(12) United States Patent
Wan et al.

(10) Patent No.: US 12,281,118 B2
(45) Date of Patent: Apr. 22, 2025

(54) NITROGEN-CONTAINING FUSED HETEROCYCLIC SHP2 INHIBITOR COMPOUND, PREPARATION METHOD, AND USE

(71) Applicant: SHANGHAI RINGENE BIOPHARMA CO., LTD., Shanghai (CN)

(72) Inventors: Huixin Wan, Nantong (CN); Jianfeng Pan, Nantong (CN); Jingui Ma, Nantong (CN); Chuantao Cha, Nantong (CN)

(73) Assignee: SHANGHAI RINGENE BIOPHARMA CO., LTD., Shanghai (CN)

( * ) Notice: Subject to any disclaimer, the term of this patent is extended or adjusted under 35 U.S.C. 154(b) by 825 days.

(21) Appl. No.: 17/292,027

(22) PCT Filed: Nov. 7, 2019

(86) PCT No.: PCT/CN2019/116386
§ 371 (c)(1),
(2) Date: May 7, 2021

(87) PCT Pub. No.: WO2020/094104
PCT Pub. Date: May 14, 2020

(65) Prior Publication Data
US 2022/0127271 A1 Apr. 28, 2022

(30) Foreign Application Priority Data

Nov. 7, 2018 (CN) .................... 201811317588.8
Dec. 26, 2018 (CN) .................... 201811594644.2
Feb. 22, 2019 (CN) .................... 201910131491.6

(51) Int. Cl.
A23K 50/10 (2016.01)
A23K 20/158 (2016.01)
A61K 9/00 (2006.01)
A61P 35/02 (2006.01)
C07D 471/04 (2006.01)
C07D 487/04 (2006.01)
C07D 519/00 (2006.01)
C07K 16/28 (2006.01)

(52) U.S. Cl.
CPC .......... C07D 487/04 (2013.01); A61K 9/0019 (2013.01); A61K 9/0053 (2013.01); A61P 35/02 (2018.01); C07D 471/04 (2013.01); C07D 519/00 (2013.01); C07K 16/2827 (2013.01)

(58) Field of Classification Search
None
See application file for complete search history.

(56) References Cited

U.S. PATENT DOCUMENTS

| 10,093,646 B2 | 10/2018 | Chen |
| 10,844,079 B2 | 11/2020 | Zheng et al. |
| 2011/0237565 A1 | 9/2011 | Borchardt et al. |
| 2016/0289238 A1 | 10/2016 | He et al. |
| 2020/0407372 A1 | 12/2020 | Koltun et al. |
| 2021/0053989 A1 | 2/2021 | Zou et al. |

FOREIGN PATENT DOCUMENTS

| AU | 2019386036 A1 | 5/2021 |
| CN | 102869666 A | 1/2013 |
| CN | 107660205 A | 2/2018 |
| CN | 110156786 A | 8/2019 |
| CN | 110655520 A | 1/2020 |
| CN | 111138412 A | 5/2020 |
| CN | 111433205 A | 7/2020 |
| JP | 2013522222 A | 6/2013 |
| JP | 2017503000 A | 1/2017 |
| JP | 2018510193 A | 4/2018 |
| WO | 2014044025 A1 | 3/2014 |
| WO | 2015107493 A1 | 7/2015 |
| WO | 2018136265 A1 | 7/2018 |
| WO | 2018172984 A1 | 9/2018 |
| WO | 2019118909 A1 | 6/2019 |
| WO | 2019158019 A1 | 8/2019 |
| WO | 2020072656 A1 | 4/2020 |
| WO | 2020094018 A1 | 5/2020 |
| WO | 2020108590 A1 | 6/2020 |

OTHER PUBLICATIONS

Jan. 13, 2020 International Search Report issued in International Patent Application No. PCT/CN2019/116386.

(Continued)

Primary Examiner — Layla Soroush
(74) Attorney, Agent, or Firm — SZDC Law PC

(57) ABSTRACT

Disclosed are a nitrogen-containing fused heterocyclic SHP2 inhibitor compound, a preparation method, and use. The nitrogen-containing fused heterocyclic SHP2 inhibitor compound is represented by formula I below. The compound has high inhibitory activity for an SHP2 enzyme and tumor cell proliferation, and has good druggability.

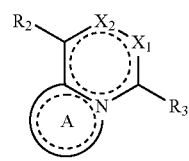

6 Claims, No Drawings

(56) References Cited

OTHER PUBLICATIONS

Jan. 13, 2020 Written Opinion of the International Searching Authority issued in International Patent Application No. PCT/CN2019/116386.
Priority document CN 201811317588.8.
Priority document CN 201811594644.2.
Priority document CN 201910131491.6.
Sep. 9, 2020 First Office Action issued in Chinese Patent Application No. 2019110834093.
Apr. 8, 2021 Second Office Action issued in Chinese Patent Application No. 2019110834093.
First Office Action issued in Japanese Patent Application No. 2021524993 dated Sep. 21, 2023.
Third Chinese Office Action issued in Chinese Application No. 2019110834093, dated Aug. 18, 2021.
Extended European Search Report issued in European Patent Application No. 19882124.1 dated Nov. 10, 2022.
Office Action issued in Japanese Patent Application No. 2021524993 dated Jul. 2, 2024.
First Office Action issued in Korea Patent Application No. KR 10-2021-7017327 dated Nov. 24, 2024.
First Office Action issued in European Patent Application No. EP19 882 124.1 dated Dec. 12, 2024.

NITROGEN-CONTAINING FUSED HETEROCYCLIC SHP2 INHIBITOR COMPOUND, PREPARATION METHOD, AND USE

This application is the national stage application of PCT/CN2019/116386, filed on Nov. 7, 2019, which claims priority of Chinese patent application 201811317588.8 filed on Nov. 7, 2018, Chinese patent application 201811594644.2 filed on Dec. 26, 2018, and Chinese patent application 201910131491.6 filed on Feb. 22, 2019. The contents of the Chinese patent applications are incorporated herein by reference in their entireties.

TECHNICAL FIELD

The invention relates to a nitrogen-containing fused heterocyclic SHP2 inhibitor compound, a preparation method and a use thereof.

BACKGROUND

Protein tyrosine phosphatase (PTP) plays an important role in the regulation of a variety of cell processes, such as cell growth, proliferation, cell differentiation, and carcinogenic transformation. The balance between dephosphorylation caused by the PTP and phosphorylation caused by a tyrosine kinase, a counterpart of PTP, is critical for normal physiological functions. The PTP is increasingly recognized as a valuable drug target. For example, Src homology-2 (SH2) domain-containing protein-tyrosine phosphatase-2 (SHP 2) encoded by Protein Tyrosine Phosphatase non-receptor type 11 (PTPN11) is a non-receptor protein tyrosine phosphatase (PTP) containing two tandem Src homology-2 (SH2) domains. SHP2 is broadly expressed in most tissues and plays an active role in multiple signal transduction pathways at downstreams of growth factor and cytokine receptors to regulate multiple cellular functions. The catalytic activity of the SHP2 is required for full activation of Ras-ERK1/2 cascade, which is mediated by dephosphorylation of a SHP2-catalyzed substrate that is negatively regulated by phosphorylation of a tyrosine. SHP2 is identified as a true oncogene; gain-of-function SHP2 mutations result in the Noonan syndrome caused by increased phosphatase activity, and various forms of leukemia (e.g., juvenile myelomonocytic leukemia, acute myelogenous leukemia, myelodysplastic syndrome, acute lymphoid leukemia) and multiple solid tumors (e.g., lung adenocarcinoma, colon cancer, neuroblastoma, glioblastoma, melanoma, hepatocellular carcinoma, and prostate cancer). Thus, SHP2 represents a promising target for a variety of cancers (e.g., triple-negative and HER2+breast cancer, cancers caused by abnormal activation of receptor protein tyrosine kinase (PTK), some of which respond poorly to kinase inhibitor monotherapy), and attracts more and more attention in the development of SHP2 inhibitors.

Therefore, discovering and searching for SHP2 inhibitors with good druggability has gradually become a hot research field in industry and academia.

Content of the Invention

The present disclosure provides a nitrogen-containing fused heterocyclic SHP2 inhibitor compound, a preparation method and a use thereof which are different from the prior art. The nitrogen-containing fused heterocyclic SHP2 inhibitor compound of the present disclosure has high inhibitory activity for an SHP2 enzyme and tumor cell proliferation, and has good druggability.

The present disclosure provides a nitrogen-containing fused heterocyclic compound represented by formula I, a pharmaceutically acceptable salt thereof, an enantiomer thereof, a diastereomer thereof, a tautomer thereof, a solvate thereof, a polymorph thereof or a prodrug thereof,

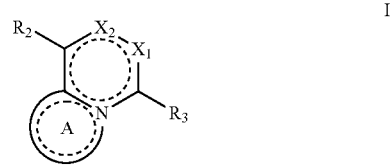

wherein $X_1$ and $X_2$ are independently N or $CR_1$;

each $R_1$ is independently hydrogen, halogen, hydroxyl, amino, acylamino, sulfonamido, $C_1$-$C_6$ alkyl, $C_1$-$C_6$ alkoxy, cyano, alkenyl, alkynyl, 3-8 membered cycloalkyl or heterocycloalkyl, 5-8 membered aryl or heteroaryl;

$R_2$ is -$L_2$-$R_y$, wherein $L_2$ is a direct bond, —O—, —S(O)n- or —$NR_b$—, and $R_y$ is 5-10 membered cycloalkyl or heterocycloalkyl or aryl or heteroaryl; n=0-2; $R_b$ is hydrogen, $C_1$-$C_6$ alkyl or alkoxy, 3-8 membered cycloalkyl or heterocycloalkyl;

$R_3$ is —$OR_c$, —$SR_c$, —$C(R_aR_b)R_c$, —$NR_bR_c$, —$COR_c$, —$CONR_bR_c$, —$NR_bCOR_c$, —$SO_2NR_bR_c$, —$NR_bSO_2R_c$, —$NR_bCONR_bR_c$, —$NR_bSO_2NR_bR_c$, —$NR_bCSNR_bR_c$, —$COOR_c$, —$OOCR_c$, —$OCONR_bR_c$, —$NR_bCOOR_c$, —$NR_bCSR_c$, and —$CSNR_bR_c$, wherein $R_b$ is independently selected from hydrogen, $C_1$-$C_6$ alkyl or alkoxy, 3-8 membered cycloalkyl or heterocycloalkyl upon each occurrence; $R_c$ is independently selected from $C_1$-$C_6$ alkyl, 3-12 membered monocyclic or polycyclic cycloalkyl, 3-12 membered monocyclic or polycyclic heterocycloalkyl; or $R_c$ and $R_a$ or $R_b$ form 3-12 membered monocyclic or polycyclic cycloalkyl, 3-12 membered monocyclic or polycyclic heterocycloalkyl, 3-12 membered Spiro or fused cycloalkyl, 3-12 membered Spiro or fused heterocycloalkyl, 13-20 membered polycyclic heterocycloalkyl, 13-20 membered Spiro heterocycloalkyl, or 13-20 membered fused heterocycloalkyl;

one or more hydrogen atoms on any of the above groups may be substituted with a substituent selected from the group consisting of deuterium, halogen, hydroxyl, amino or cycloamino, cyano, nitro, sulfone or sulfoxide, $C_1$-$C_8$ alkyl, 3-8 membered cycloalkyl or heterocycloalkyl, $C_1$-$C_8$ alkoxy, $C_1$-$C_8$ alkylamino, alkenyl, alkynyl, acyl or sulfonyl, urea or sulfonylurea, 5-8 membered aryl or heteroaryl, amino substituted with $R^{2-1}$, $C_1$-$C_4$ alkyl substituted with $R^{2-2}$,

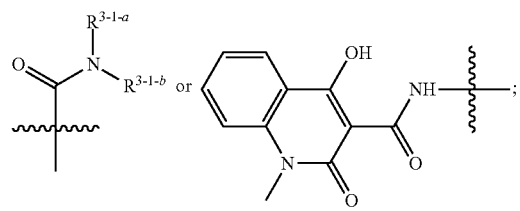

alternatively, 4-8 membered heterocycloalkyl formed by 2 hydrogen atoms on any of the groups described above and the

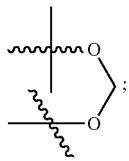

$R^{2-1}$ is $C_1$-$C_4$ alkyl or a 3-6 membered cycloalkyl;

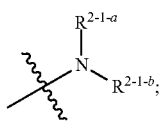

$R^{2-2}$ is halogen or;
$R^{2-1-a}$, $R^{2-1-b}$, $R^{3-1-a}$ and $R^{3-1-b}$ are independently $C_1$-$C_4$ alkyl;
wherein the heteroaryl comprises 1-3 heteroatoms selected from the group consisting of N, O, P, or S; the heterocycloalkyl comprises 1-3 heteroatoms selected from the group consisting of N, O, P, or S; the ring system comprises a spiro ring, a bridged ring, a fused ring, a fused saturated or partially unsaturated ring system; the above ring systems may be further substituted with $C_1$-$C_6$ alkyl, hydroxy, amino, halogen or alkoxy.

In the present disclosure, some substituents of the nitrogen-containing fused heterocyclic compound represented by formula I or T-a, a pharmaceutically acceptable salt thereof, an enantiomer thereof, a diastereomer thereof, a tautomer thereof, a solvate thereof, a polymorph thereof or a prodrug thereof may be defined below, and definitions of substituents not mentioned are as described in any embodiment above.

In a preferred embodiment, in the nitrogen-containing fused heterocyclic compound represented by formula I, a pharmaceutically acceptable salt thereof, an enantiomer thereof, a diastereomer thereof, a tautomer thereof, a solvate thereof, a polymorph thereof or a prodrug thereof,
the A is any of the following groups:

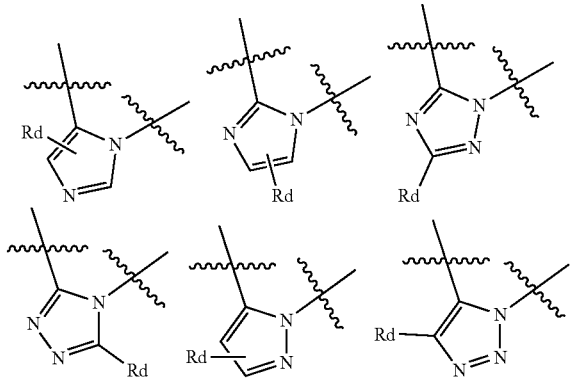

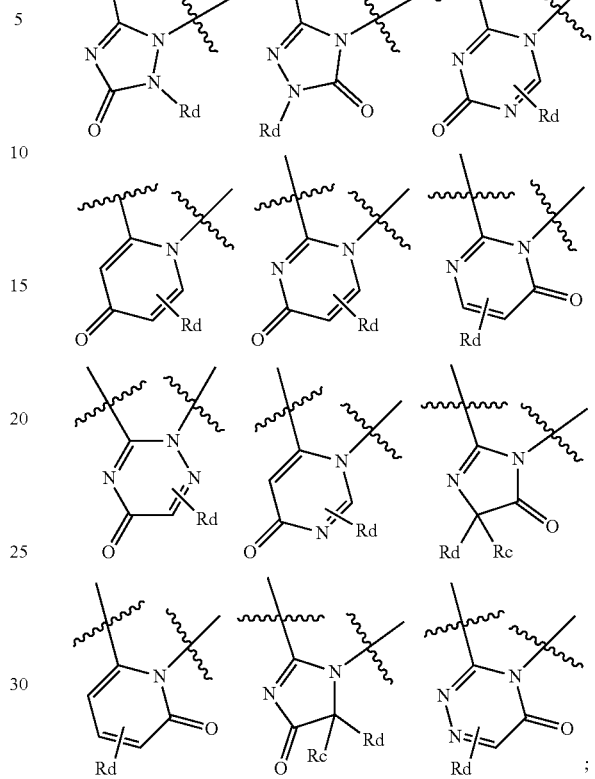

$R_d$ is hydrogen, halogen, hydroxyl, amino, $C_1$-$C_6$ alkyl, $C_1$-$C_6$ alkoxy, $C_1$-$C_6$ alkylamino, cyano, alkenyl, alkynyl, 3-8 membered cycloalkyl or heterocycloalkyl, 5-8 membered aryl or heteroaryl.

In a preferred embodiment, in the nitrogen-containing fused heterocyclic compound represented by formula I, a pharmaceutically acceptable salt thereof, an enantiomer thereof, a diastereomer thereof, a tautomer thereof, a solvate thereof, a polymorph thereof or a prodrug thereof,
the $R_a$ is independently hydrogen, $C_1$-$C_6$ alkyl or alkoxy, 3-8 membered cycloalkyl or heterocycloalkyl.

In some preferred embodiment, a nitrogen-containing fused heterocyclic compound represented by formula I, a pharmaceutically acceptable salt thereof, an enantiomer thereof, a diastereomer thereof, a tautomer thereof, a solvate thereof, a polymorph thereof or a prodrug thereof is not any of the following compounds:

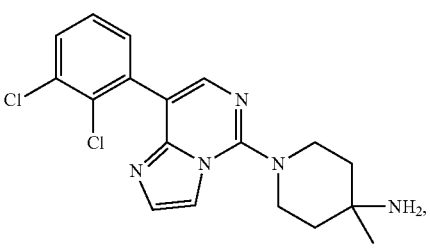

-continued

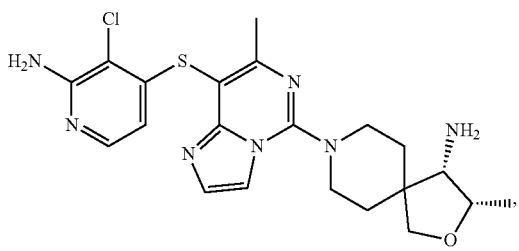

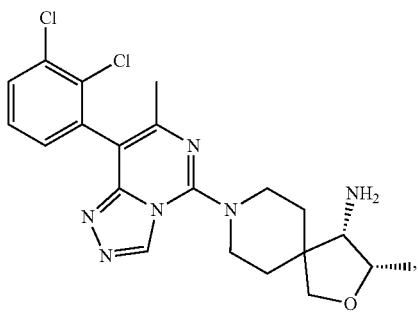

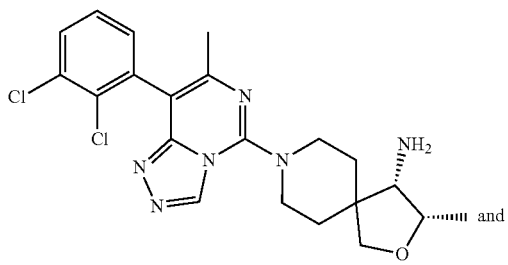

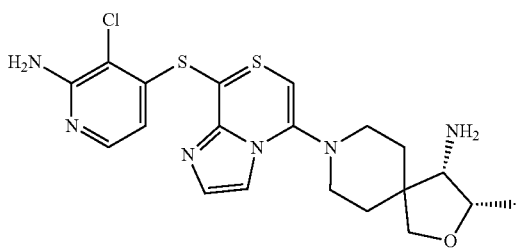

In a preferred embodiment, when $R_3$ is —$NR_bR_c$; the —$NR_bR_c$ is 3-12 membered monocyclic heterocycloalkyl, 3-12 membered monocyclic heterocycloalkyl or 13-20 membered polycyclic heterocycloalkyl, further may be

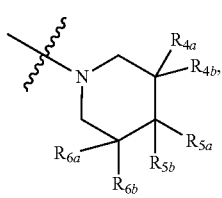

and furthermore may be

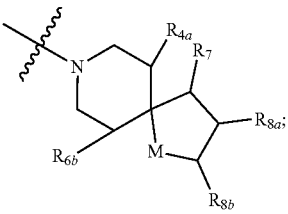

wherein $R_{5a}$ is $C_1$-$C_6$ alkyl, hydroxy, amino or aminomethyl;

$R_{5b}$ is hydroxy, amino, halogen, $C_1$-$C_6$ alkyl, 3-8 membered cycloalkyl or heterocycloalkyl, hydroxyalkyl, alkoxyalkyl, cycloalkylalkyl, alkoxyacyl, 5-8 membered aryl or heteroaryl;

alternatively, $R_{5a}$ and $R_{5b}$ together with carbon atoms to which the $R_{5a}$ and the $R_{5b}$ are linked form 3-12 membered monocyclic or polycyclic saturated or unsaturated alkyl, 3-12 membered monocyclic or polycyclic saturated or unsaturated heterocycloalkyl, 3-12 membered spiro or fused cycloalkyl, and 3-12 membered spiro or fused heterocycloalkyl;

one or more hydrogen atoms of $R_{5a}$ and $R_{5b}$ described above, or groups obtained in such a way that "$R_{5a}$ and $R_{5b}$ together with carbon atoms to which the $R_{5a}$ and the $R_{5b}$ are linked form 3-12 membered monocyclic or polycyclic saturated or unsaturated alkyl, 3-12 membered monocyclic or polycyclic saturated or unsaturated heterocycloalkyl, 3-12 membered spiro or fused cycloalkyl, and 3-12 membered spiro or fused heterocycloalkyl" may be substituted with substituent(s) selected from the group consisting of deuterium, halogen, hydroxy, alkoxy, amino, alkylamino, alkyl, cycloalkyl and heterocycloalkyl;

M is —O—, —S—, —$SO_2$—, —$CR_{9a}R_{9b}$— or —$NR_{10}$—;

$R_7$ is hydrogen, halogen, $C_1$-$C_6$ alkyl, hydroxy, amino or alkoxy;

$R_{9a}$ and $R_{9b}$ are independently deuterium, hydrogen, oxygen, hydroxyl, halogen, amino or $C_1$-$C_6$ alkyl;

$R_{10}$ is hydrogen or $C_1$-$C_{10}$ alkyl;

$R_{8a}$ and $R_{8b}$ are independently hydrogen, halogen or $C_1$-$C_6$ alkyl;

alternatively, $R_{8a}$ and $R_{8b}$ together with carbon atoms or heteroatoms to which the $R_{8a}$ and the $R_{8b}$ are linked form a 3-12 membered saturated or partially unsaturated or aromatic ring system, wherein the formed ring system can continue to be substituted with one or more substituents;

when one or more hydrogen atoms on the ring system are substituted with a substituent, the substituent is $R^{8a-1}$, wherein $R^{8a-1}$ is halogen or $C_1$-$C_8$ alkoxy.

The present disclosure also provides a nitrogen-containing fused heterocyclic compound represented by formula I-a, a pharmaceutically acceptable salt thereof, an enantiomer thereof, a diastereomer thereof, a tautomer thereof, a solvate thereof, a polymorph thereof or a prodrug thereof:

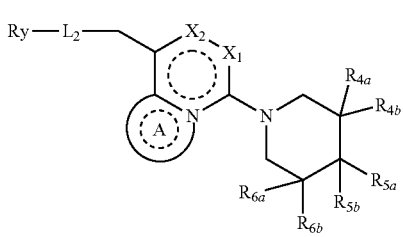

wherein $L_2$ is a direct bond or —S—;
$X_1$ is N or $CR_1$;
$X_2$ is $CR_1$;
each $R_1$ is independently H, amino or $C_1$-$C_6$ alkyl;
A is

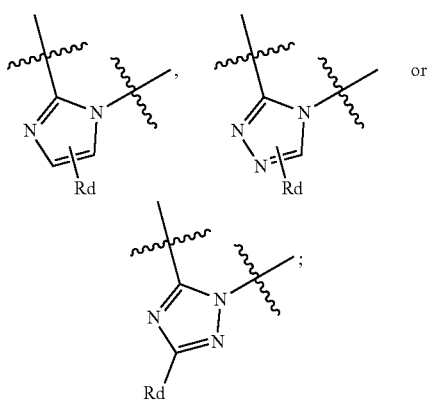

$R_d$ is H or $C_1$-$C_6$ alkyl;
$R_y$ is 5-10 membered aryl or 5-10 membered heteroaryl;
$R_{4a}$, $R_{4b}$, $R_{6a}$ and $R_{6b}$ are independently hydrogen;
$R_{5a}$ and $R_{5b}$ are independently amino or $C_1$-$C_6$ alkyl;
alternatively, $R_{5a}$ and $R_{5b}$ together with atoms to which the $R_{5a}$ and the $R_{5b}$ are linked form 3-12 membered monocyclic saturated cycloalkyl, 3-12 membered fused cycloalkyl, or 3-12 membered fused heterocycloalkyl, wherein the 3-12 membered fused heterocycloalkyl contains 1-3 heteroatoms selected from the group consisting of N, O, P, or S,
wherein one or more hydrogen atoms on $R_1$ and $R_y$ described above may be substituted with a substituent selected from the group consisting of halogen, hydroxy, amino, $C_1$-$C_8$ alkyl, 3-8 membered cycloalkyl, $C_1$-$C_8$ alkoxy, amino substituted with $R^{2-1}$, $C_1$-$C_4$ alkyl substituted with $R^{2-2}$, or

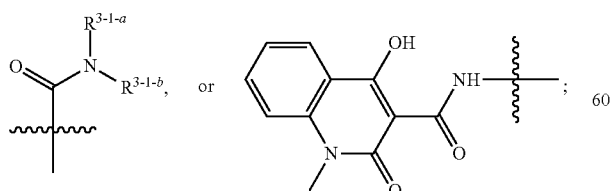

alternatively, 2 hydrogen atoms on $R_1$ and $R_y$ described above are substituted with

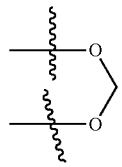 [SMILES: *OCO*]

to form 4-8 membered heterocycloalkyl;
one or more hydrogen atoms on $R_{5a}$ and $R_{5b}$ described above, or groups obtained in such a way that "$R_{5a}$ and $R_{5b}$ together with atoms to which the $R_{5a}$ and the $R_{5b}$ are linked form 3-12 membered monocyclic saturated alkyl, 3-12 membered fused cycloalkyl, or 3-12 membered fused heterocycloalkyl" may be substituted with substituent(s) selected from the group consisting of halogen, alkoxy and amino.

In a preferred embodiment, in the nitrogen-containing fused heterocyclic compound represented by formula I, a pharmaceutically acceptable salt thereof, an enantiomer thereof, a diastereomer thereof, a tautomer thereof, a solvate thereof, a polymorph thereof or a prodrug thereof, the nitrogen-containing fused heterocyclic compound represented by formula I is represented by formula I-a;

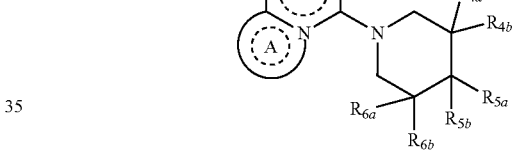

wherein $L_2$ is a direct bond or —S—;
$X_1$ is N or $CR_1$;
$X_2$ is $CR_1$;
each $R_1$ is independently H, amino or $C_1$-$C_6$ alkyl;
A is

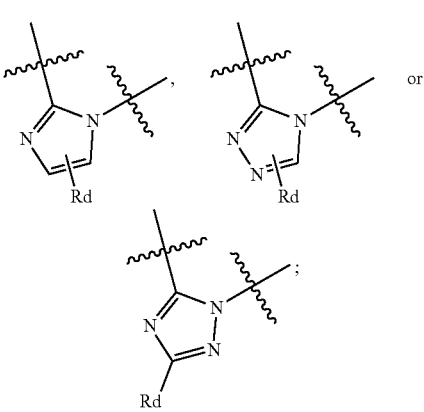

$R_d$ is H or $C_1$-$C_6$ alkyl;
$R_y$ is 5-10 membered aryl or 5-10 membered heteroaryl;
$R_{4a}$, $R_{4b}$, $R_{6a}$ and $R_{6b}$ are independently hydrogen;
$R_{5a}$ and $R_{5b}$ are independently amino or $C_1$-$C_6$ alkyl;
alternatively, $R_{5a}$ and $R_{5b}$ together with atoms to which the $R_{5a}$ and the $R_{5b}$ are linked form 3-12 membered monocyclic saturated cycloalkyl, 3-12 membered fused cycloalkyl, or 3-12 membered fused heterocycloalkyl, wherein the 3-12 membered fused heterocycloalkyl contains 1-3 heteroatoms selected from the group consisting of N, O, P, or S, wherein one or more hydrogen atoms on $R_1$ and $R_y$ described above may be substituted with a substituent selected from the group consisting of halogen, hydroxy, amino, $C_1$-$C_8$ alkyl, 3-8 membered cycloalkyl, $C_1$-$C_8$ alkoxy, amino substituted with $R^{2-1}$, $C_1$-$C_4$ alkyl substituted with $R^{2-2}$, or

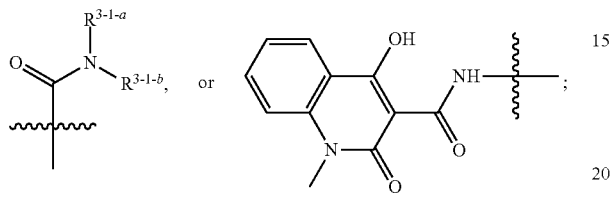

alternatively, 2 hydrogen atoms on $R_1$ and $R_y$ described above are substituted with

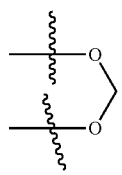 [SMILES: *OCO*]

to form 4-8 membered heterocycloalkyl;

one or more hydrogen atoms on $R_{5a}$ and $R_{5b}$ described above, or groups obtained in such a way that "$R_{5a}$ and $R_{5b}$ together with atoms to which the $R_{5a}$ and the $R_{5b}$ are linked form 3-12 membered monocyclic saturated alkyl, 3-12 membered fused cycloalkyl, or 3-12 membered fused heterocycloalkyl" may be substituted with substituent(s) selected from the group consisting of halogen, alkoxy and amino.

In a preferred embodiment, in the compound represented by formula I-a:

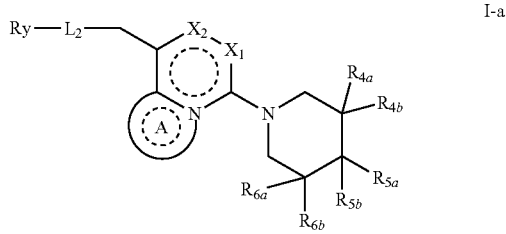

wherein $L_2$ is a direct bond or —S—;

$X_1$ is N or $CR_1$;

$X_2$ is $CR_1$;

each $R_1$ is independently H, amino or $C_1$-$C_6$ alkyl;

A is

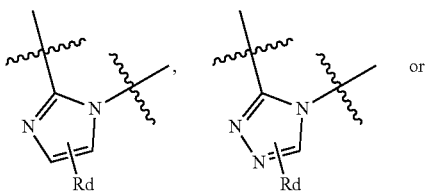

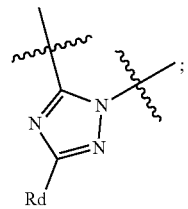

$R_d$ is H;

$R_y$ is 5-10 membered aryl or 5-10 membered heteroaryl;

$R_{4a}$, $R_{4b}$, $R_{6a}$ and $R_{6b}$ are independently hydrogen;

$R_{5a}$ and $R_{5b}$ are independently amino or $C_1$-$C_6$ alkyl;

alternatively, $R_{5a}$ and $R_{5b}$ together with atoms to which the $R_{5a}$ and the $R_{5b}$ are linked form 3-12 membered monocyclic saturated cycloalkyl, 3-12 membered fused cycloalkyl, or 3-12 membered fused heterocycloalkyl, wherein the 3-12 membered fused heterocycloalkyl contains 1-3 heteroatoms selected from the group consisting of N, O, P, or S;

when one or more hydrogen atoms on the $R_1$ are independently substituted with substituent(s), the substituent(s) is halogen substituent;

when one or more hydrogen atoms on the $R_y$ are substituted with substituent(s), the substituent(s) is (are) $R^{y-1}$, wherein the $R^{y-1}$ is one or more of halogen, amino, amino substituted with $R^{2-1}$, and $C_1$-$C_4$ alkyl substituted with $R^{2-2}$;

$R^{2-1}$ is 3-6 membered cycloalkyl;

$R^{2-2}$ is halogen;

$R^{2-a}$, $R^{2-1-b}$, $R^{3-1-a}$ and $R^{3-1-b}$ are independently $C_1$-$C_4$ alkyl;

one or more hydrogen atoms on groups obtained in such a way that "$R_{5a}$ and $R_{5b}$ together with atoms to which the $R_{5a}$ and the $R_{5b}$ are linked form 3-12 membered monocyclic saturated alkyl, 3-12 membered fused cycloalkyl, or 3-12 membered fused heterocycloalkyl" may be substituted with substituent(s), wherein the substituent(s) is (are) $R^{5a-1}$, and the $R^{5a-1}$ is one or more of halogen, $C_1$-$C_8$ alkoxy and amino.

In a preferred embodiment, $R_{5a}$ and $R_{5b}$ may independently be amino or $C_1$-$C_6$ alkyl.

In a preferred embodiment, $R_{5a}$ and $R_{5b}$ together with atoms to which the $R_{5a}$ and the $R_{5b}$ are linked form 3-12 membered monocyclic saturated cycloalkyl.

In a preferred embodiment, $R_{5a}$ and $R_{5b}$ together with atoms to which the $R_{5a}$ and the $R_{5b}$ are linked form 3-12 membered fused cycloalkyl or 3-12 membered fused heterocycloalkyl.

In a preferred embodiment, A is

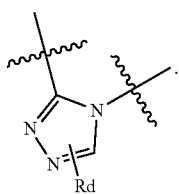

In a preferred embodiment, A is

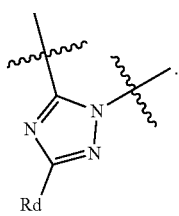

In a preferred embodiment, when each $R_1$ is independently $C_1$-$C_6$ alkyl, the $C_1$-$C_6$ alkyl may not be substituted, or one or more hydrogen atoms on the $C_1$-$C_6$ alkyl are substituted only by a substituent.

In a preferred embodiment, when each $R_1$ is independently $C_1$-$C_6$ alkyl, the $C_1$-$C_6$ alkyl may be $C_1$-$C_3$ alkyl, further may be methyl, ethyl, n-propyl or isopropyl, and further may be the methyl.

In a preferred embodiment, when one or more hydrogen atoms on each $R_1$ are independently substituted with a halogen, the halogen may be F, Cl, Br or I, and further may be F.

In a preferred embodiment, when one or more hydrogen atoms on each $R_1$ are independently substituted with halogen, the $C_1$-$C_6$ alkyl may be —$CH_2F$.

In a preferred embodiment, when $R_y$ is 5-10 membered aryl, the 5-10 membered aryl may not be substituted, or one or more hydrogen atoms on the 5-10 membered aryl are substituted only by a substituent.

In a preferred embodiment, when $R_y$ is 5-10 membered aryl, the 5-10 membered aryl may be 6-10 membered aryl (phenyl or naphthyl), or further may be the phenyl.

In a preferred embodiment, when $R_y$ is 5-10 membered aryl, and one or more hydrogen atoms on the 5-10 membered aryl are substituted with a substituent, the substituent is $R^{y-1}$, and each of the $R^{y-1}$ is independently halogen, wherein the halogen may be F, Cl, Br or I, or may be the Cl.

In a preferred embodiment, when $R_y$ is 5-10 membered aryl, and one or more hydrogen atoms on the 5-10 membered aryl are substituted with a substituent, the number of the substituent may be 1 or 2, or may be 2. When the number of the substituents is 2, the substituents may be the same or different.

In a preferred embodiment, when $R_y$ is 5-10 membered aryl, and one or more hydrogen atoms on the 5-10 membered aryl are substituted with a substituent, the substituent may be located in an ortho-position and/or a meta-position of $L_2$, or may be located in an ortho-position and a meta-position of $L_2$.

In a preferred embodiment, when $R_y$ is 5-10 membered aryl, the number of ring systems of the 5-10 membered aryl may be 1 or 2, or may be 1.

In a preferred embodiment, when $R_y$ is 5-10 membered heteroaryl, the 5-10 membered heteroaryl may not be substituted, or one or more hydrogen atoms on the 5-10 membered heteroaryl are substituted.

In a preferred embodiment, when $R_y$ is 5-10 membered heteroaryl, the 5-10 membered heteroaryl may be 6-8 membered heteroaryl.

In a preferred embodiment, when $R_y$ is 5-10 membered heteroaryl, heteroatoms in the 5-10 membered heteroaryl may be N and the number may be 1.

In a preferred embodiment, when $R_y$ is 5-10 membered heteroaryl, the number of ring systems of the 5-10 membered heteroaryl may be 1 or 2, or may be 1.

In a preferred embodiment, when $R^{y-1}$ is halogen, the halogen may be F, Cl, Br or I, and may be Cl.

In a preferred embodiment, when $R^{y-1}$ is $C_1$-$C_4$ alkyl substituted with $R^{22}$, the $C_1$-$C_4$ alkyl may be methyl, ethyl, n-propyl, isopropyl, n-butyl, sec-butyl, isobutyl or tert-butyl, or may be the methyl.

In a preferred embodiment, when $R^{2-1}$ is 3-6 membered cycloalkyl, the 3-6 membered cycloalkyl may be cyclopropyl, cyclobutyl, cyclopentyl or cyclohexyl, or may be cyclopropyl.

In a preferred embodiment, when $R^{2-2}$ is halogen, the halogen may be F, Cl, Br or I, or may be the F.

In a preferred embodiment, when $R_y$ is 5-10 membered aryl, and one or more hydrogen atoms on the 5-10 membered aryl are substituted only, the 5-10 membered aryl may be

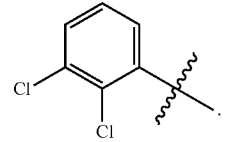 [SMILES: *c1cccc(Cl)c1Cl]

In a preferred embodiment, when $R_y$ is 5-10 membered heteroaryl, and one or more hydrogen atoms on the 5-10 membered heteroaryl are substituted, the 5-10 membered heteroaryl may be

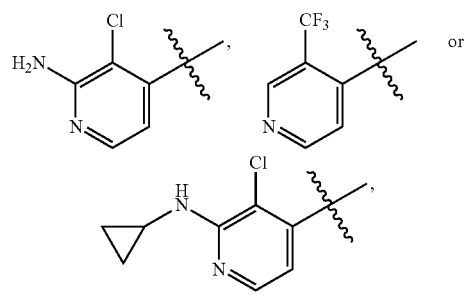

or may be

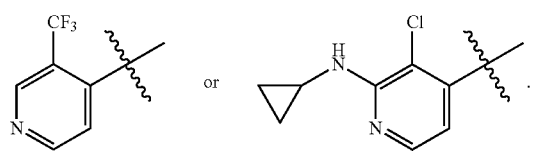 [SMILES: *c1ccncc1C(F)(F)F ; *c1ccnc(NC2CC2)c1Cl]

In a preferred embodiment, R$_y$ is

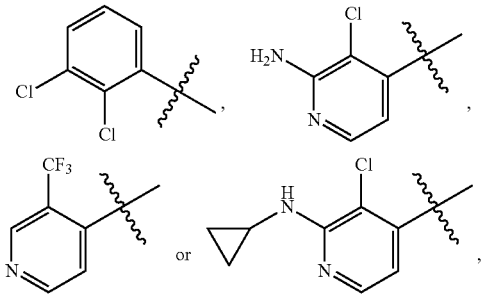

or may be

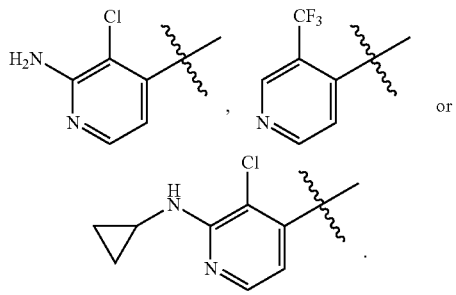

In a preferred embodiment, when R$_{5a}$ and R$_{5b}$ are independently C$_1$-C$_6$ alkyl, the C$_1$-C$_6$ alkyl may not be substituted, or one or more hydrogen atoms on the C$_1$-C$_6$ alkyl are substituted only.

In a preferred embodiment, when R$_{5a}$ and R$_{5b}$ are independently C$_1$-C$_6$ alkyl, the C$_1$-C$_6$ alkyl may be C$_1$-C$_3$ alkyl, further may be methyl, ethyl, n-propyl or isopropyl, or further may be the methyl.

In a preferred embodiment, when R$_{5a}$ and R$_{5b}$ together with atoms to which the R$_{5a}$ and the R$_{5b}$ are linked form 3-12 membered monocyclic saturated cycloalkyl, the 3-12 membered monocyclic saturated cycloalkyl may not be substituted, or one or more hydrogen atoms on the 3-12 membered monocyclic saturated cycloalkyl may be substituted only.

In a preferred embodiment, when R$_{5a}$ and R$_{5b}$ together with atoms to which the R$_{5a}$ and the R$_{5b}$ are linked form 3-12 membered monocyclic saturated alkyl, the 3-12 membered monocyclic saturated alkyl may be 3-6 membered monocyclic saturated alkyl, further may be cyclopropyl, cyclobutyl, cyclopentyl or cyclohexyl, or further may be the cyclopentyl.

In a preferred embodiment, when R$_{5a}$ and R$_{5b}$ together with atoms to which the R$_{5a}$ and the R$_{5b}$ are linked form 3-12 membered fused cycloalkyl, the 3-12 membered fused cycloalkyl may not be substituted, or one or more hydrogen atoms on the 3-12 membered fused cycloalkyl are substituted.

In a preferred embodiment, when R$_{5a}$ and R$_{5b}$ together with atoms to which the R$_{5a}$ and the R$_{5b}$ are linked form 3-12 membered fused cycloalkyl, the number of rings of the 3-12 membered fused cycloalkyl may be 2, and further may be fused cycloalkyl

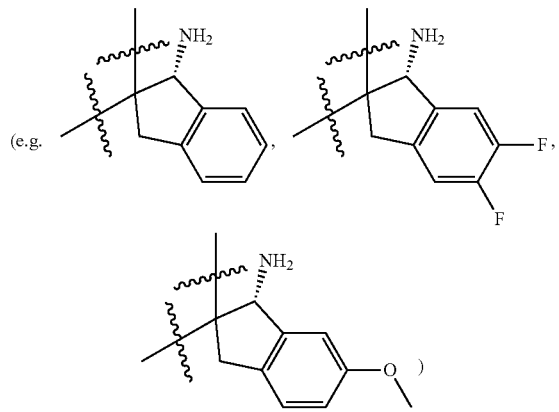 [SMILES: *C1(*)Cc2ccccc2[C@H]1N ; *C1(*)Cc2cc(F)c(F)cc2[C@H]1N ; *C1(*)Cc2ccc(OC)cc2[C@H]1N]

(e.g.

formed by fusing monocyclic saturated cycloalkyl to aryl,
wherein when the 3-12 membered fused cycloalkyl is the fused cycloalkyl formed by fusing the monocyclic saturated cycloalkyl to the aryl, the monocyclic saturated cycloalkyl may be 3-6 membered monocyclic saturated cycloalkyl, further may be cyclopropyl, cyclobutyl, cyclopentyl or cyclohexyl, or may be the cyclopentyl;
wherein when the 3-12 membered fused cycloalkyl is the fused cycloalkyl formed by fusing the monocyclic saturated cycloalkyl to the aryl, the aryl may be 6-10 membered aryl, or further may be phenyl;
wherein when the 3-12 membered fused cycloalkyl is the fused cycloalkyl formed by fusing the monocyclic saturated cycloalkyl to the aryl, the monocyclic saturated cycloalkyl may be linked to

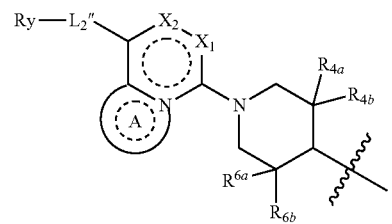

by a C atom;
wherein when the 3-12 membered fused cycloalkyl is the fused cycloalkyl formed by fusing the monocyclic saturated cycloalkyl to the aryl, and the R$^{5a-1}$ is amino, the number of the R$^{5a-1}$ may be 1;
wherein when the 3-12 membered fused cycloalkyl is the fused cycloalkyl formed by fusing the monocyclic saturated cycloalkyl to the aryl, and the R$^{5a-1}$ is amino, the substitution position of the R$^{5a-1}$ may be on the monocyclic saturated cycloalkyl;
wherein when the 3-12 membered fused cycloalkyl is the fused cycloalkyl formed by fusing the monocyclic saturated cycloalkyl to the aryl, and R$^{5a-1}$ is halogen and/or C$_1$-C$_8$ alkoxy, the number of the R$^{5a-1}$ may be 1 or 2.
wherein when the 3-12 membered fused cycloalkyl is the fused cycloalkyl formed by fusing the monocyclic saturated cycloalkyl to the aryl, and R$^{5a-1}$ is halogen and/or C$_1$-C$_8$ alkoxy, the substitution position of the R$^{5a-1}$ may be on the aryl.

In a preferred embodiment, when $R_{5a}$ and $R_{5b}$ together with atoms to which the $R_{5a}$ and the $R_{5b}$ are linked form 3-12 membered fused cycloalkyl, the 3-12 membered fused cycloalkyl may be 6-9 membered fused cycloalkyl.

In a preferred embodiment, when $R^{5a}$ and $R^{5b}$ together with atoms to which the $R^{5a}$ and the $R^{5b}$ are linked form 3-12 membered fused cycloalkyl, and one or more hydrogen atoms on the 3-12 membered fused cycloalkyl are substituted with a substituent and a C atom at the substitution position is a chiral C atom, the stereo configuration of the chiral C atom may be R type or S type, or may be S type.

In a preferred embodiment, when $R^{5a}$ and $R^{5b}$ together with atoms to which the $R^{5a}$ and the $R^{5b}$ are linked form 3-12 membered fused cycloalkyl, and one or more hydrogen atoms on the 3-12 membered fused cycloalkyl are substituted with substituent(s), the number of the substituent(s) may be 1, 2 or 3. When the number of the substituent is 2 or 3, the substituent may be the same or different.

In a preferred embodiment, when $R^{5a-1}$ is halogen, the halogen may be F, Cl, Br or I, or may be F.

In a preferred embodiment, when $R^{5a-1}$ is $C_1$-$C_8$ alkoxy, the $C_1$-$C_8$ alkoxy may be $C_1$-$C_3$ alkoxy, further may be methoxy, ethoxy, n-propoxy or isopropoxy, or further may be the methoxy.

In a preferred embodiment, when $R^{5a}$ and $R^{5b}$ together with atoms to which the $R^{5a}$ and the $R^{5b}$ are linked form 3-12 membered fused cycloalkyl, and one or more hydrogen atoms on the 3-12 membered fused cycloalkyl are substituted, the 3-12 membered fused cycloalkyl may be

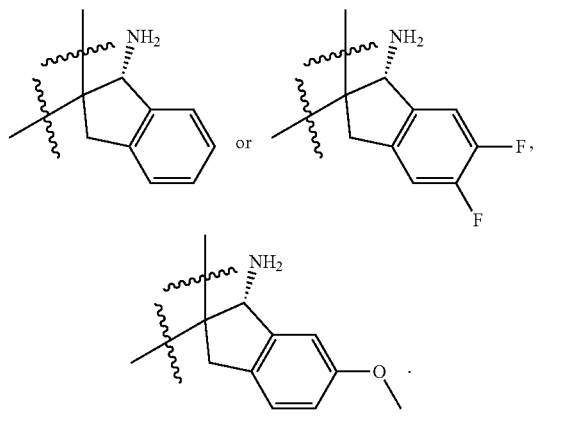 [SMILES: *C1(*)Cc2ccccc2[C@H]1N ; *C1(*)Cc2cc(F)c(F)cc2[C@H]1N ; *C1(*)Cc2ccc(OC)cc2[C@H]1N]

In a preferred embodiment, when $R_{5a}$ and $R_{5b}$ together with atoms to which the $R_{5a}$ and the $R_{5b}$ are linked form 3-12 membered fused heterocyclyl, the 3-12 membered fused heterocyclyl may not be substituted, or one or more hydrogen atoms on the 3-12 membered fused heterocyclyl are substituted only.

In a preferred embodiment, when $R_{5a}$ and $R_{5b}$ together with atoms to which the $R_{5a}$ and the $R_{5b}$ are linked form 3-12 membered fused heterocyclyl, the number of rings of the 3-12 membered fused heterocyclyl may be 2; the 3-12 membered fused heterocyclyl further may be fused heterocyclyl formed by fusing "monocyclic saturated cycloalkyl, or monocyclic saturated heterocycloalkyl" to "aryl or heteroaryl", or further may be fused heterocyclyl formed by fusing the monocyclic saturated cycloalkyl to the heteroaryl, or fused heterocyclyl

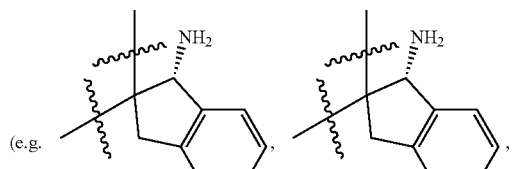

formed by fusing monocyclic saturated heterocycloalkyl to aryl;

wherein when the 3-12 membered fused heterocyclyl is the fused cycloalkyl formed by fusing the "monocyclic saturated cycloalkyl or monocyclic saturated heterocycloalkyl" to the "aryl or heteroaryl", the monocyclic saturated cycloalkyl may be 3-6 membered monocyclic saturated cycloalkyl, further may be cyclopropyl, cyclobutyl, cyclopentyl or cyclohexyl, or may be the cyclopentyl;

wherein when the 3-12 membered fused heterocyclyl is fused heterocyclyl formed by fusing the "monocyclic saturated cycloalkyl, or monocyclic saturated heterocycloalkyl" to the "aryl or heteroaryl", the heterocyclic saturated cycloalkyl may be 3-6 membered heterocyclic saturated cycloalkyl, and further may be tetrahydrofuranyl;

wherein when the 3-12 membered fused heterocyclyl is the fused cycloalkyl formed by fusing the "monocyclic saturated cycloalkyl or monocyclic saturated heterocycloalkyl" to the "aryl or heteroaryl", the aryl may be 6-10 membered aryl, further may be phenyl or phenanthrenyl, or further may be the phenyl;

wherein when the 3-12 membered fused heterocycloalkyl is the fused heterocycloalkyl formed by fusing the "monocyclic saturated cycloalkyl, or monocyclic saturated heterocycloalkyl" to the "aryl or heteroaryl", the heteroaryl may be 5-10 membered heteroaryl, a heteroatom is S and/or N, and the heteroaryl further may be pyridyl or

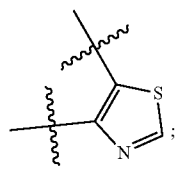 [SMILES: *c1ncsc1*]

wherein when the 3-12 membered fused heterocycloalkyl is fused heterocyclyl formed by fusing the "monocyclic saturated cycloalkyl, or monocyclic saturated heterocycloalkyl" to the "aryl or heteroaryl", the "monocyclic saturated cycloalkyl, or monocyclic saturated heterocycloalkyl" may be linked to

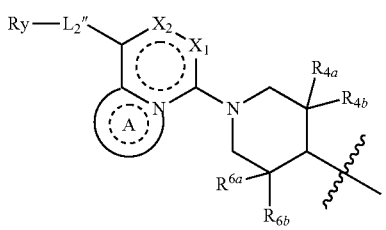

by a C atom.

- wherein when the 3-12 membered fused heterocycloalkyl is the fused heterocycloalkyl formed by fusing the "monocyclic saturated cycloalkyl, or monocyclic saturated heterocycloalkyl" to the "aryl or heteroaryl", and $R^{5a-1}$ is amino, the number of $R^{5a-1}$ may be 1;
- wherein when the 3-12 membered fused heterocycloalkyl is the fused heterocycloalkyl formed by fusing the "monocyclic saturated cycloalkyl, or monocyclic saturated heterocycloalkyl" to the "aryl or heteroaryl", and $R^{5a-1}$ is amino, the substitution position of the $R^{5a-1}$ may be on the monocyclic saturated cycloalkyl, or on the monocyclic saturated heterocycloalkyl.

In a preferred embodiment, when $R^{5a}$ and $R^{5b}$ together with atoms to which the $R^{5a}$ and the $R^{5b}$ are linked form 3-12 membered fused heterocycloalkyl, the 3-12 membered fused heterocycloalkyl may be 6-9 membered fused heterocycloalkyl.

In a preferred embodiment, when $R^{5a}$ and $R^{5b}$ together with atoms to which the $R^{5a}$ and the $R^{5b}$ are linked form 3-12 membered fused heterocycloalkyl, and one or more hydrogen atoms on the 3-12 membered fused heterocycloalkyl are substituted with a substituent, and a C atom at the substitution position is a chiral C atom, the stereo configuration of the chiral C atom may be R type or S type, or may be S type.

In a preferred embodiment, when $R^{5a}$ and $R^{5b}$ together with atoms to which the $R^{5a}$ and the $R^{5b}$ are linked form 3-12 membered fused heterocycloalkyl, heteroatoms in the 3-12 membered fused heterocycloalkyl may be one or more of O, S and N, with a number of 1 or 2.

In a preferred embodiment, when $R^{5a}$ and $R^{5b}$ together with atoms to which the $R^{5a}$ and the $R^{5b}$ are linked form 3-12 membered fused heterocycloalkyl, and one or more hydrogen atoms on the 3-12 membered fused heterocycloalkyl are substituted with a substituent, the number of the substituent may be 1.

In a preferred embodiment, when $R^{5a}$ and $R^{5b}$ together with atoms to which the $R^{5a}$ and the $R^{5b}$ are linked form 3-12 membered fused heterocycloalkyl, and one or more hydrogen atoms on the 5-12 membered fused heterocycloalkyl are substituted, the 5-12 membered fused heterocycloalkyl may be

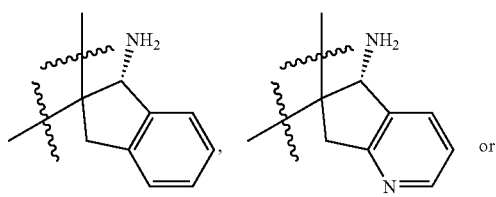

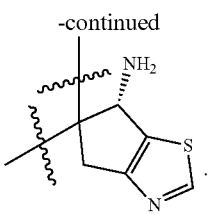

In a preferred embodiment,

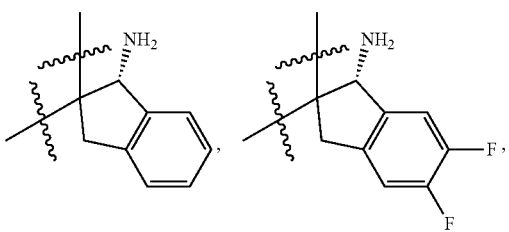

may be or may be

-continued

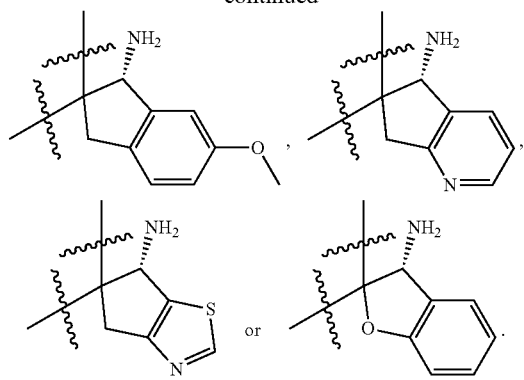

In a preferred embodiment, carbon atoms in the cycloalkyl are not oxidized.

In a preferred embodiment, nitrogen, carbon or sulfur atoms in the heterocyclyl are not oxidized, and the nitrogen atoms are not quaternized.

In a preferred embodiment, nitrogen, carbon or sulfur atoms in the heteroaryl are not oxidized, and the nitrogen atoms are not quaternized.

In a preferred embodiment, the $X_1$ is N.

In a preferred embodiment, the $R_1$ is amino.

In a preferred embodiment, the $L_2$ is —S—.

In a preferred embodiment, the A is

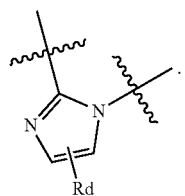

In a preferred embodiment, the $R_{5a}$ and $R_{5b}$ together with atoms to which the $R_{5a}$ and the $R_{5b}$ are linked form 3-6 membered cycloalkyl, 5-12 membered fused cycloalkyl or 5-12 membered fused heterocycloalkyl, more preferably 5-12 membered fused cycloalkyl or 5-12 membered fused heterocycloalkyl.

In a preferred embodiment, the nitrogen-containing fused heterocyclic compound represented by formula I-a is a compound represented by formula I-b:

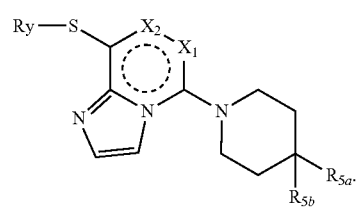

In a preferred embodiment, the nitrogen-containing fused heterocyclic compound represented by formula I-b is a compound represented by formula I-c:

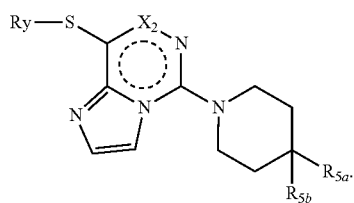

wherein $R_{5a}$ and $R_{5b}$ together with atoms to which the $R_{5a}$ and the $R_{5b}$ are linked form 3-6 membered cycloalkyl, 5-12 membered fused cycloalkyl, or 5-12 membered fused heterocycloalkyl.

In a preferred embodiment, the nitrogen-containing fused heterocyclic compound represented by formula I-a is: $R_y$ is

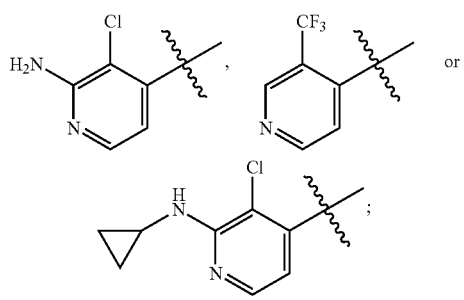

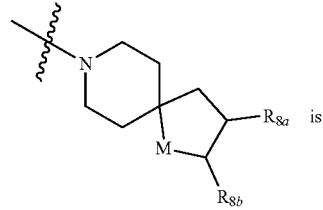

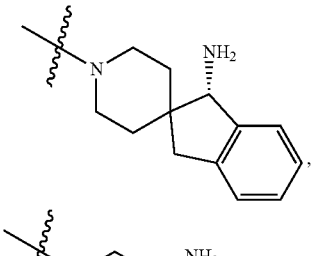

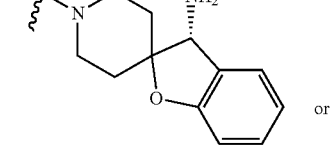

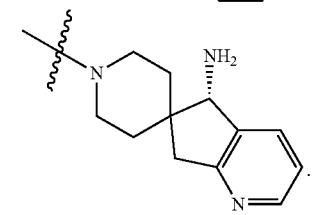

In a preferred embodiment, the nitrogen-containing fused heterocyclic compound represented by formula I-c is a compound represented by formula I-d:

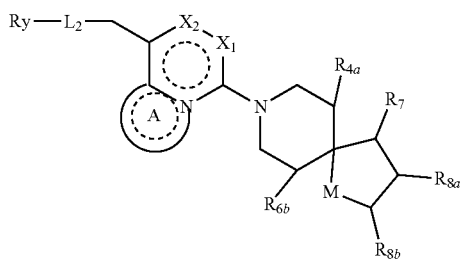

I-d wherein $R_{4a}$ and $R_{6b}$ are hydrogen;
$R_7$ is amino;
M is O or C;
$R_{8a}$ and $R_{8b}$ are hydrogen,
alternatively, $R_{8a}$ and $R_{8b}$ together with carbon atoms or heteroatoms to which the $R_{8a}$ and the $R_{8b}$ are linked form a 3-12 membered aromatic ring system, wherein the heteroatoms comprise 1-3 heteroatoms selected from the group consisting of N, O, P, or S;
the formed ring system can continue to be substituted with one or more substituents;
when one or more hydrogen atoms on the ring system are substituted with a substituent, the substituent is $R^{8a-1}$, wherein $R^{8a-1}$ is halogen and/or $C_1$-$C_8$ alkoxy.

In a preferred embodiment, the nitrogen-containing fused heterocyclic compound represented by formula I-d is a compound represented by formula I-d-1 and/or a compound represented by formula I-d-2:

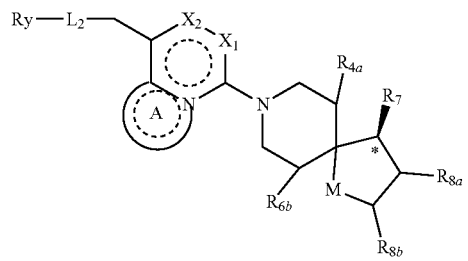

I-d-1

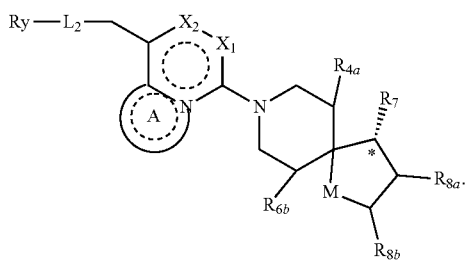

I-d-2

In a preferred embodiment, when $R_{8a}$ and $R_{8b}$ together with carbon atoms or heteroatoms to which the $R_{8a}$ and the $R_{8b}$ are linked form a 3-12 membered aromatic ring system, the aromatic ring system may be 1 or 2 aromatic ring systems, or may be 1 aromatic ring system;
wherein when $R_{8a}$ and $R_{8b}$ together with carbon atoms or heteroatoms to which the $R_{8a}$ and the $R_{8b}$ are linked form a 3-12 membered aromatic ring system, the 3-12 membered aromatic ring system may be 3-12 membered aryl or 3-12 membered heteroaryl;
wherein when the 3-12 membered aromatic ring system is the 3-12 membered aryl, the 3-12 membered aryl may be 6-10 membered aryl, further may be phenyl or a naphthyl, or further may be the phenyl;
wherein when the 3-12 membered aromatic ring system is 4-18 membered heteroaryl, the 4-18 membered heteroaryl may be 4-6 membered heteroaryl;
wherein when the 3-12 membered aromatic ring system is 4-18 membered heteroaryl, the heteroatoms in the 4-18 membered heteroaryl may be S or N, and the number of the heteroatoms may be 1 or 2;
wherein when $R^{8a-1}$ is halogen, the halogen may be F, Cl, Br or I, or may be F;
wherein when $R^{8a-1}$ is $C_1$-$C_8$ alkoxy, the $C_1$-$C_8$ alkoxy, the $C_1$-$C_8$ alkoxy may be $C_1$-$C_3$ alkoxy, further may be methoxy, ethoxy, n-propoxy or isopropoxy, or further may be the methoxy.

In a preferred embodiment, when one or more hydrogen atoms on the ring system are substituted with a substituent, the ring system may be

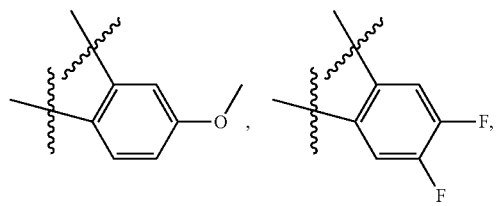

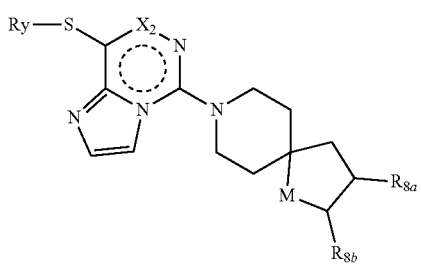

In a preferred embodiment, the nitrogen-containing fused heterocyclic compound represented by formula I-d is represented by formula I-e:

I-e wherein $R_{8a}$ and $R_{8b}$ together with carbon atoms or heteroatoms to which the $R_{8a}$ and the $R_{8b}$ are linked form a 3-12 membered aromatic ring system, wherein the 3-12 membered aromatic ring system is 3-12 membered aryl or 3-12 membered heteroaryl;

In a preferred embodiment, the nitrogen-containing fused heterocyclic compound represented by formula I is any of the following compounds:

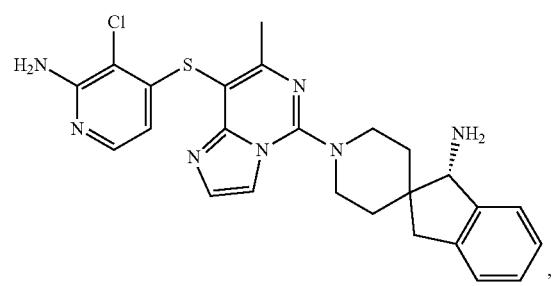
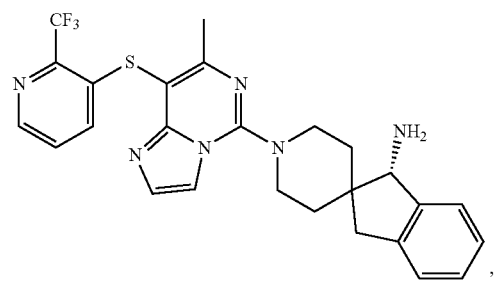
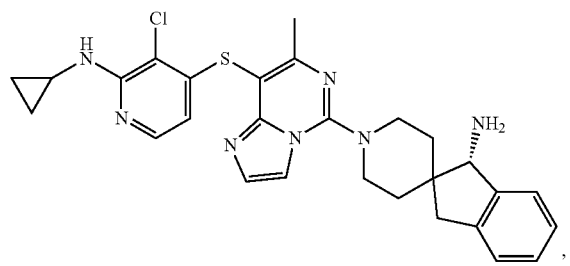
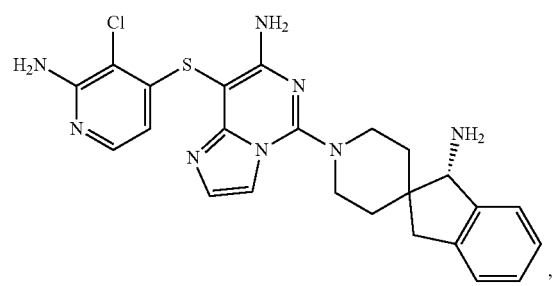
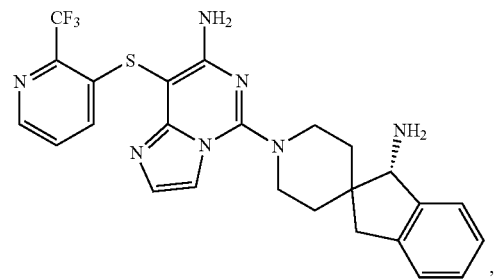
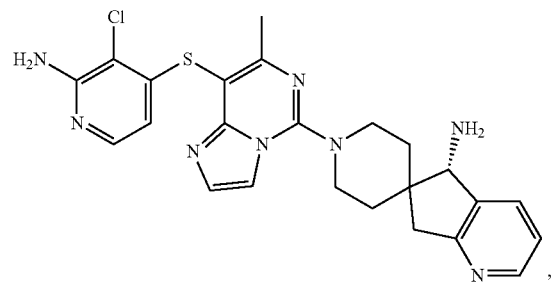
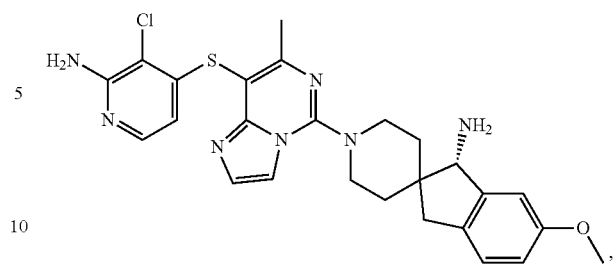
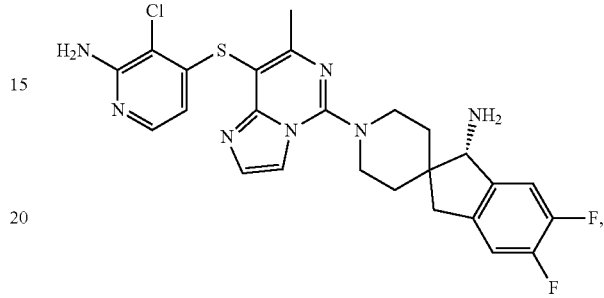
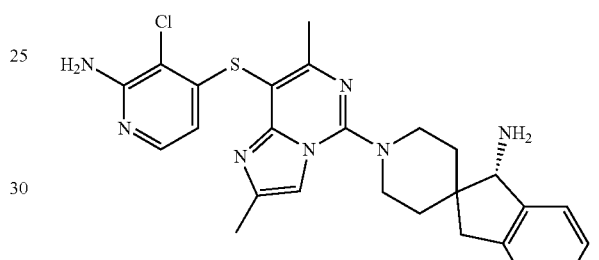
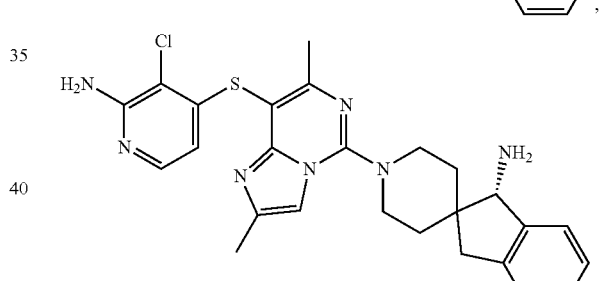
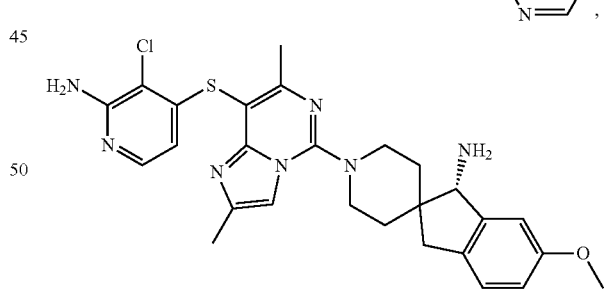
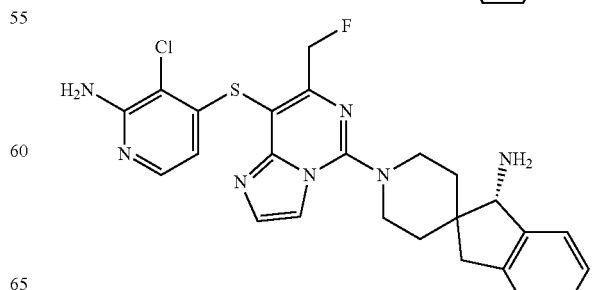

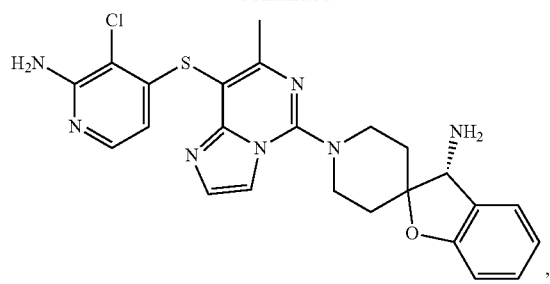
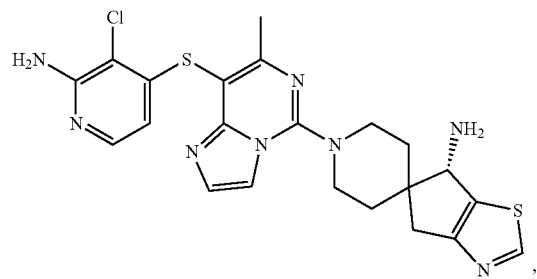
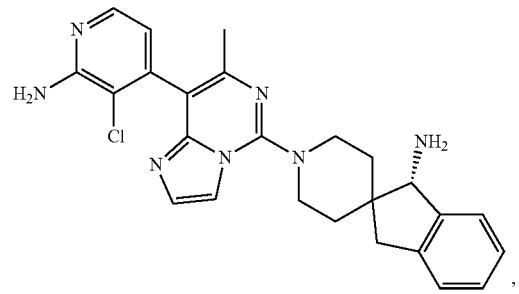
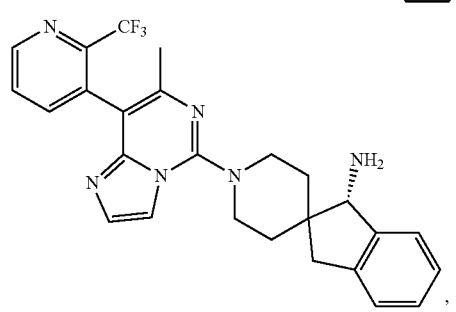
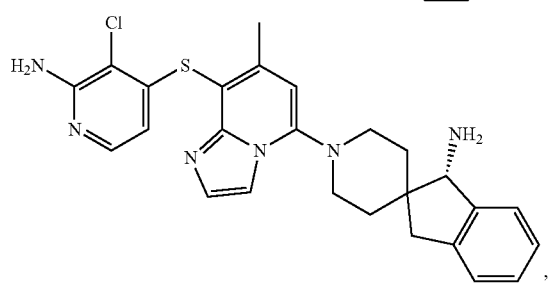
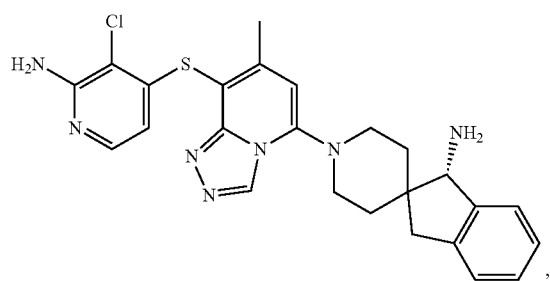
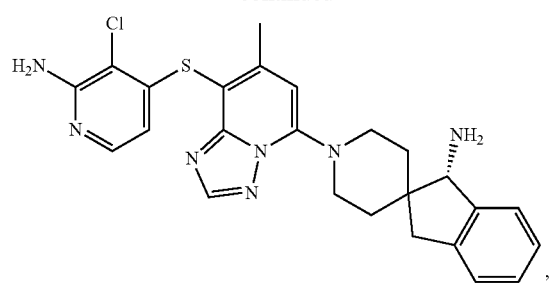
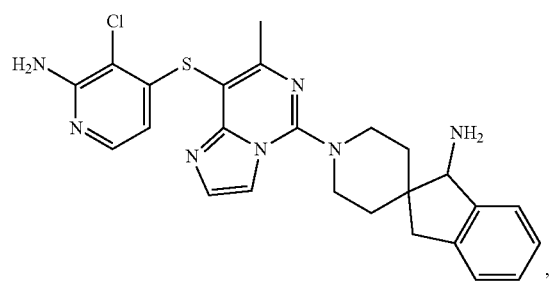
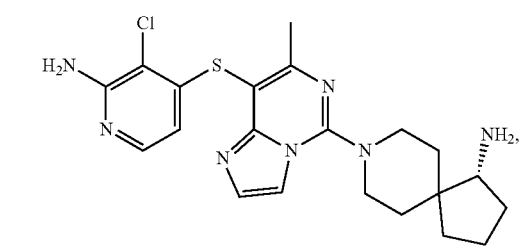
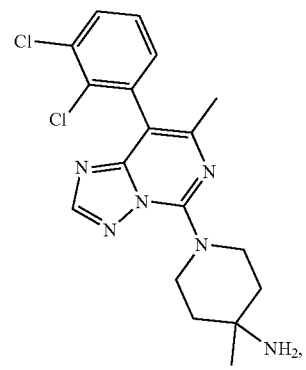
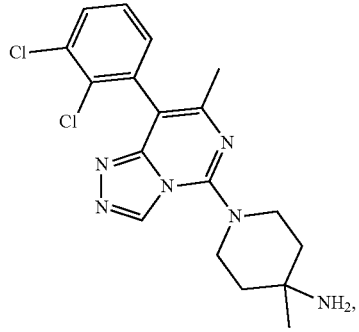

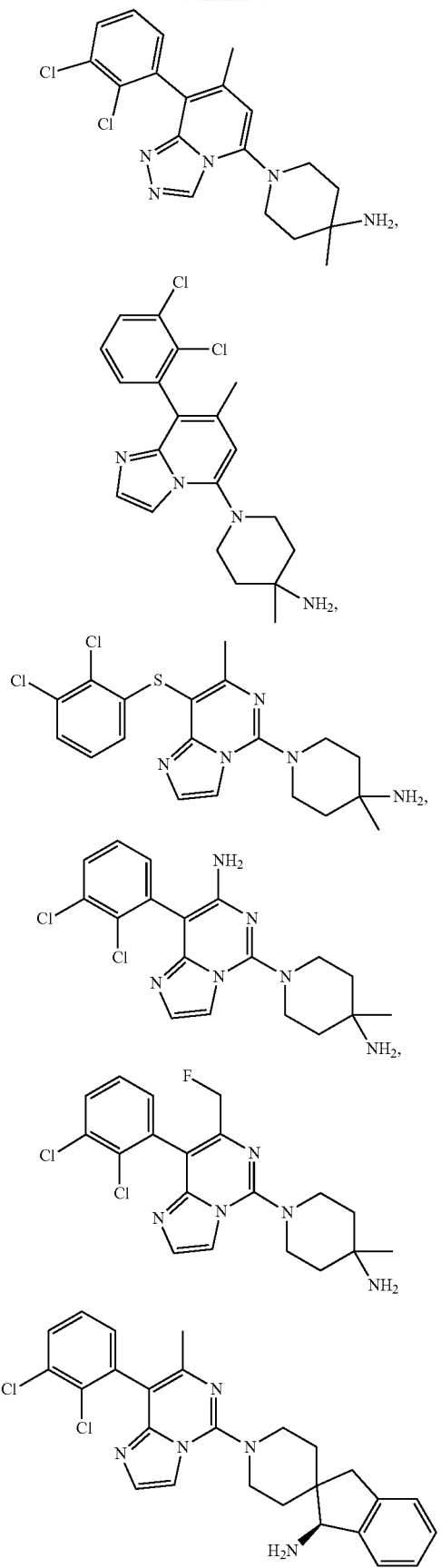
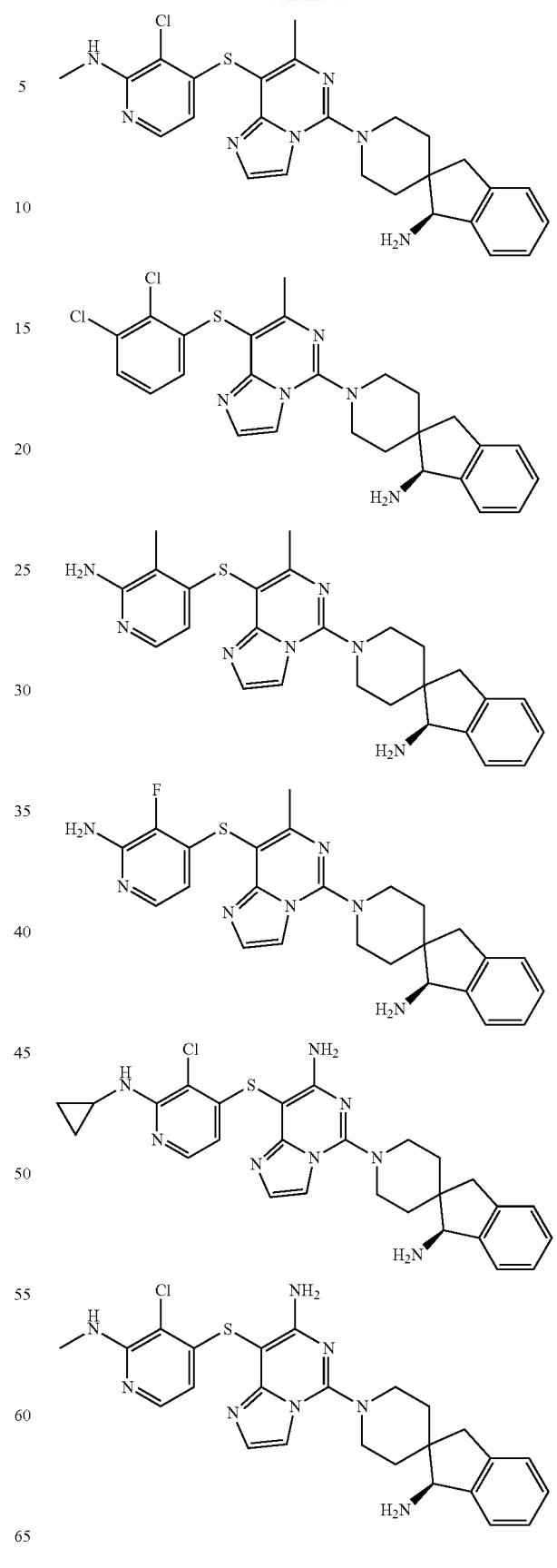

-continued
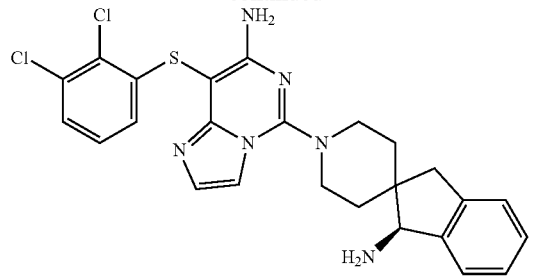
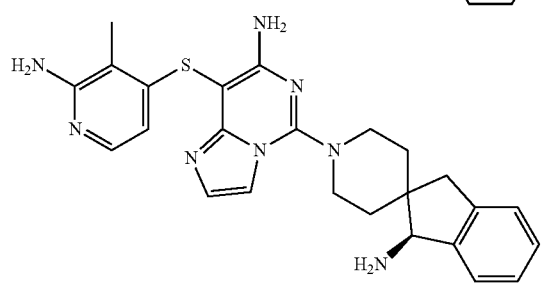
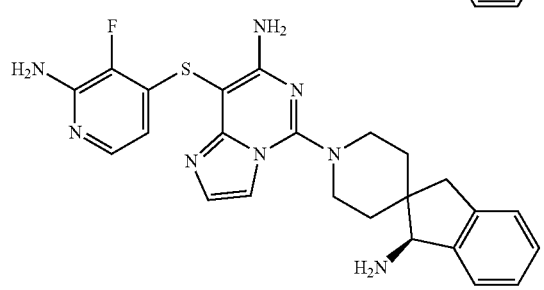
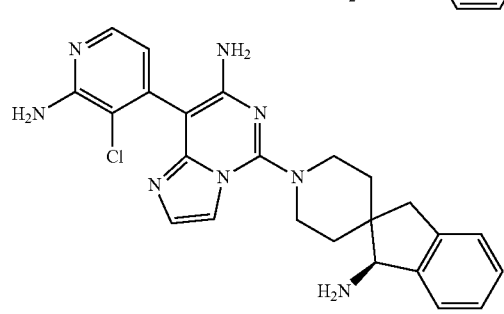
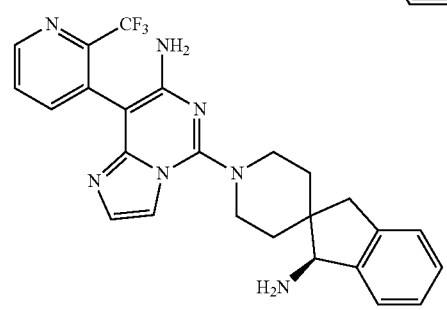
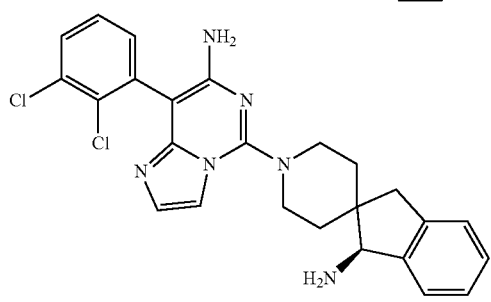
-continued
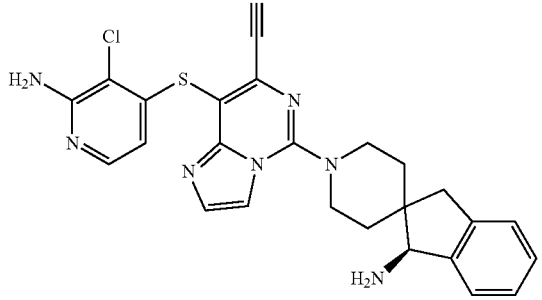
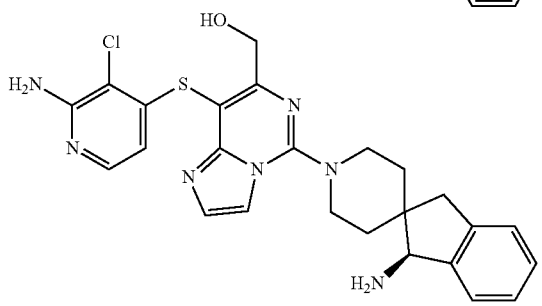
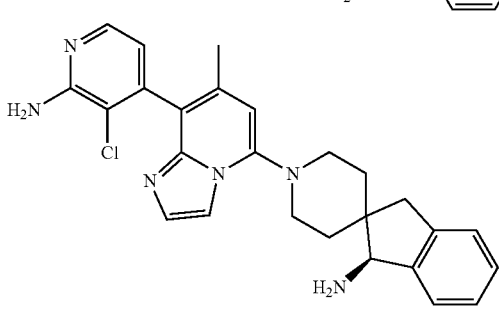
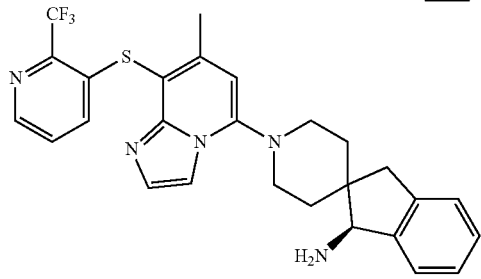
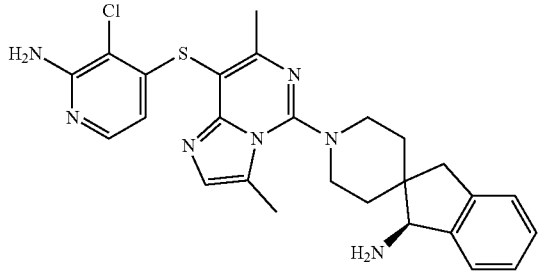
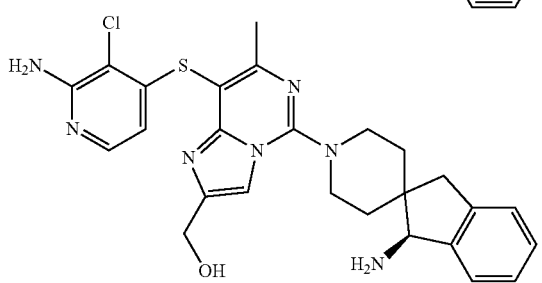

31
-continued
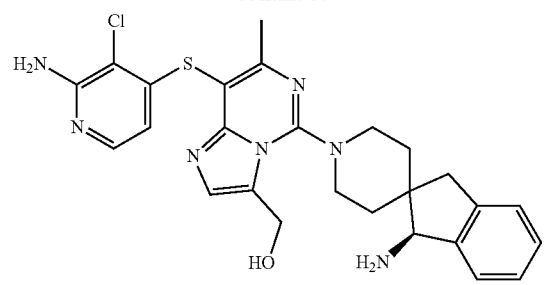
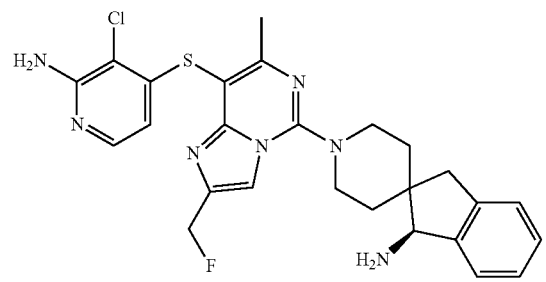
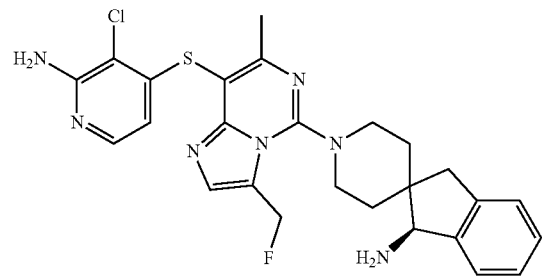
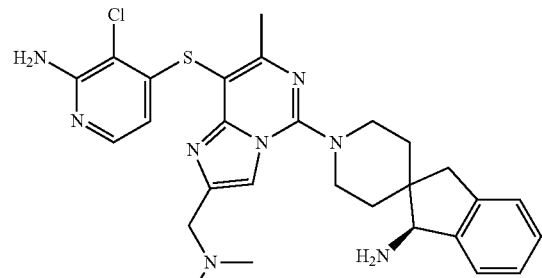
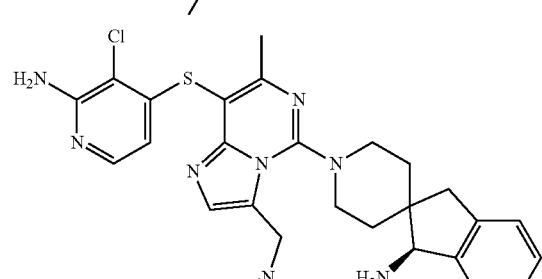
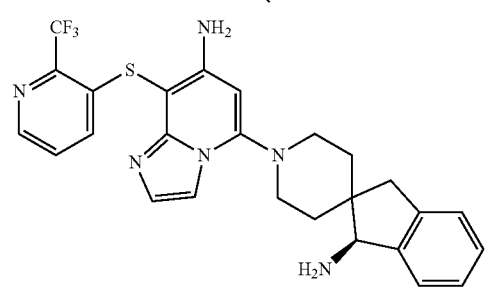
32
-continued
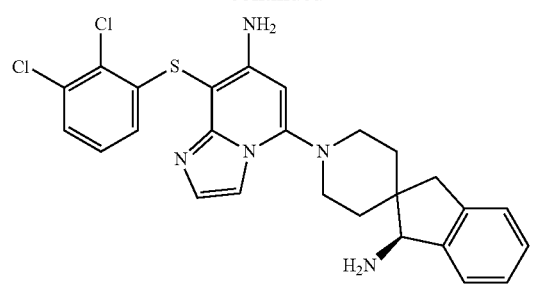
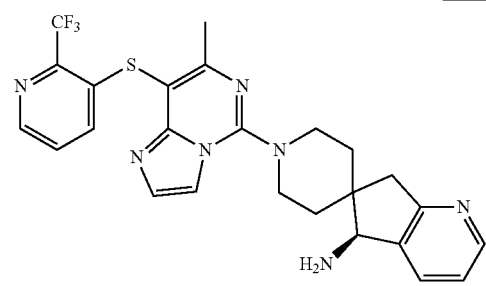
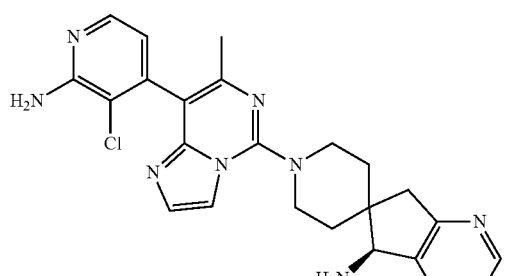
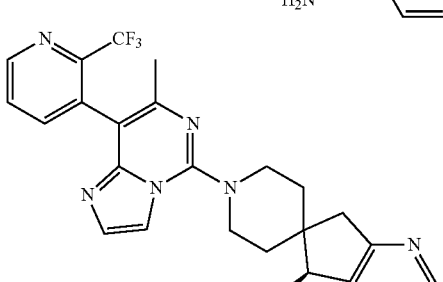
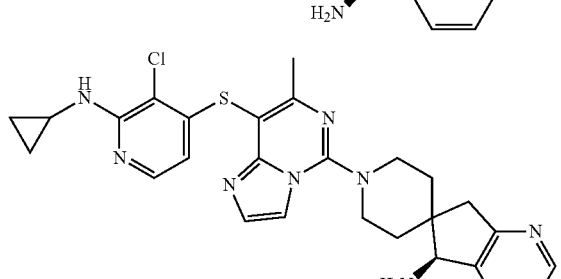
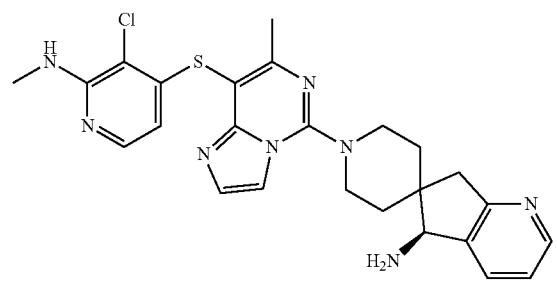

33
-continued
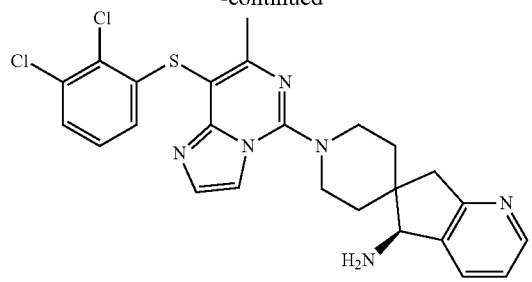
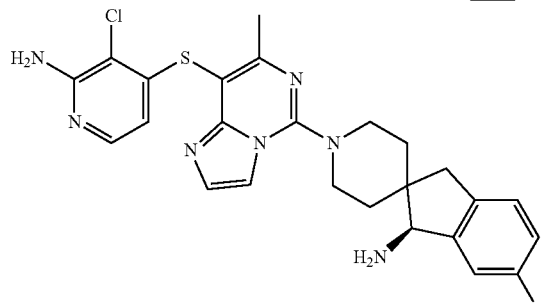
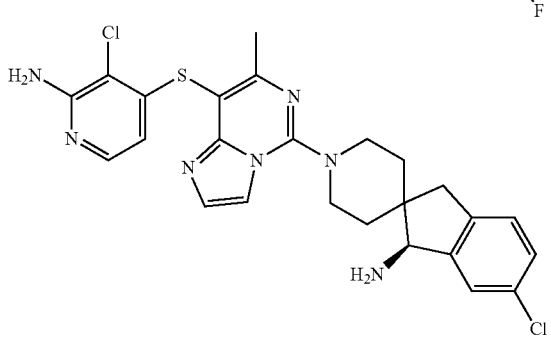
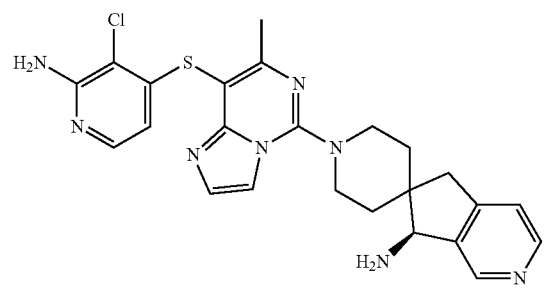
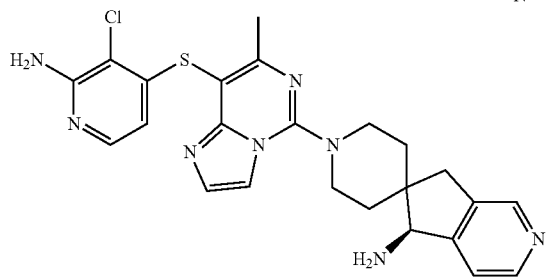
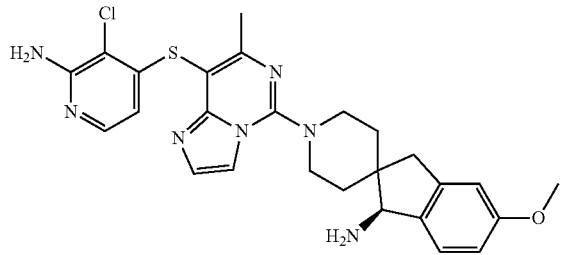
34
-continued
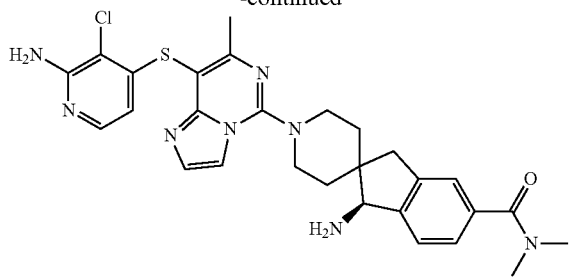
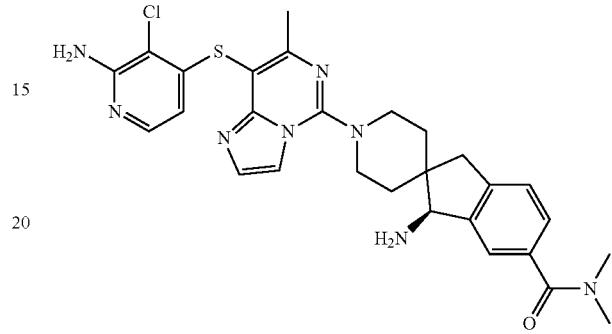
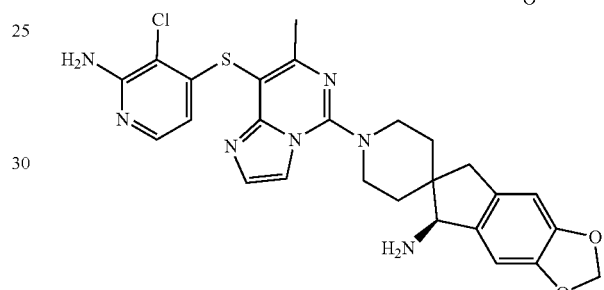
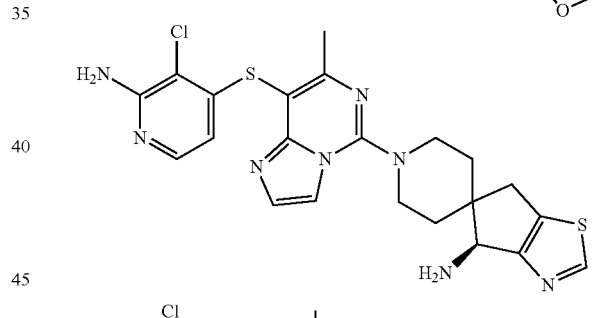
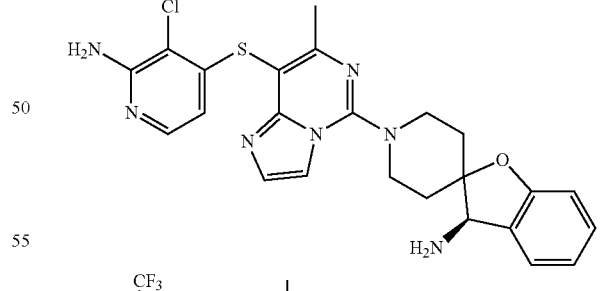
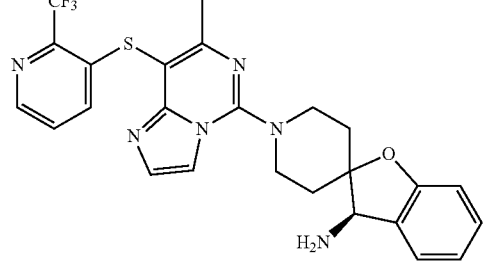

35
-continued
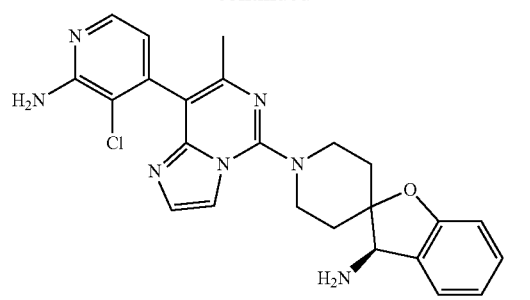
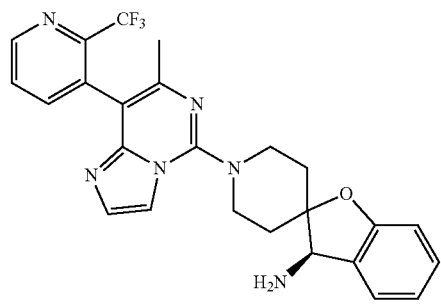
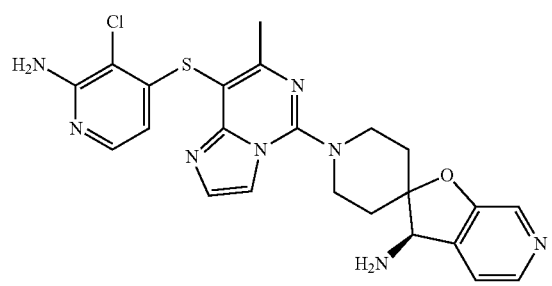
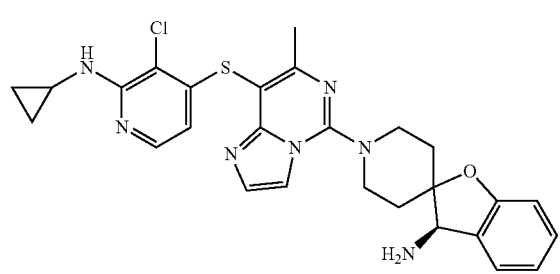
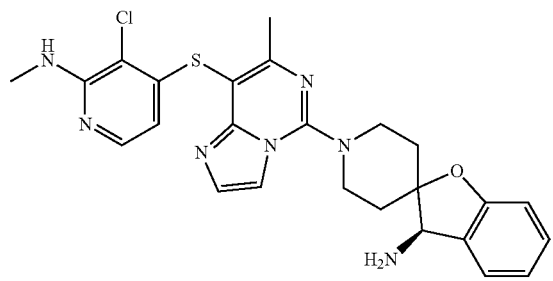
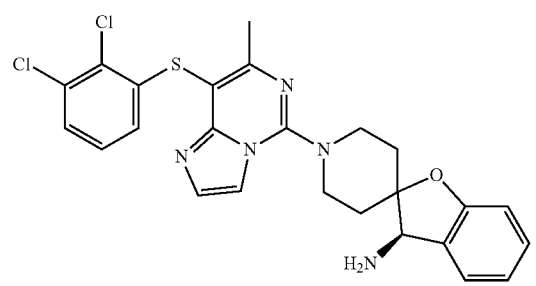
36
-continued
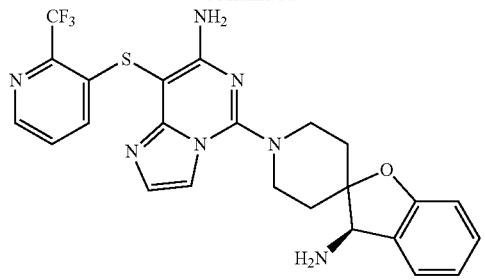
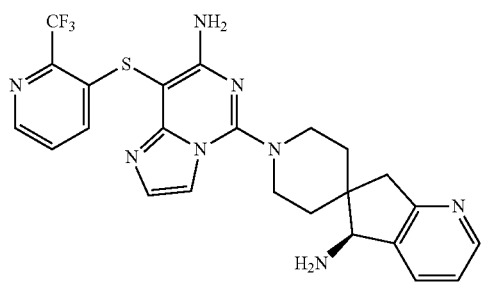
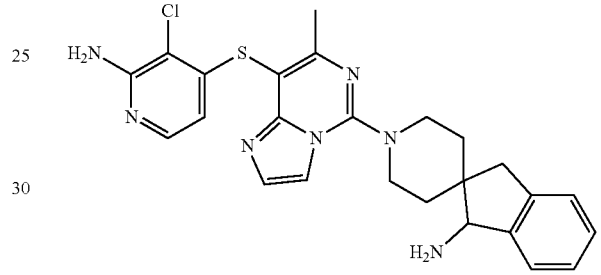
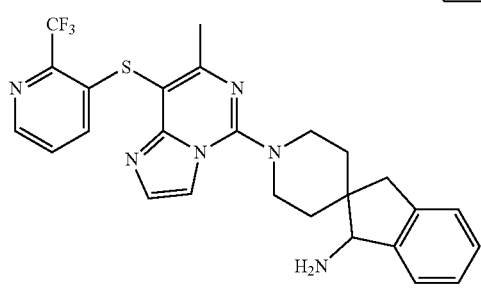
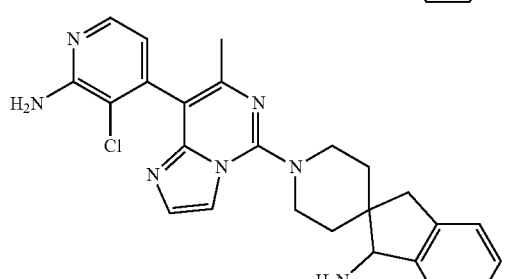
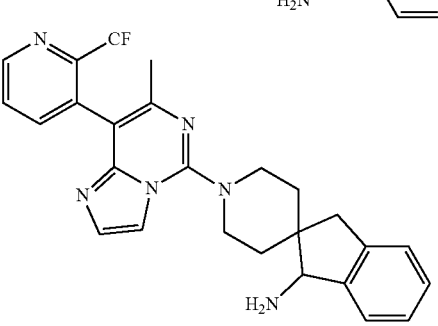

37
-continued
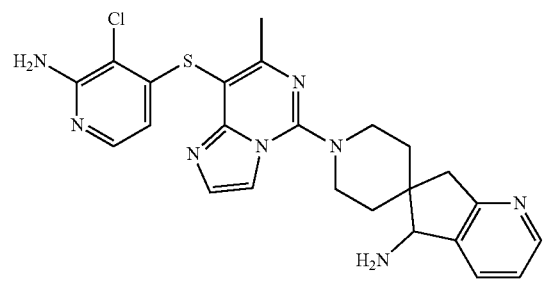
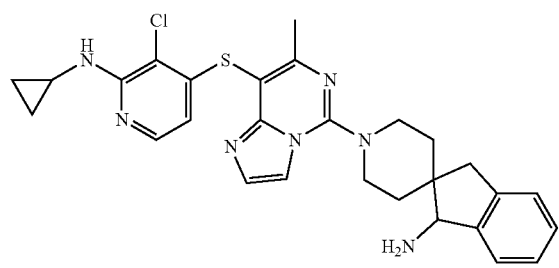
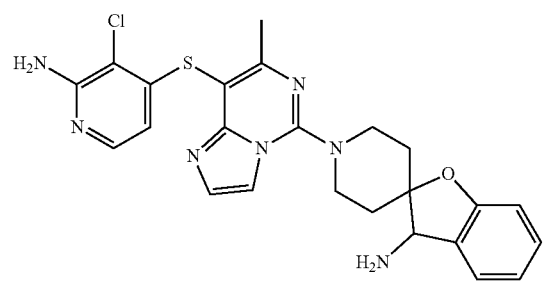
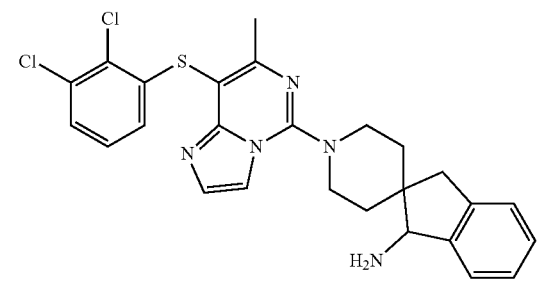
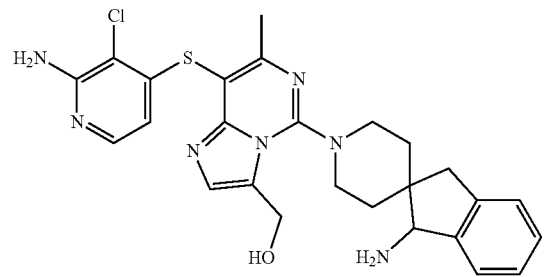
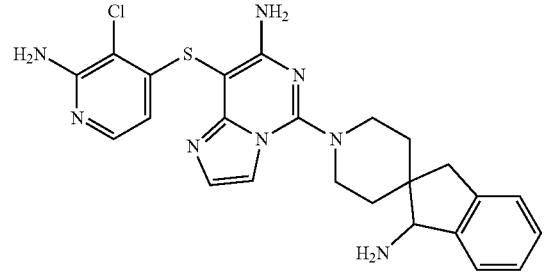
38
-continued
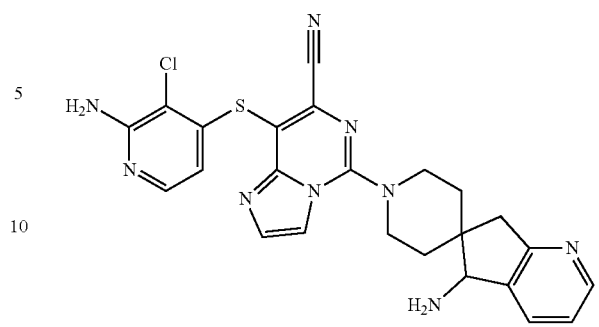
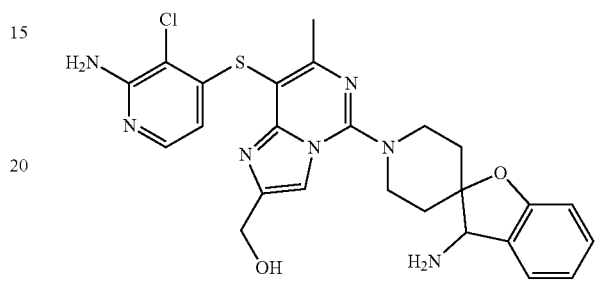
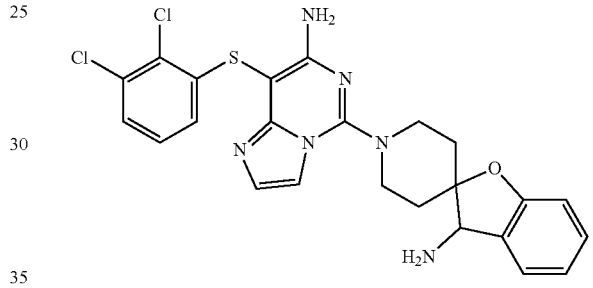
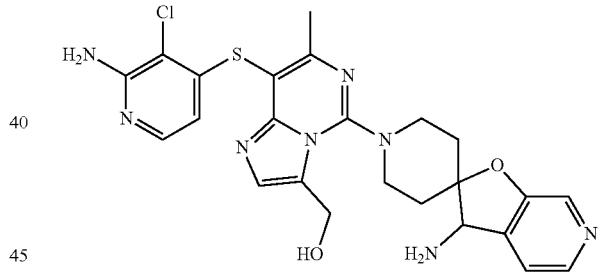
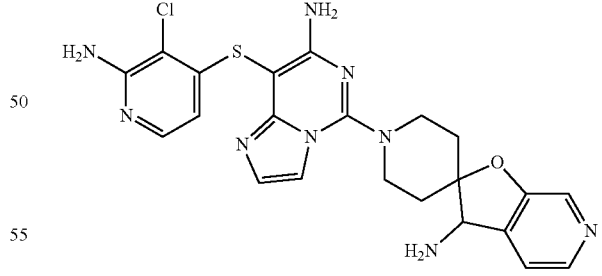
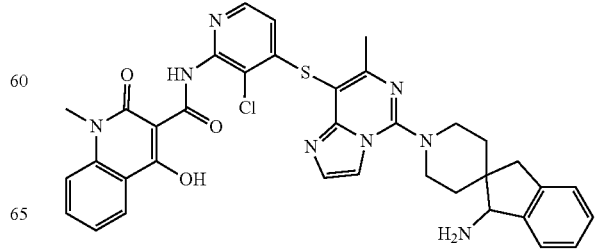

-continued

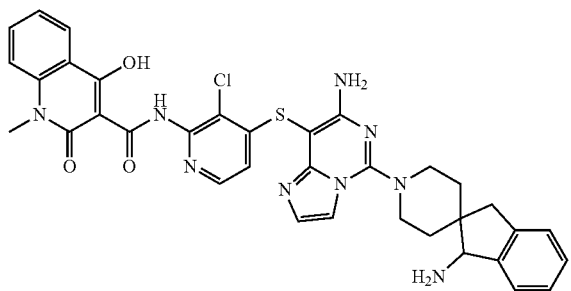

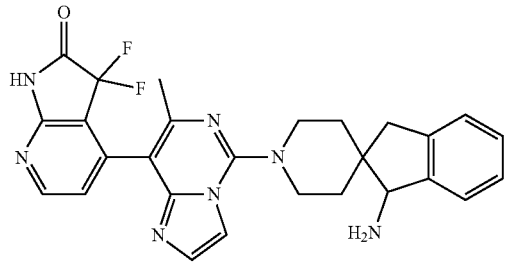

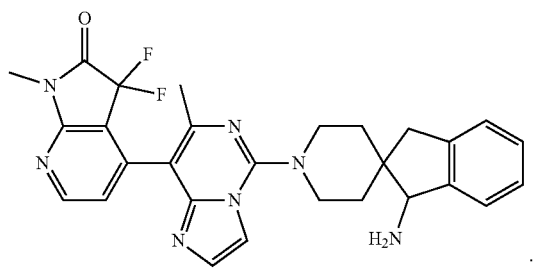

The present disclosure also provides a preparation method for a nitrogen-containing fused heterocyclic compound represented by formula I, comprising the following steps of deprotecting the compound represented by formula II in a solvent under acidic conditions, and thus obtaining the nitrogen-containing fused heterocyclic compound represented by formula I;

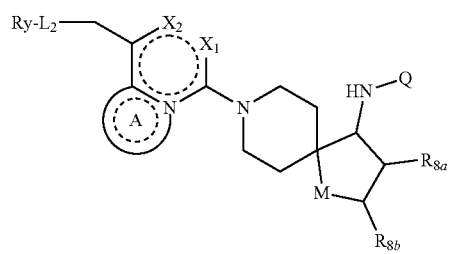

or

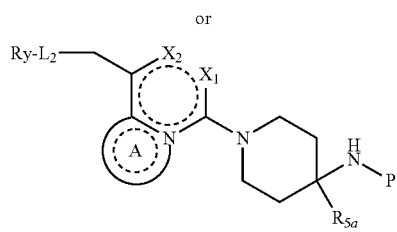

II

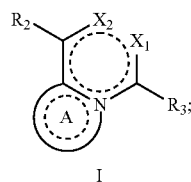

I wherein P and Q are amino protective groups, and definitions of $L_2$, $X_1$, $X_2$, $R_y$, A, M, $R_{5a}$, $R_{8a}$ and $R_{8b}$ are the same as described above.

The present disclosure also provides a compound represented by formula II-1:

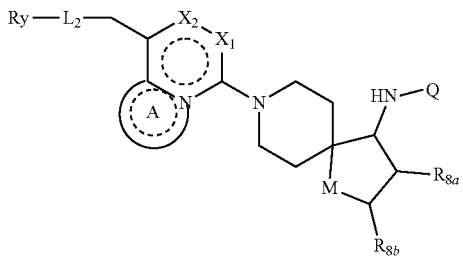

wherein Q is an amino protective group, and definitions of $X_1$, $X_2$, $R_y$, A, M, $R_{8a}$ and $R_{8b}$ are the same as described above.

In formula II-1, the amino protective group is preferably

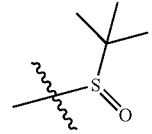

The compound represented by formula II-1 is preferably any of the following compounds:

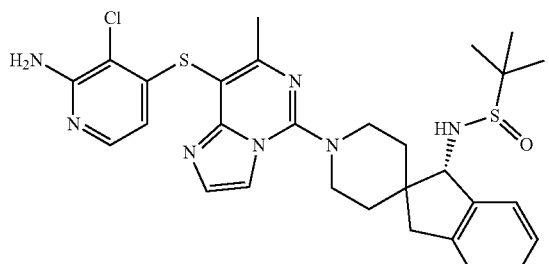

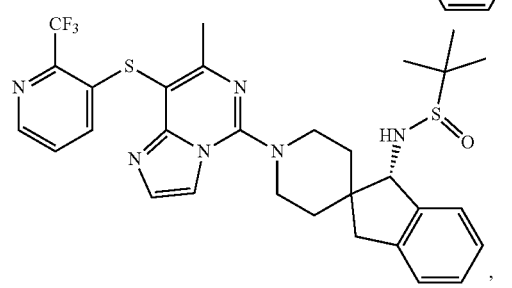

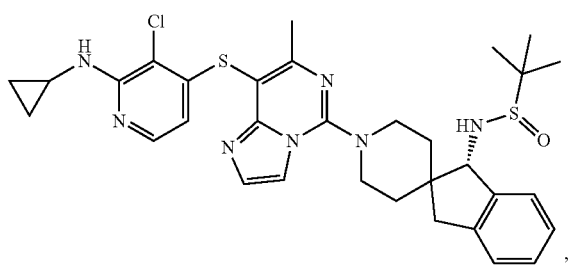
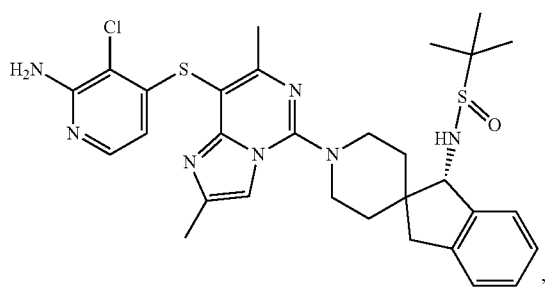
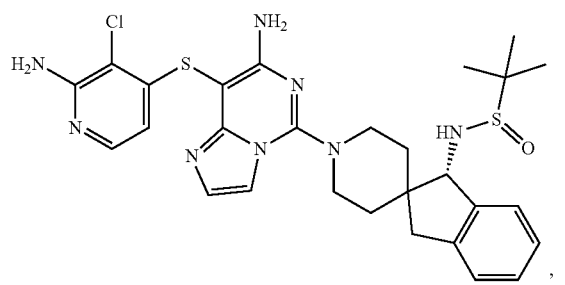
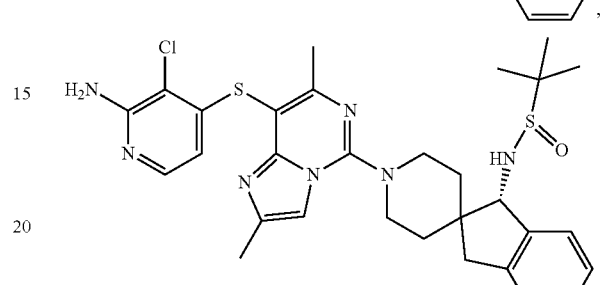
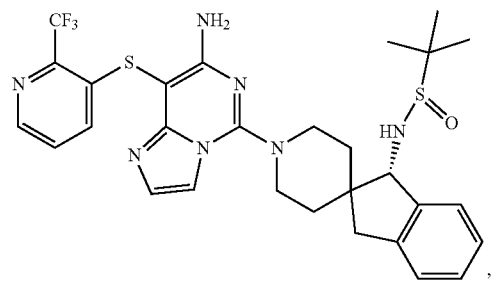
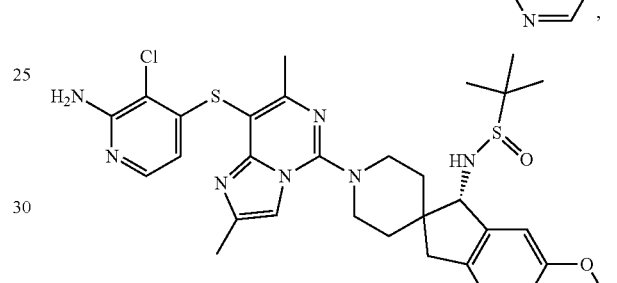
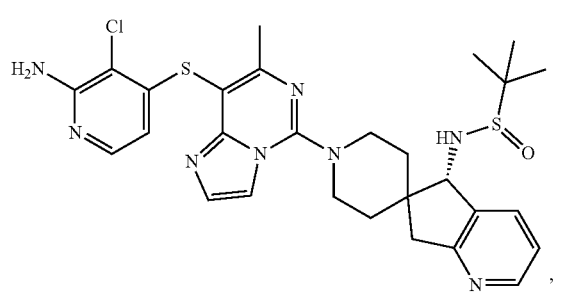
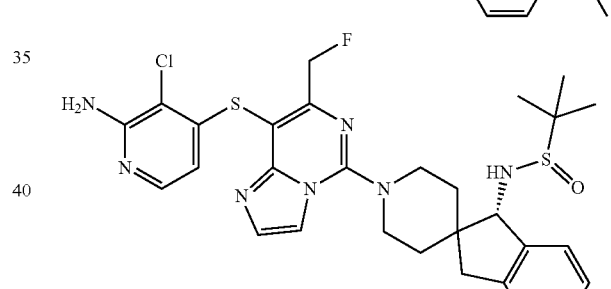
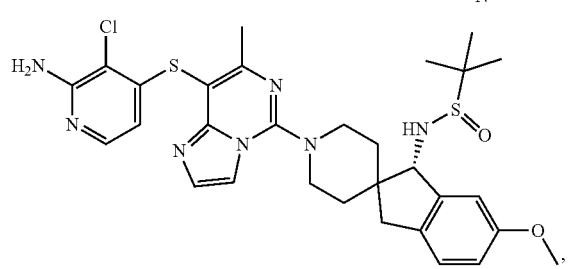
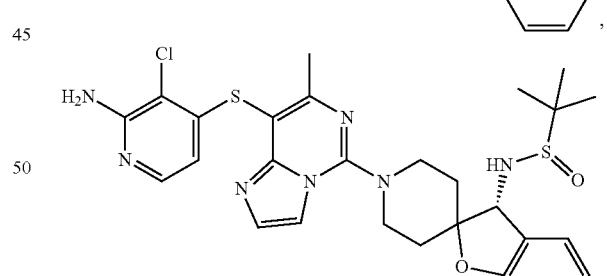
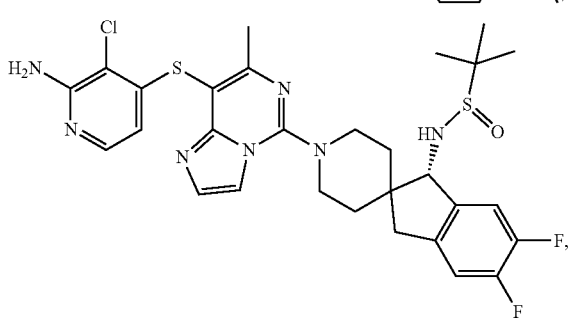
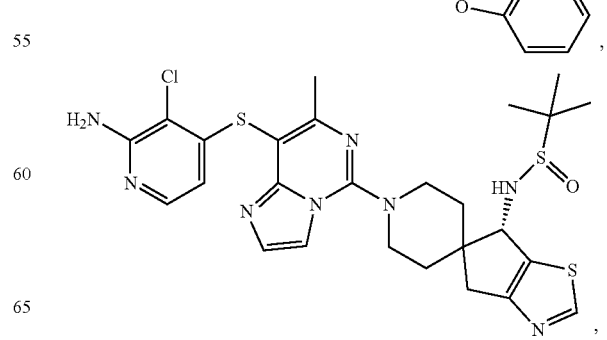

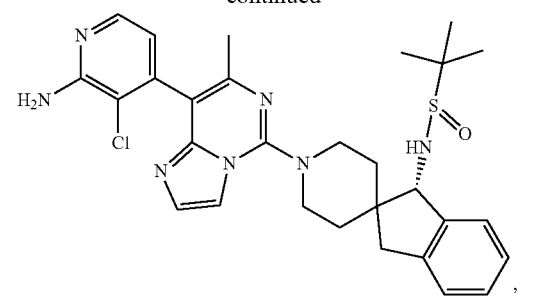
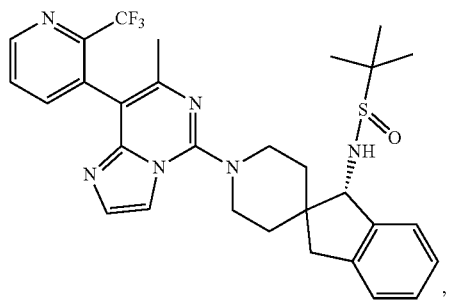
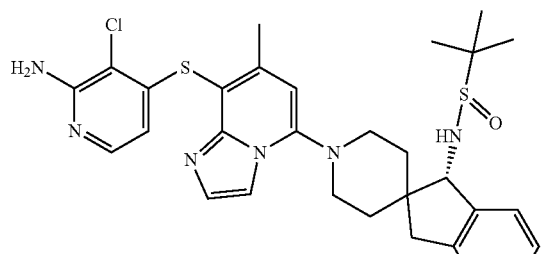
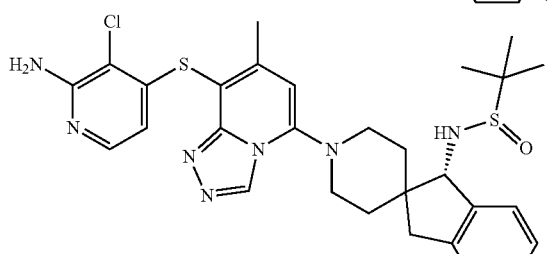
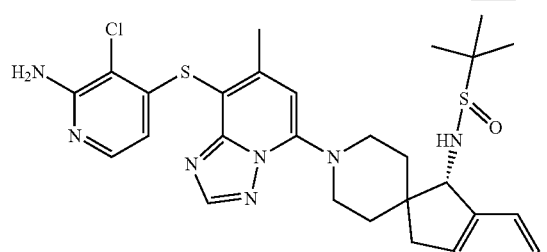
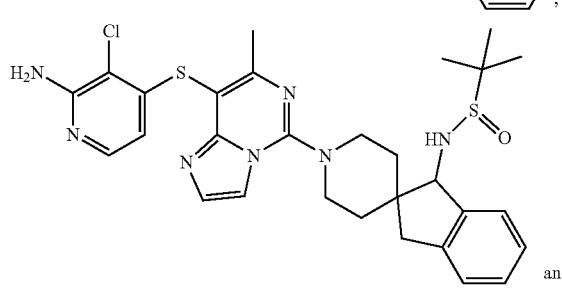
and
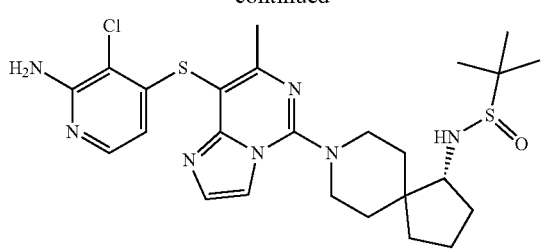
The present disclosure also provides a compound represented by formula II-2:
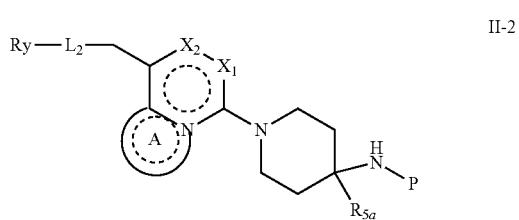
wherein P is an amino protective group, and definitions of $X_1$, $X_2$, $R_y$, A, M and $R_{5a}$ are the same as described above.
In formula II-2, the amino protective group is preferably
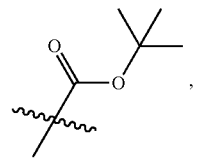
The present disclosure also provides a compound represented by formula I-2:
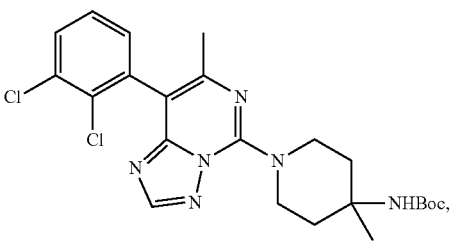
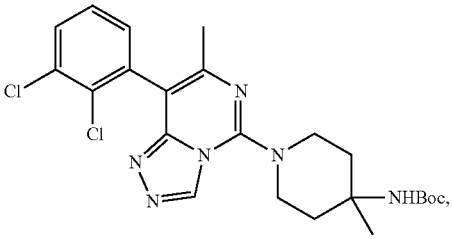

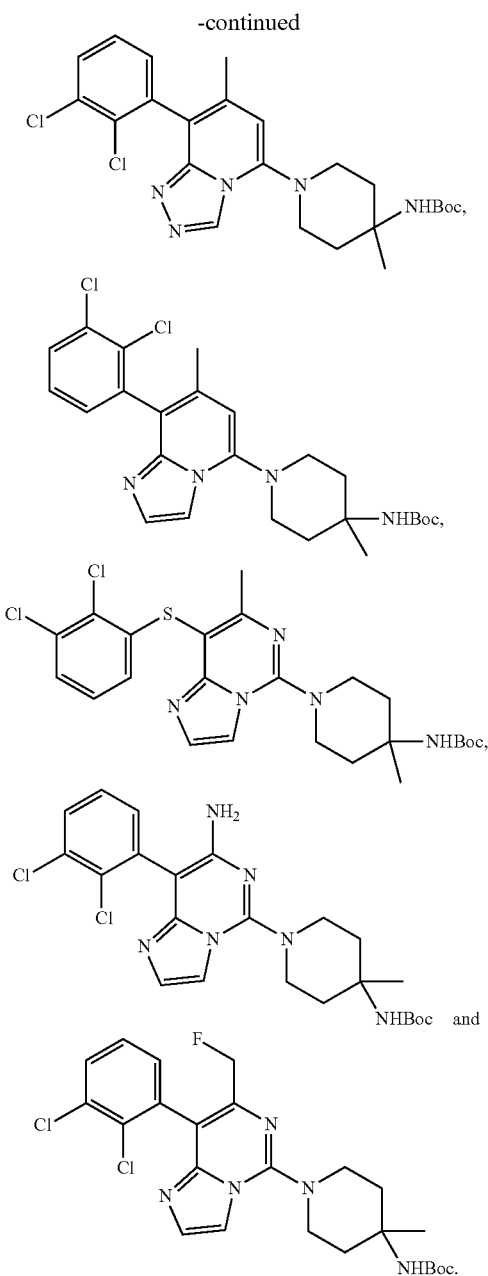

The present disclosure also provides a pharmaceutical composition A comprising the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof, and a pharmaceutically acceptable carrier.

The present disclosure also provides a pharmaceutical combination comprising the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof, and a PD-1 inhibitor,
  wherein the PD-1 inhibitor may be a PD-L1 antibody and further may be an anti-mouse PD-L1 (B7-H1) (Clone: 10F.9G2, Lot: 66571701B).

In the pharmaceutical combination, the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof, and a PD-1 inhibitor can be administered alone or in combination with the PD-1 inhibitor.

In the pharmaceutical combination, the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof and the PD-1 inhibitor can be administered by injection.

In the pharmaceutical combination, the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof can be administered according to the body weight of a subject, e.g., 2 mg/kg (referring to a single dose).

In the pharmaceutical combination, the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof can be administered once daily at the dose described above.

In the pharmaceutical combination, the PD-1 inhibitor can be administered according to the body weight of the subject, e.g., 10 mg/kg (referring to a single dose).

In the pharmaceutical combination, the PD-1 inhibitor can be administered twice a week at the dose described above.

The present disclosure also provides a pharmaceutical composition B comprising the pharmaceutical combination and pharmaceutically acceptable excipients described above.

The present disclosure also provides a use of the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof, the pharmaceutical composition described above, the pharmaceutical composition A described above or the pharmaceutical composition B described above in the preparation of a drug.

The present disclosure also provides a use of the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof, the pharmaceutical composition described above, the pharmaceutical composition A described above or the pharmaceutical composition B described above in the preparation of a drug, wherein the drug is used to prevent and/or treat an SHP2 protein activity or expression associated disease,
  wherein the SHP2 protein activity or expression associated disease may be one or more of a tumor, an immune disease, and an inflammatory disease. The tumor is preferably a tumor caused by an abnormal Ras-Raf-ERK or PD1/L1 signaling pathway, further preferably oesophageal cancer cells, lung cancer cells, colorectal cancer cells, pancreas cancer cells, leukemia cells, lung cancer cells, lung cancer, gastric cancer, lung cancer, lung cancer or gastric cancer, and furthermore preferably oesophageal cancer cells, lung cancer cells, colorectal cancer cells, pancreas cancer cells, leukemia cells, lung cancer cells, lung cancer or gastric cancer.

The present disclosure also provides a use of the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof, the pharmaceutical composition described above, the pharmaceutical composition A described above or the pharmaceutical composition B described above in the preparation of a drug, wherein the drug is used to prevent and/or treat a disease associated with one or more of a tumor, an immune disease, and an inflammatory disease;

wherein the tumor, the immune disease and the inflammatory disease are the same as described above.

The present disclosure also provides a use of the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof, the pharmaceutical composition described above, the pharmaceutical composition A described above or the pharmaceutical composition B described above in the preparation of an SHP2 inhibitor.

The present disclosure also provides a method for preventing and/or treating a disease, comprising administering to a subject in need of the treatment an effective amount of the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof, the pharmaceutical composition described above, the pharmaceutical composition A described above or the pharmaceutical composition B described above; wherein the disease is an SHP2 protein activity or expression associated disease.

In the method, the disease is the same as described above.

The present disclosure also provides a method for preventing and/or treating a disease, comprising administering to a subject in need of the treatment an effective amount of the nitrogen-containing fused heterocyclic compound represented by formula I or I-a described above, a pharmaceutically acceptable salt thereof, an enantiomer thereof, a diastereomer thereof, a tautomer thereof, a solvate thereof, a polymorph thereof or a prodrug thereof, the pharmaceutical composition described above, the pharmaceutical composition A described above or the pharmaceutical composition B described above; wherein the disease is one or more of a tumor, an immune disease, and an inflammatory disease.

In the method, the tumor, the immune disease and the inflammatory disease are the same as described above.

In the method, the mode of administering the subject in need of treatment may be oral.

In the method, the frequency of administering the subject in need of treatment may be once daily.

In the method, the cycle for the mode of administering the subject in need of treatment may be 21 days.

In the method, the effective amount of administering the subject in need of treatment may be given according to the body weight of the subject, and may be 2-10 mg/kg (single dose), e.g. 0.8 mg/kg, 2 mg/kg, 2.5 mg/kg, 5 mg/kg, 6 mg/kg.

A preferred embodiment includes a nitrogen-containing fused heterocyclic compound represented by formula I-1, or a pharmaceutically acceptable salt thereof, or an enantiomer, a diastereomer, a tautomer, a solvate, a polymorph or a prodrug thereof,

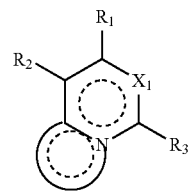

I-1 where
$X_1$ is selected from N and $CR_a$, and $R_a$ is selected from hydrogen, halogen, $C_1$-$C_6$ alkyl, $C_1$-$C_6$ alkoxy, etc.;
$R_1$ is selected from hydrogen, halogen, hydroxyl, amino, acylamino, sulfonamido, $C_1$-$C_6$ alkyl, $C_1$-$C_6$ alkoxy, cyano, alkenyl, alkynyl, 3-8 membered cycloalkyl or heterocycloalkyl, 5-8 membered aryl or heteroaryl;
$R_2$ is selected from -$L_2$-$R_y$; wherein $L_2$ is a direct bond, —O—, —S(O)n-, —$NR_b$—, etc., and $R_y$ is 5-10 membered cycloalkyl or heterocycloalkyl or aryl or heteroaryl; n=0-2; $R_b$ is selected from hydrogen, $C_1$-$C_6$ alkyl or alkoxy, 3-8 membered cycloalkyl or heterocycloalkyl, etc.;
$R_3$ is selected from —$OR_c$, —$SR_c$, —$C(R_aR_b)R_c$, —$NR_bR_c$, —$COR_c$, —$CONR_bR_c$, —$NR_bCOR_c$, —$SO_2NR_bR_c$, —$NR_bSO_2R_c$, —$NR_bCONR_bR_c$, —$NR_bSO_2NR_bR_c$, —$NR_bCSNR_bR_c$, —$COOR_c$, —$OOCR_c$, —$OCONR_bR_c$, —$NR_bCOOR_c$, —$NR_bCSR_c$, —$CSNR_bR_c$, etc., wherein $R_b$ is independently selected from hydrogen, $C_1$-$C_6$ alkyl or alkoxy, 3-8 membered cycloalkyl or heterocycloalkyl upon each occurrence; $R_c$ is independently selected from $C_1$-$C_6$ alkyl, 3-12 membered monocyclic or polycyclic cycloalkyl, 3-12 membered monocyclic or polycyclic heterocycloalkyl; or $R_c$ with $R_a$ or $R_b$ may form 3-12 membered monocyclic or polycyclic cycloalkyl, 3-12 membered monocyclic or polycyclic heterocycloalkyl, 3-12 membered spiro or fused cycloalkyl, and 3-12 membered spiro or fused heterocycloalkyl;
one or more hydrogen atoms on any of the above groups may be substituted with a substituent selected from the group consisting of, including but not limited, deuterium, halogen, hydroxyl, amino or cycloamino, cyano, nitro, sulfone or sulfoxide, $C_1$-$C_8$ alkyl, 3-8 membered cycloalkyl or heterocycloalkyl, $C_1$-$C_8$ alkoxy, $C_1$-$C_8$ alkylamino, alkenyl, alkynyl, acyl or sulfonyl, urea or sulfonylurea, 5-8 membered aryl or heteroaryl; wherein the heteroaryl comprises 1-3 heteroatoms selected from the group consisting of N, O, P, or S; the heterocycloalkyl comprises 1-3 heteroatoms selected from the group consisting of N, O, P, or S; the ring system comprises a spiro ring, a bridged ring, a fused ring, a fused saturated or partially unsaturated ring system; the above ring systems may be further substituted with $C_1$-$C_6$ alkyl, hydroxy, amino, halogen or alkoxy, etc.

A further embodiment includes a compound represented by formula (I-1), or a pharmaceutically acceptable salt thereof, or an enantiomer, a diastereomer, a tautomer, a solvate, a polymorph or a prodrug thereof, preferably the compound represented by formula (II), or the pharmaceutically acceptable salt thereof, or the enantiomer, the diastereomer, the tautomer, the solvate, the polymorph or the prodrug thereof:

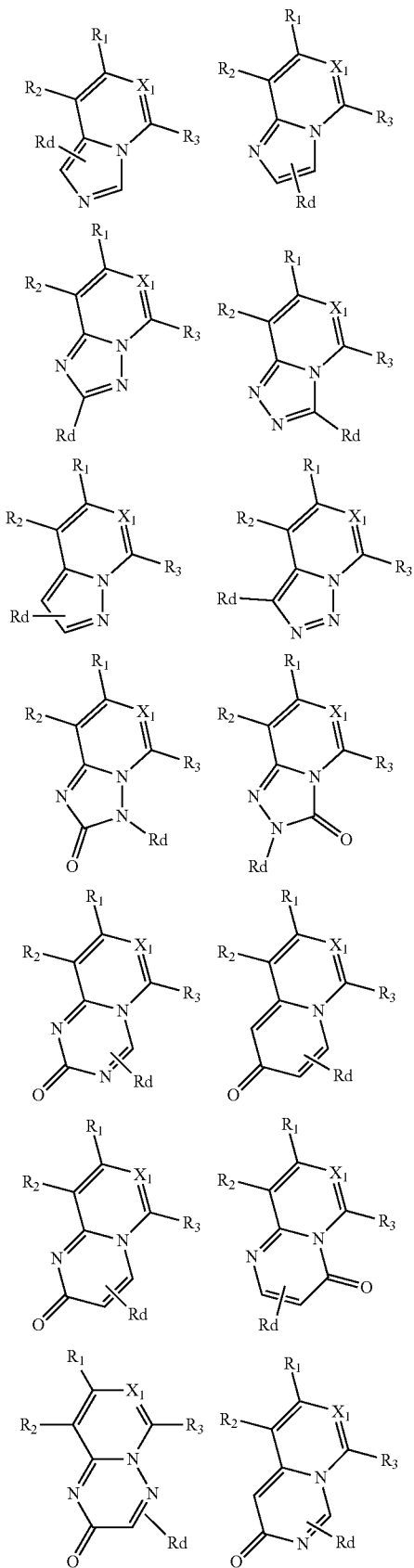

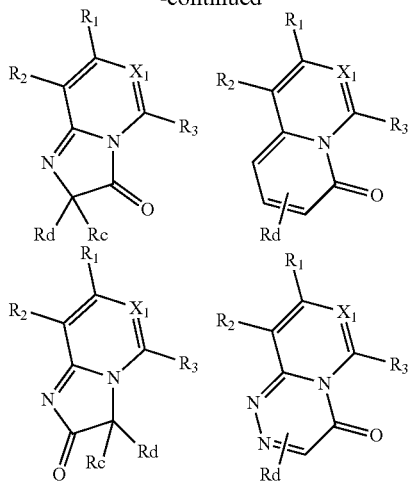

-continued (II)

wherein $R_d$ is selected from hydrogen, halogen, hydroxyl, amino, $C_1$-$C_6$ alkyl, $C_1$-$C_6$ alkoxy, $C_1$-$C_6$ alkylamino, cyano, alkenyl, alkynyl, 3-8 membered cycloalkyl or heterocycloalkyl, 5-8 membered aryl or heteroaryl; $R_1$, $R_2$, $R_3$ and $X_1$ are defined as described above.

In a further embodiment, the present disclosure is preferably a compound represented by the following formula (III), or a pharmaceutically acceptable salt thereof, or an enantiomer, a diastereomer, a tautomer, a solvate, a polymorph or a prodrug thereof:

III

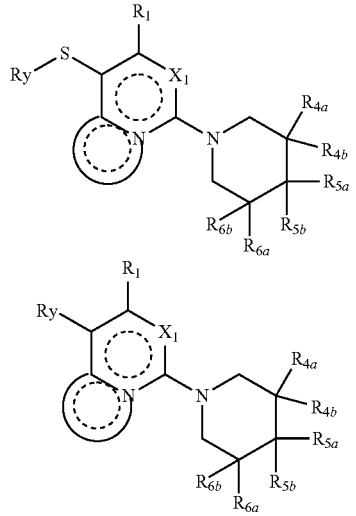

wherein $R_{4a}$, $R_{4b}$, $R_{6a}$, and $R_{6b}$ are independently selected from hydrogen, halogen, hydroxyl, amino, etc., respectively, and cannot be simultaneously substituted with the hydroxyl or the hydroxyl and fluorine at the same carbon atom; $R_{5a}$ is selected from $C_1$-$C_6$ alkyl, hydroxyl, amino, aminomethyl, etc.; $R_{5b}$ is selected from hydroxyl, amino, halogen, $C_1$-$C_6$ alkyl, 3-8 membered cycloalkyl or heterocycloalkyl, hydroxyalkyl, alkoxyalkyl, cycloalkylalkyl, alkoxyacyl, 5-8 membered aryl or heteroaryl, etc.;

alternatively, $R_{5a}$ and $R_{5b}$ may be linked by carbon atoms to form 3-12 membered monocyclic or polycyclic saturated or unsaturated alkyl, 3-12 membered monocyclic or polycyclic saturated or unsaturated heterocycloalkyl, 3-12 membered spiro or fused cycloalkyl, and 3-12 membered spiro or fused heterocycloalkyl;

and each hydrogen atom on the $R_{5a}$ and $R_{5b}$ groups described above may be respectively substituted with the following groups of deuterium, halogen, hydroxyl, alkoxy, amino, alkylamino, alkyl, cycloalkyl, heterocycloalkyl, etc.;

more preferably a compound represented by formula IV:

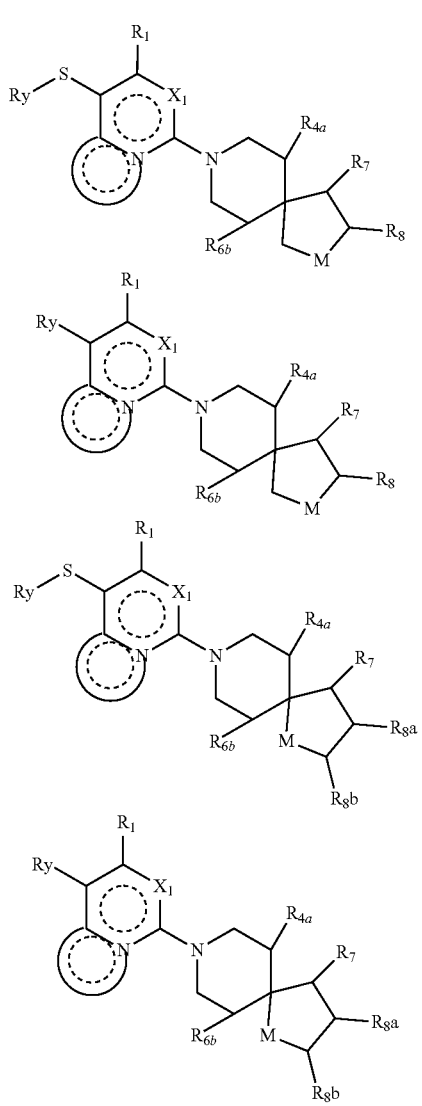

wherein M is selected from —O—, —S—, —SO$_2$—, —CR$_{9a}$R$_{9b}$—, —NR$_{10}$—, etc.; R$_7$ is selected from hydrogen, halogen, C$_1$-C$_6$ alkyl, hydroxy, amino, alkoxy, etc.; R$_8$ is selected from hydroxyl, halogen, C$_1$-C$_6$ alkyl, etc.; R$_{9a}$ and R$_{9b}$ are independently selected from deuterium, hydrogen, oxygen, hydroxyl, halogen, amino, C$_1$-C$_6$ alkyl, etc.; R$_{10}$ is selected from hydrogen, C$_1$-C$_{10}$ alkyl, etc.; R$_{8a}$ and R$_{8b}$ are independently selected from hydrogen, halogen, C$_1$-C$_6$ alkyl, etc., respectively; alternatively, R$_{8a}$ and R$_{8b}$ are linked by carbon atoms or heteroatoms to form a 3-12 membered saturated or partially unsaturated or aromatic ring system; wherein the formed ring system can continue to be substituted with one or more substituents; R$_1$, R$_y$, and X$_1$ are defined as described above.

A method for preparing a compound represented by formula I, wherein the method comprises steps a-b:
a) converting a compound represented by formula (A) and a block R$_2$ to a compound B represented by formula through a metal-catalyzed coupling reaction, wherein an R$_2$ fragment is a boric acid, a boric acid ester, a trifluoroborate, or a sulfide, etc.; and
b) obtaining a compound represented by formula (I) by a cross-coupling reaction between the compound B represented by formula and a block R$_3$ in the presence of a transition metal catalyst, wherein an R$_3$ fragment is an amine, an alcohol, an alkene, an alkyne, a metal alkyl reagent, an alkylboronic acid, an alkylboronic acid ester, an alkyl trifluoroborate, etc.;

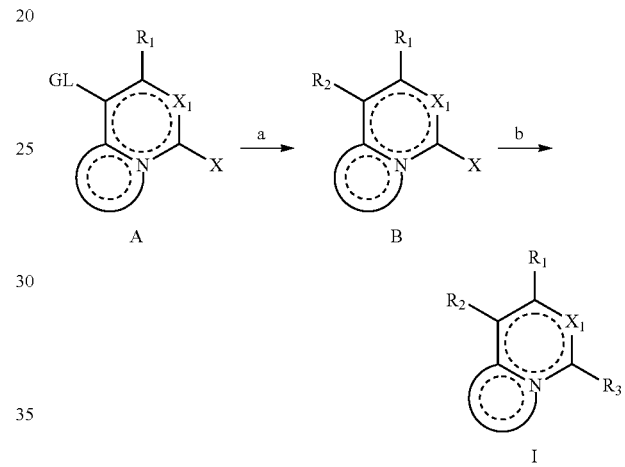

wherein LG is a leaving group which is selected from halogen, trifluoromethanesulfonate, benzenesulfonate, etc., and each of the group is defined as described above.

Preferably, the steps a) and b) are respectively carried out in a solvent and the solvent is selected from the group consisting of water, methanol, ethanol, isopropanol, butanol, ethylene glycol, ethylene glycol monomethylether, N-methylpyrrolidone, dimethyl sulfoxide, tetrahydrofuran, toluene, dichloromethane, 1,2-dichloroethane, acetonitrile, N,N-dimethylformamide, N,N-dimethylacetamide, dioxane, or a composition thereof.

Preferably, the transition metal catalyst is selected from the group consisting of tris (dibenzylideneacetone) dipalladium (Pd$_2$(dba)$_3$), tetrakis (triphenylphosphine) palladium (Pd(PPh$_3$)$_4$), palladium acetate, palladium chloride, dichlorobis (triphenylphosphine) palladium, palladium trifluoroacetate, palladium triphenylphosphine acetate, [1,1'-bis (diphenylphosphino) ferrocene] palladium dichloride, bis (tri-o-phenylphosphine) palladium dichloride, 1,2-bis (diphenylphosphino) ethane palladium dichloride, or a composition thereof; the catalyst ligand is selected from the group consisting of tri-tert-butylphosphine, tri-tert-butylphosphine tetrafluoroborate, tri-n-butylphosphine, triphenylphosphine, tri-p-benzylphosphine, tricyclohexylphosphine, tri-o-benzylphosphine, or a composition thereof.

Preferably, the inorganic base is selected from the group consisting of sodium hydride, potassium hydroxide, sodium acetate, potassium acetate, potassium tert-butoxide, sodium tert-butoxide, potassium fluoride, cesium fluoride, potassium phosphate, potassium carbonate, potassium bicarbonate, sodium carbonate, sodium bicarbonate, or a composition thereof; the organic base is selected from the group consisting of pyridine, triethylamine, N,N-diisopropylethylamine, 1,8-diazabicyclo [5.4.0] undec-7-ene (DBU), hexamethyl disilithium, sodium hexamethyl disilyl, dimethylpyridine, or a composition thereof.

The present disclosure provides a class of preferred compounds represented by formula (I-1), including, but not limited to, the following structures:

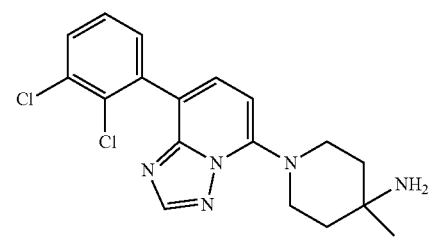

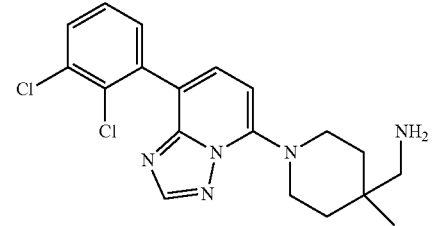

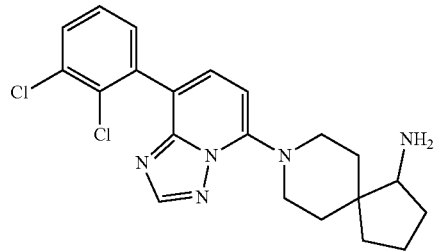

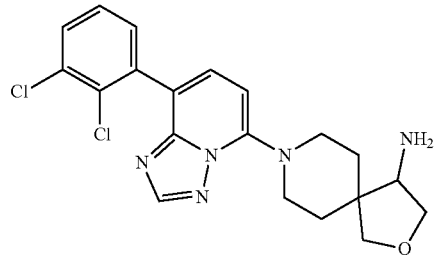

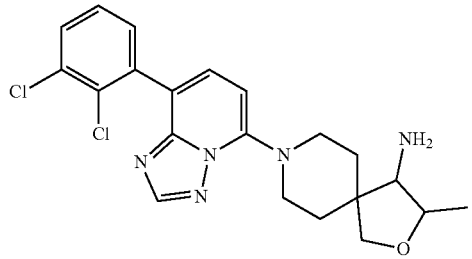

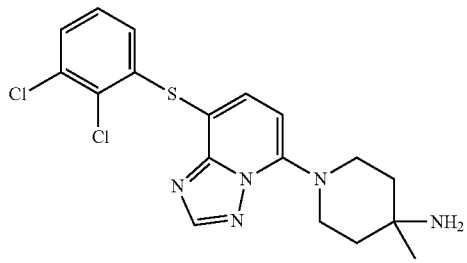

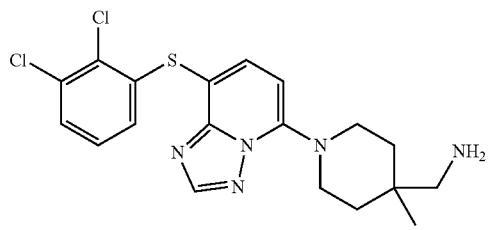

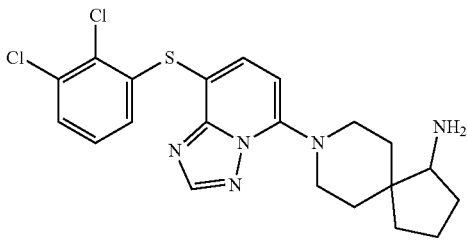

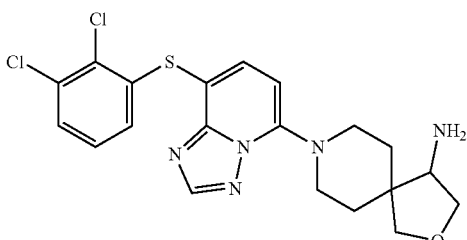

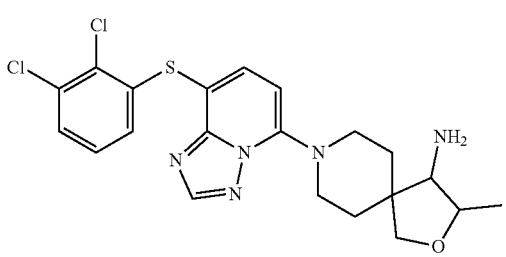

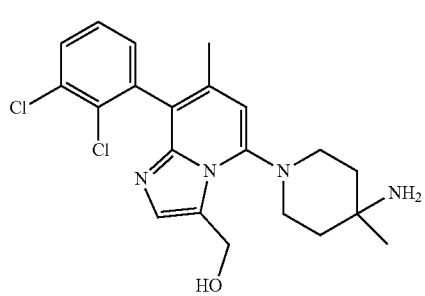

-continued
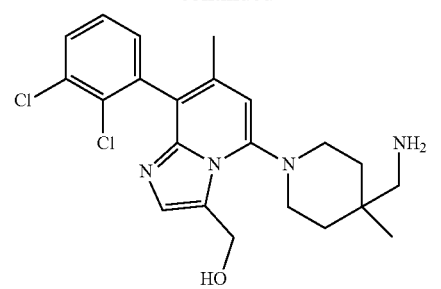
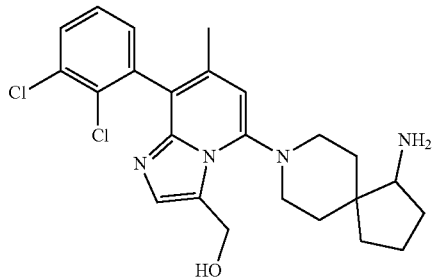
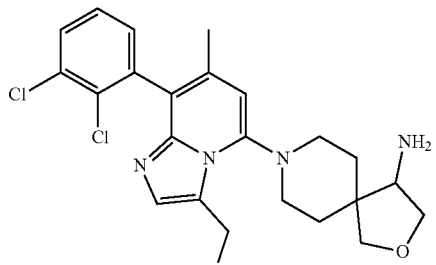
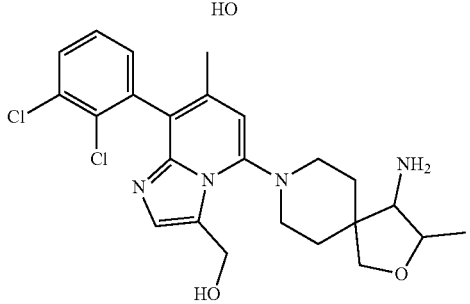
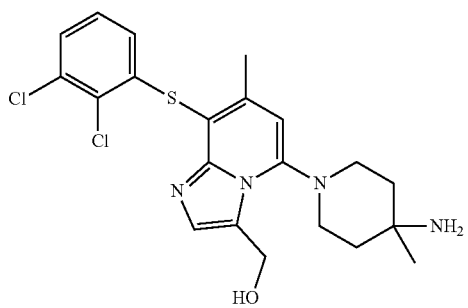
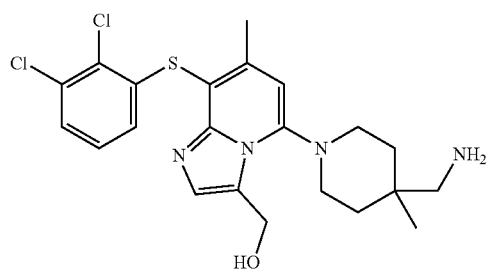
-continued
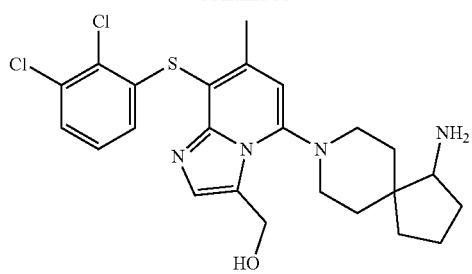
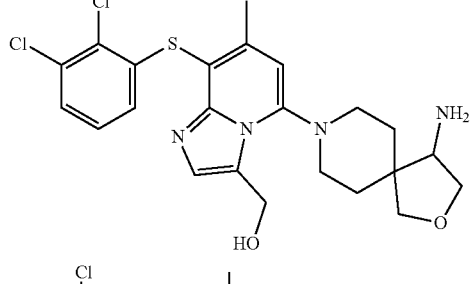
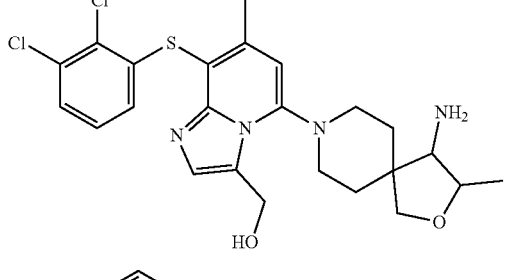
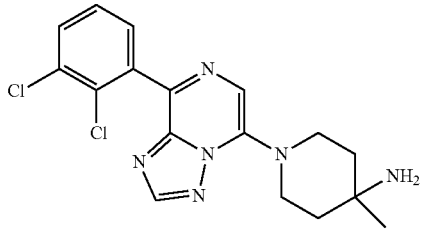
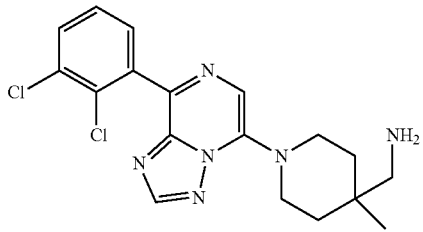
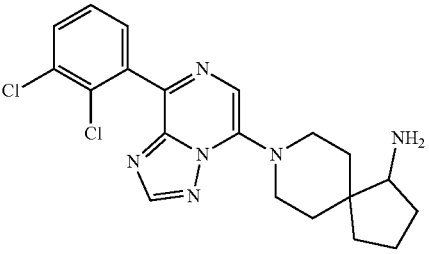

57
-continued
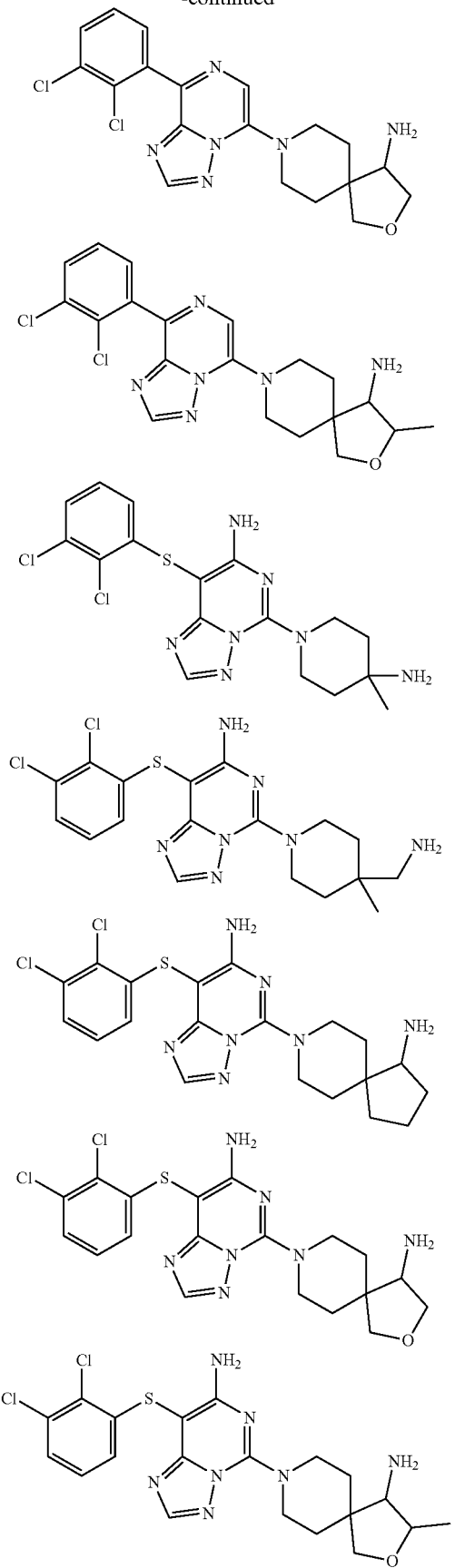
58
-continued
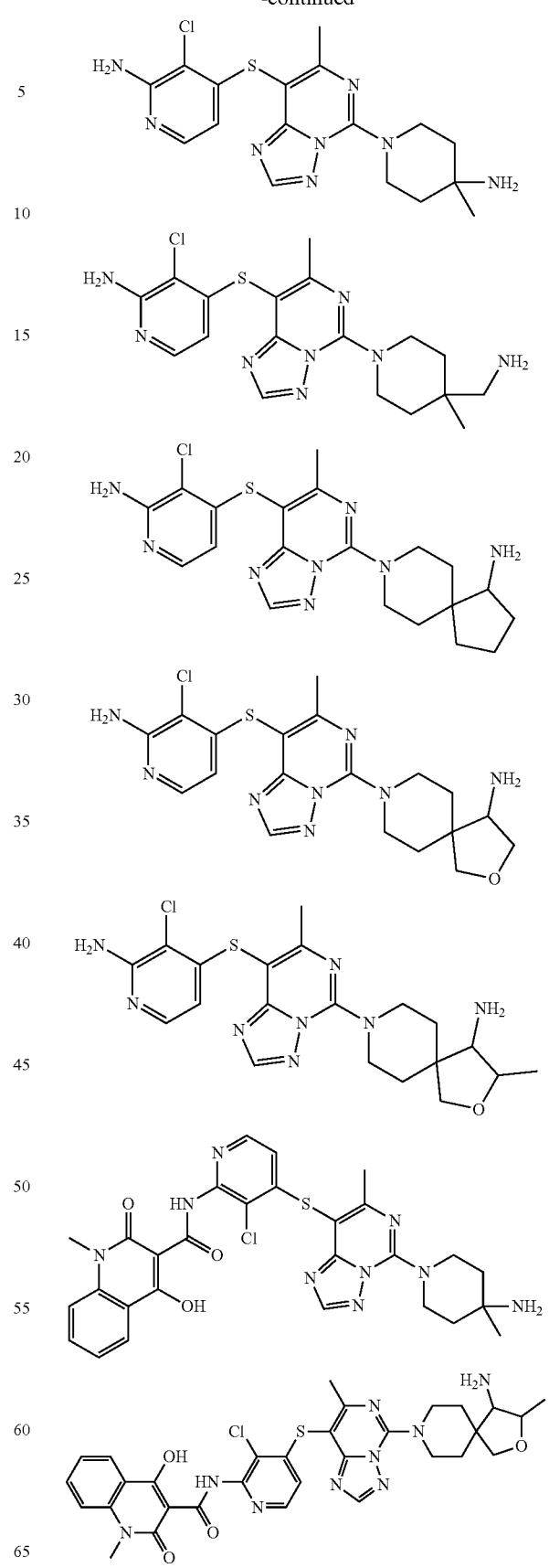

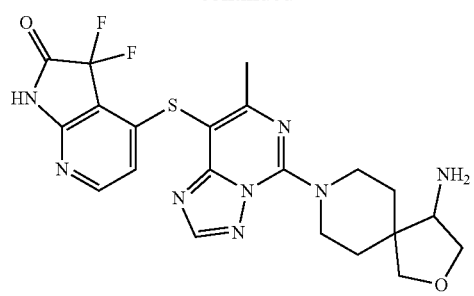
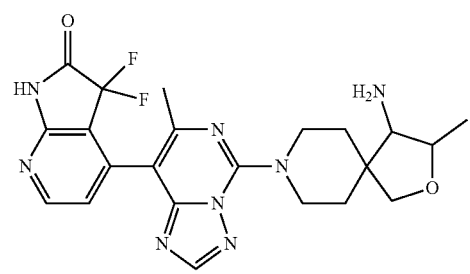
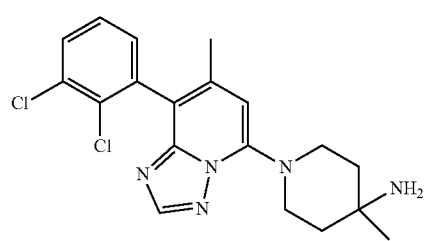
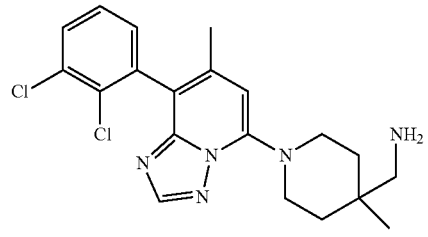
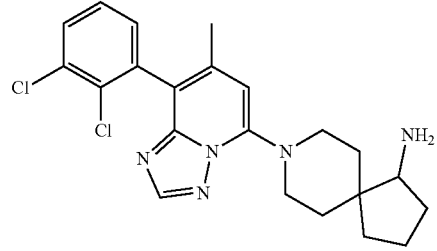
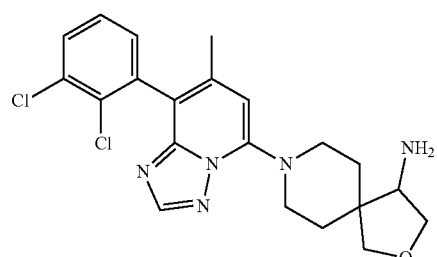
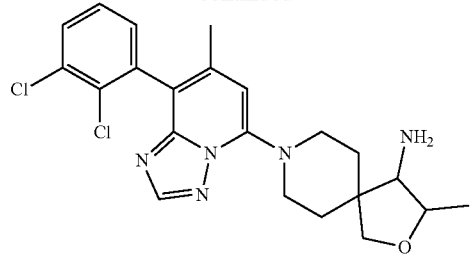
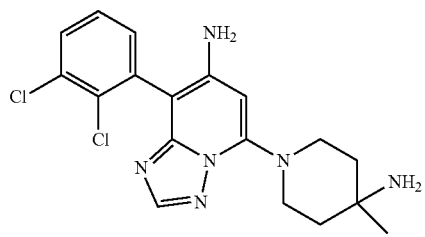
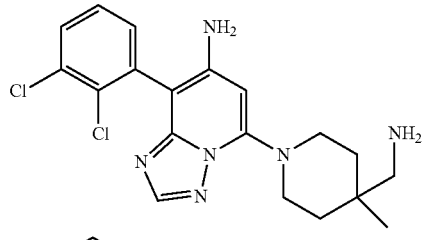
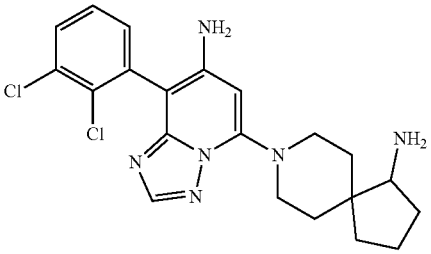
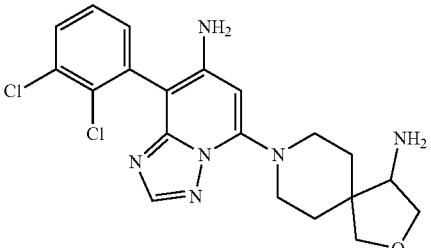
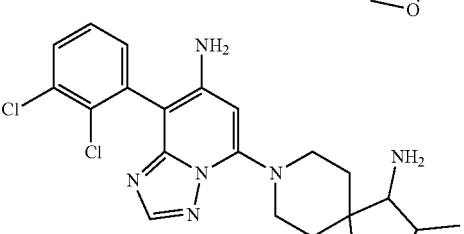
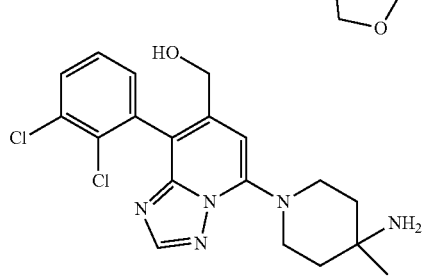

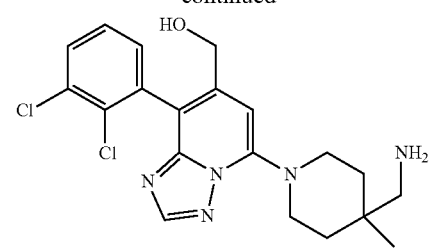
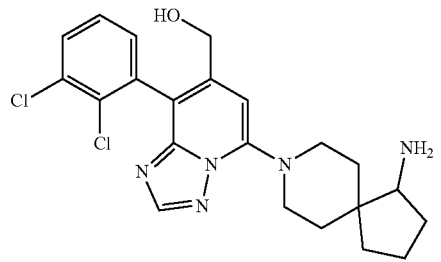
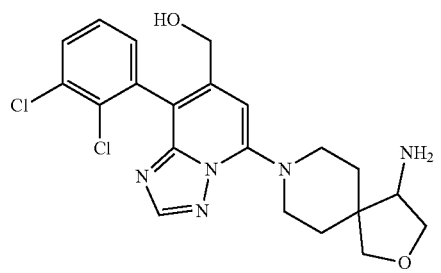
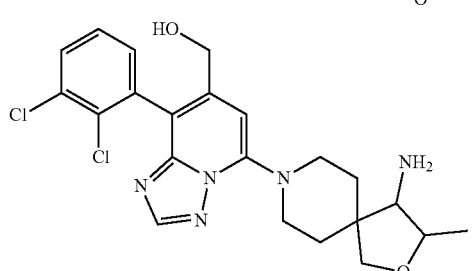
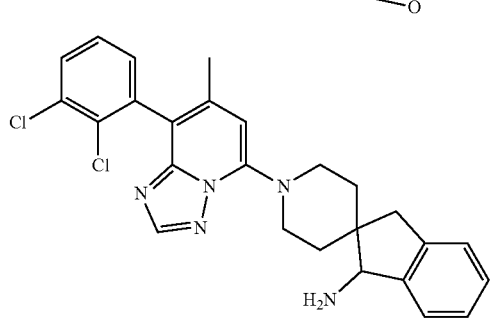
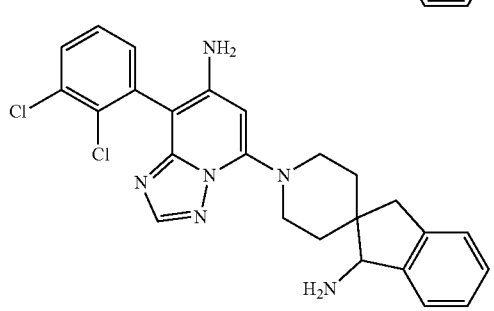
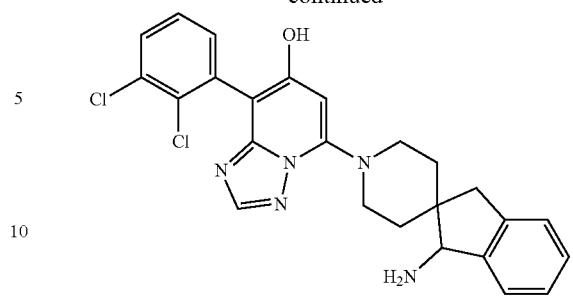
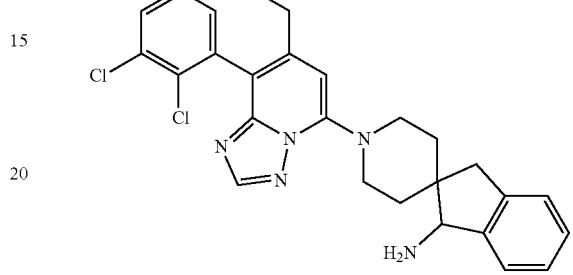
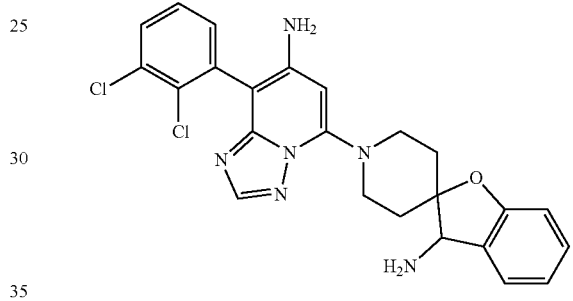
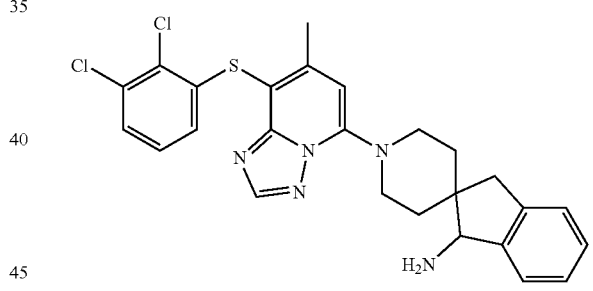
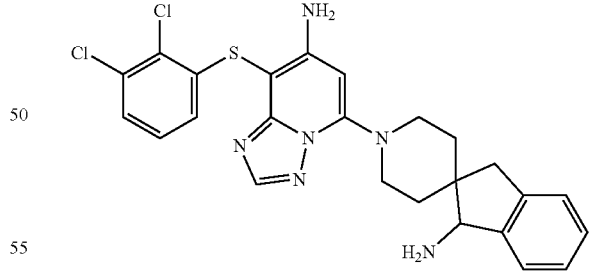
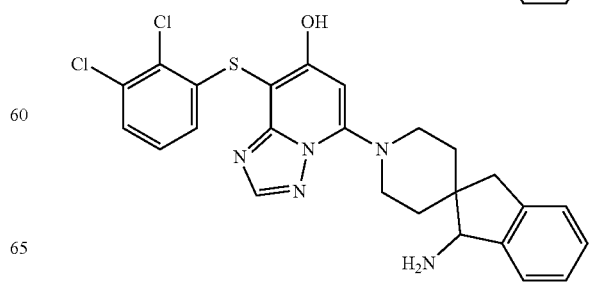

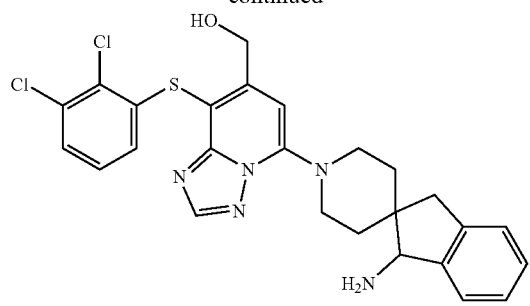
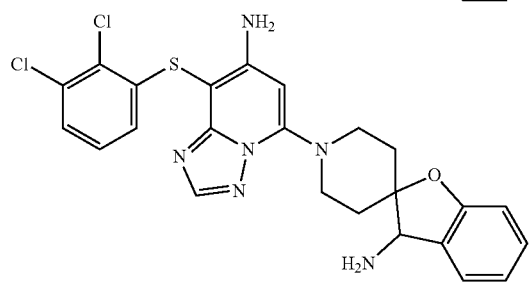
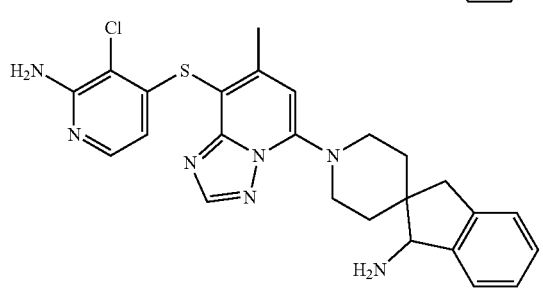
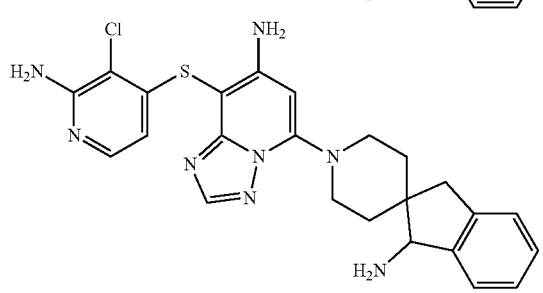
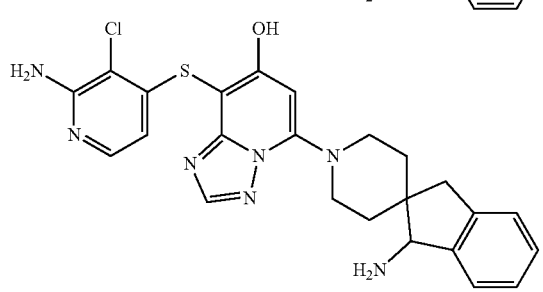
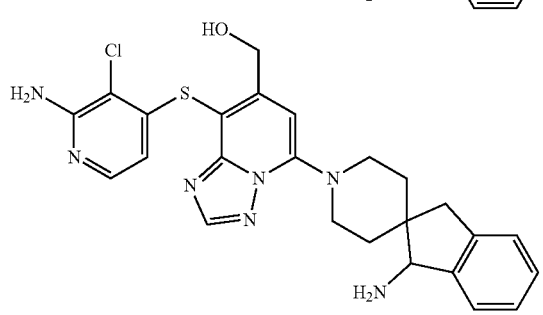
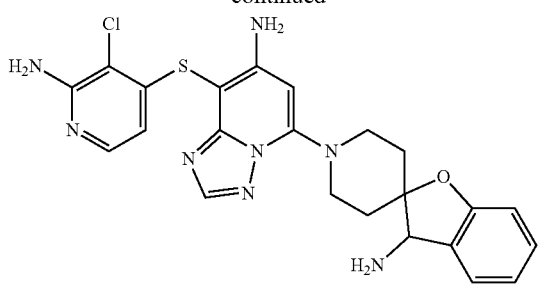
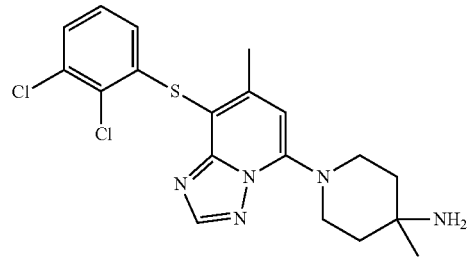
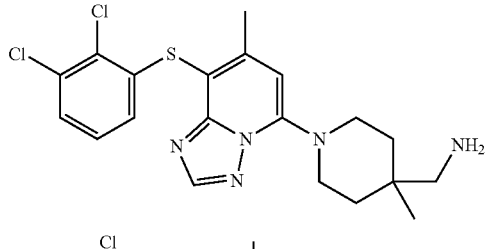
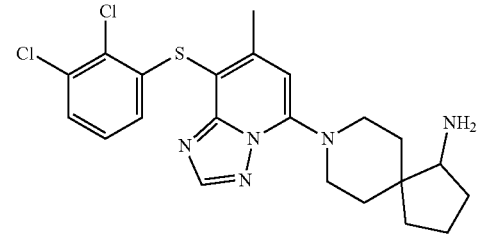
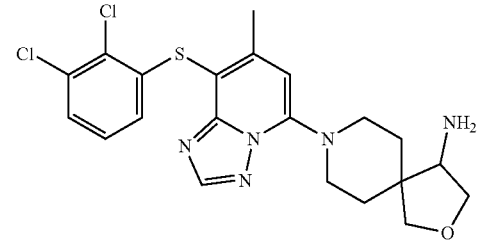
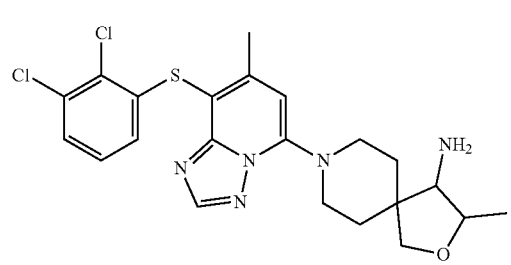

-continued
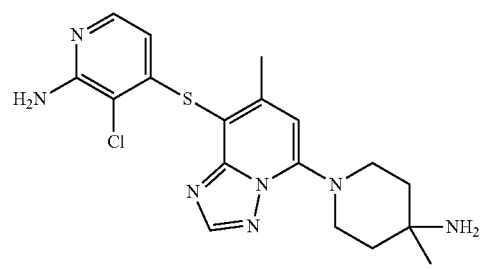
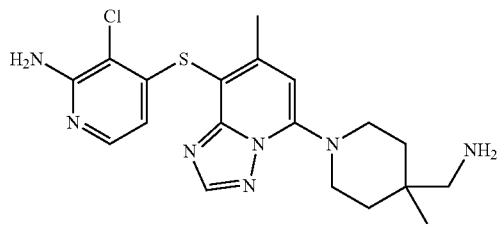
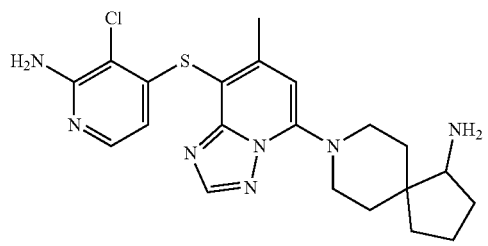
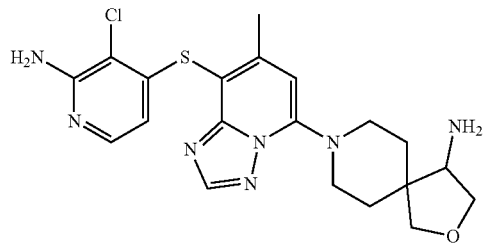
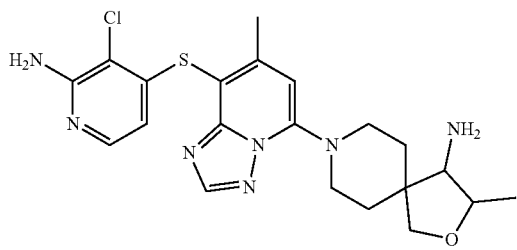
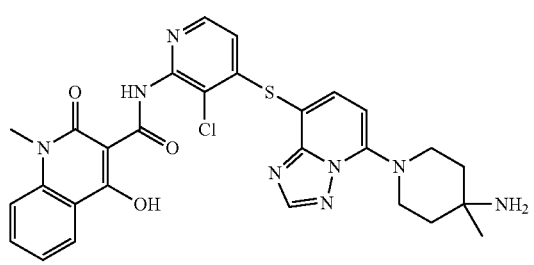
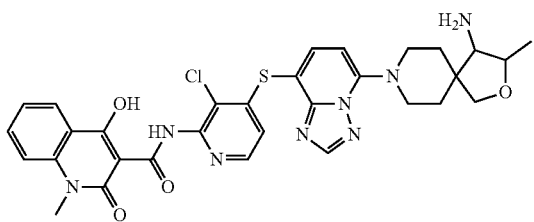
-continued
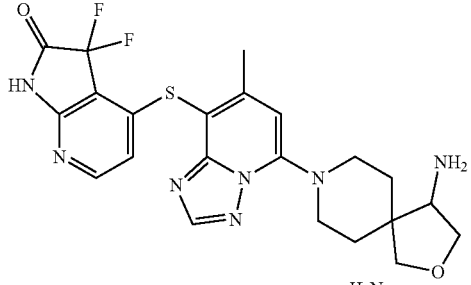
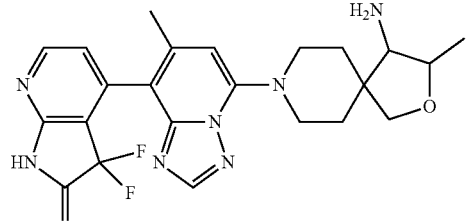
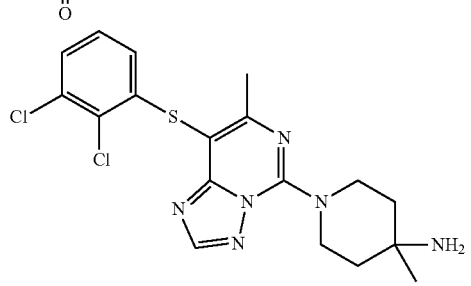
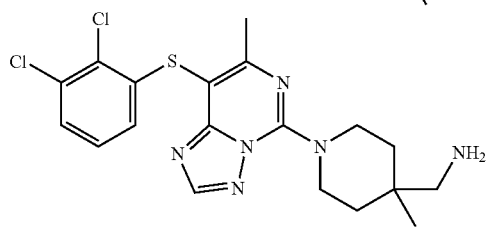
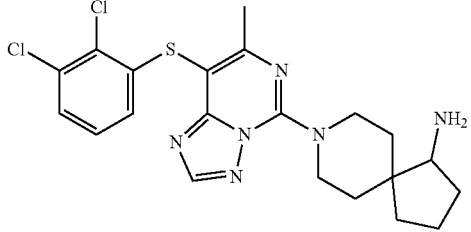
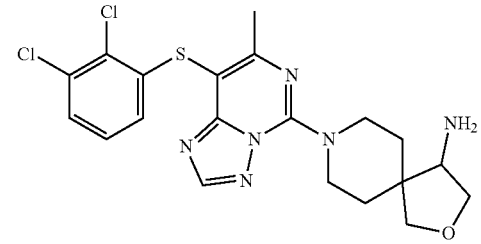
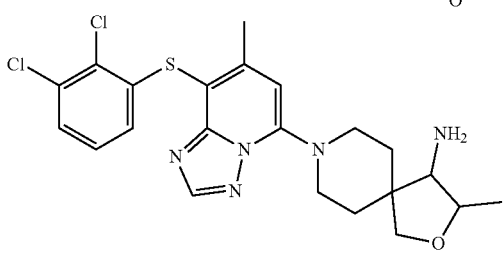

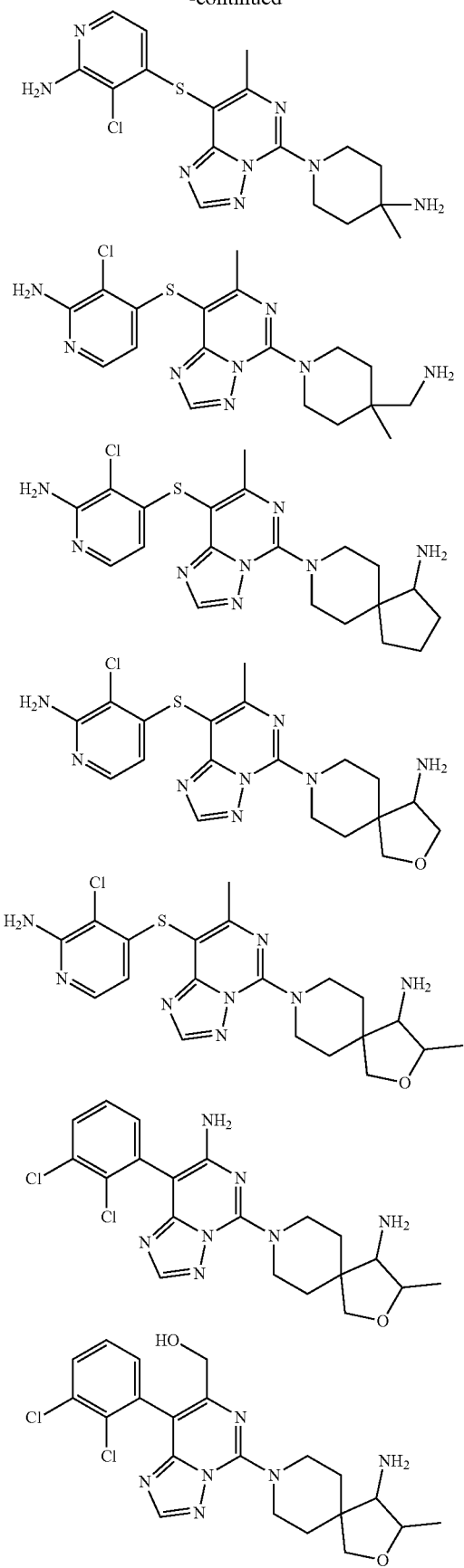
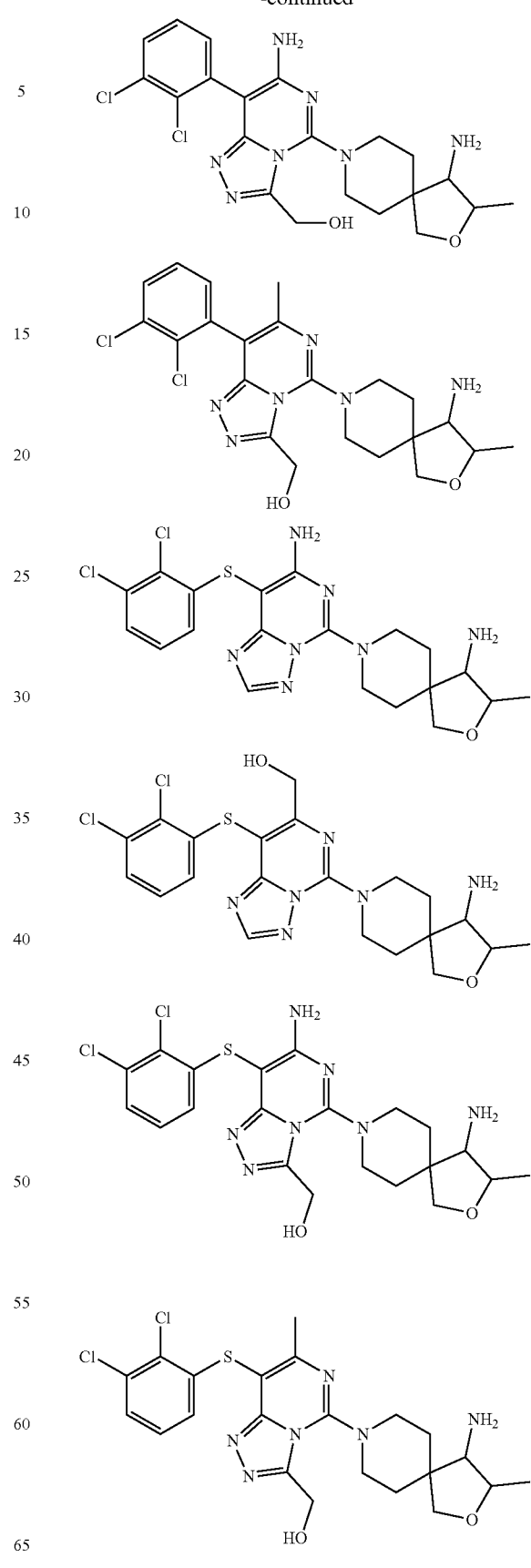

-continued
69
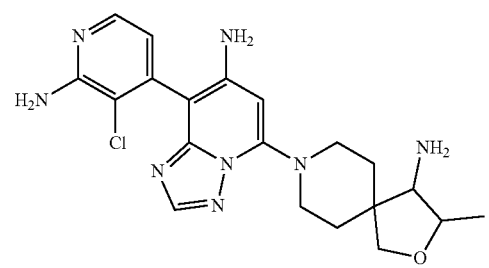
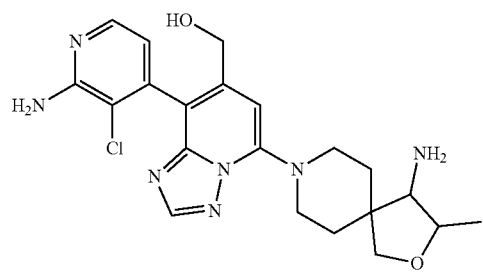
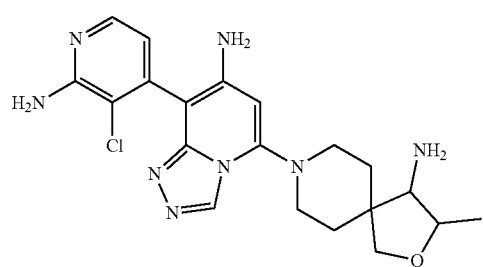
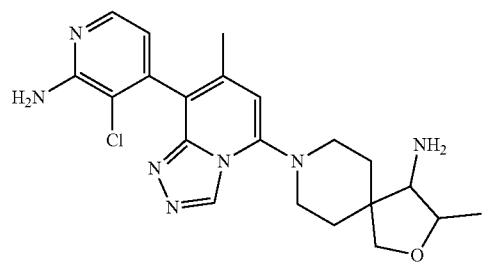
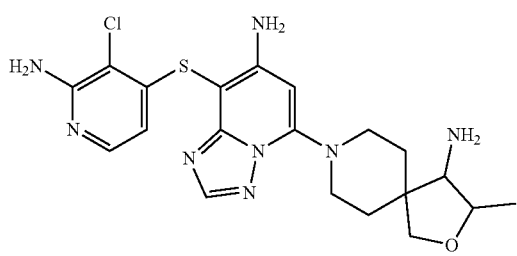
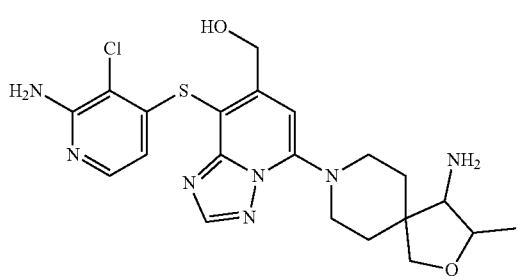
70
-continued
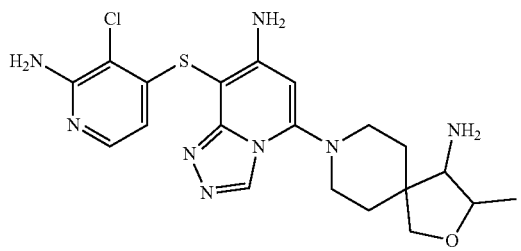
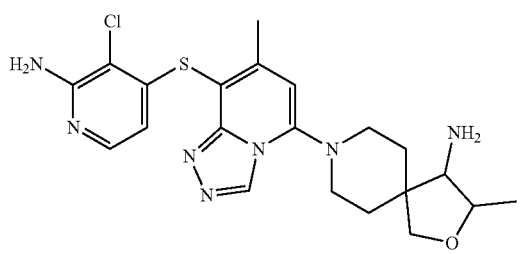
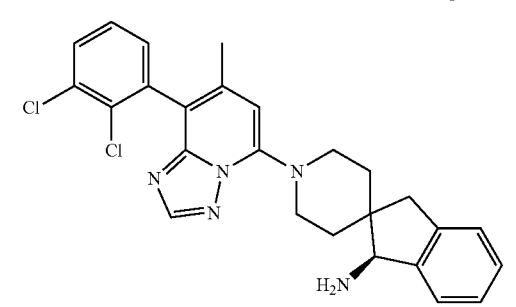
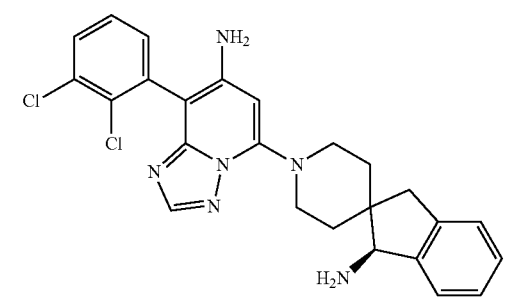
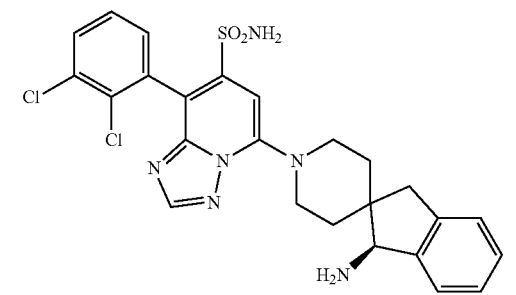
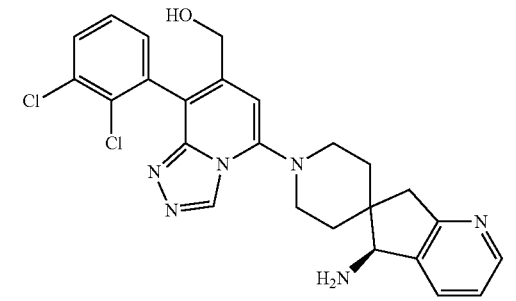

-continued
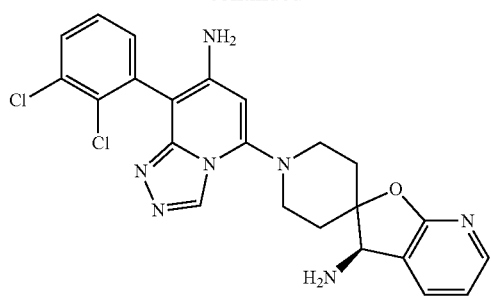
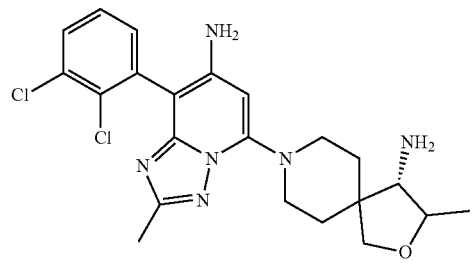
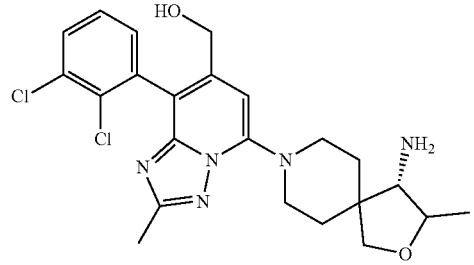
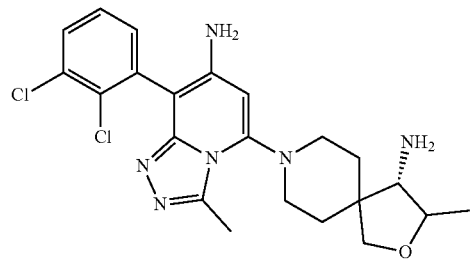
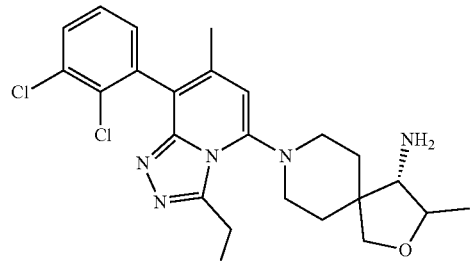
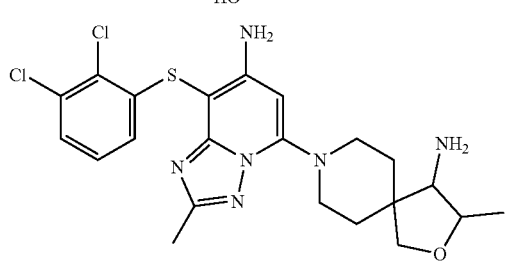
-continued
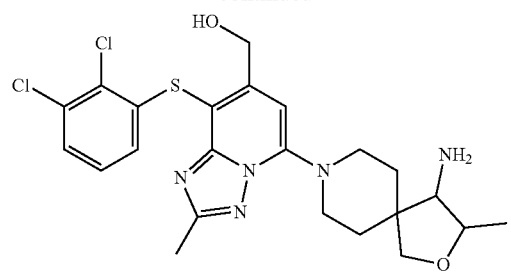
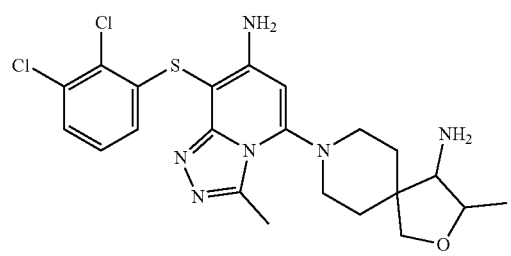
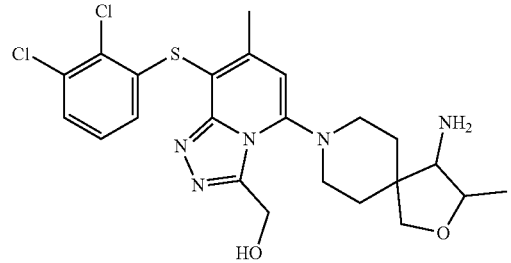
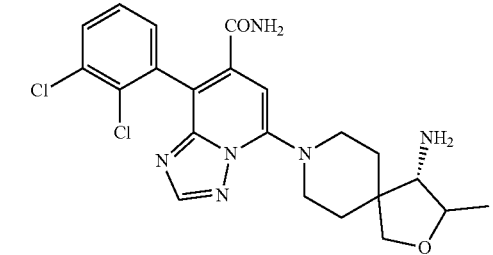
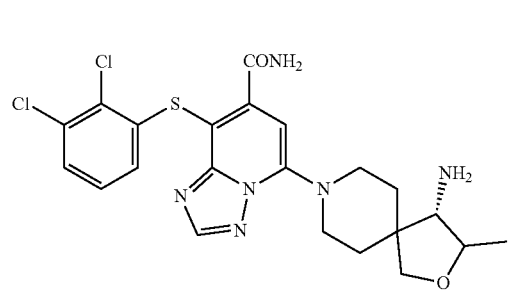
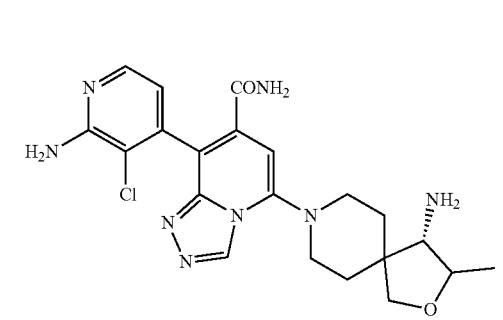

-continued
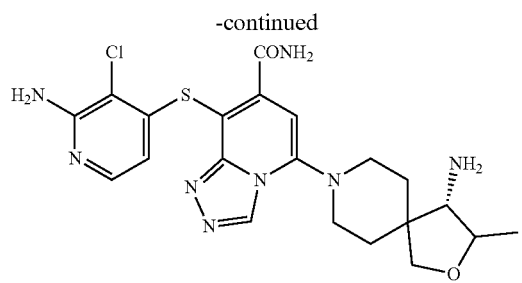
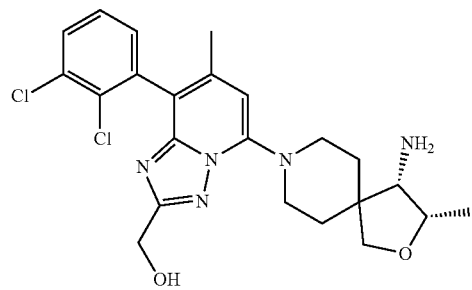
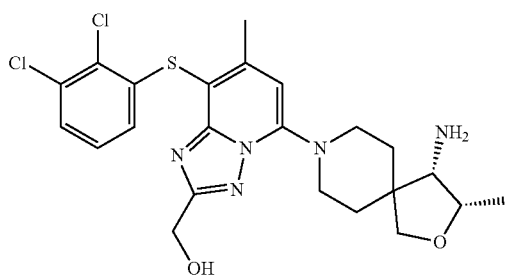
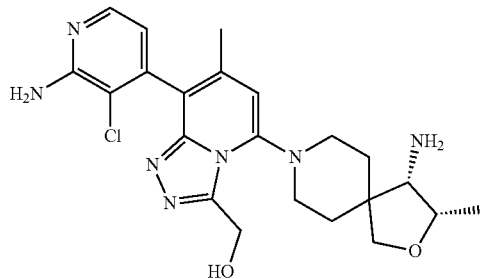
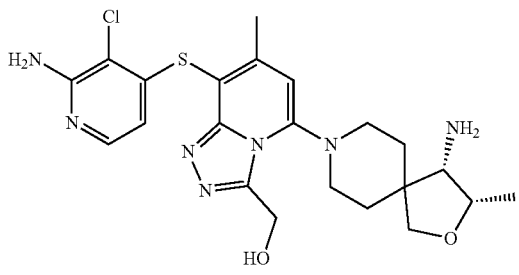
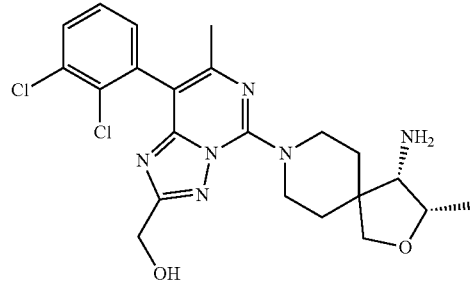
-continued
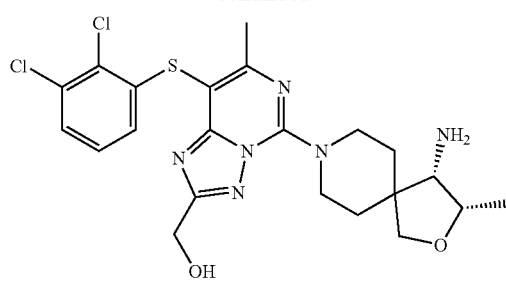
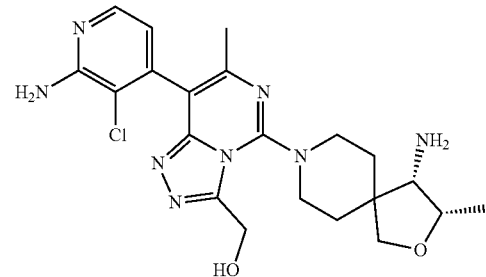
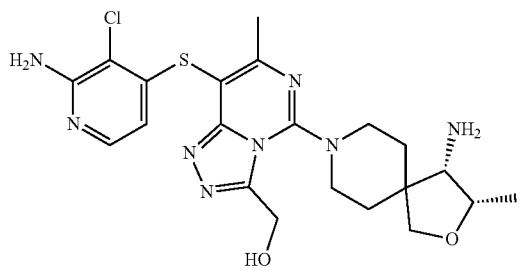
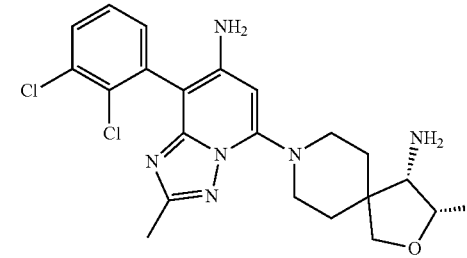
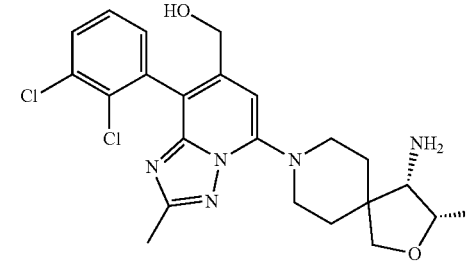
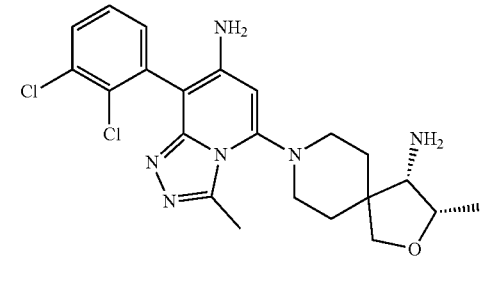

75
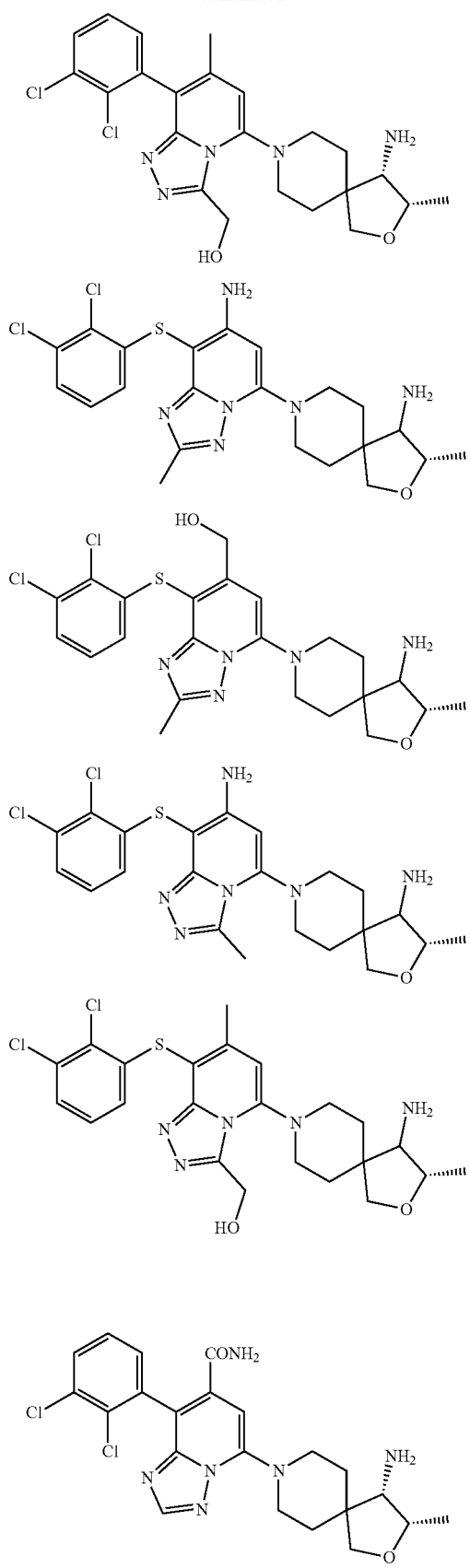
76
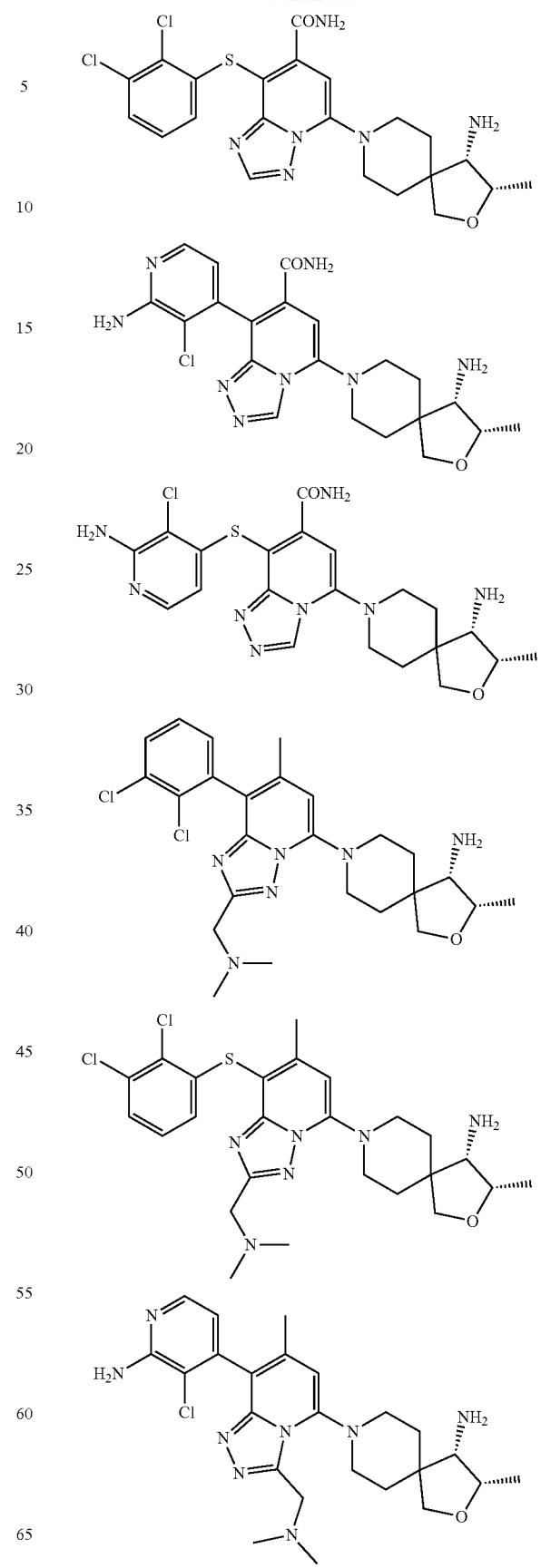

77
-continued
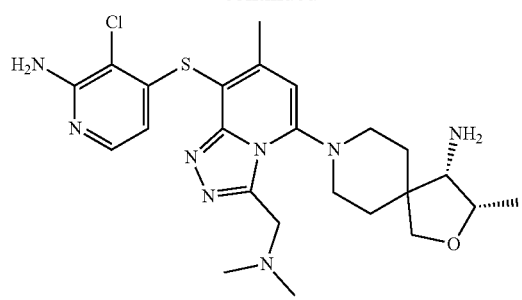
78
-continued
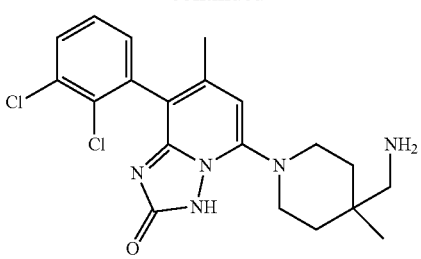
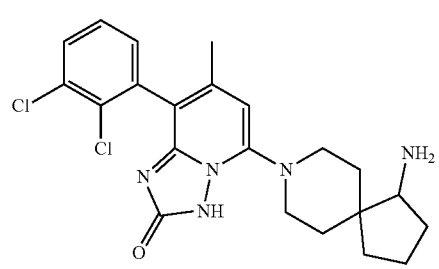
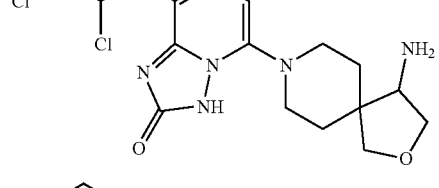
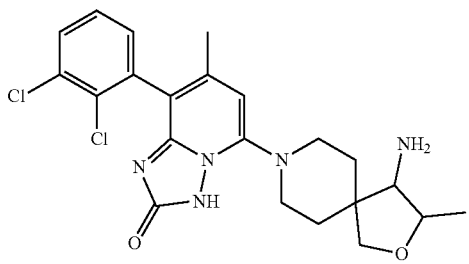
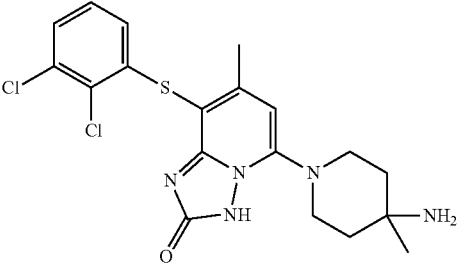
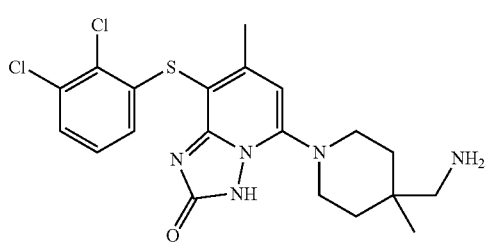

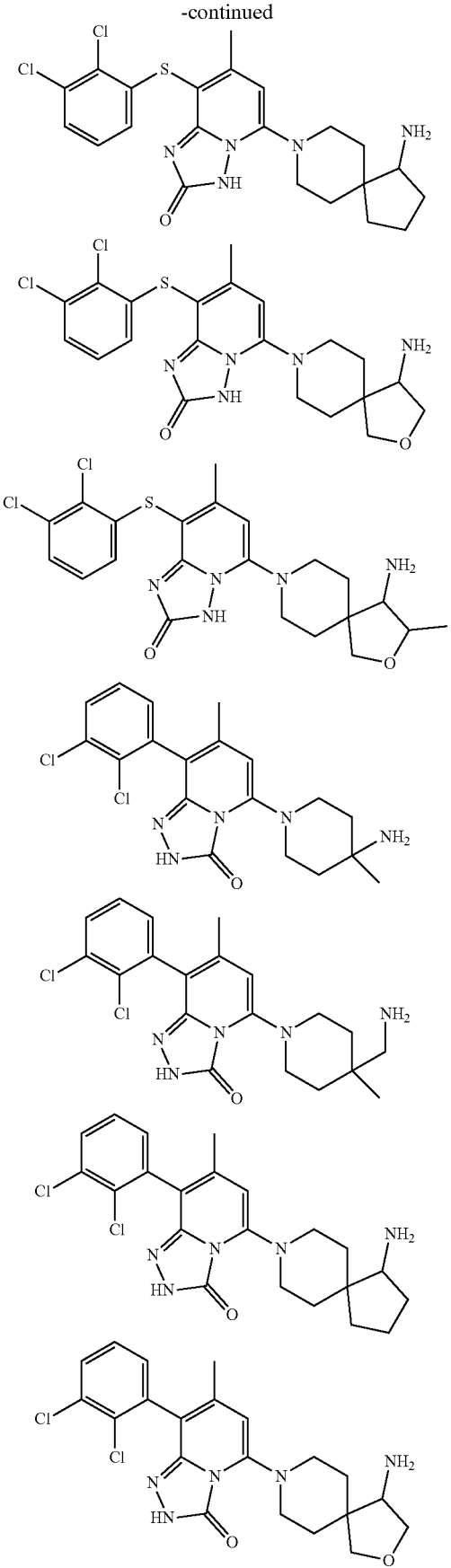

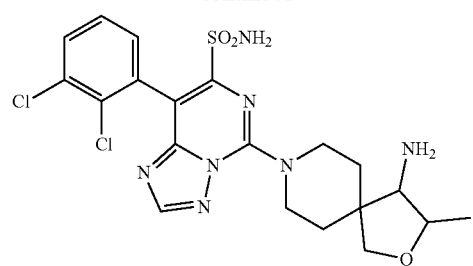
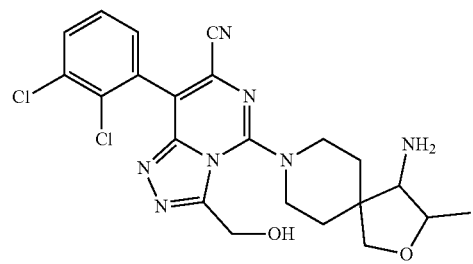
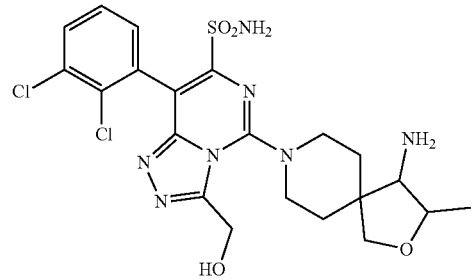
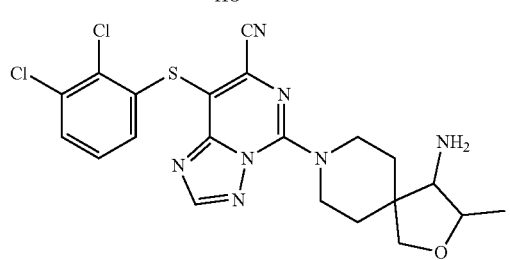
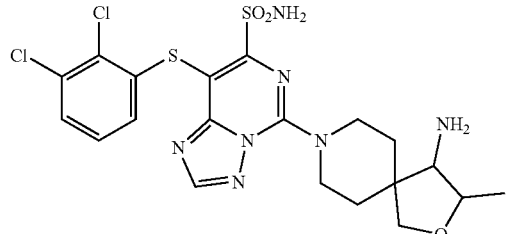
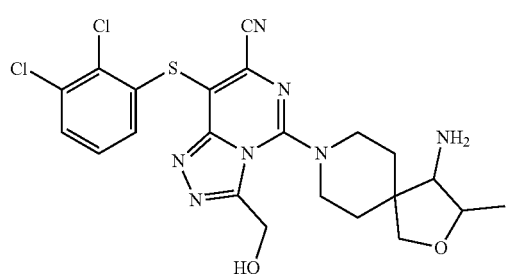
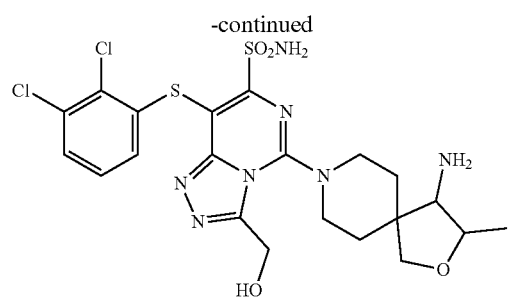
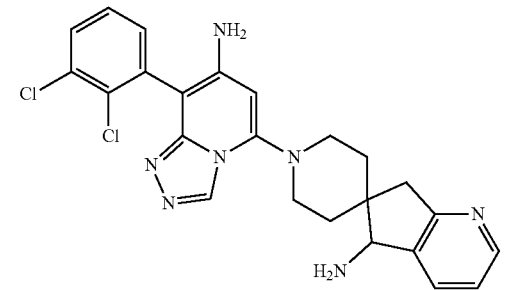
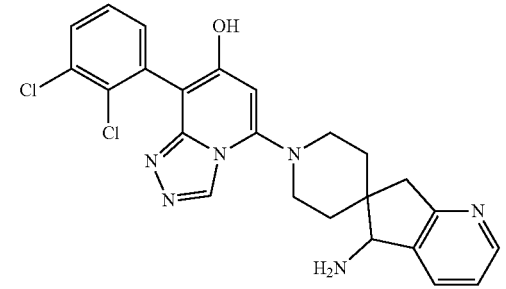
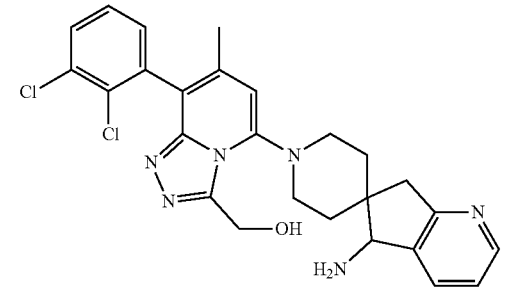
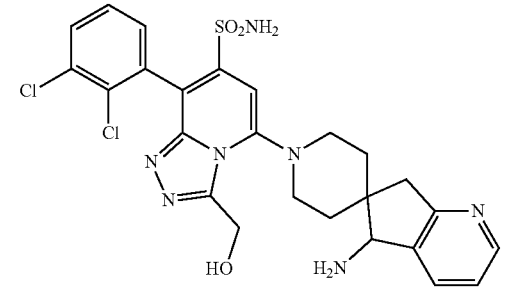
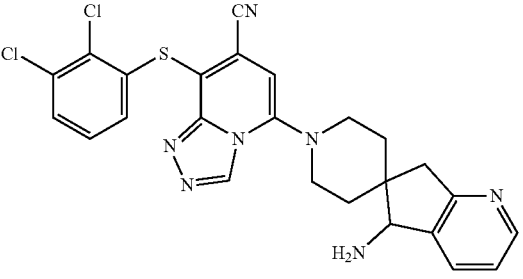

-continued
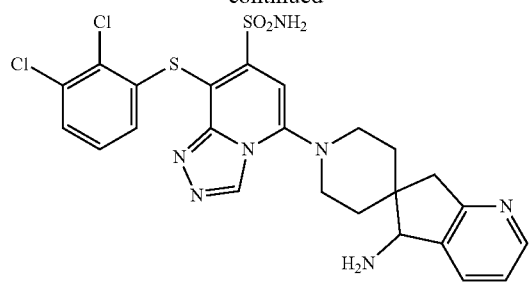
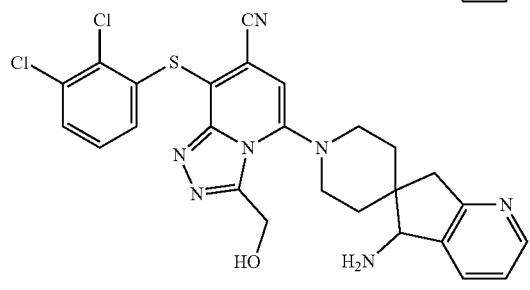
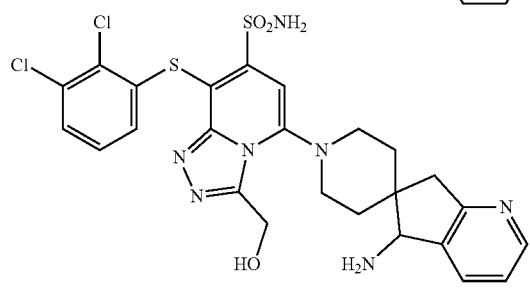
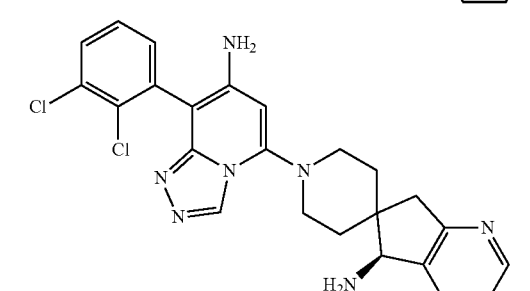
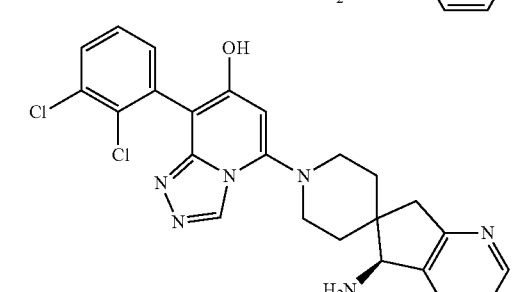
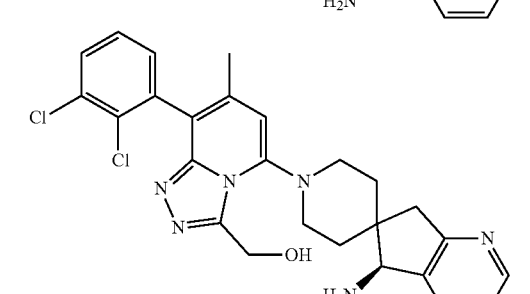
-continued
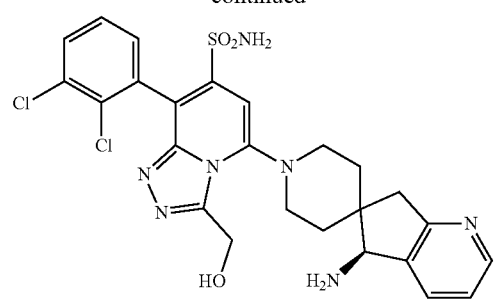
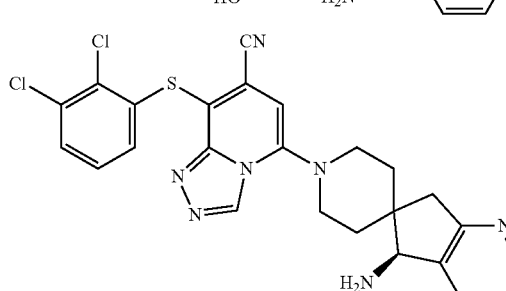
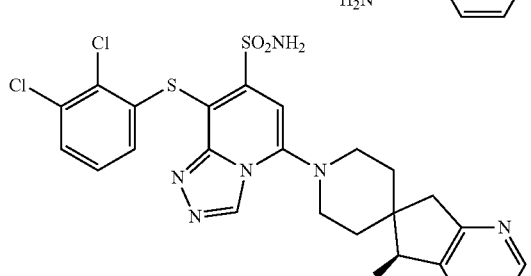
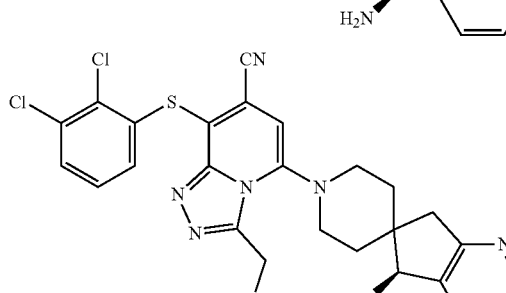
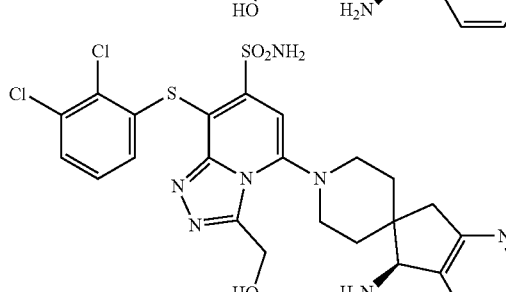
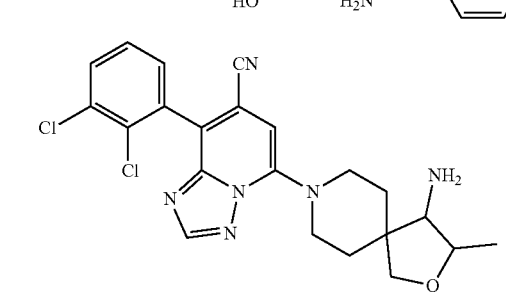

-continued
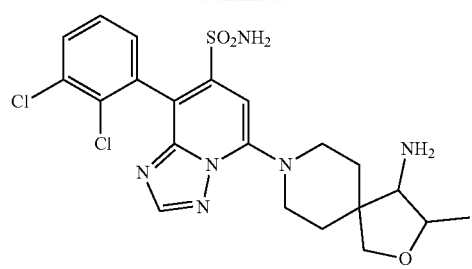
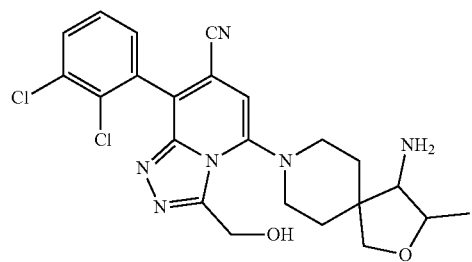
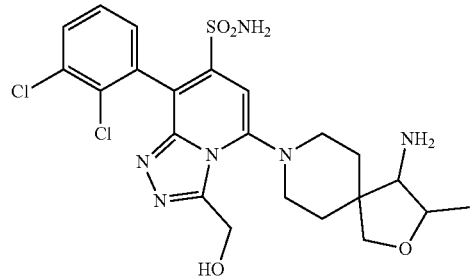
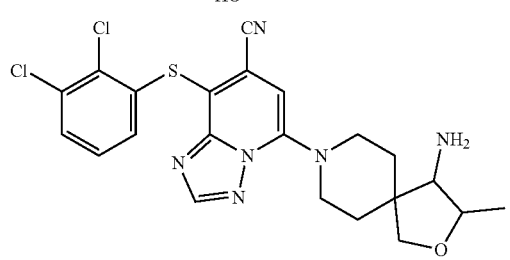
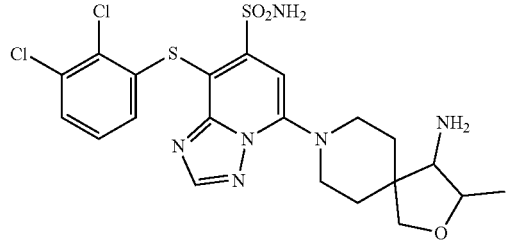
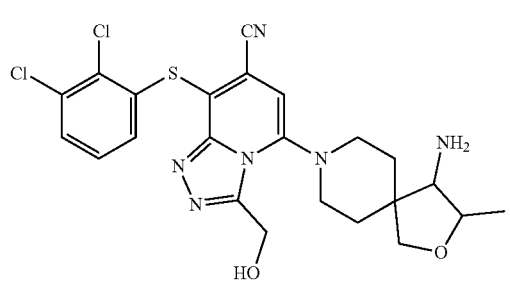
-continued
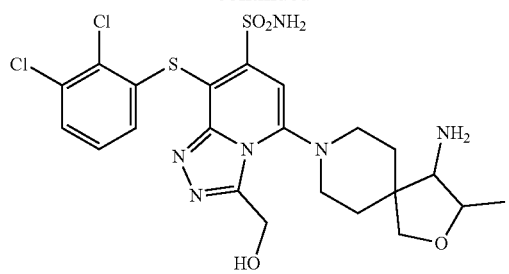
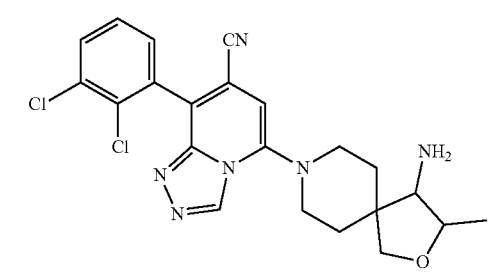
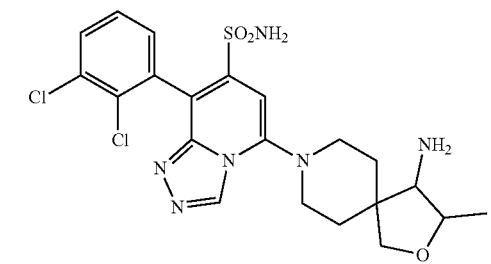
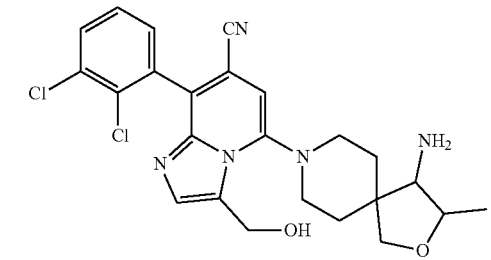
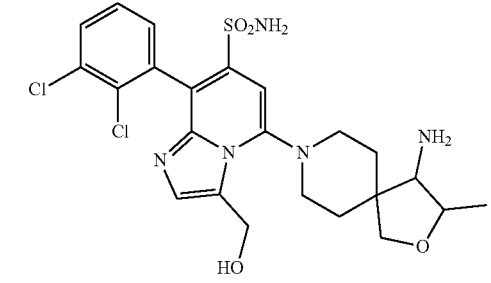
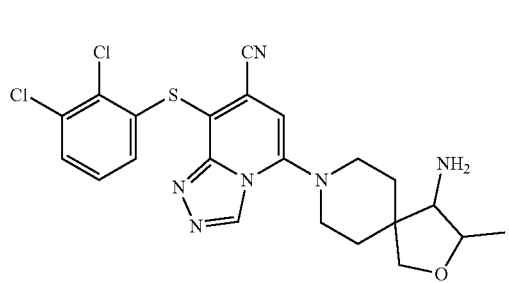

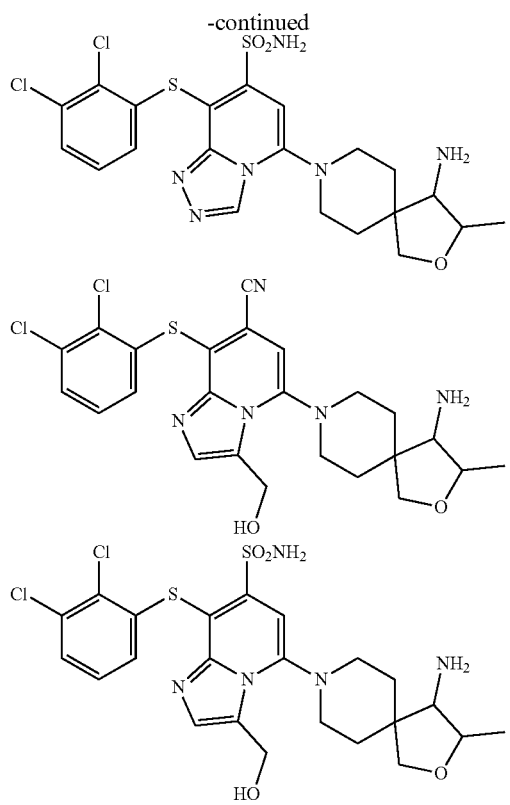

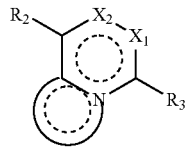

Another object of the present disclosure is to provide a drug for treating or preventing tumors and a composition thereof. The technical scheme to achieve the above object is as follows:

A pharmaceutical composition for treating tumors, comprising a nitrogen-containing fused heterocyclic compound represented by formula (I-1) described above, or a pharmaceutically acceptable salt thereof, or an enantiomer, a diastereomer, a tautomer, a solvate, a polymorph or a prodrug thereof, and a pharmaceutically acceptable carrier.

Another object of the present disclosure is to provide a use of one of the compounds described above. The technical scheme to achieve the above object is as follows:

The nitrogen-containing fused heterocyclic compound represented by formula (I-1), or a pharmaceutically acceptable salt thereof, or an enantiomer, a diastereomer, a tautomer, a solvate, a polymorph or a prodrug thereof is used to prepare a drug for treating diseases associated with the activity or expression of proteins such as SHP2, particularly a drug for treating a tumor, an immune disease and an inflammatory disease.

The present disclosure relates to a compound with structural characteristics of a formula (I-1), wherein the compound can inhibit a variety of tumor cells, particularly can efficiently kill tumors associated with abnormal signaling pathways such as Ras-ERK, PD-L1, etc., and is a class of therapeutic drugs with a novel mechanism of action.

A preferred embodiment includes a nitrogen-containing fused heterocyclic compound represented by formula I-2, or a pharmaceutically acceptable salt thereof, or an enantiomer, a diastereomer, a tautomer, a solvate, a polymorph or a prodrug thereof, where:

$X_1$ and $X_2$ are independently selected from N and $CR_1$, respectively, wherein $R_1$ is selected from hydrogen, halogen, hydroxyl, amino, amido, sulfonamido, $C_1$-$C_6$ alkyl, $C_1$-$C_6$ alkoxy, cyano, alkenyl, alkynyl, 3-8 membered cycloalkyl or heterocycloalkyl, 5-8 membered aryl or heteroaryl;

$R_2$ is selected from -$L_2$-$R_y$; wherein $L_2$ is a direct bond, —O—, —S(O)n-, —$NR_b$—, etc., and $R_y$ is 5-10 membered cycloalkyl or heterocycloalkyl or aryl or heteroaryl; n=0-2; $R_b$ is selected from hydrogen, $C_1$-$C_6$ alkyl or alkoxy, 3-8 membered cycloalkyl or heterocycloalkyl, etc.;

$R_3$ is selected from —$OR_c$, —$SR_c$, —$C(R_aR_b)$ $R_c$, —$NR_bR_c$, —$COR_c$, —$CONR_bR_c$, —$NR_bCOR_c$, —$SO_2NR_bR_c$, —$NR_bSO_2R_c$, —$NR_bCONR_bR_c$, —$NR_bSO_2NR_bR_c$, —$NR_bCSNR_bR_c$, —$COOR_c$, —$OOCR_c$, —$OCONR_bR_c$, —$NR_bCOOR_c$, —$NR_bCSR_c$, —$CSNR_bR_c$, etc., wherein $R_b$ is independently selected from hydrogen, $C_1$-$C_6$ alkyl or alkoxy, 3-8 membered cycloalkyl or heterocycloalkyl upon each occurrence; $R_c$ is independently selected from $C_1$-$C_6$ alkyl, 3-12 membered monocyclic or polycyclic cycloalkyl, 3-12 membered monocyclic or polycyclic heterocycloalkyl; or $R_c$ with $R_a$ or $R_b$ may form 3-12 membered monocyclic or polycyclic cycloalkyl, 3-12 membered monocyclic or polycyclic heterocycloalkyl, 3-12 membered spiro or fused cycloalkyl, and 3-12 membered spiro or fused heterocycloalkyl;

one or more hydrogen atoms on any of the above groups may be substituted with a substituent selected from the group consisting of, including but not limited, deuterium, halogen, hydroxyl, amino or cycloamino, cyano, nitro, sulfone or sulfoxide, $C_1$-$C_8$ alkyl, 3-8 membered cycloalkyl or heterocycloalkyl, $C_1$-$C_8$ alkoxy, $C_1$-$C_8$ alkylamino, alkenyl, alkynyl, acyl or sulfonyl, urea or sulfonylurea, 5-8 membered aryl or heteroaryl; wherein the heteroaryl comprises 1-3 heteroatoms selected from the group consisting of N, O, P, or S; the heterocycloalkyl comprises 1-3 heteroatoms selected from the group consisting of N, O, P, or S; the ring system comprises a spiro ring, a bridged ring, a fused ring, a fused saturated or partially unsaturated ring system; the above ring systems may be further substituted with $C_1$-$C_6$ alkyl, hydroxy, amino, halogen or alkoxy, etc.

A further embodiment includes a compound represented by formula (I-2), or a pharmaceutically acceptable salt thereof, or an enantiomer, a diastereomer, a tautomer, a solvate, a polymorph or a prodrug thereof, preferably the compound represented by formula (IIA), or the pharmaceutically acceptable salt thereof, or the enantiomer, the diastereomer, the tautomer, the solvate, the polymorph or the prodrug thereof:

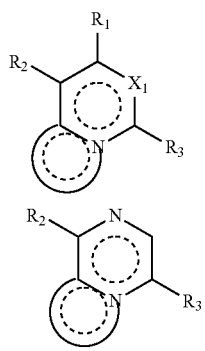
(IIA)
Further preferred is formula IIB:
(IIB)
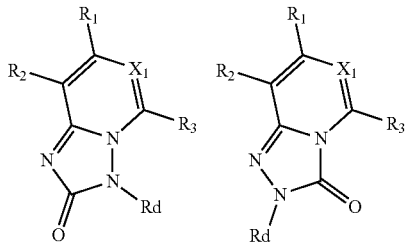
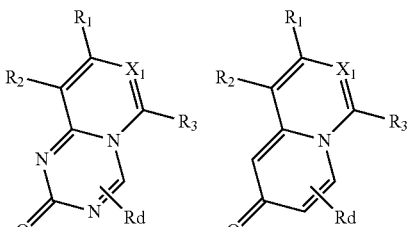
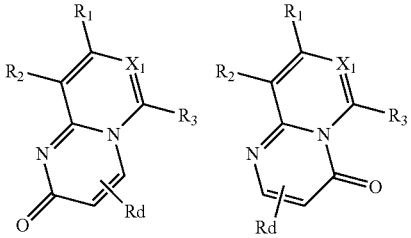
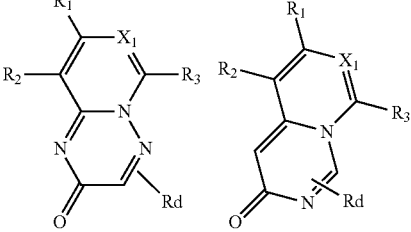
-continued
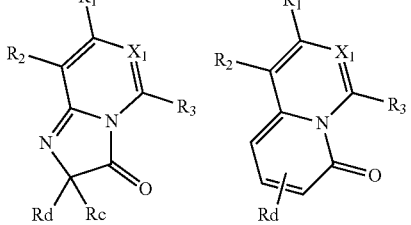
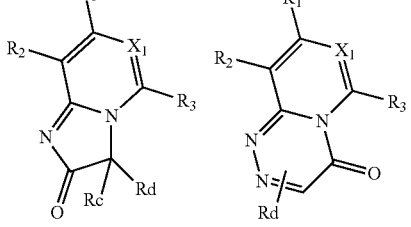
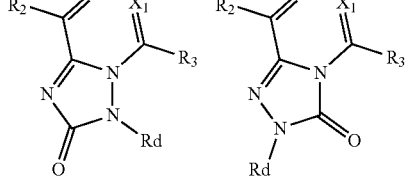

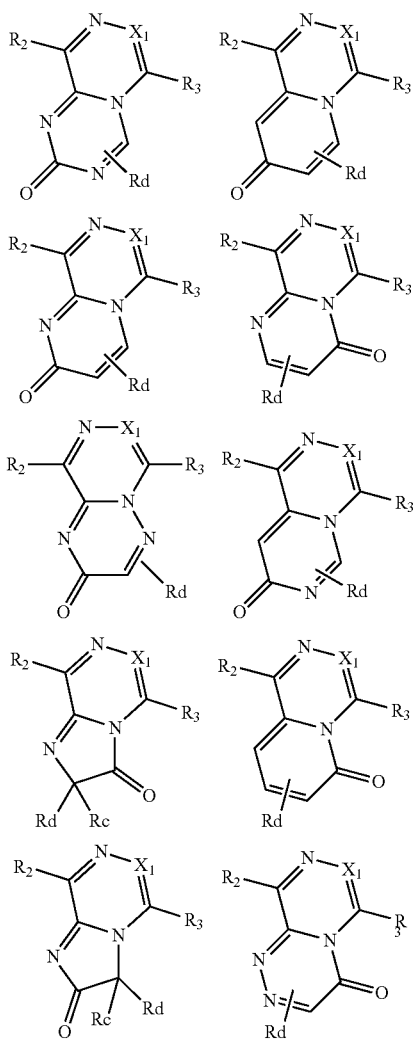

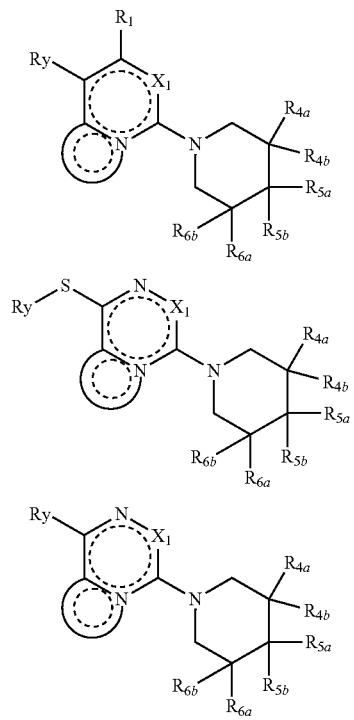

wherein $R_{4a}$, $R_{4b}$, $R_{6a}$, an $R_{6b}$ are independently selected from hydrogen, halogen, hydroxyl, amino, etc., respectively, and cannot be simultaneously substituted with the hydroxyl or the hydroxyl and fluorine at the same carbon atom; $R_{5a}$ is selected from $C_1$-$C_6$ alkyl, hydroxyl, amino, aminomethyl, etc.; $R_{5b}$ is selected from hydroxyl, amino, halogen, $C_1$-$C_6$ alkyl, 3-8 membered cycloalkyl or heterocycloalkyl, hydroxyalkyl, alkoxyalkyl, cycloalkylalkyl, alkoxyacyl, 5-8 membered aryl or heteroaryl, etc.;

alternatively, $R_{5a}$ and $R_{5b}$ may be linked by carbon atoms to form 3-12 membered monocyclic or polycyclic saturated or unsaturated alkyl, 3-12 membered monocyclic or polycyclic saturated or unsaturated heterocycloalkyl, 3-12 membered spiro or fused cycloalkyl, and 3-12 membered spiro or fused heterocycloalkyl;

and each hydrogen atom on the $R_{5a}$ and $R_{5b}$ groups described above may be respectively substituted with the following groups of deuterium, halogen, hydroxyl, alkoxy, amino, alkylamino, alkyl, cycloalkyl, heterocycloalkyl, etc.;

more preferably a compound represented by formula IV:

wherein $R_d$ is selected from hydrogen, halogen, hydroxyl, amino, $C_1$-$C_6$ alkyl, $C_1$-$C_6$ alkoxy, $C_1$-$C_6$ alkylamino, cyano, alkenyl, alkynyl, 3-8 membered cycloalkyl or heterocycloalkyl, 5-8 membered aryl or heteroaryl; $R_1$, $R_2$, $R_3$ and $X_1$ are defined as described above.

In a further embodiment, the present disclosure is preferably a compound represented by the following formula (III), or a pharmaceutically acceptable salt thereof, or an enantiomer, a diastereomer, a tautomer, a solvate, a polymorph or a prodrug thereof:

III

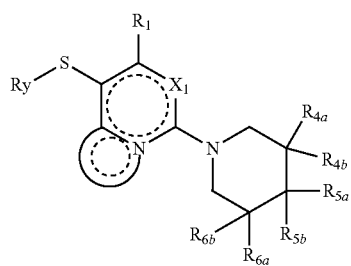

IV

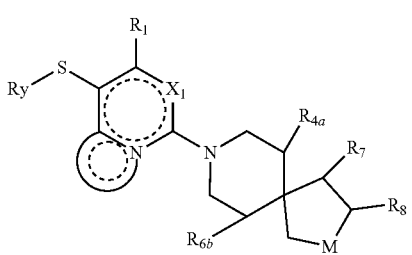

-continued

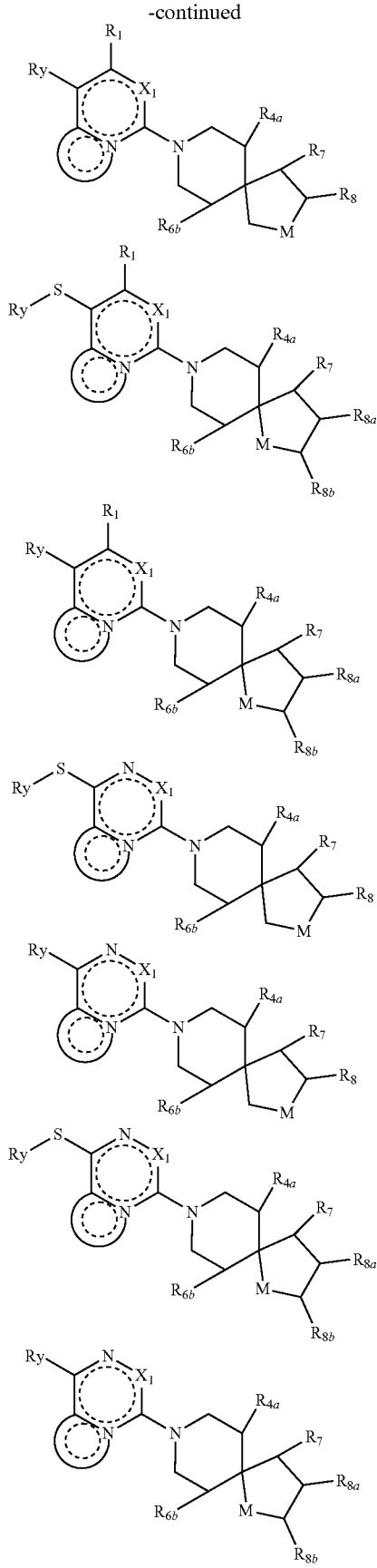

wherein M is selected from —O—, —S—, —SO$_2$—, —CR$_{9a}$R$_{9b}$—, —NR10-, etc.; R$_7$ is selected from hydrogen, halogen, C$_1$-C$_6$ alkyl, hydroxy, amino, alkoxy, etc.; R$_8$ is selected from hydroxyl, halogen, C$_1$-C$_{10}$ alkyl, etc.; R$_{9a}$ and R$_{9b}$ are independently selected from deuterium, hydrogen, oxygen, hydroxyl, halogen, amino, C$_1$-C$_6$ alkyl, etc.; R$_{10}$ is selected from hydrogen, C$_1$-C$_{10}$ alkyl, etc.; R$_{8a}$ and R$_{8b}$ are independently selected from hydrogen, halogen, C$_1$-C$_6$ alkyl, etc., respectively; alternatively, R$_{8a}$ and R$_{8b}$ are linked by carbon atoms or heteroatoms to form a 3-12 membered saturated or partially unsaturated or aromatic ring system; wherein the formed ring system can continue to be substituted with one or more substituents; R$_1$, R$_y$, and X$_1$ are defined as described above.

A method for preparing a compound represented by formula I-2, wherein the method comprises steps a-b:
  a) converting a compound represented by formula (A) and a block R$_2$ to a compound B represented by formula through a metal-catalyzed coupling reaction, wherein an R$_2$ fragment is a boric acid, a boric acid ester, a trifluoroborate, a tin reagent, a zinc reagent or a sulfide, etc.; and
  b) obtaining a compound represented by formula (I) by a cross-coupling reaction between the compound B represented by formula and a block R$_3$ in the presence of a base catalyzed substitution or a transition metal catalyst, wherein an R$_3$ fragment is an amine, an alcohol, an alkene, an alkyne, a metal alkyl reagent, an alkylboronic acid, an alkylboronic acid ester, an alkyl trifluoroborate, etc.;

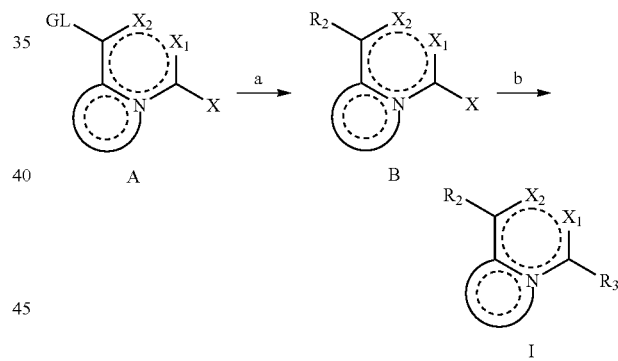

wherein LG is a leaving group which is selected from halogen, trifluoromethanesulfonate, benzenesulfonate, etc., and each of the group is defined as described above.

Preferably, the steps a) and b) are respectively carried out in a solvent and the solvent is selected from the group consisting of water, methanol, ethanol, isopropanol, butanol, ethylene glycol, ethylene glycol monomethylether, N-methylpyrrolidone, dimethyl sulfoxide, tetrahydrofuran, toluene, dichloromethane, 1,2-dichloroethane, acetonitrile, N,N-dimethylformamide, N,N-dimethylacetamide, dioxane, or a composition thereof.

Preferably, the transition metal catalyst is selected from the group consisting of tris (dibenzylideneacetone) dipalladium (Pd$_2$(dba)$_3$), tetrakis (triphenylphosphine) palladium (Pd(PPh$_3$)$_4$), palladium acetate, palladium chloride, dichlorobis (triphenylphosphine) palladium, palladium trifluoroacetate, palladium triphenylphosphine acetate, [1,1'-bis (diphenylphosphino) ferrocene] palladium dichloride, bis (trio-phenylphosphine) palladium dichloride, 1,2-bis(diphenylphosphino) ethane palladium dichloride, or a composition thereof; the catalyst ligand is selected from the group consisting of tri-tert-butylphosphine, tri-tert-butylphosphine tetrafluoroborate, tri-n-butylphosphine, triphenylphosphine, tri-p-benzylphosphine, tricyclohexylphosphine, tri-o-benzylphosphine, or a composition thereof.

Preferably, the inorganic base is selected from the group consisting of sodium hydride, potassium hydroxide, sodium acetate, potassium acetate, potassium tert-butoxide, sodium tert-butoxide, potassium fluoride, cesium fluoride, potassium phosphate, potassium carbonate, potassium bicarbonate, sodium carbonate, sodium bicarbonate, or a composition thereof; the organic base is selected from the group consisting of pyridine, triethylamine, N,N-diisopropylethylamine, 1,8-diazabicyclo [5.4.0] undec-7-ene (DBU), hexamethyl disilithium, sodium hexamethyl disilyl, dimethylpyridine, or a composition thereof.

The present disclosure provides a class of preferred compounds represented by formula (I), including, but not limited to, the following structures:

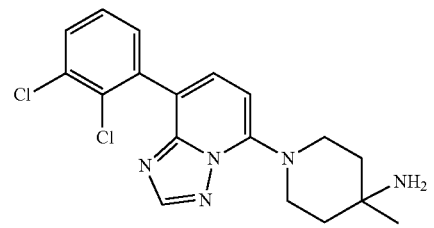

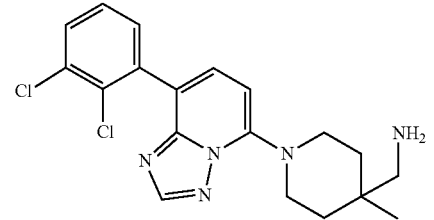

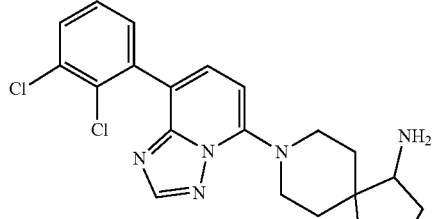

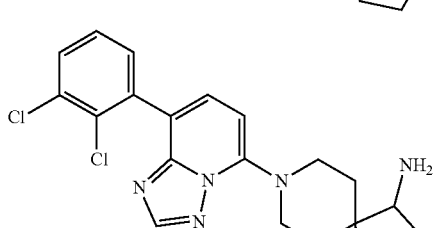

-continued

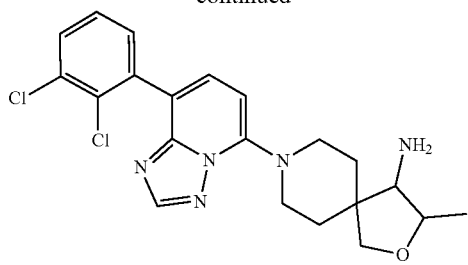

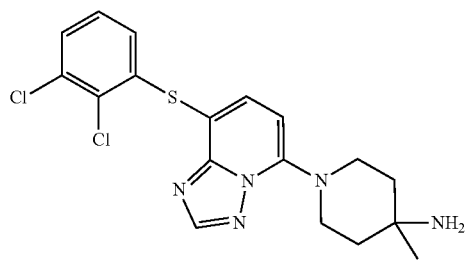

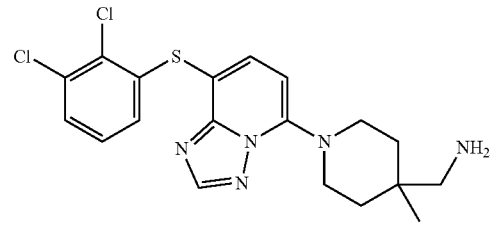

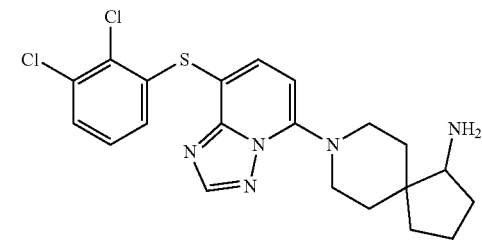

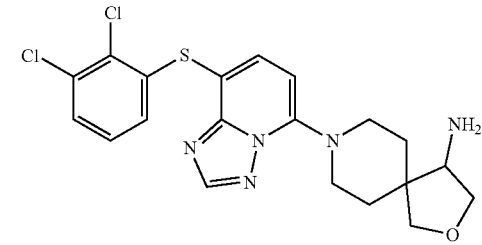

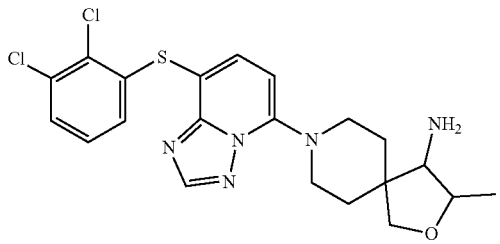

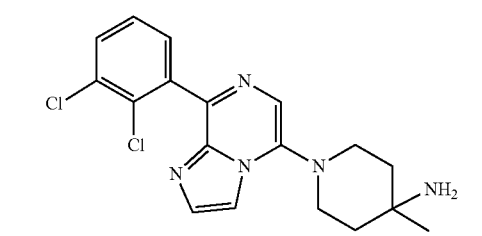

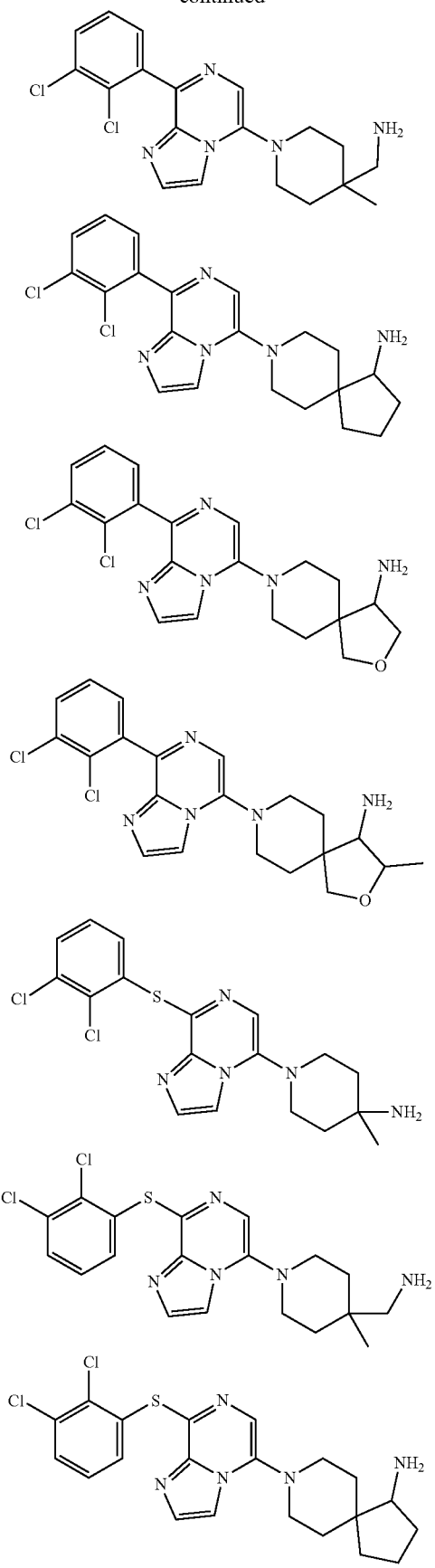
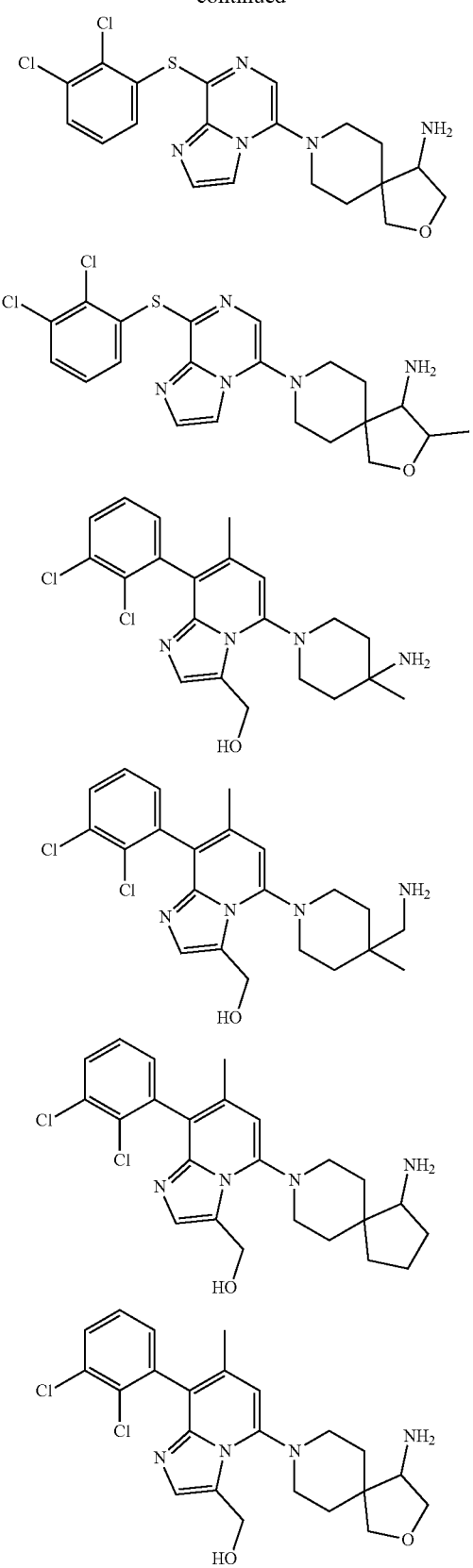

-continued
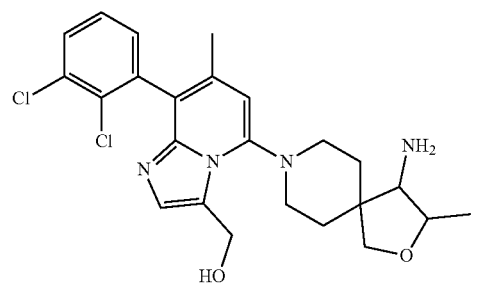
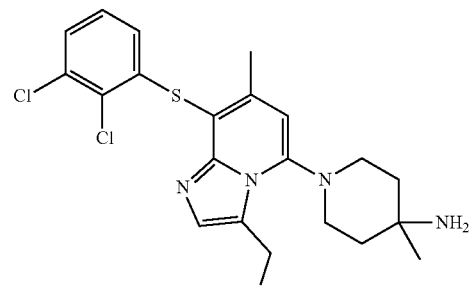
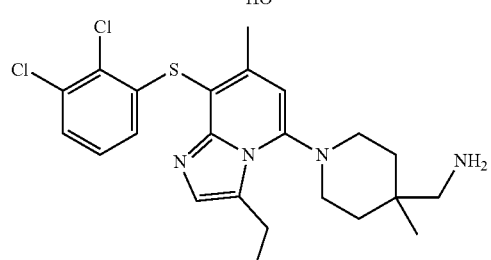
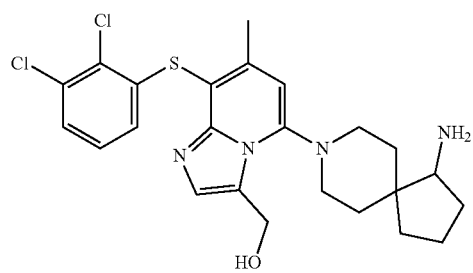
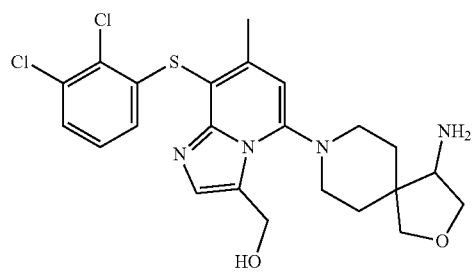
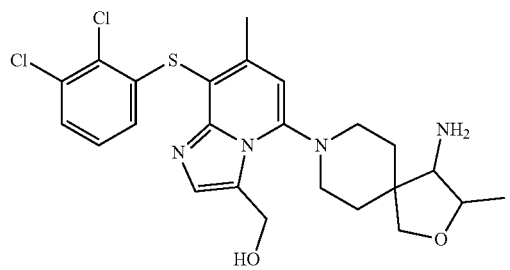
-continued
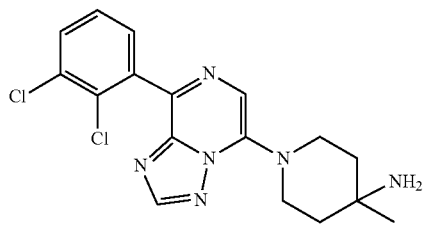
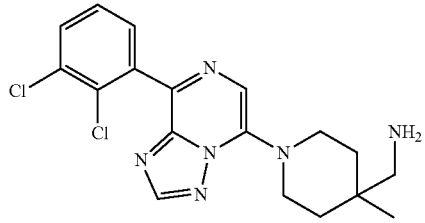
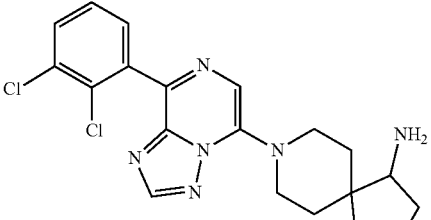
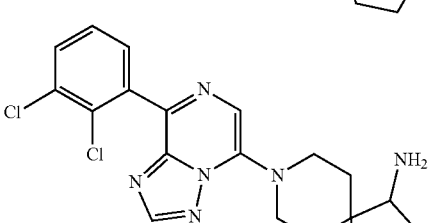
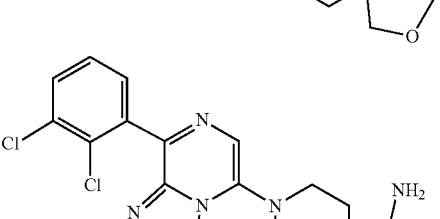
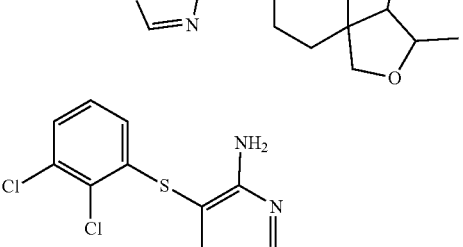
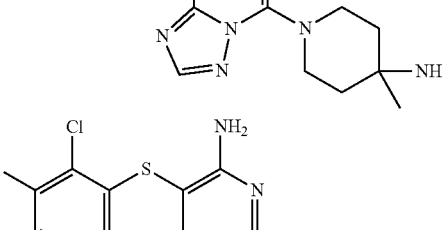
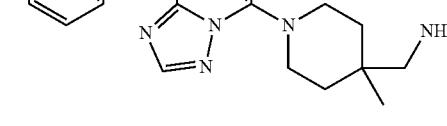

101
-continued
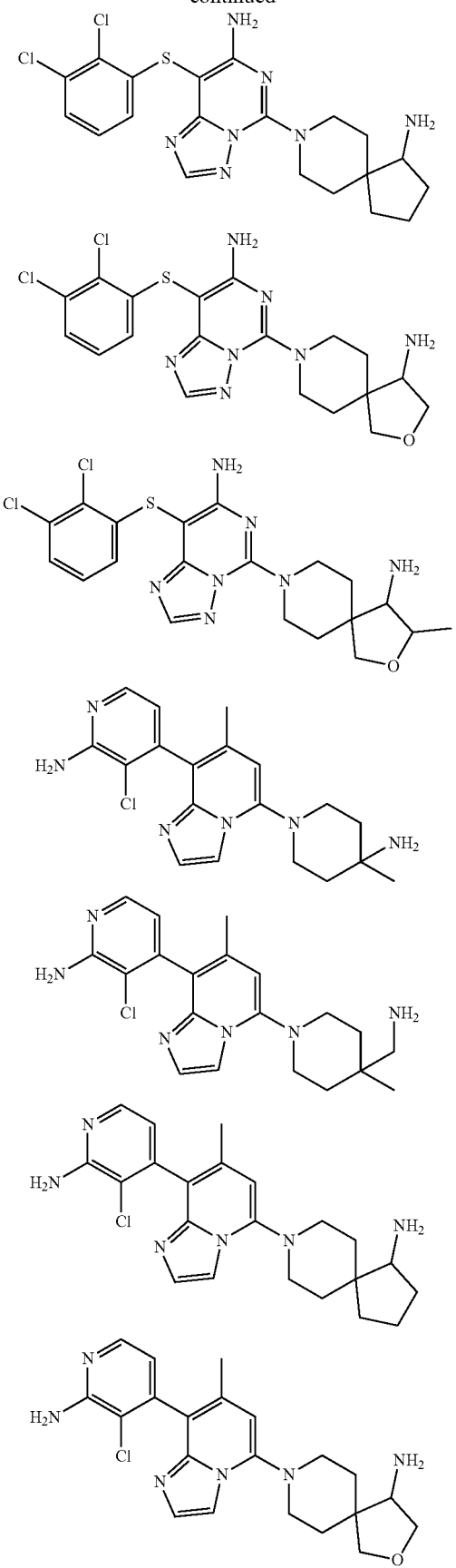
102
-continued
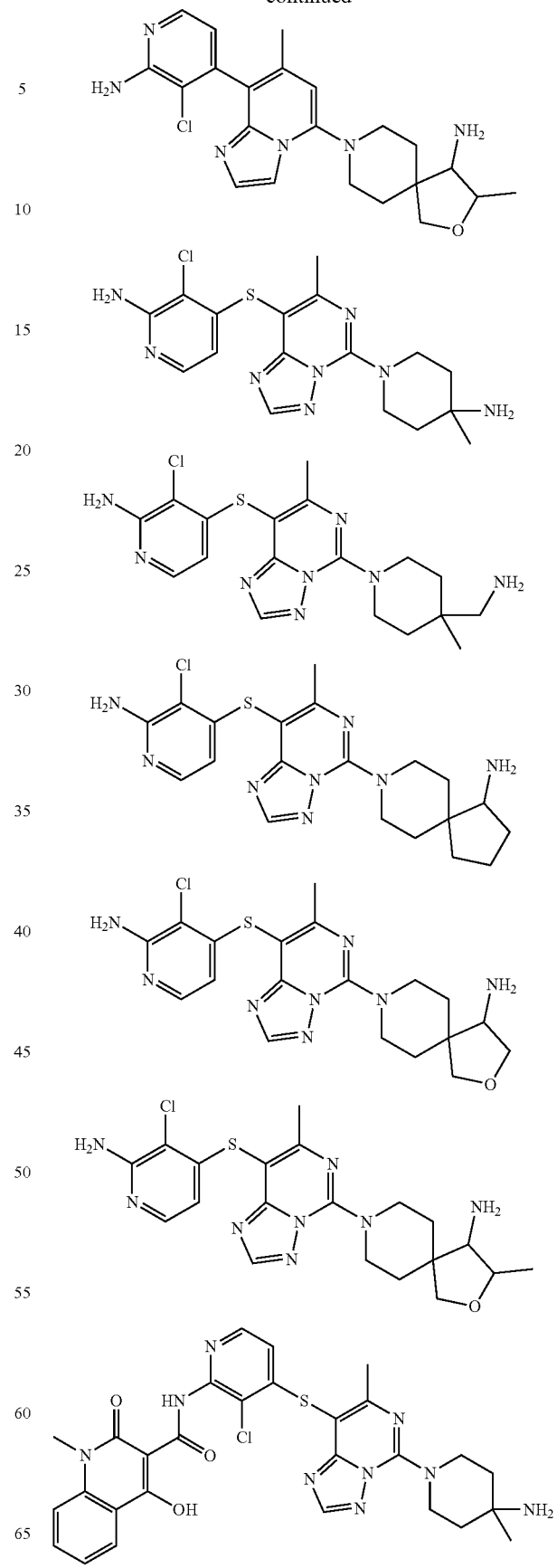

-continued
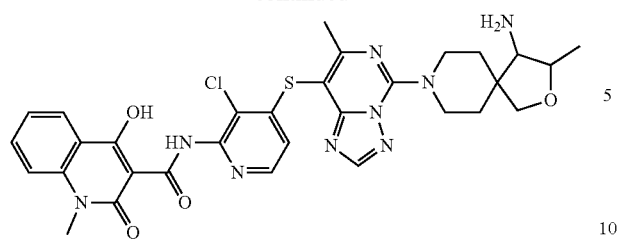
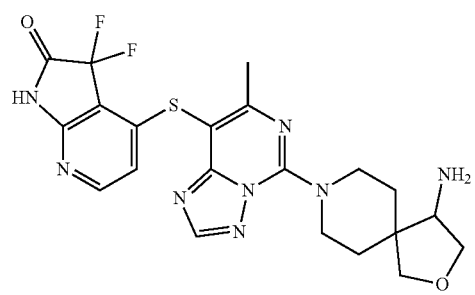
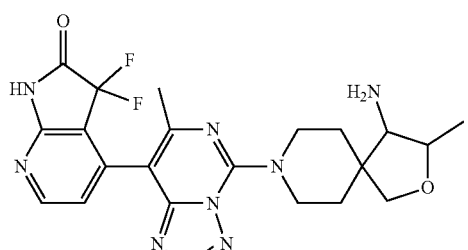
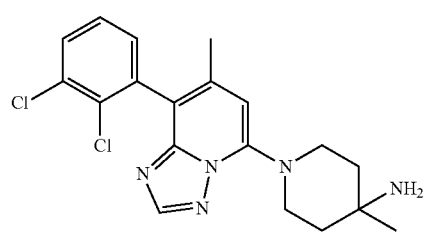
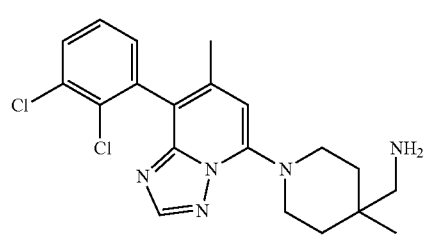
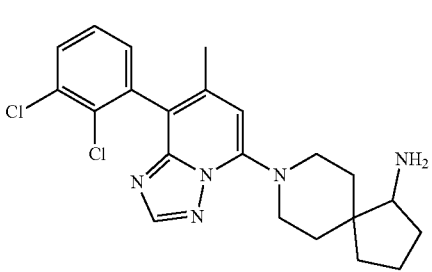
-continued
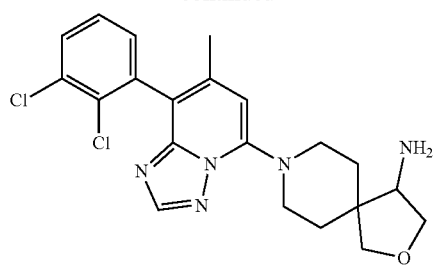
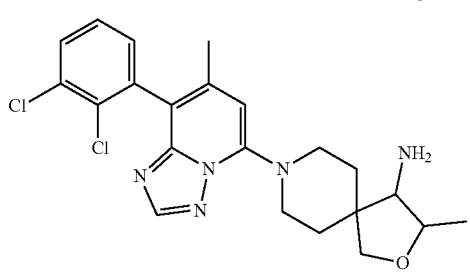
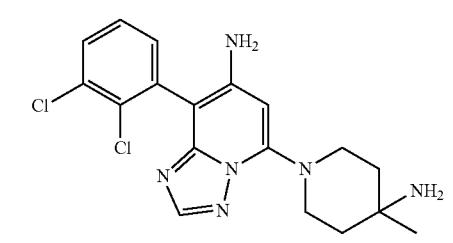
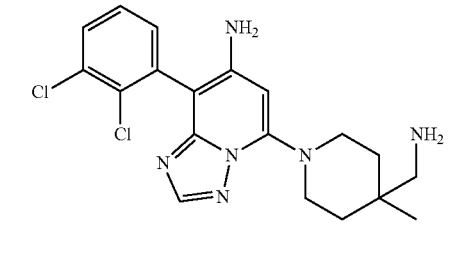
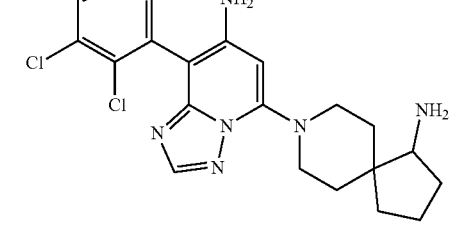

105
-continued
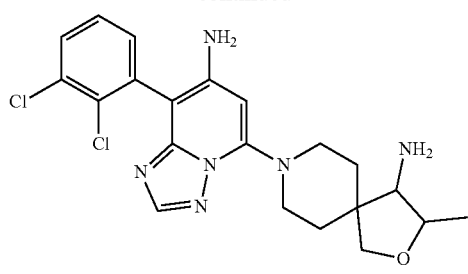
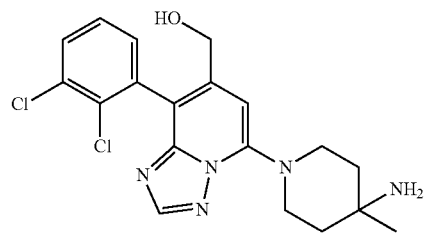
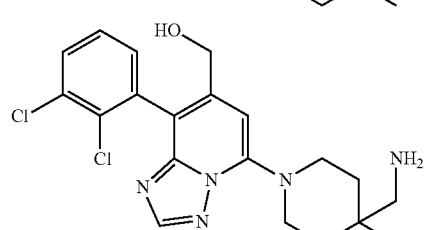
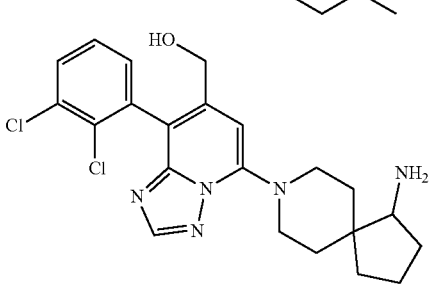
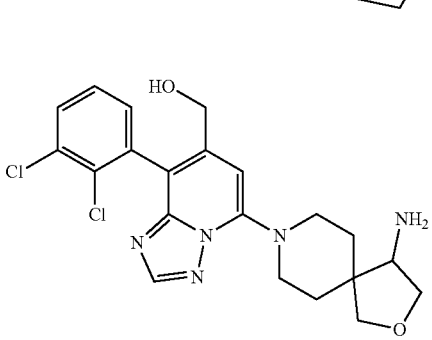
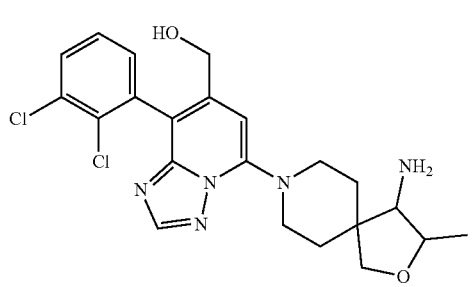
106
-continued
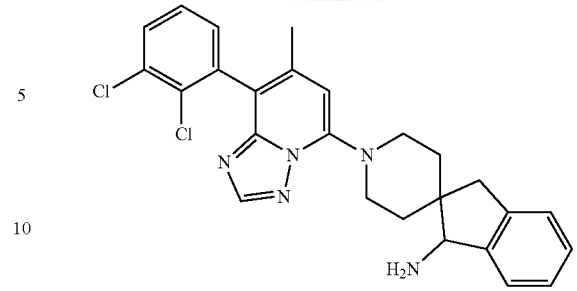
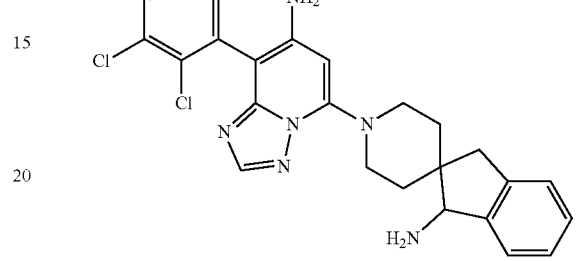
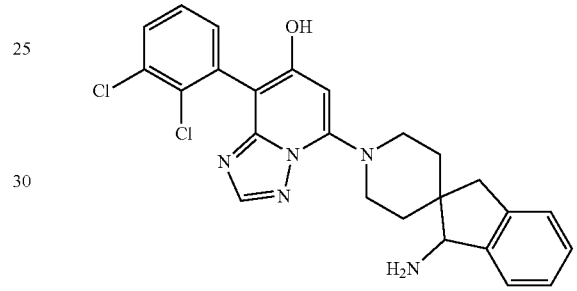
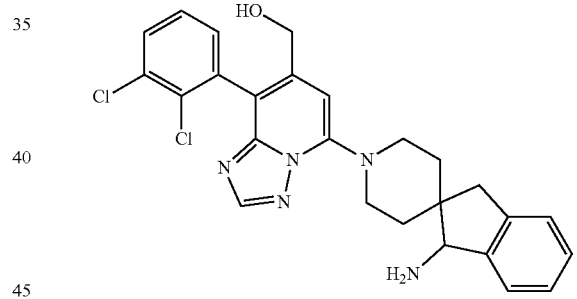
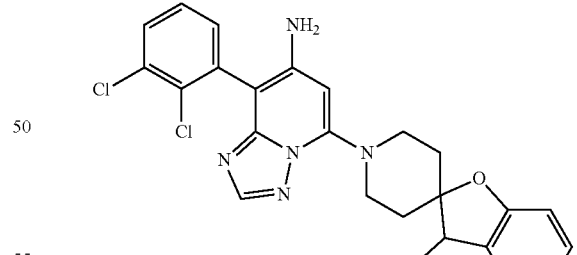
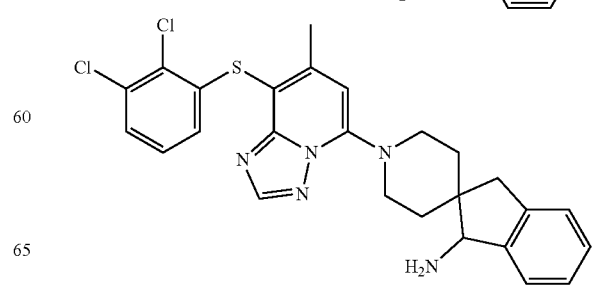

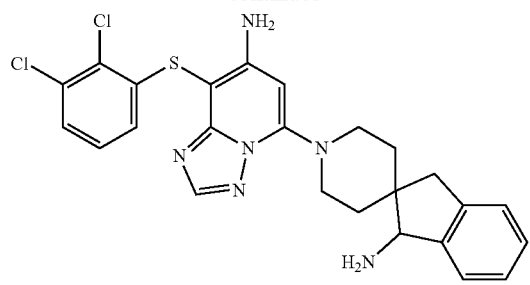
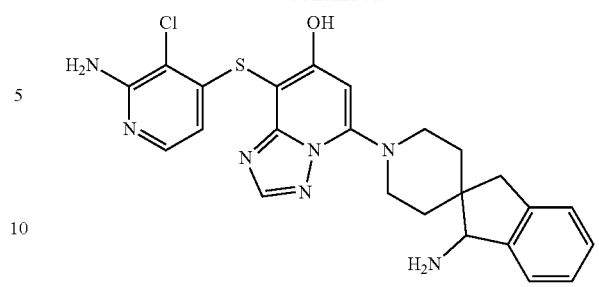
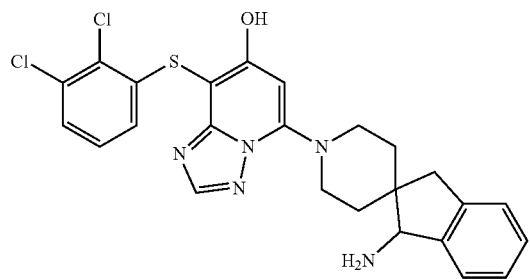
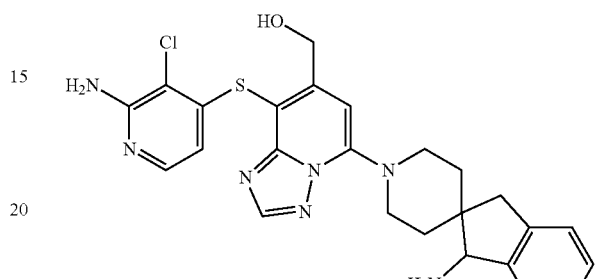
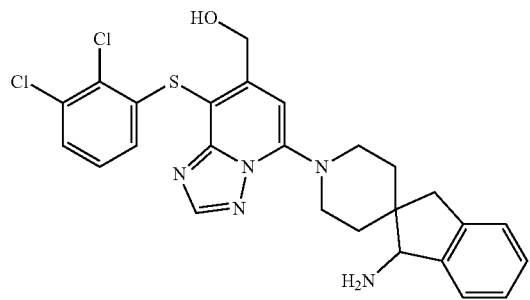
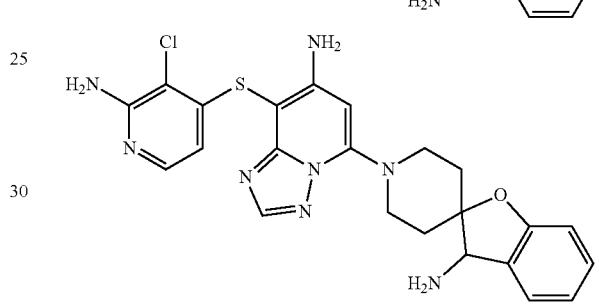
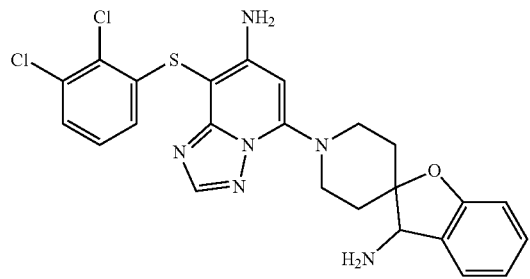
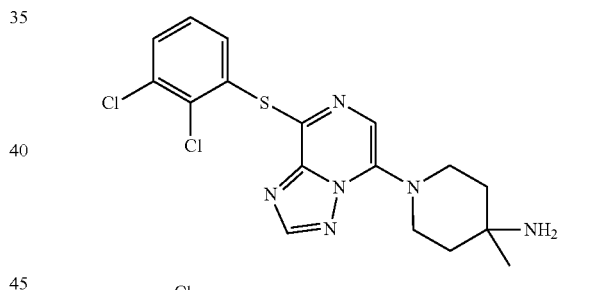
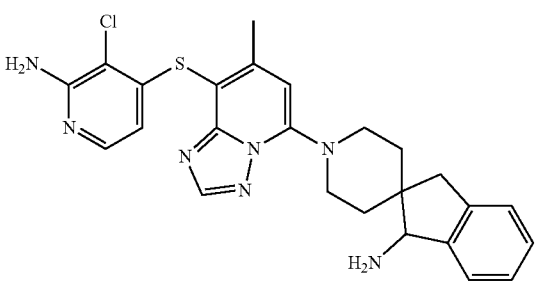
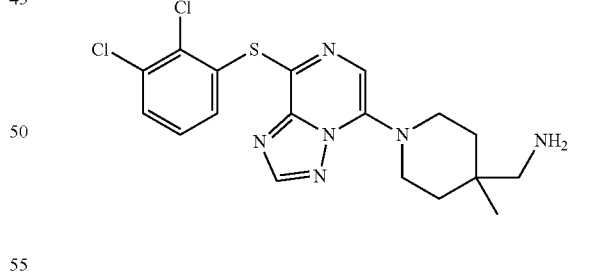
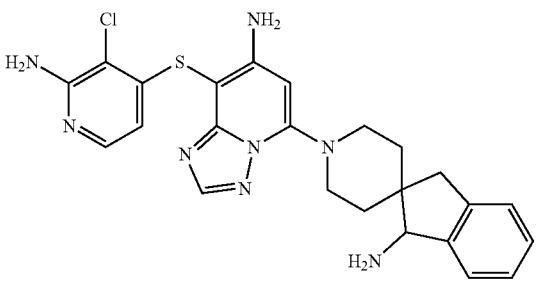
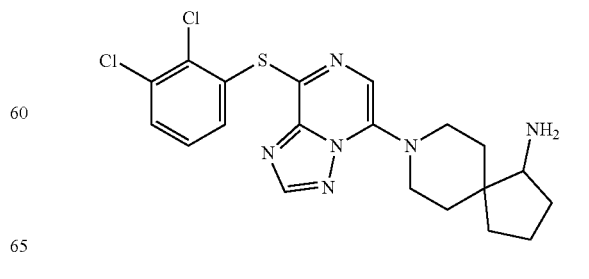

109
-continued
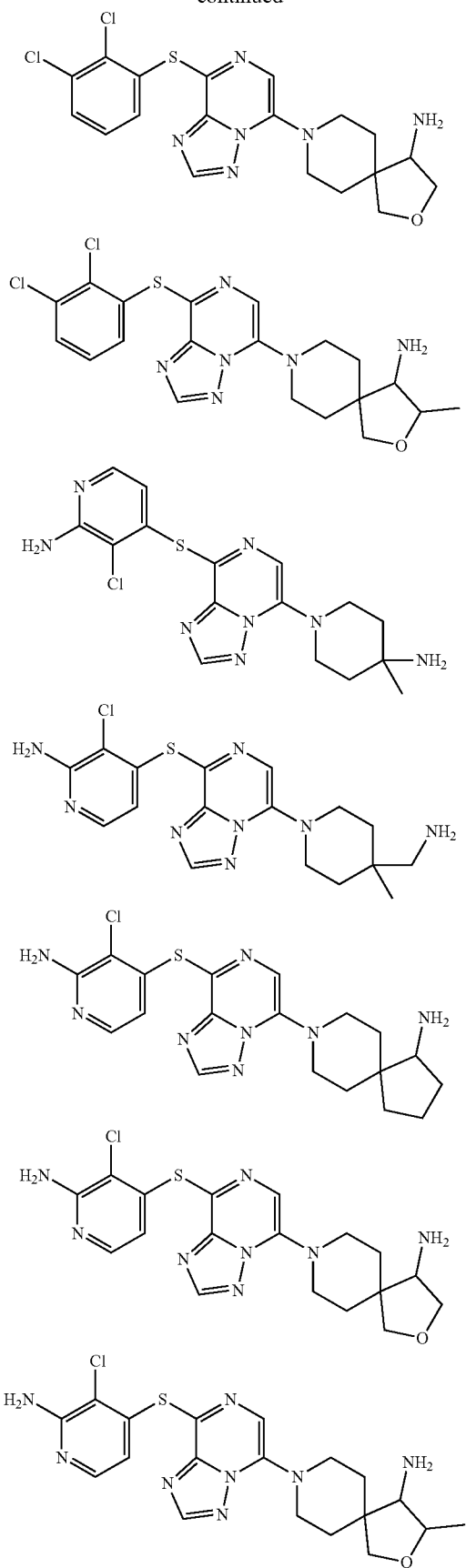
110
-continued
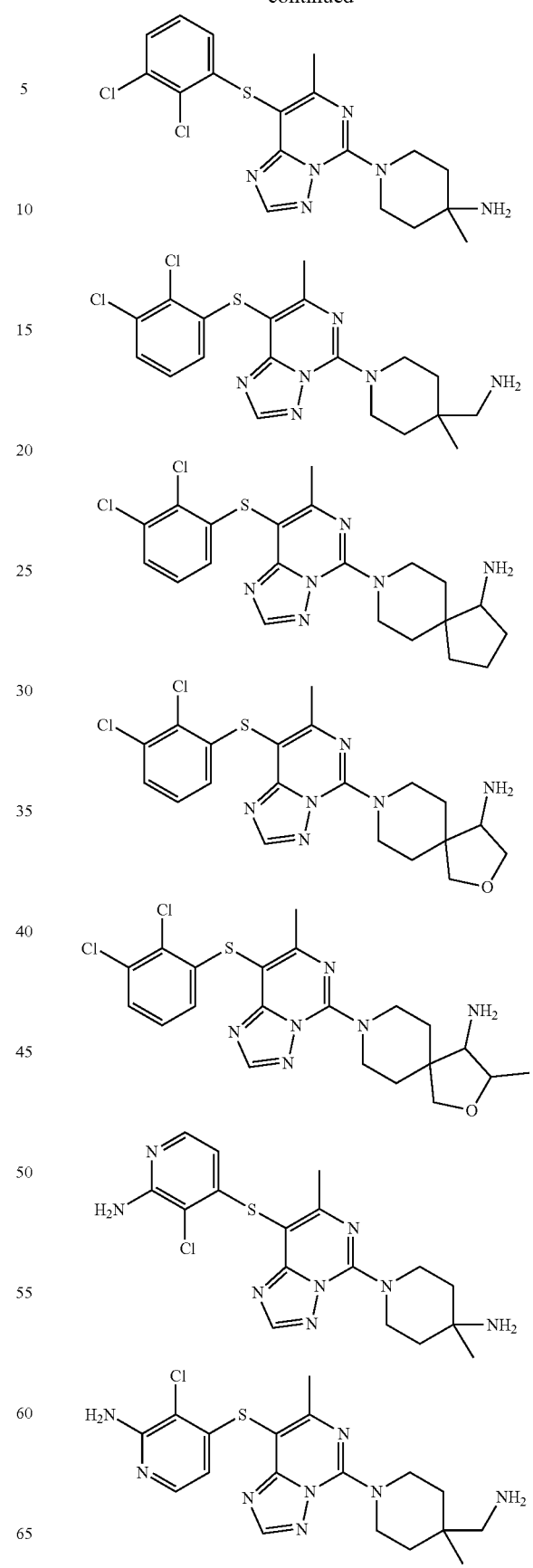

111
-continued
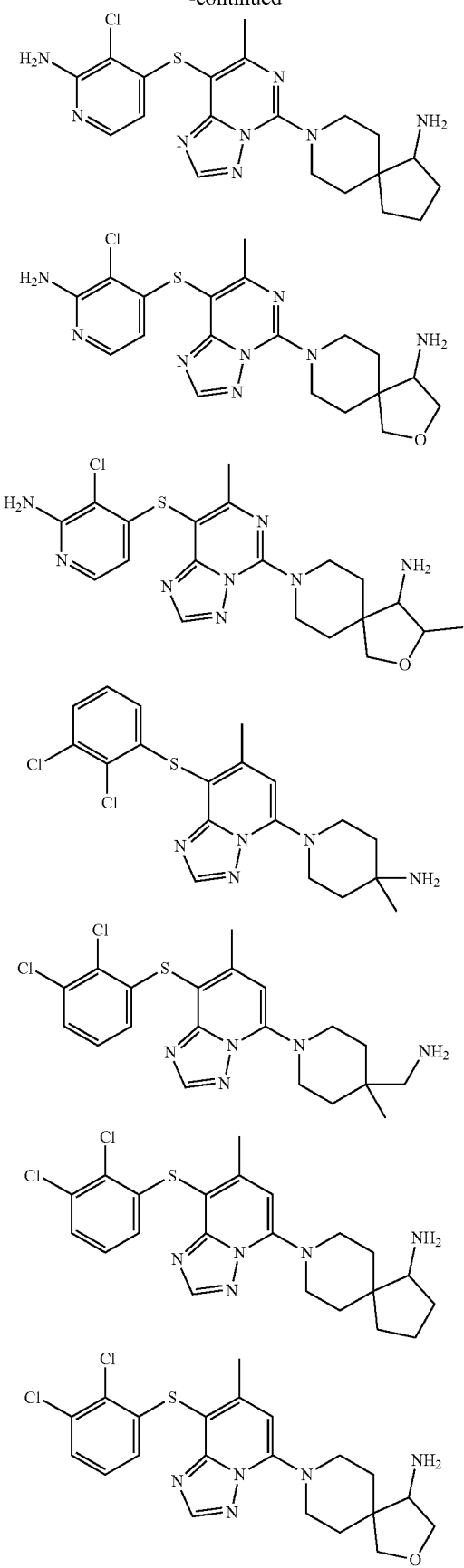
112
-continued
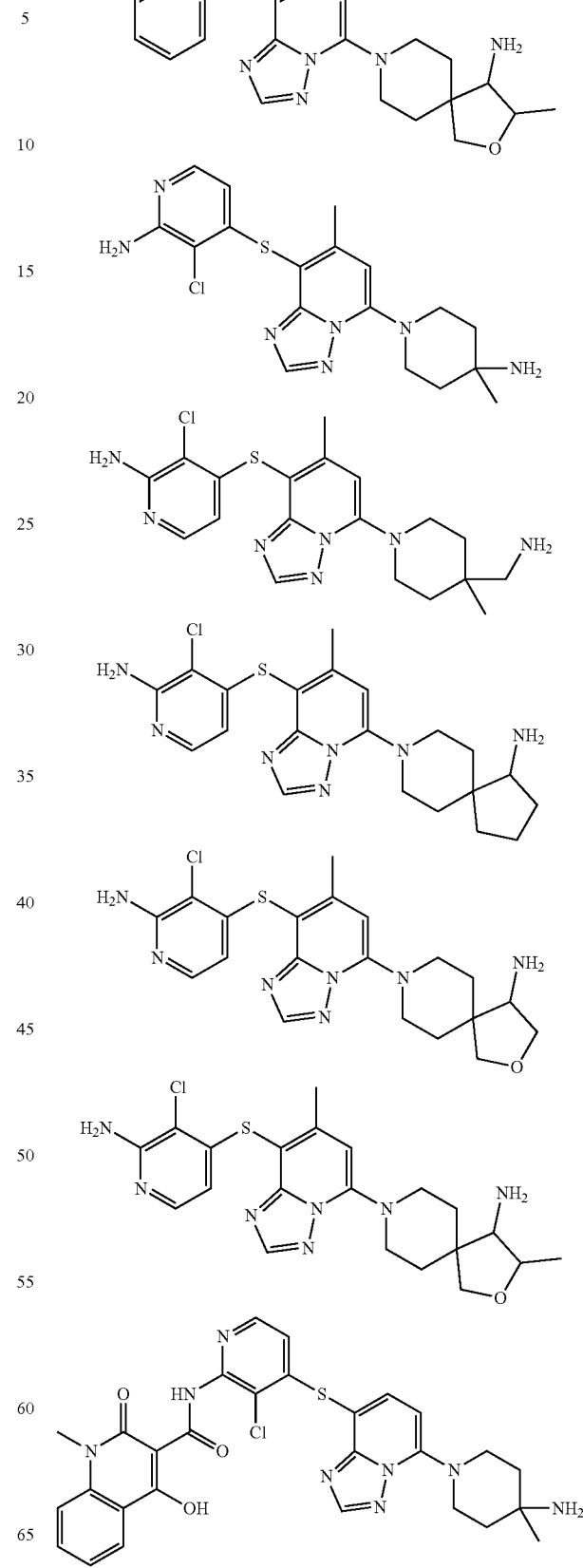

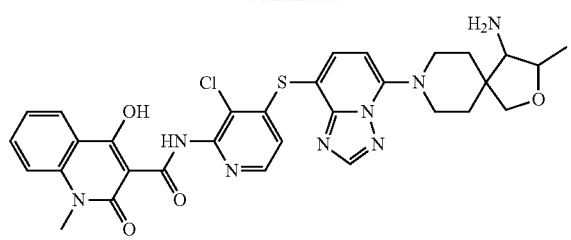
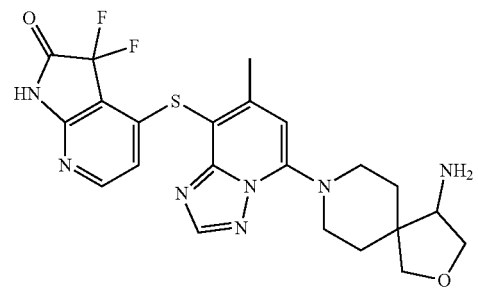
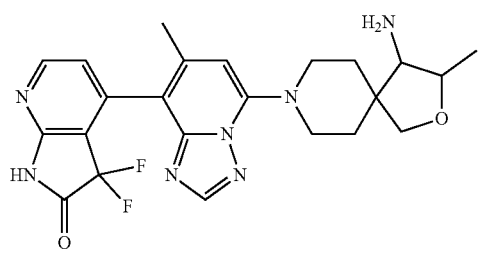
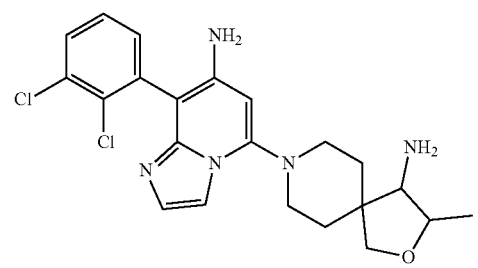
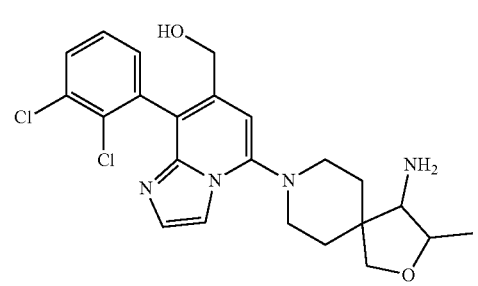
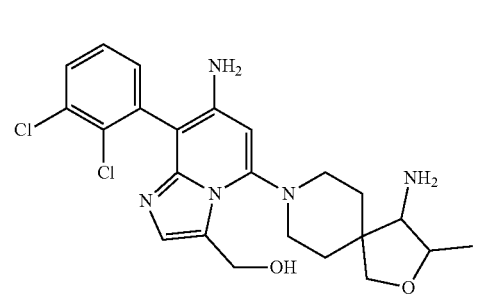
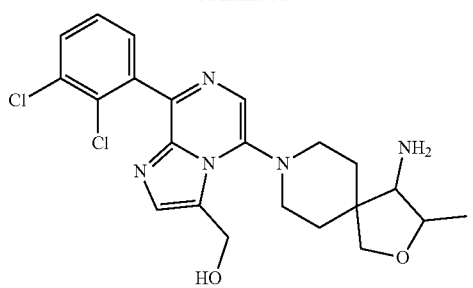
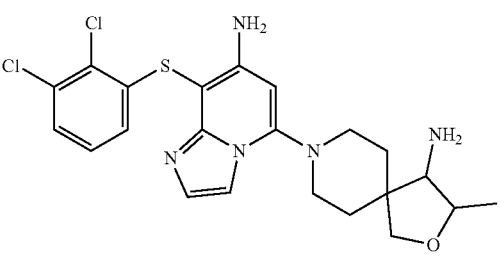
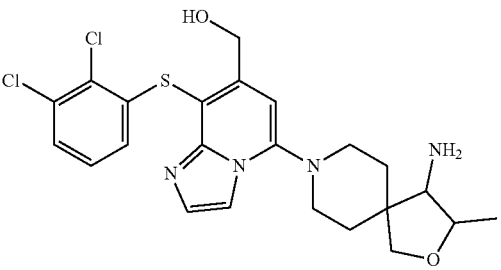
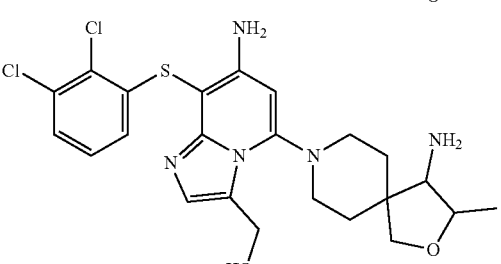
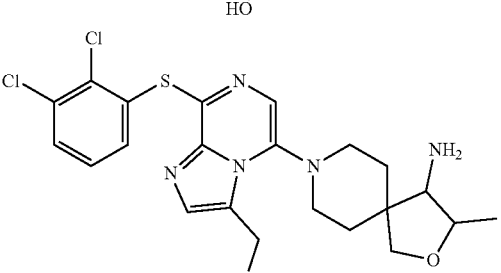
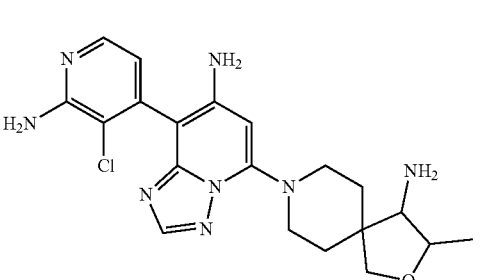

115
-continued
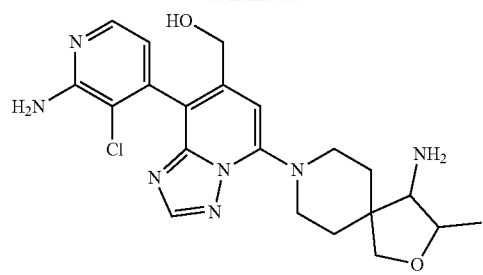
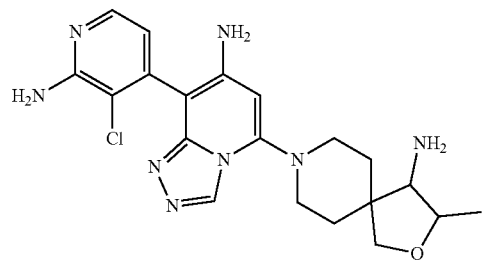
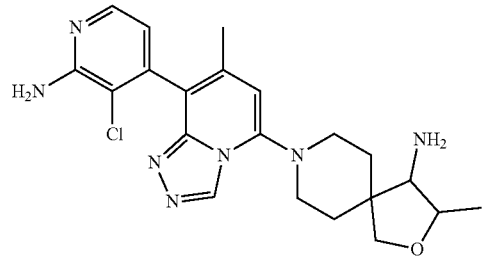
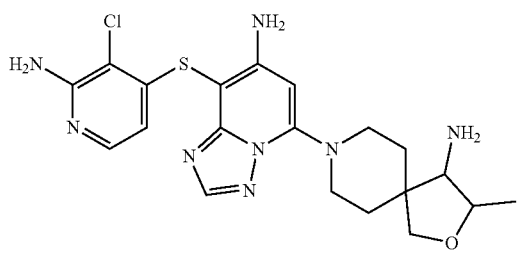
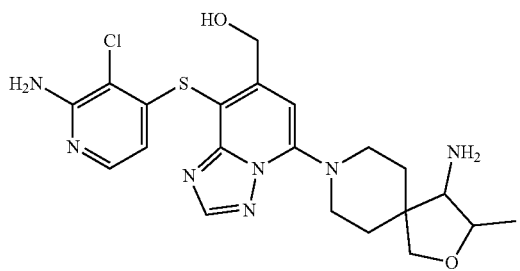
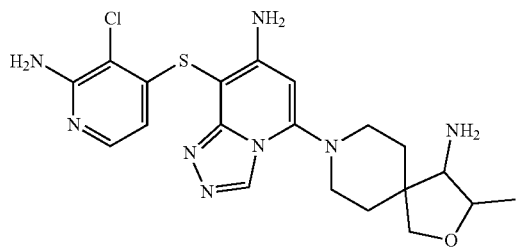
116
-continued
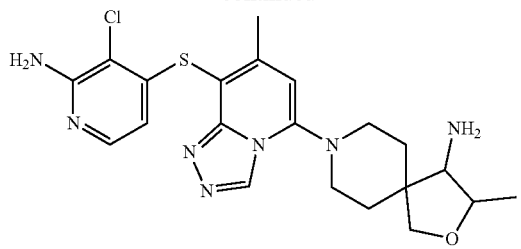
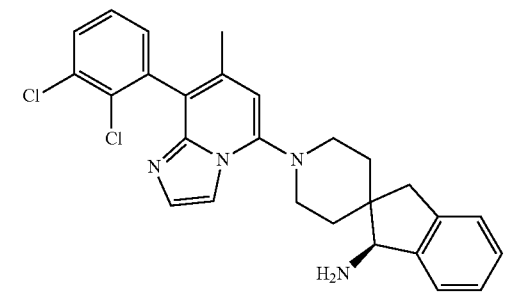
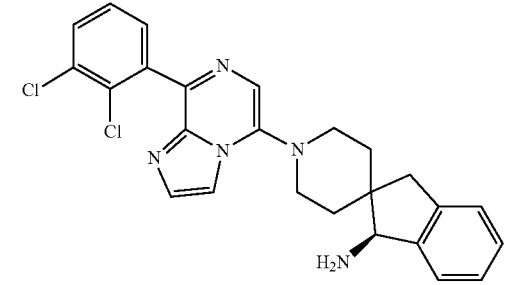
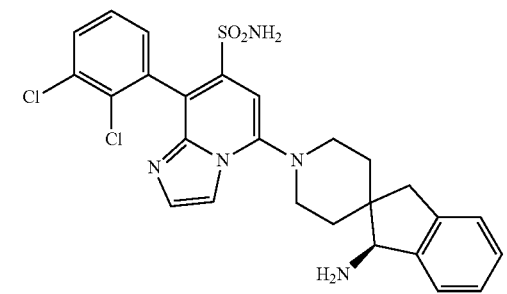
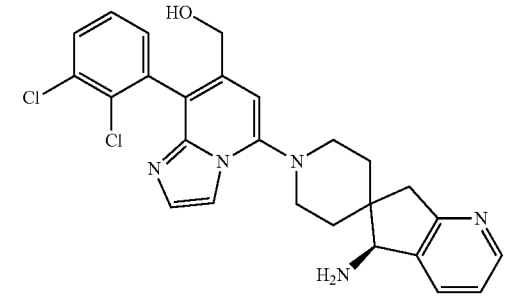
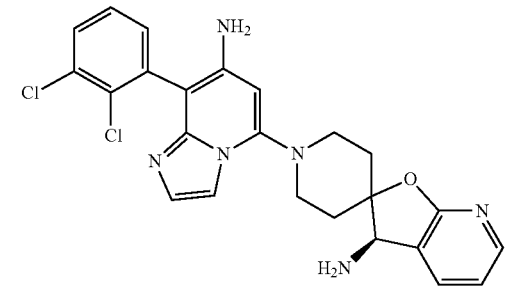

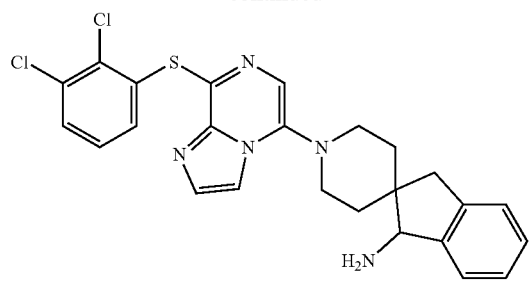
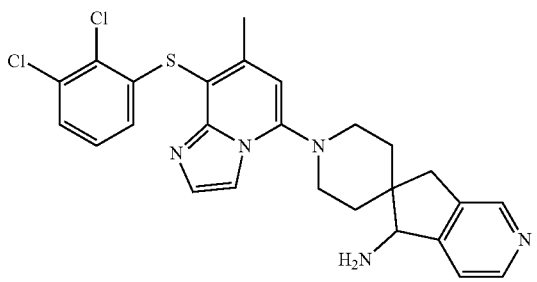
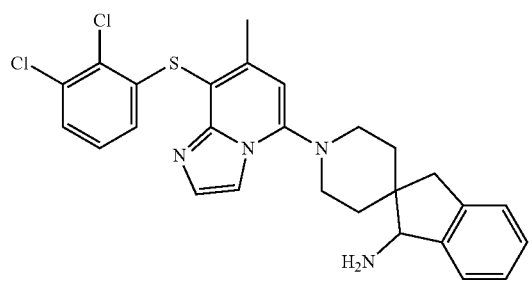
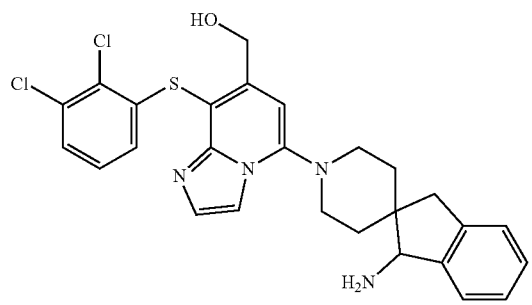
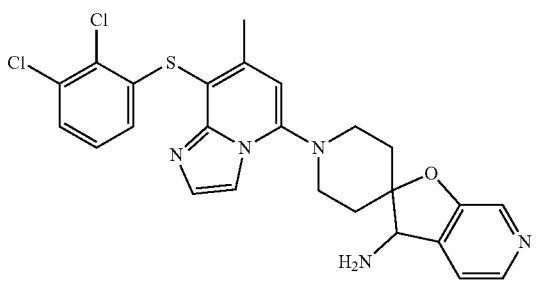
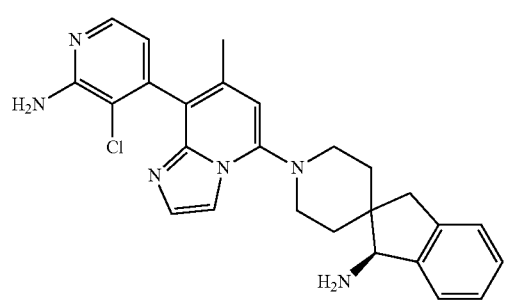
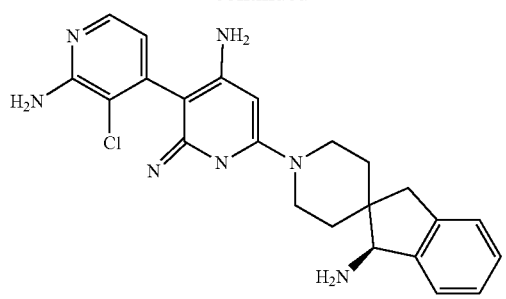
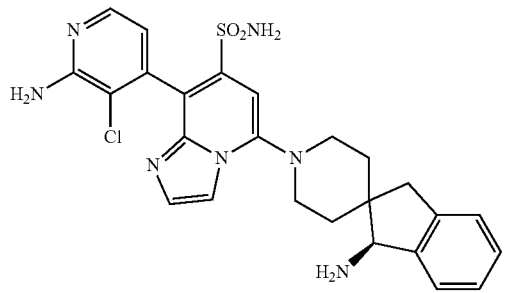
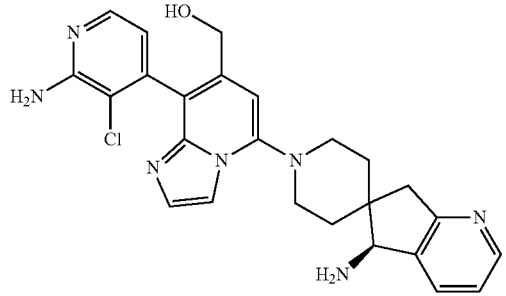
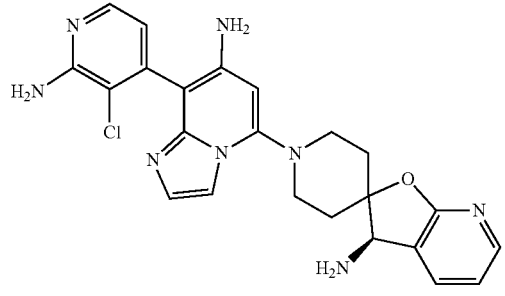
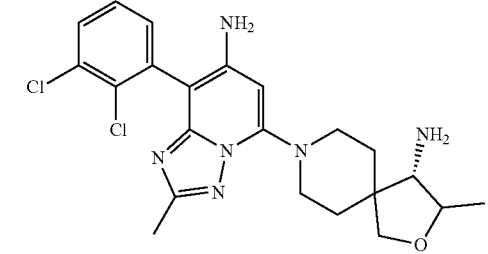
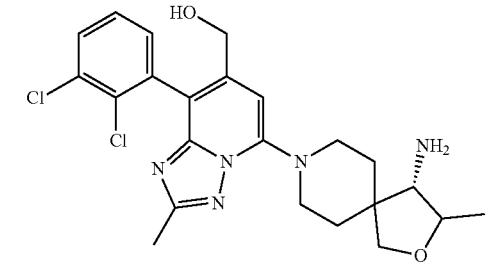

119
-continued
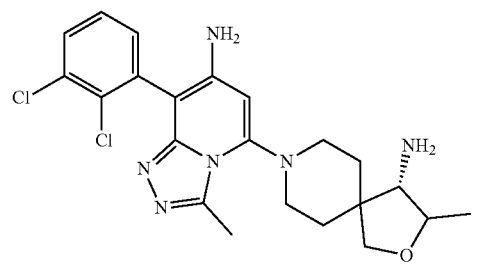
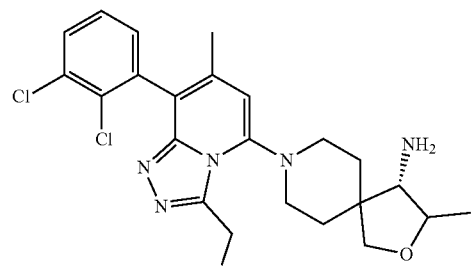
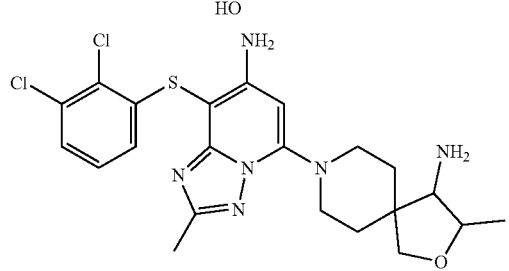
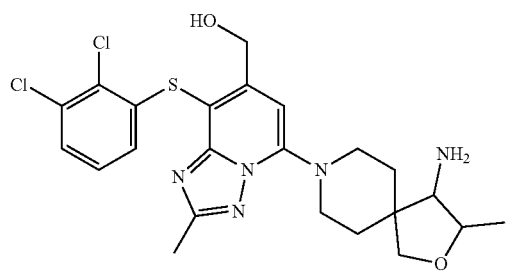
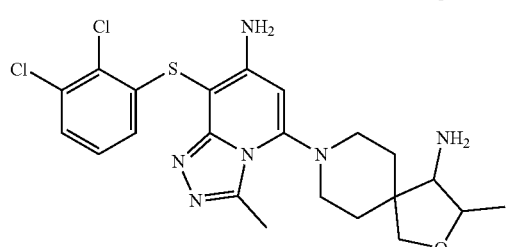
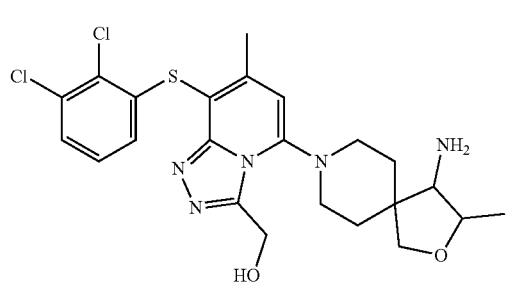
120
-continued
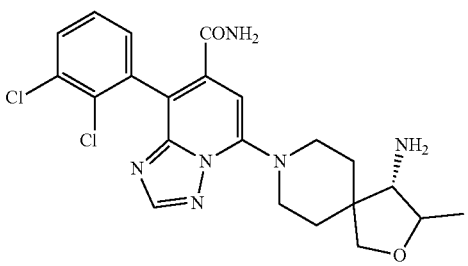
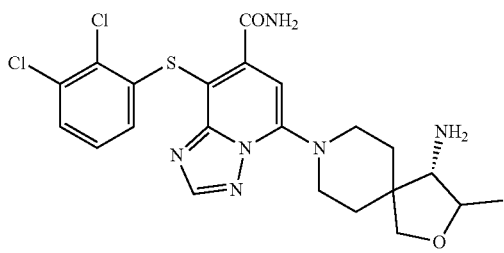
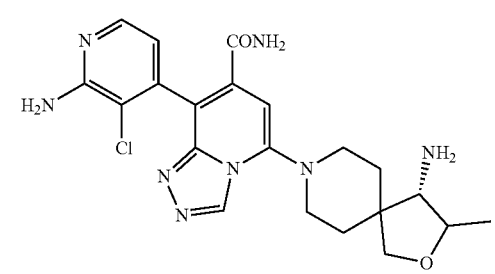
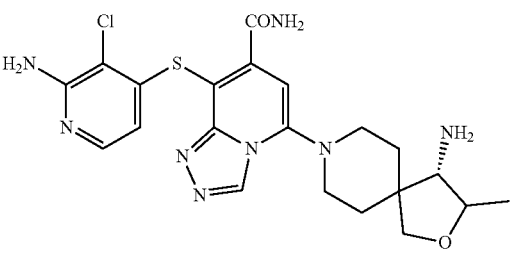
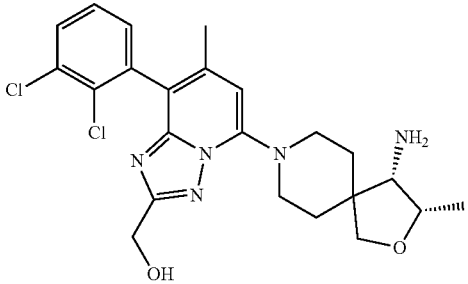
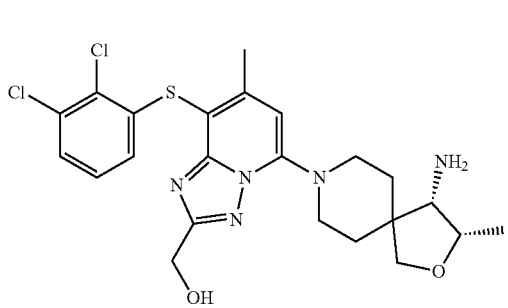

121
-continued
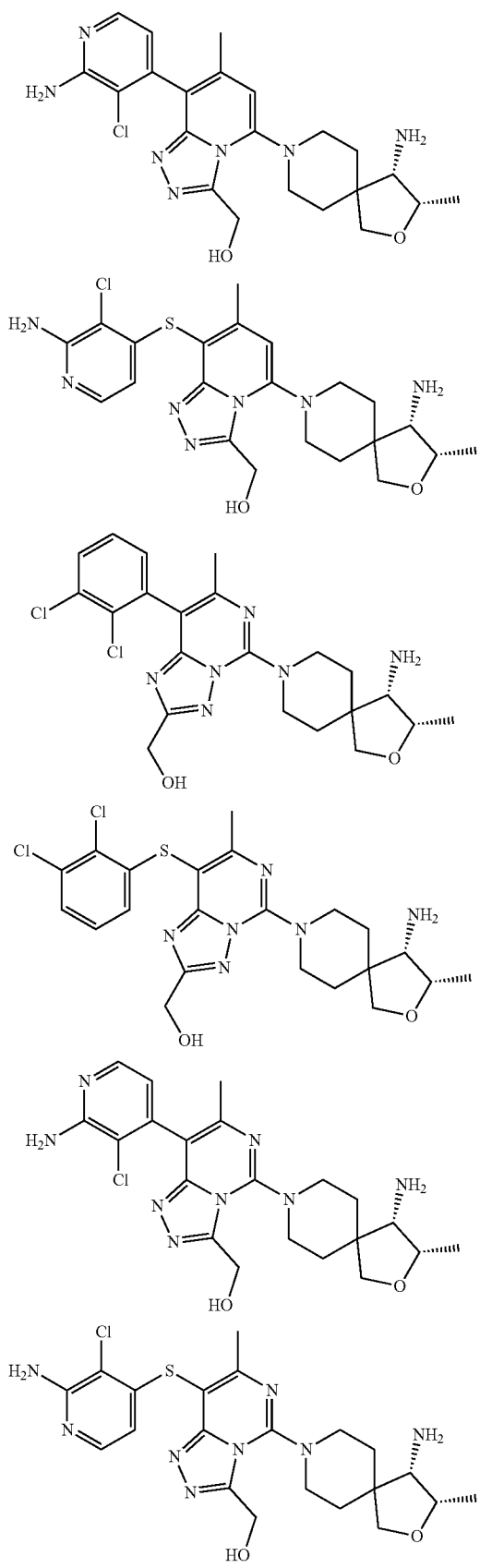
122
-continued
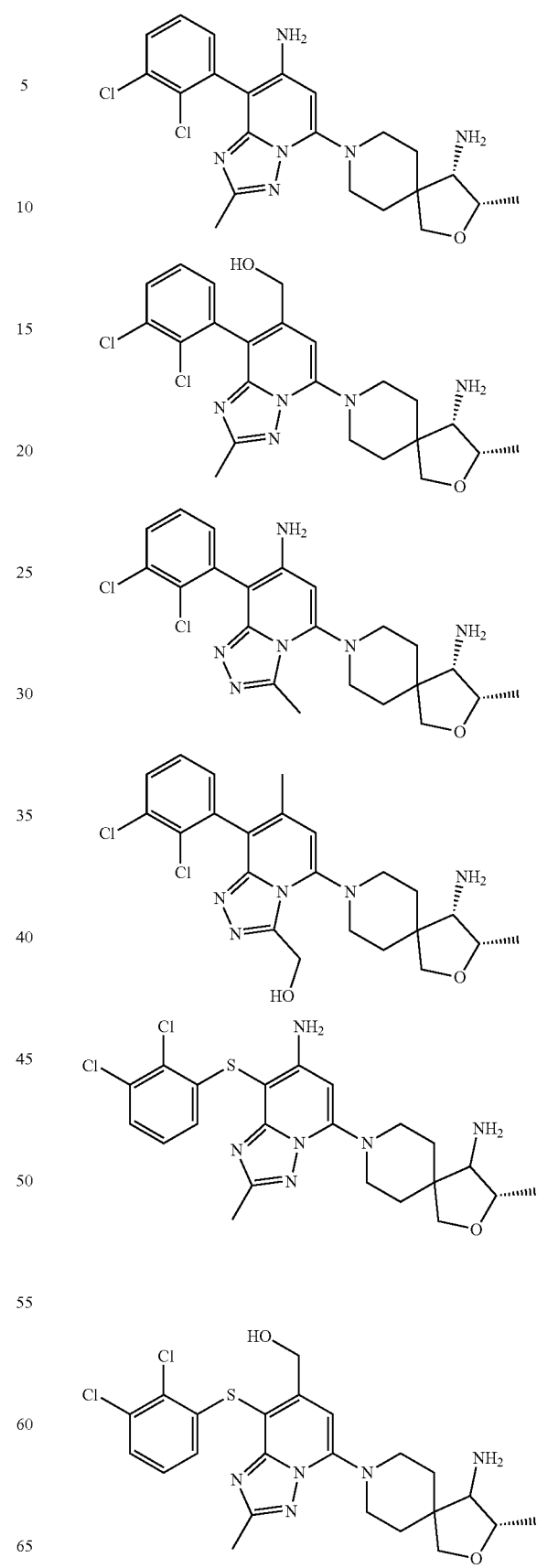

123
-continued
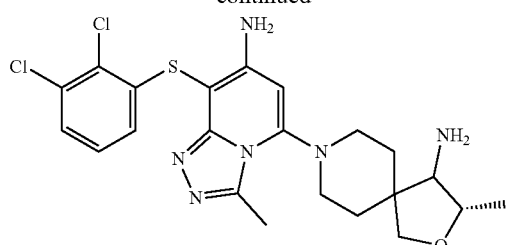
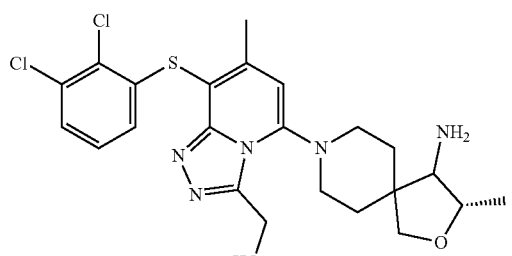
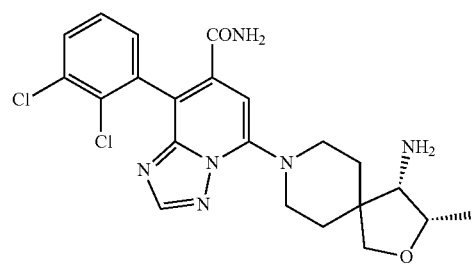
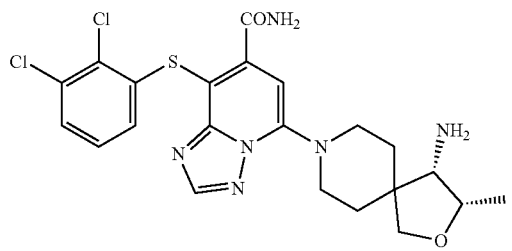
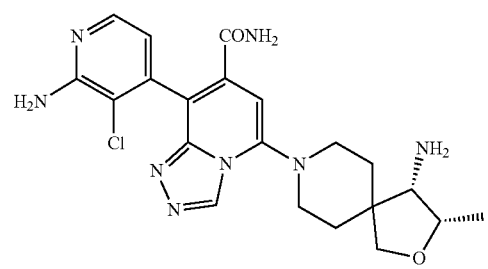
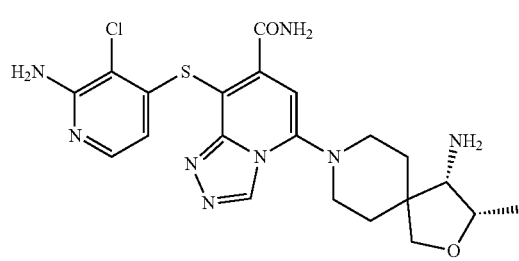
124
-continued
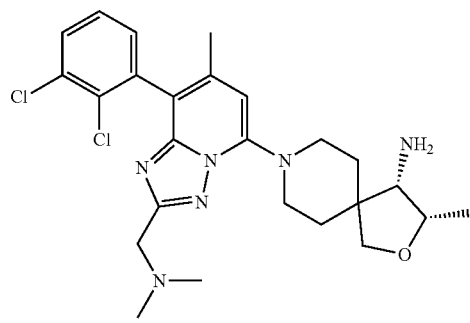
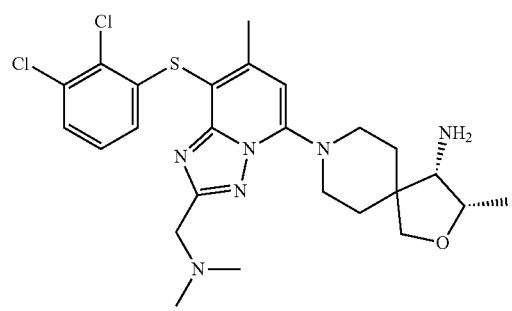
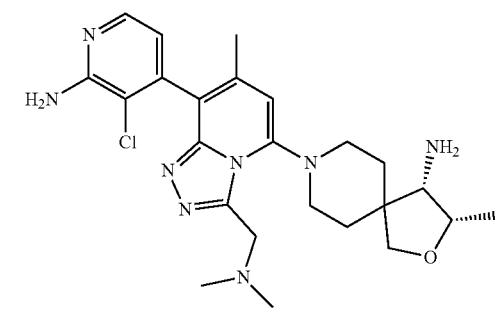
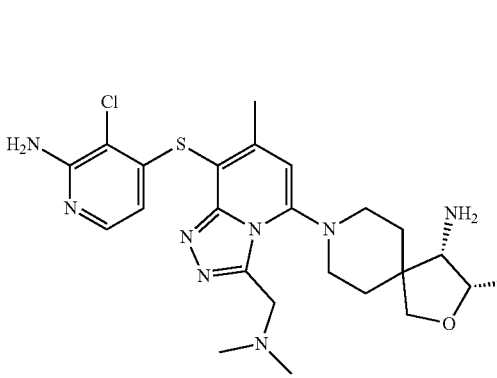
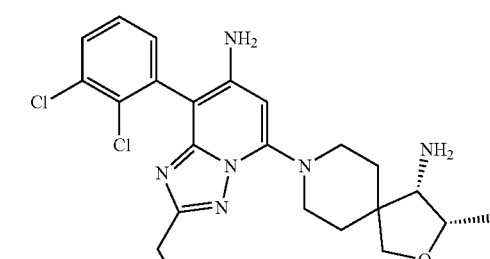

125
-continued
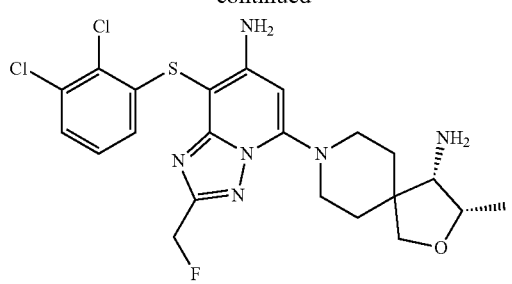
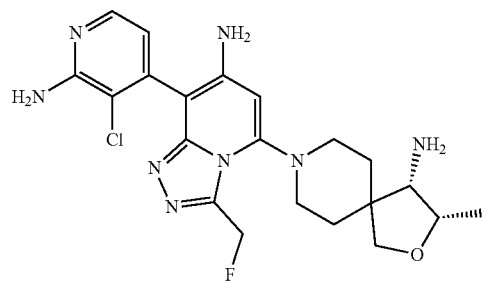
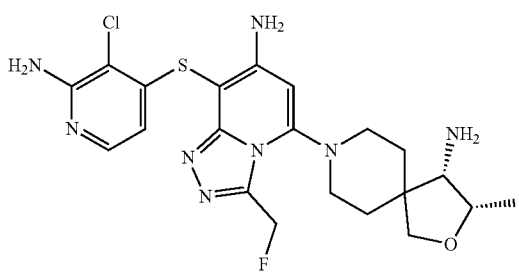
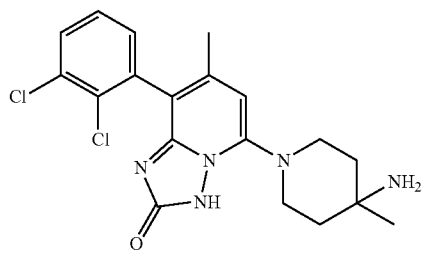
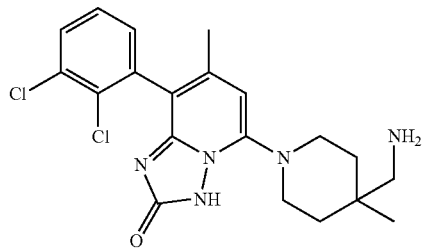
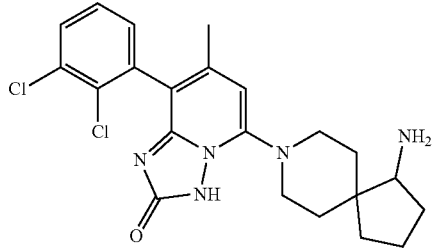
126
-continued
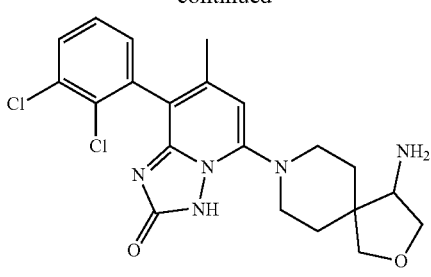
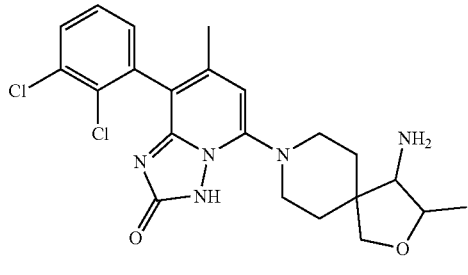
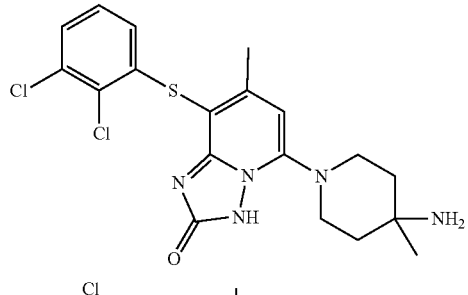
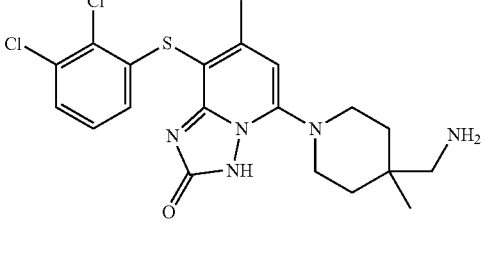
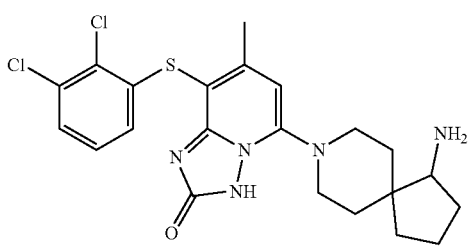
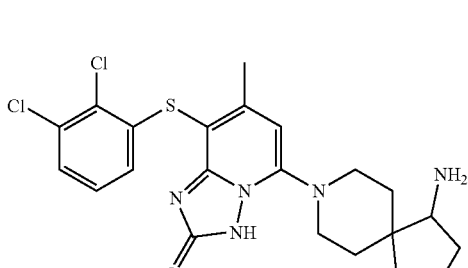

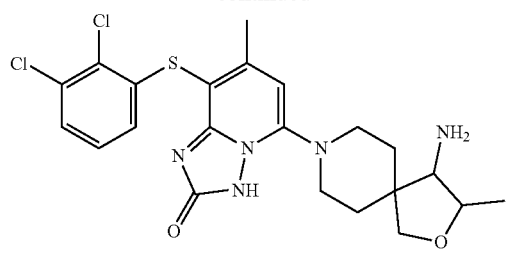
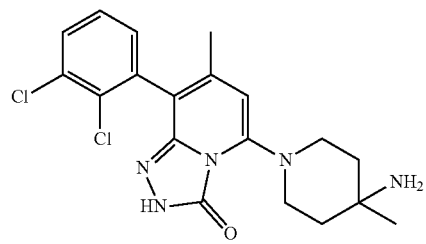
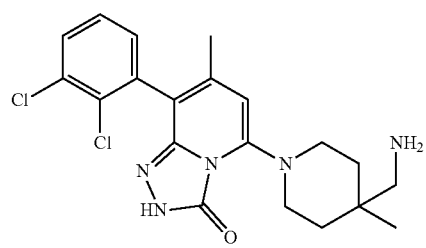
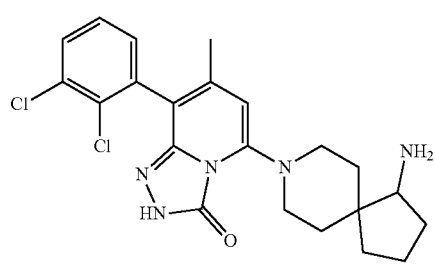
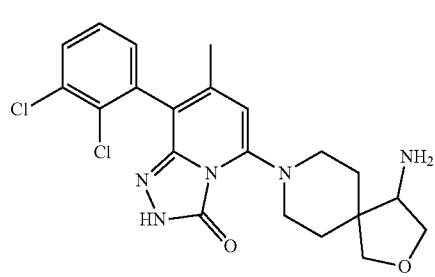
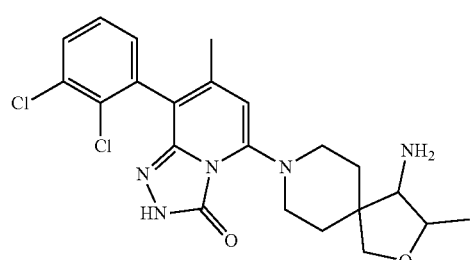
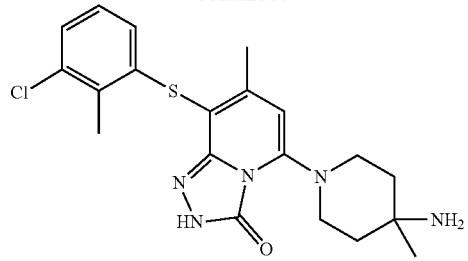
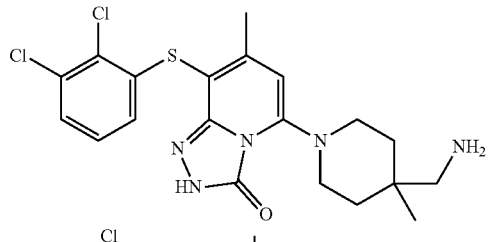
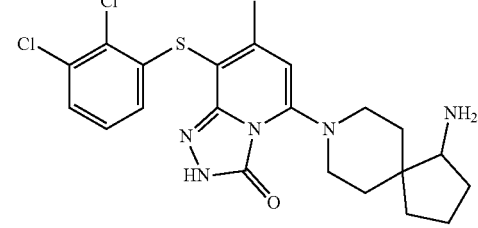
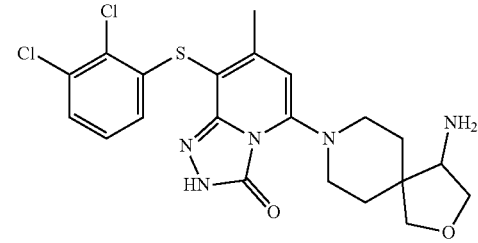
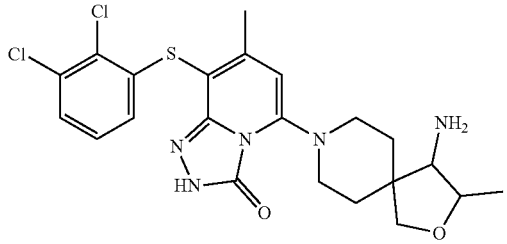
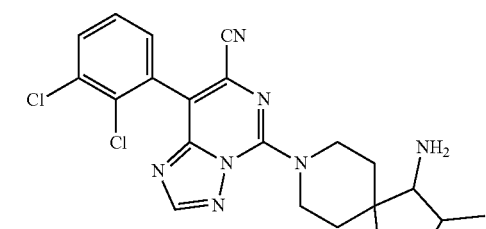
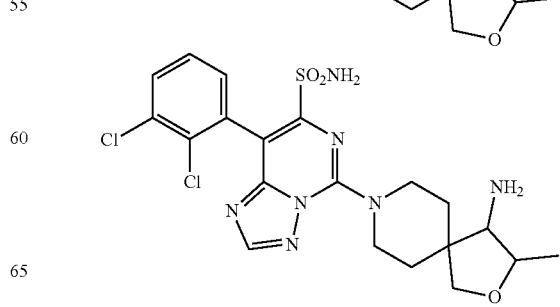

129
-continued
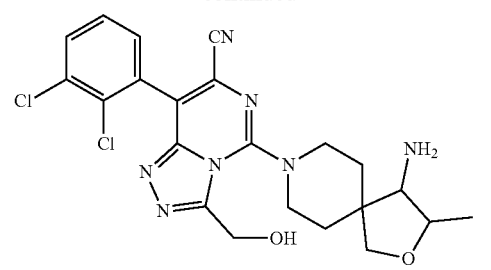
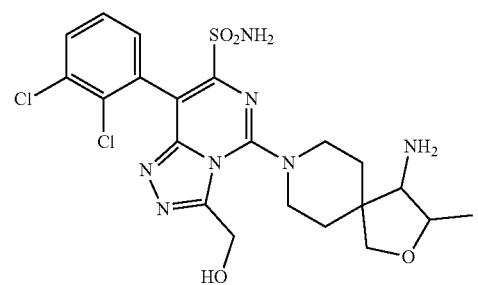
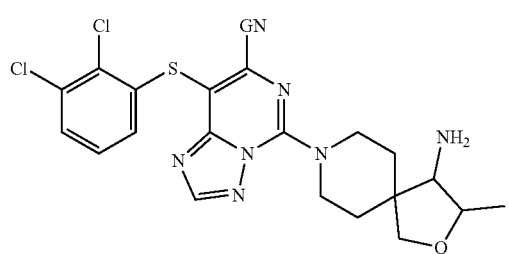
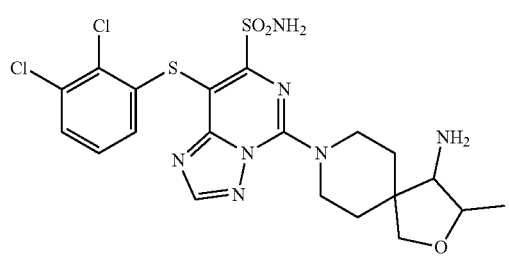
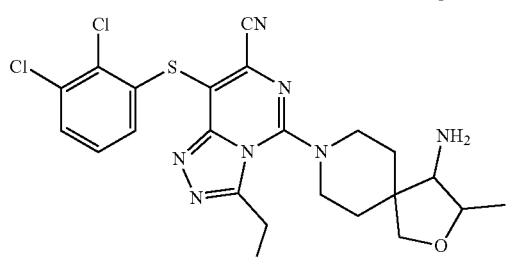
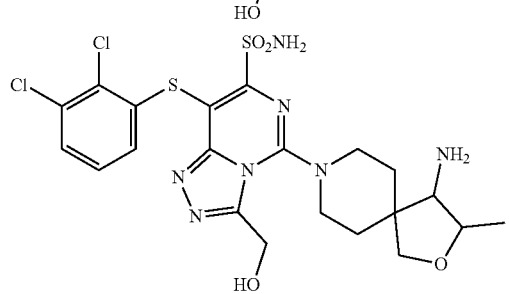
130
-continued
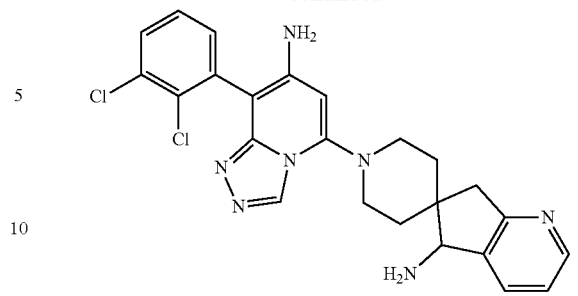
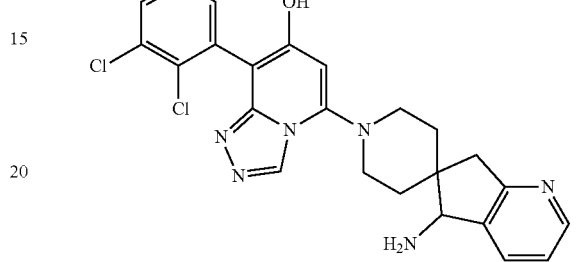
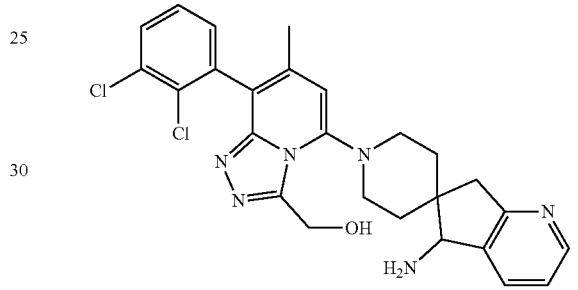
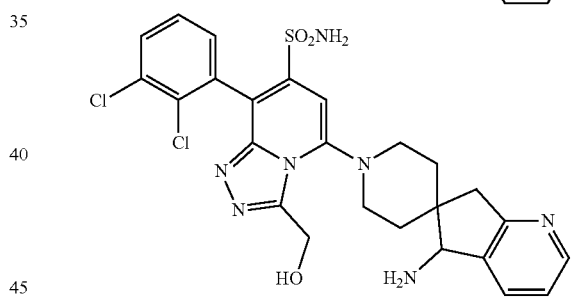
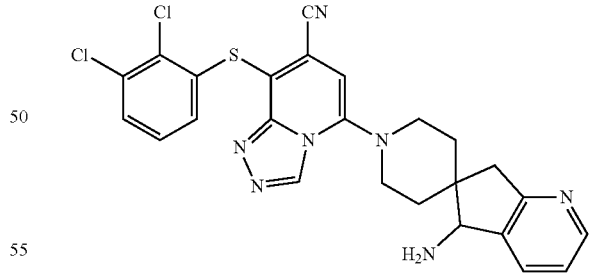
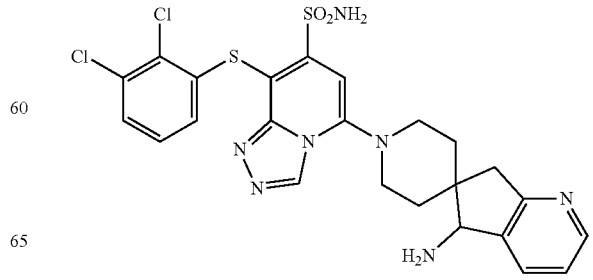

131
-continued
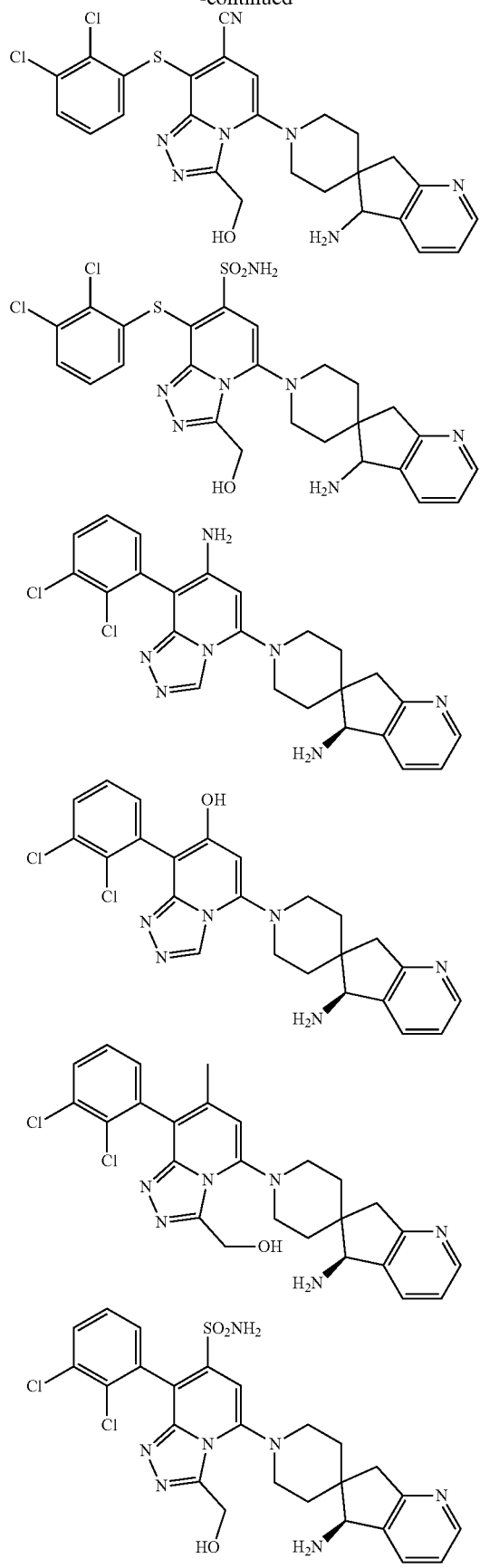
132
-continued
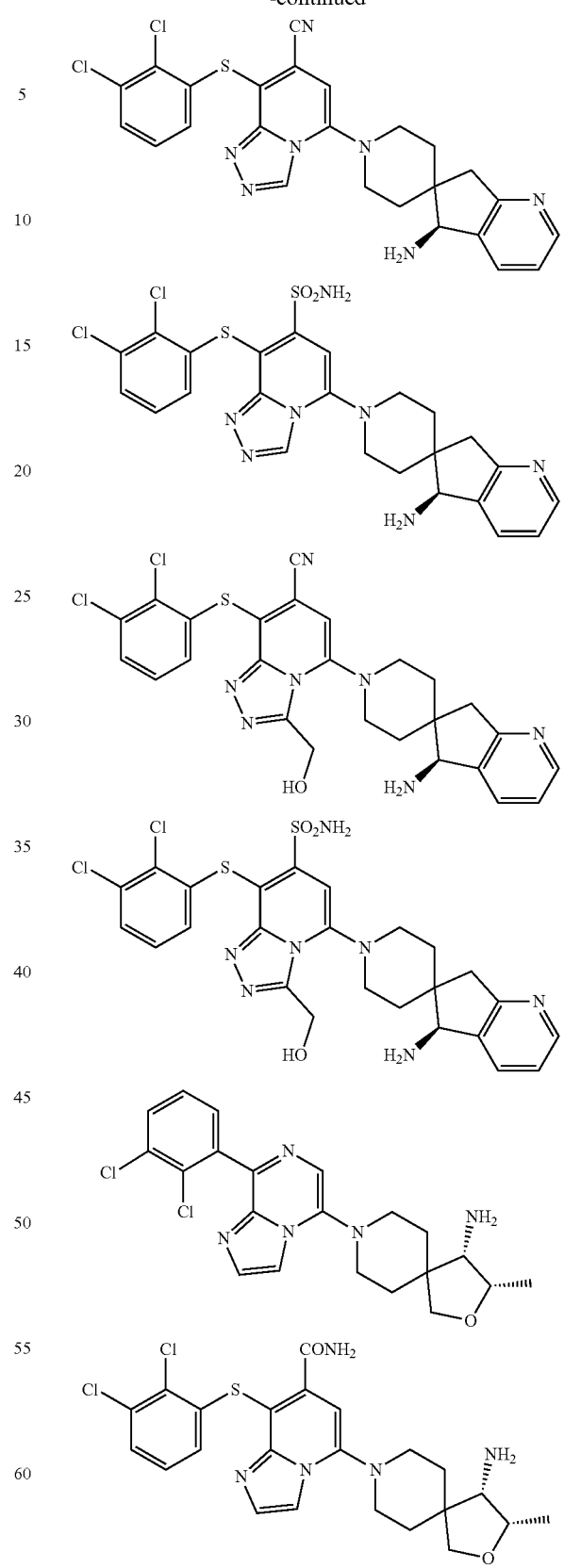

133
-continued
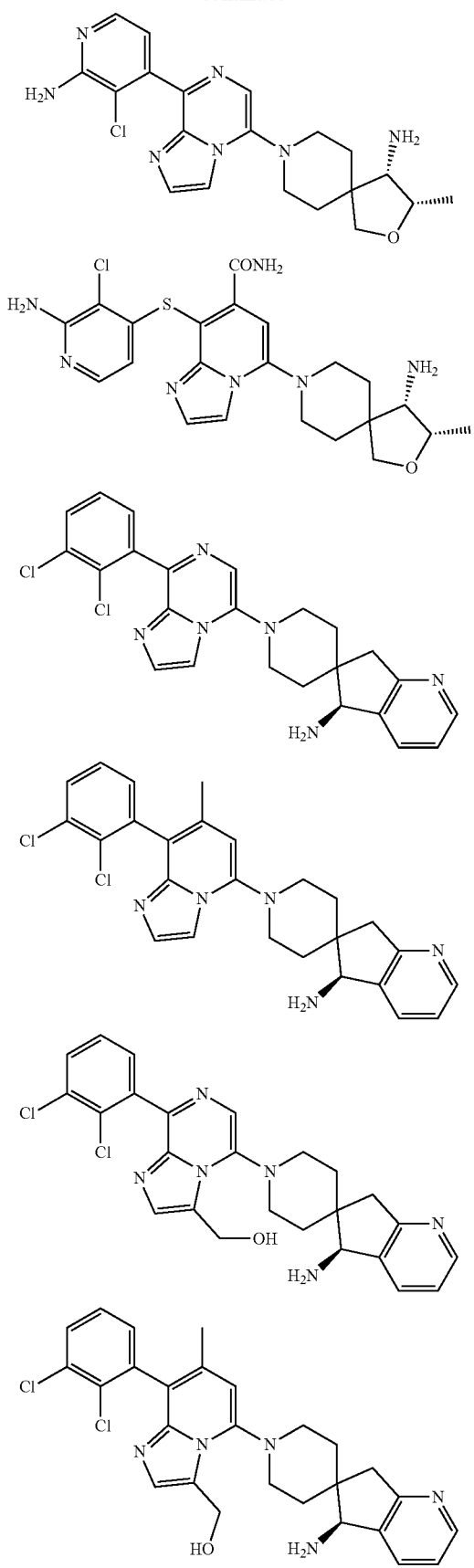
134
-continued
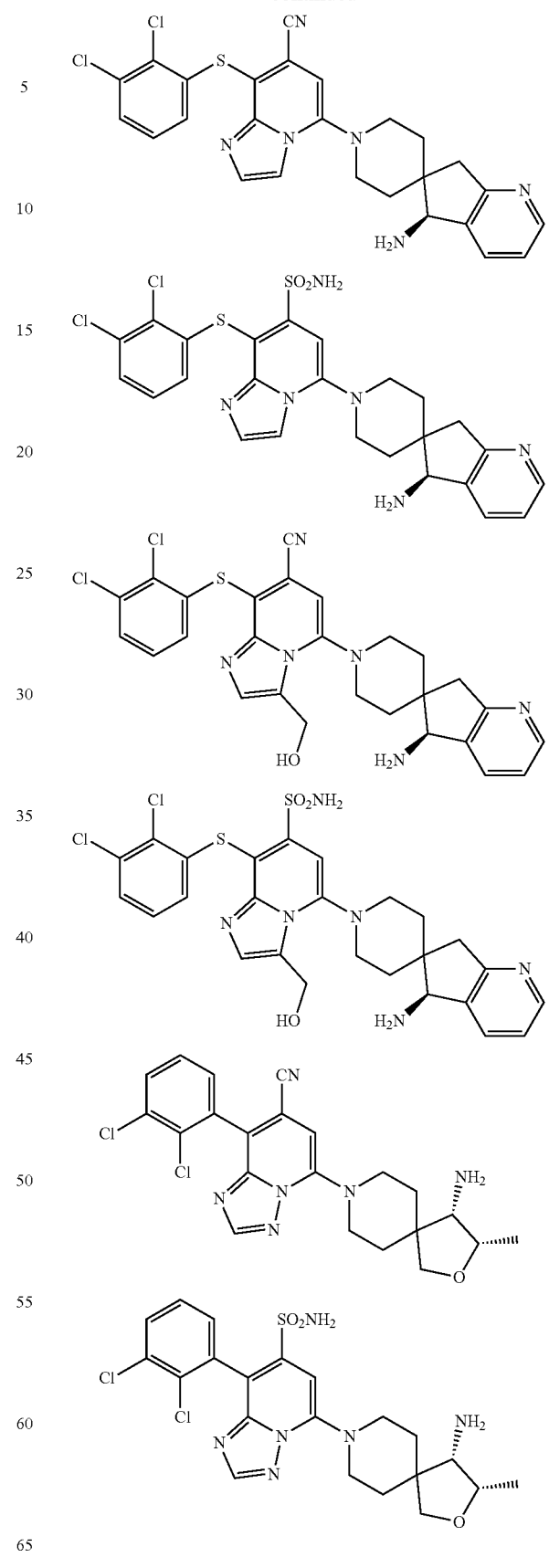

135
-continued
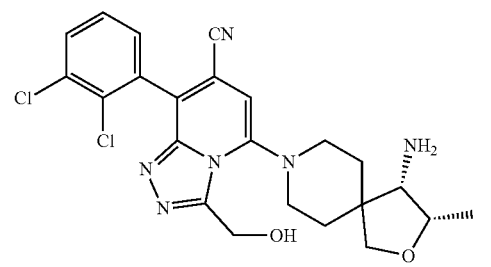
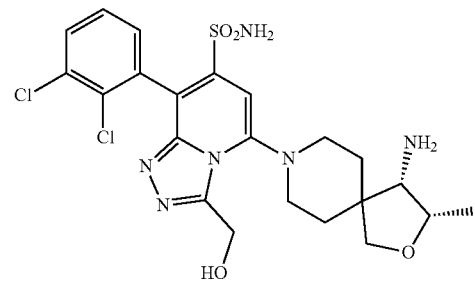
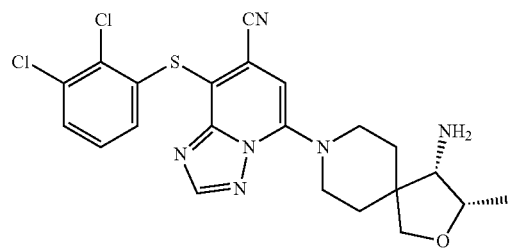
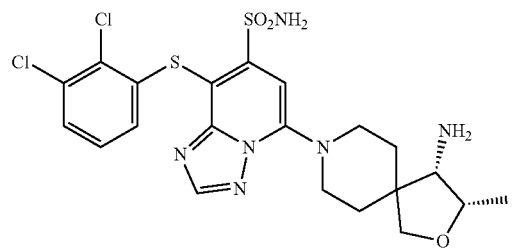
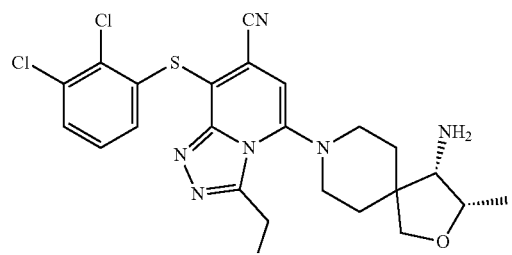
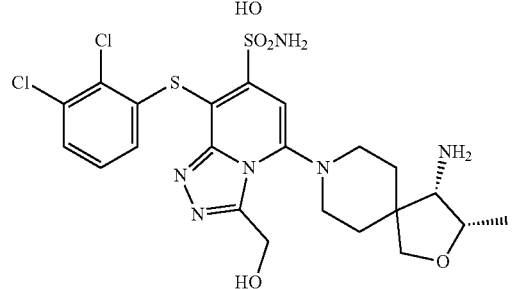
136
-continued
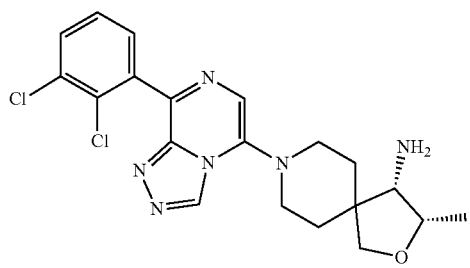
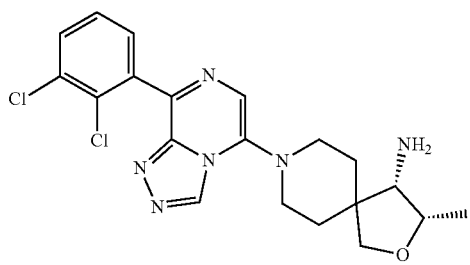
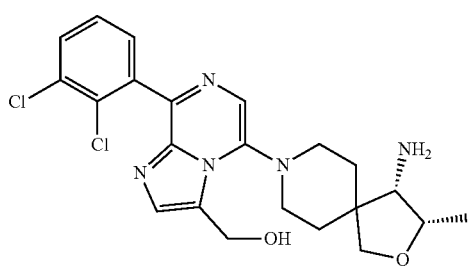
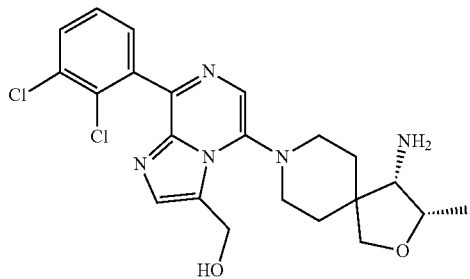
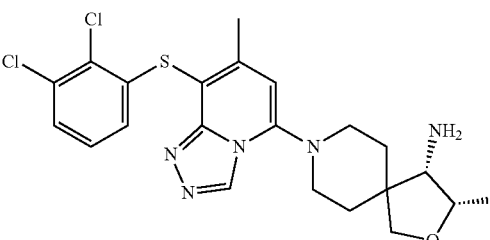
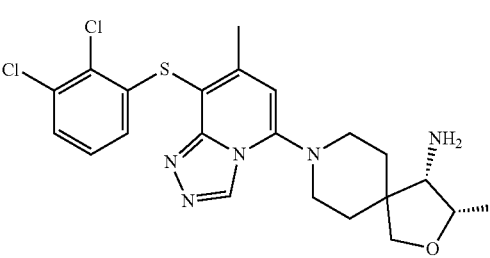

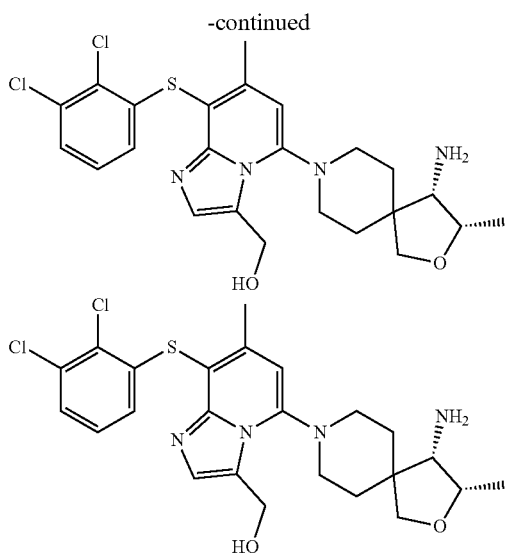

Another object of the present disclosure is to provide a drug for treating or preventing tumors and a composition thereof. The technical scheme to achieve the above object is as follows:

A pharmaceutical composition for treating tumors, comprising a nitrogen-containing fused heterocyclic compound represented by formula (I-2) described above, or a pharmaceutically acceptable salt thereof, or an enantiomer, a diastereomer, a tautomer, a solvate, a polymorph or a prodrug thereof, and a pharmaceutically acceptable carrier.

Another object of the present disclosure is to provide a use of one of the compounds described above. The technical scheme to achieve the above object is as follows:

The nitrogen-containing fused heterocyclic compound represented by formula (I-2), or a pharmaceutically acceptable salt thereof, or an enantiomer, a diastereomer, a tautomer, a solvate, a polymorph or a prodrug thereof is used to prepare a drug for treating diseases associated with the activity or expression of proteins such as SHP2, particularly a drug for treating a tumor, an immune disease and an inflammatory disease.

The present disclosure relates to a compound with structural characteristics of a formula (I-2), wherein the compound can inhibit a variety of tumor cells, particularly can efficiently kill tumors associated with abnormal signaling pathways such as Ras-ERK, PD-L1, etc., and is a class of therapeutic drugs with a novel mechanism of action.

In a preferred embodiment, a nitrogen-containing fused heterocyclic compound represented by formula I-3, or a pharmaceutically acceptable salt thereof, or an enantiomer, a diastereomer, a tautomer, a solvate, a polymorph or a prodrug thereof,

I-3

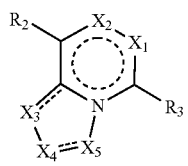

wherein $X_1$, $X_2$, $X_3$, $X_4$ and $X_5$ are independently selected from N and $CR_1$, respectively, wherein $R_1$ is selected from hydrogen, halogen, hydroxyl, substituted or unsubstituted amino, substituted or unsubstituted acylamino, substituted or unsubstituted sulfonamido, $C_1$-$C_6$ substituted or unsubstituted alkyl, $C_1$-$C_6$ substituted or unsubstituted alkoxy, cyano, alkenyl, alkynyl, 3-8 membered substituted or unsubstituted cycloalkyl or heterocycloalkyl, 5-8 membered substituted or unsubstituted aryl or heteroaryl;

$R_2$ is selected from -$L_2$-$R_y$; wherein $L_2$ is a direct bond, —O—, —S(O)n-, —$NR_b$—, etc., and $R_y$ is 5-10 membered cycloalkyl or heterocycloalkyl or aryl or heteroaryl; n=0-2; $R_b$ is selected from hydrogen, $C_1$-$C_6$ alkyl or alkoxy, 3-8 membered cycloalkyl or heterocycloalkyl, etc.;

$R_3$ is selected from —$OR_c$, —$SR_c$, —$C(R_aR_b)R_c$, —$NR_bR_c$, —$COR_c$, —$CONR_bR_c$, —$NR_bCOR_c$, —$SO_2NR_bR_c$, —$NR_bSO_2R_c$, —$NR_bCONR_bR_c$, —$NR_bSO_2NR_bR_c$, —$NR_bCSNR_bR_c$, —$COOR_c$, —$OOCR_c$, —$OCONR_bR_c$, —$NR_bCOOR_c$, —$NR_bCSR_c$, —$CSNR_bR_c$, etc., wherein $R_b$ is independently selected from hydrogen, $C_1$-$C_6$ alkyl or alkoxy, 3-8 membered cycloalkyl or heterocycloalkyl upon each occurrence; $R_c$ is independently selected from $C_1$-$C_6$ alkyl, 3-12 membered monocyclic or polycyclic cycloalkyl, 3-12 membered monocyclic or polycyclic heterocycloalkyl; or $R_c$ with $R_a$ or $R_b$ may form 3-12 membered monocyclic or polycyclic cycloalkyl, 3-12 membered monocyclic or polycyclic heterocycloalkyl, 3-12 membered spiro or fused cycloalkyl, and 3-12 membered spiro or fused heterocycloalkyl;

$C_1$-$C_8$ alkyl, 3-8 membered cycloalkyl or heterocycloalkyl, $C_1$-$C_8$ alkoxy, $C_1$-$C_8$ alkylamino, alkenyl, alkynyl, acyl or sulfonyl, urea or sulfonylurea, 5-8 membered aryl or heteroaryl; wherein the heteroaryl comprises 1-3 heteroatoms selected from the group consisting of N, O, P, or S; the heterocycloalkyl comprises 1-3 heteroatoms selected from the group consisting of N, O, P, or S; the ring system comprises a spiro ring, a bridged ring, a fused ring, a fused saturated or partially unsaturated ring system; the above ring systems may be further substituted with $C_1$-$C_6$ alkyl, hydroxy, amino, halogen or alkoxy, etc.

A further embodiment includes a compound represented by formula (I-3), or a pharmaceutically acceptable salt thereof, or an enantiomer, a diastereomer, a tautomer, a solvate, a polymorph or a prodrug thereof, preferably the compound represented by formula (IIA), or the pharmaceutically acceptable salt thereof, or the enantiomer, the diastereomer, the tautomer, the solvate, the polymorph or the prodrug thereof:

(IIA)

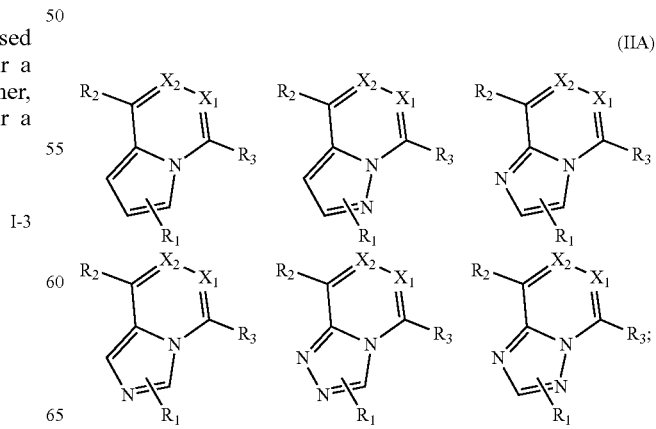

More preferably a compound represented by formula (IIB):

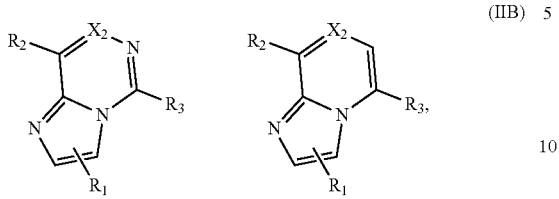

wherein $R_1$, $R_2$, $R_3$, $X_1$, and $X_2$ are as defined as described above.

In a further embodiment, the present disclosure is preferably a compound represented by the following formula (III), or a pharmaceutically acceptable salt thereof, or an enantiomer, a diastereomer, a tautomer, a solvate, a polymorph or a prodrug thereof:

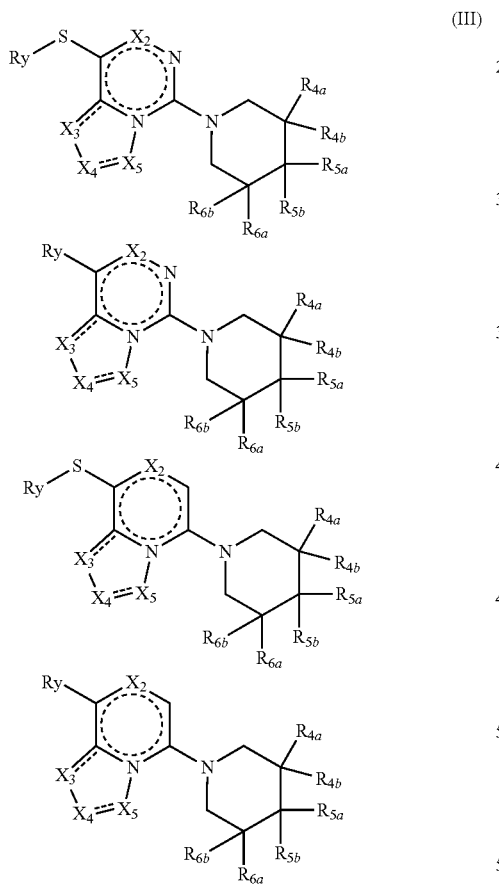

wherein $R_{4a}$, $R_{4b}$, $R_{6a}$, and $R_{6b}$ are independently selected from hydrogen, halogen, hydroxyl, amino, etc., respectively, and cannot be simultaneously substituted with the hydroxyl or the hydroxyl and fluorine at the same carbon atom; $R_{5a}$ is selected from $C_1$-$C_6$ alkyl, hydroxyl, amino, aminomethyl, etc.; $R_{5b}$ is selected from hydroxyl, amino, halogen, $C_1$-$C_6$ alkyl, 3-8 membered cycloalkyl or heterocycloalkyl, hydroxyalkyl, alkoxyalkyl, cycloalkylalkyl, alkoxyacyl, 5-8 membered aryl or heteroaryl, etc.;

alternatively, $R_{5a}$ and $R_{5b}$ may be linked by carbon atoms to form 3-12 membered monocyclic or polycyclic saturated or unsaturated alkyl, 3-12 membered monocyclic or polycyclic saturated or unsaturated heterocycloalkyl, 3-12 membered spiro or fused cycloalkyl, and 3-12 membered spiro or fused heterocycloalkyl;

and each hydrogen atom on the $R_{5a}$ and $R_{5b}$ groups described above may be respectively substituted with the following groups of deuterium, halogen, hydroxyl, alkoxy, amino, alkylamino, alkyl, cycloalkyl, heterocycloalkyl, etc.;

more preferably a compound represented by formula IV:

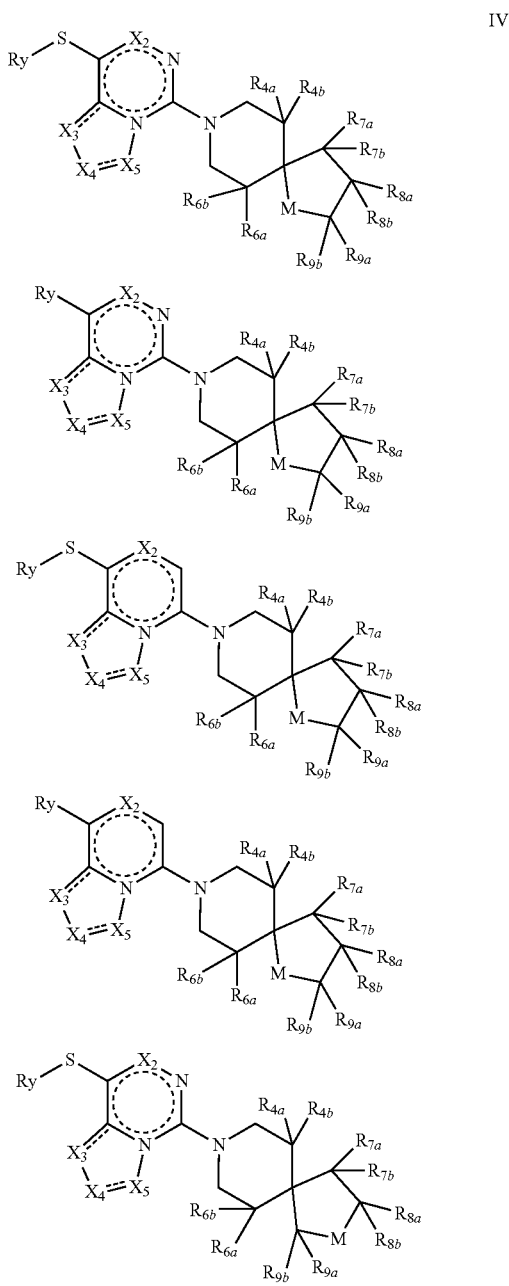

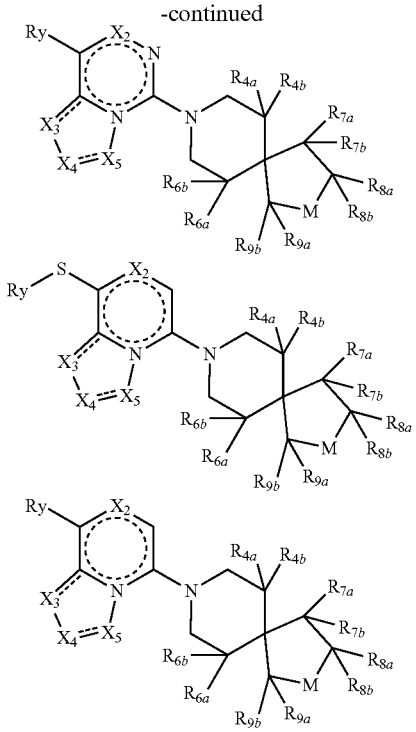

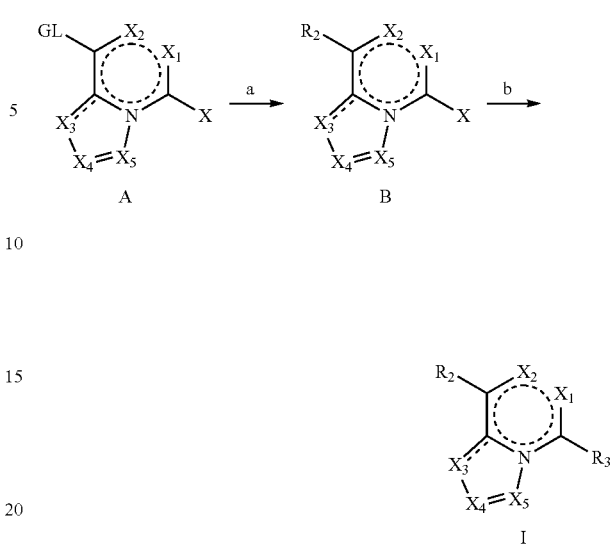

wherein M is selected from —O—, —S—, —SO$_2$—, —CR$_{9a}$R$_{9b}$—, —NR$_{10}$—, etc.; R$_{7a}$ and R$_{7b}$ are independently selected from hydrogen, halogen, C$_1$-C$_6$ alkyl, hydroxyl, amino, alkoxy, etc., respectively; R$_{8a}$ and R$_{8b}$ are independently selected from hydroxyl, halogen, C$_1$-C$_6$ alkyl, etc., respectively; R$_{9a}$ and R$_{9b}$ are independently selected from deuterium, hydrogen, oxygen, hydroxyl, halogen, amino, C$_1$-C$_6$ alkyl, etc., respectively; R$_{10a}$ and R$_{10b}$ are independently selected from hydrogen, deuterium, halogen, oxo, hydroxyl, amino, C$_1$-C$_6$ alkyl or alkoxy, respectively; R$_{10}$ is independently selected from hydrogen, C$_1$-C$_6$ substituted or unsubstituted alkyl, etc.;

alternatively, R$_{7a}$, R$_{7b}$, R$_{8a}$, R$_{8b}$, R$_{9a}$ and R$_{9b}$ are linked by carbon atoms or heteroatoms in pairs to form a 3-12 membered saturated or partially unsaturated or aromatic ring system, wherein the formed ring system can continue to be substituted with one or more substituents; R$_y$, X$_2$, X$_3$, X$_4$ and X$_5$ are defined as described above.

A method for preparing a compound represented by formula I-3, wherein the method comprises steps a-b:
a) converting a compound represented by formula (A) and a block R$_2$ to a compound B represented by formula through a metal-catalyzed coupling reaction, wherein an R$_2$ fragment is a boric acid, a boric acid ester, a trifluoroborate, a tin reagent, a zinc reagent or a sulfide, etc.; and
b) obtaining a compound represented by formula (I) by a cross-coupling reaction between the compound B represented by formula and a block R$_3$ in the presence of a base catalyzed substitution or a transition metal catalyst, wherein an R$_3$ fragment is an amine, an alcohol, an alkene, an alkyne, a metal alkyl reagent, an alkylboronic acid, an alkylboronic acid ester, an alkyl trifluoroborate, etc.;

wherein LG is a leaving group which is selected from halogen, trifluoromethanesulfonate, benzenesulfonate, etc., and each of the group is defined as described above.

Preferably, the steps a) and b) are respectively carried out in a solvent and the solvent is selected from the group consisting of water, methanol, ethanol, isopropanol, butanol, ethylene glycol, ethylene glycol monomethylether, N-methylpyrrolidone, dimethyl sulfoxide, tetrahydrofuran, toluene, dichloromethane, 1,2-dichloroethane, acetonitrile, N,N-dimethylformamide, N,N-dimethylacetamide, dioxane, or a composition thereof.

Preferably, the transition metal catalyst is selected from the group consisting of tris (dibenzylideneacetone) dipalladium (Pd$_2$(dba)$_3$), tetrakis (triphenylphosphine) palladium (Pd(PPh$_3$)$_4$), palladium acetate, palladium chloride, dichlorobis (triphenylphosphine) palladium, palladium trifluoroacetate, palladium triphenylphosphine acetate, [1,1'-bis (diphenylphosphino) ferrocene] palladium dichloride, bis (tri-o-phenylphosphine) palladium dichloride, 1,2-bis (diphenylphosphino) ethane palladium dichloride, or a composition thereof; the catalyst ligand is selected from the group consisting of tri-tert-butylphosphine, tri-tert-butylphosphine tetrafluoroborate, tri-n-butylphosphine, triphenylphosphine, tri-p-benzylphosphine, tricyclohexylphosphine, tri-o-benzylphosphine, or a composition thereof.

Preferably, the inorganic base is selected from the group consisting of sodium hydride, potassium hydroxide, sodium acetate, potassium acetate, potassium tert-butoxide, sodium tert-butoxide, potassium fluoride, cesium fluoride, potassium phosphate, potassium carbonate, potassium bicarbonate, sodium carbonate, sodium bicarbonate, or a composition thereof; the organic base is selected from the group consisting of pyridine, triethylamine, N,N-diisopropylethylamine, 1,8-diazabicyclo [5.4.0] undec-7-ene (DBU), hexamethyl disilithium, sodium hexamethyl disilyl, dimethylpyridine, or a composition thereof.

The present disclosure provides a class of preferred compounds represented by formula (I-3), including, but not limited to, the following structures:

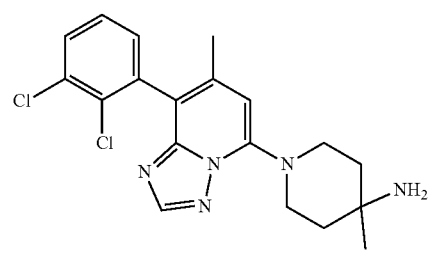
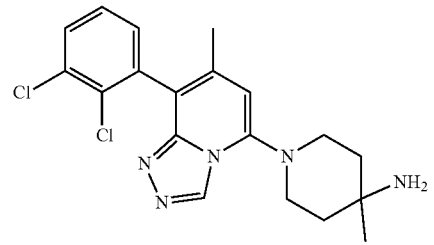
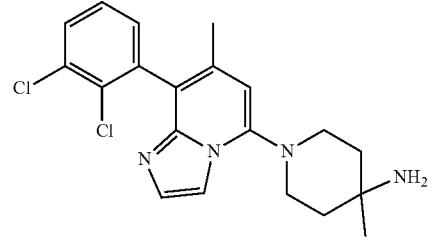
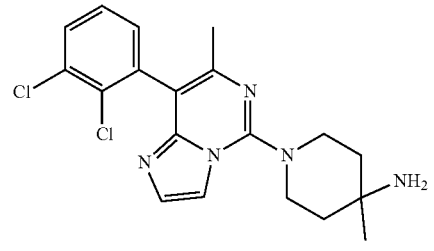
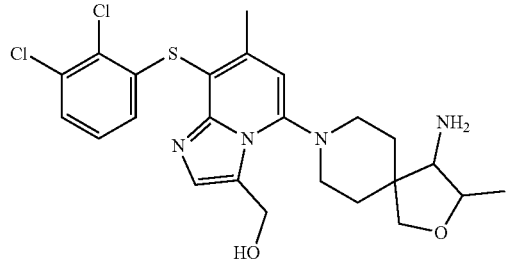
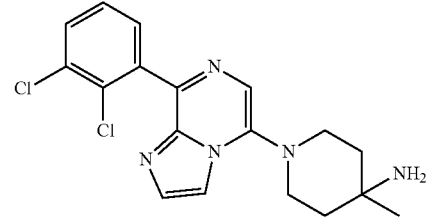
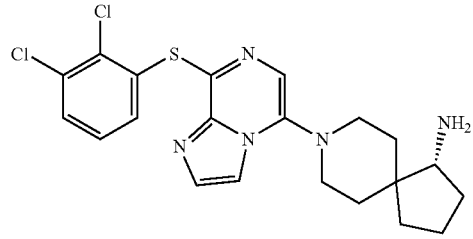
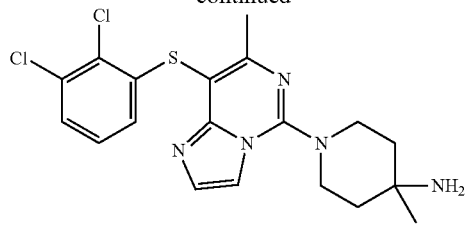
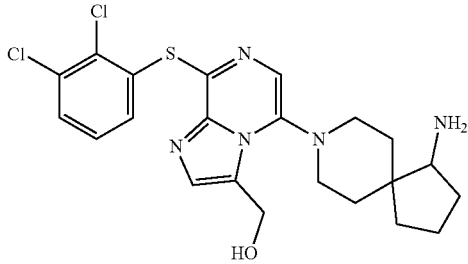
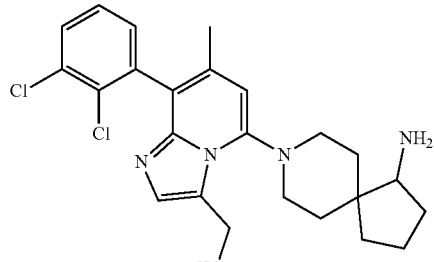
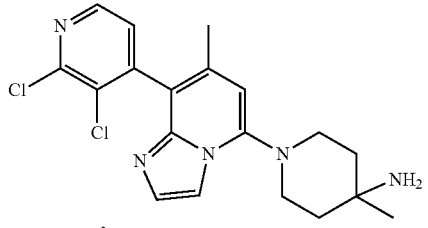
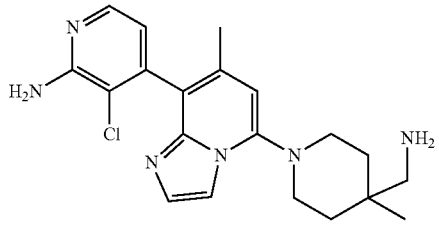
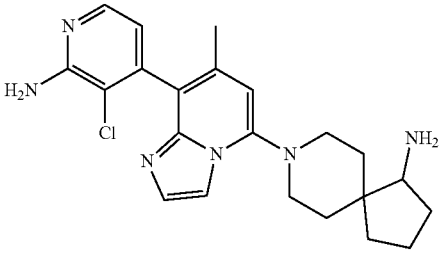
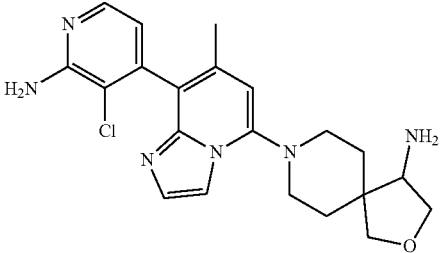

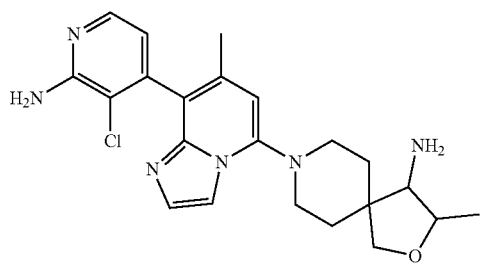
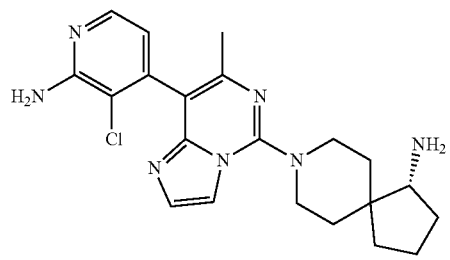
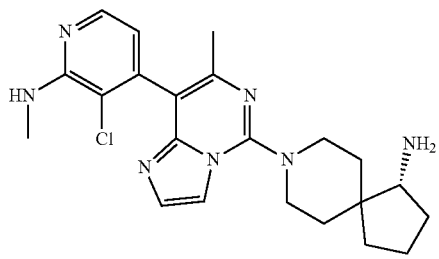
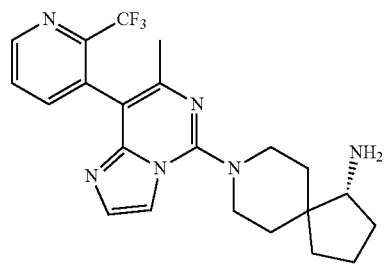
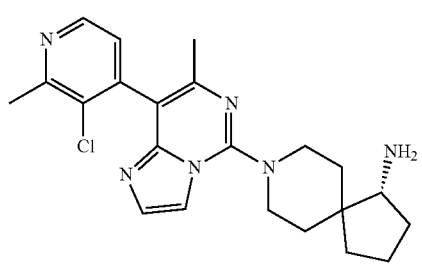
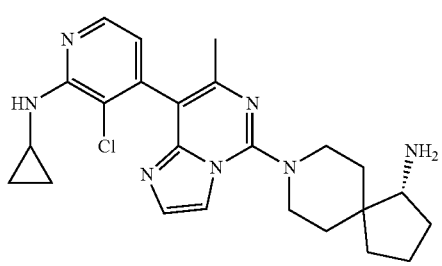
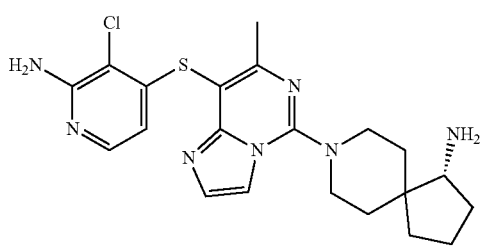
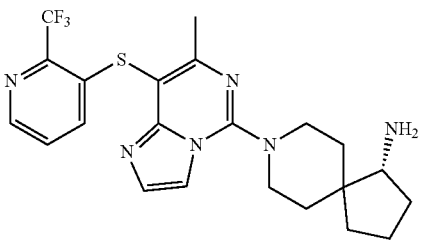
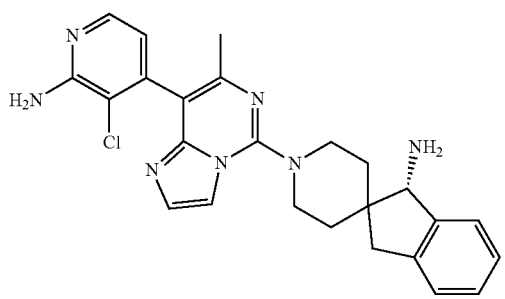
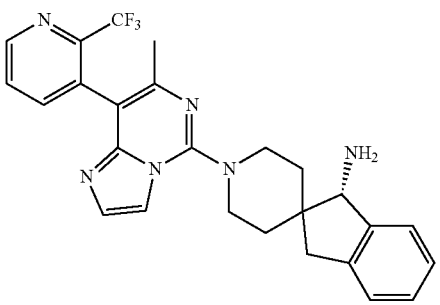
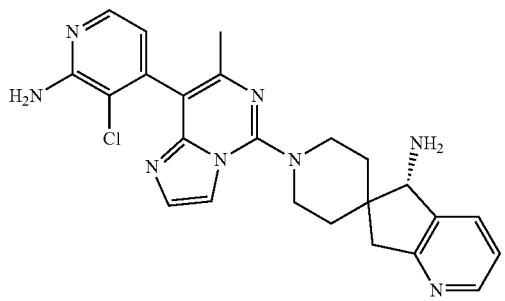
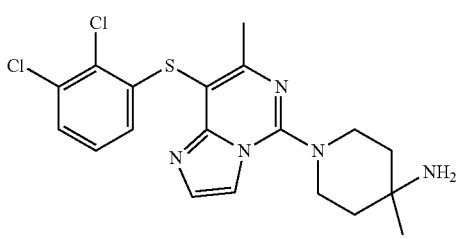

147
-continued
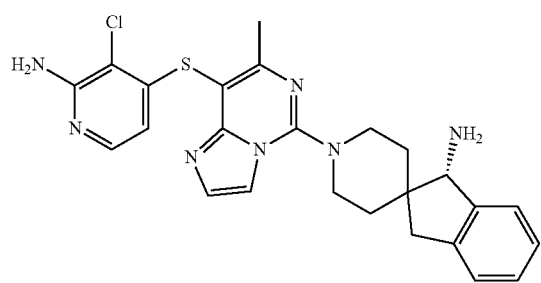
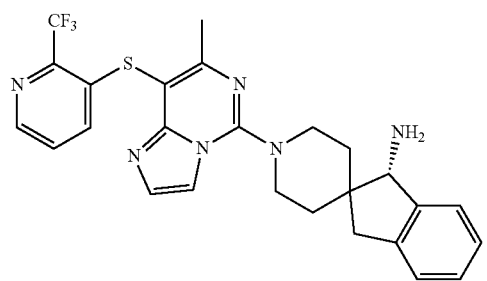
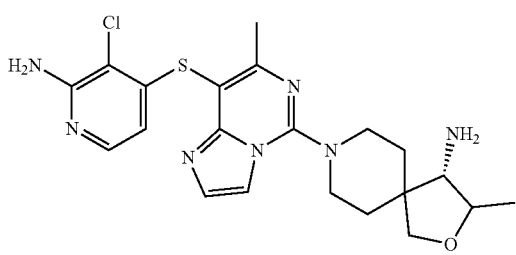
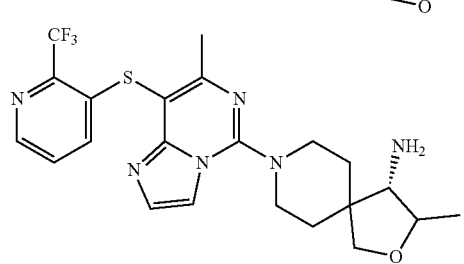
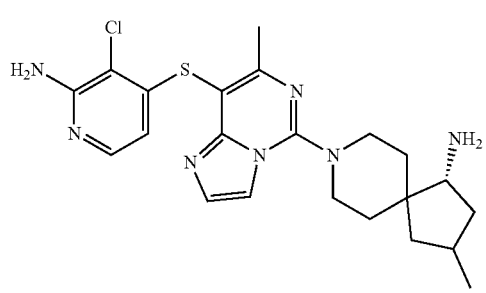
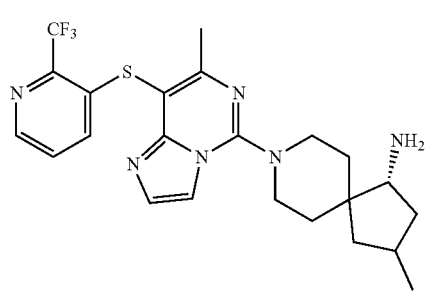
148
-continued
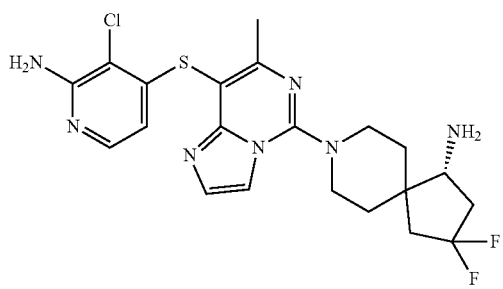
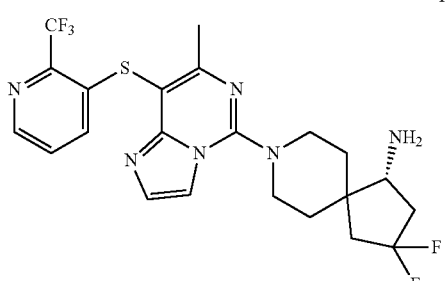
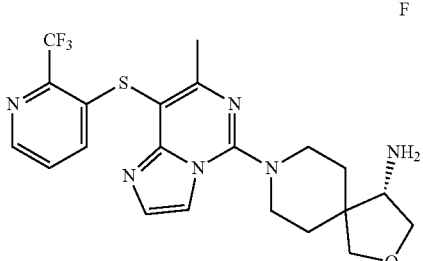
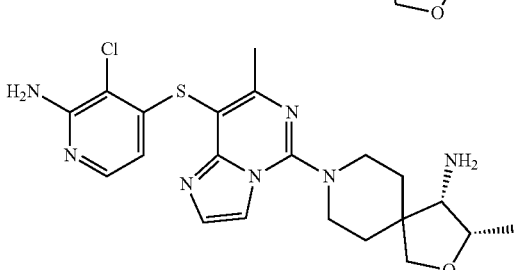
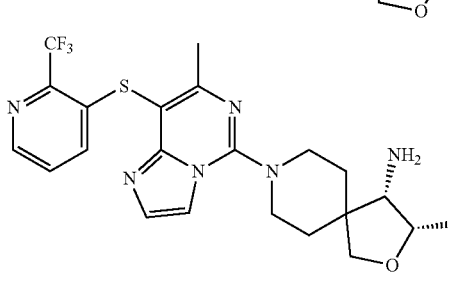
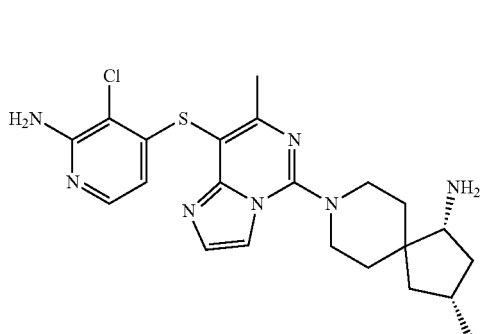

149
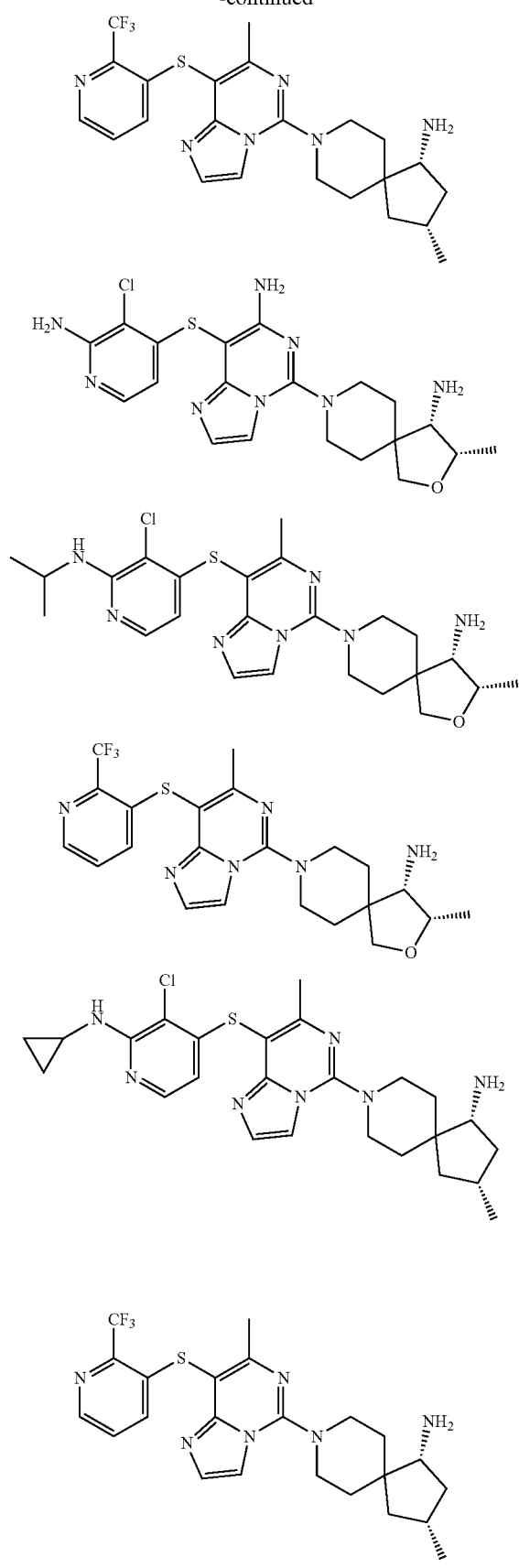
150
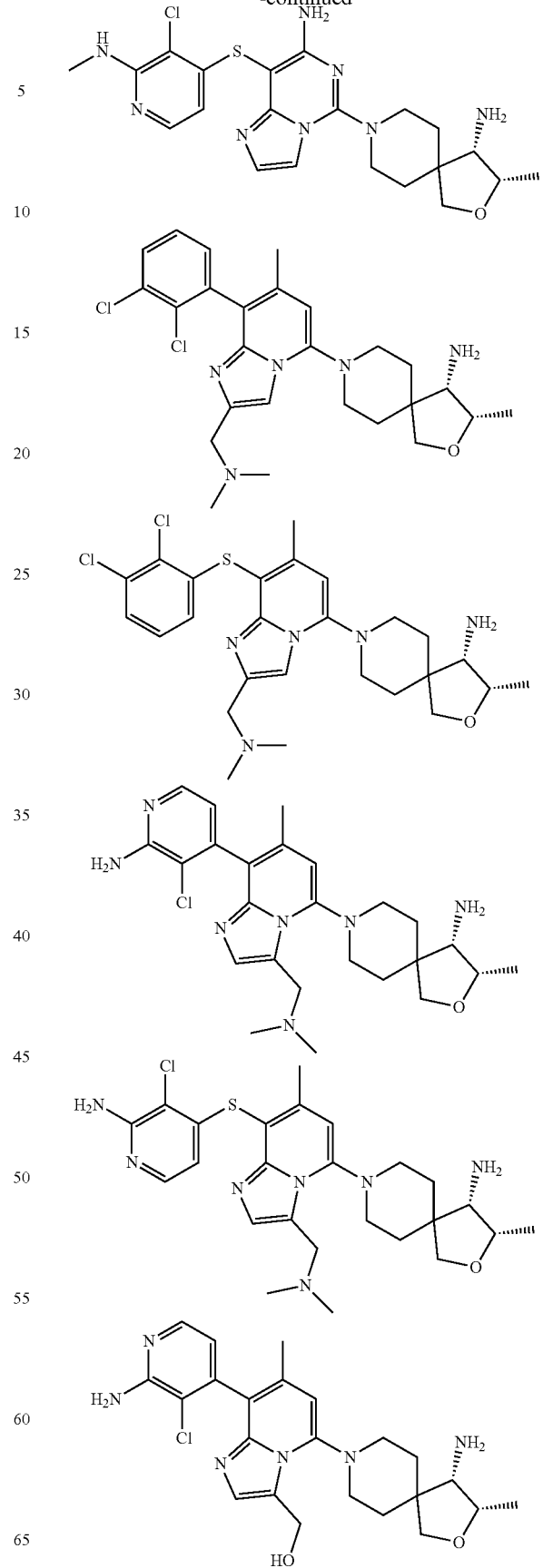

-continued
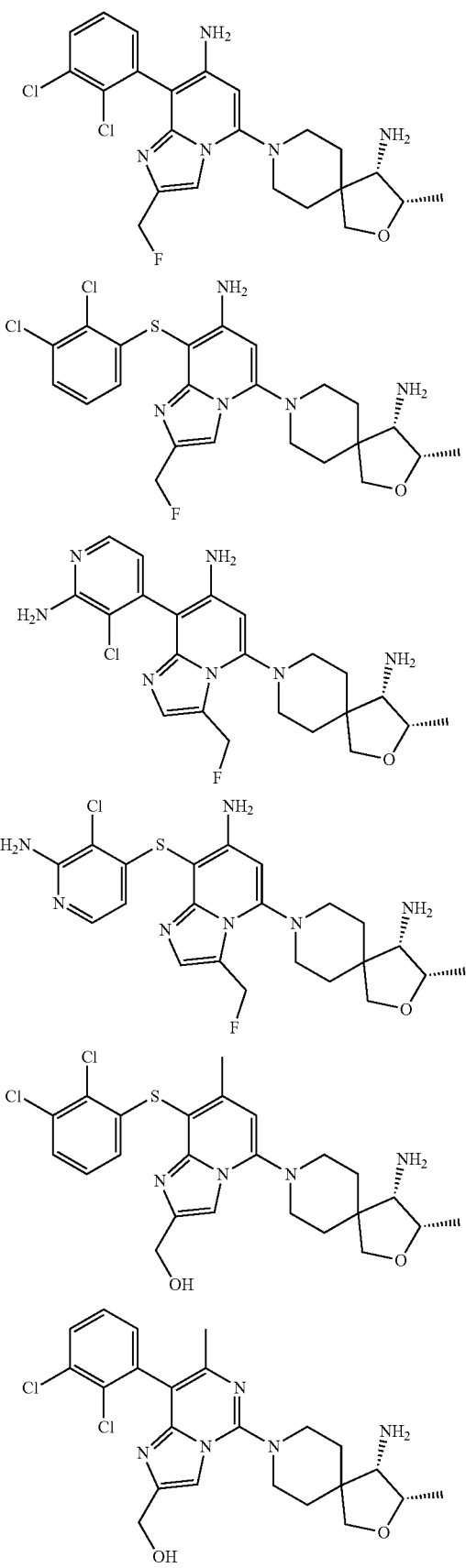 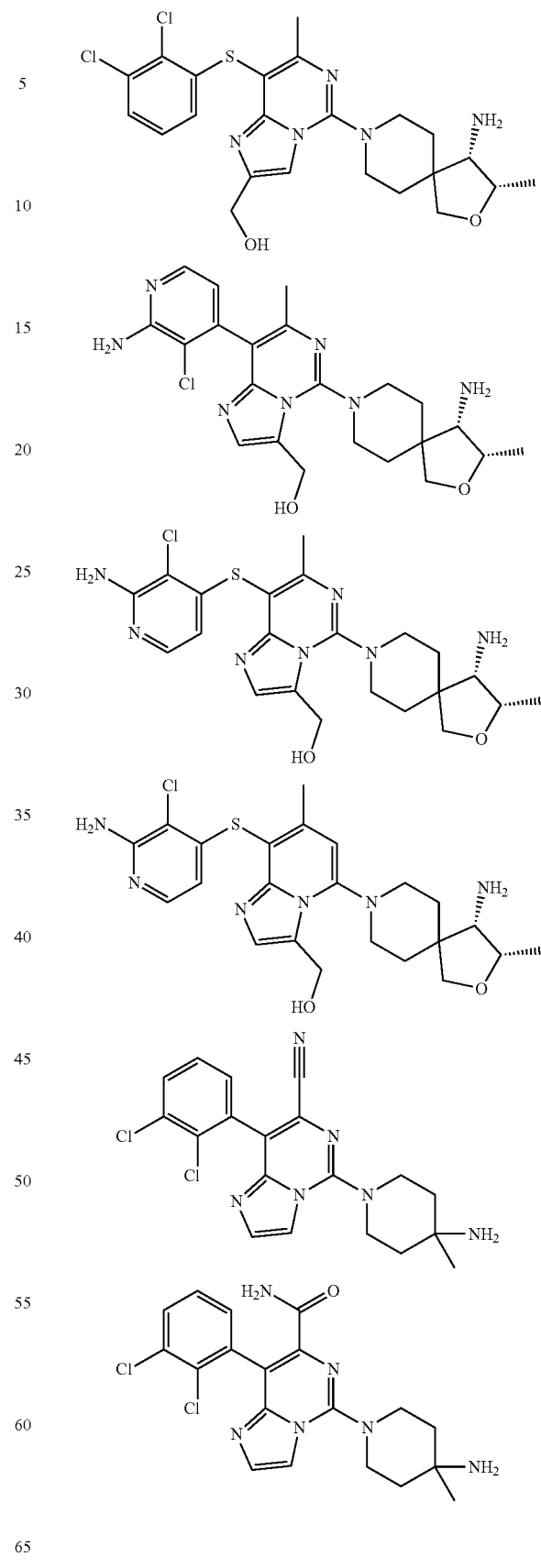

153
-continued
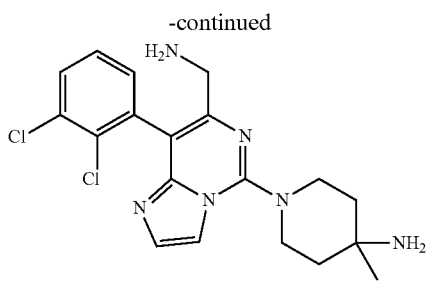
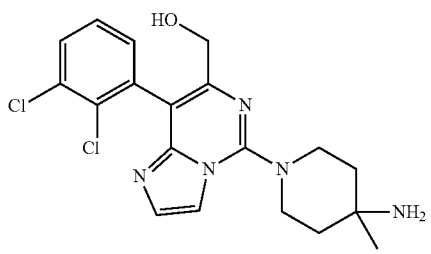
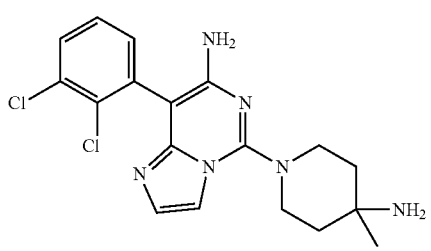
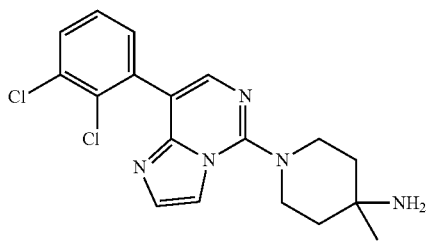
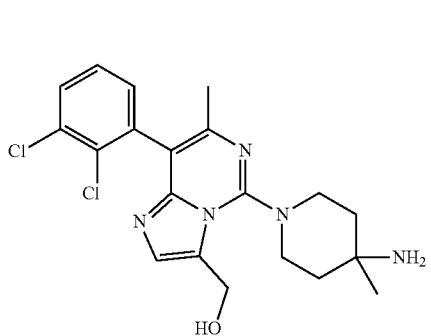
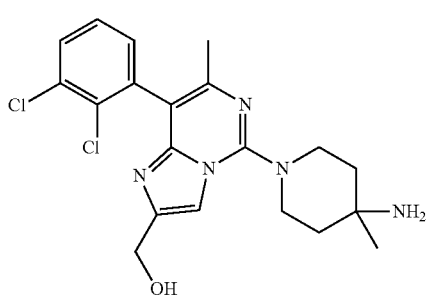
154
-continued
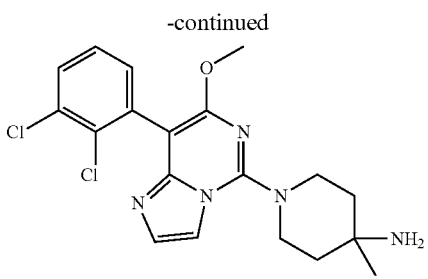
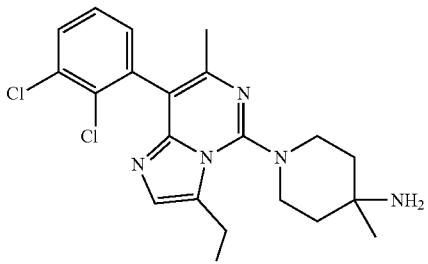
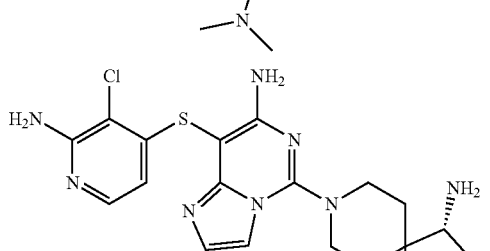
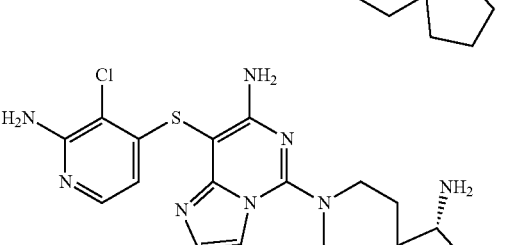
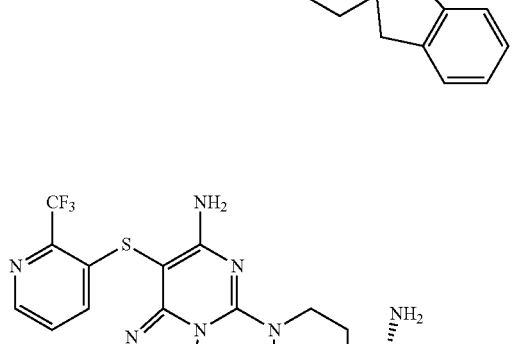
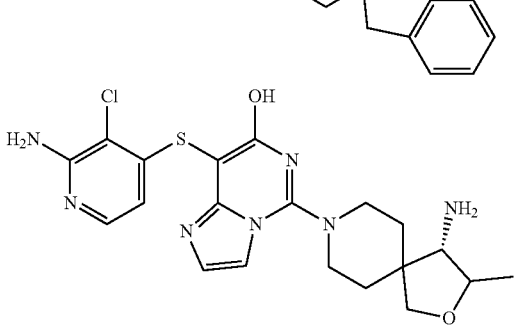

155
-continued
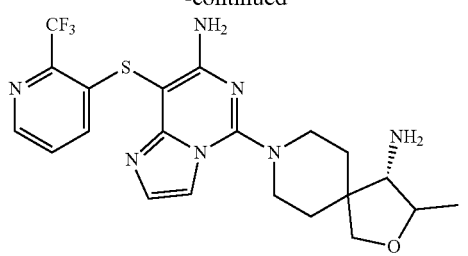
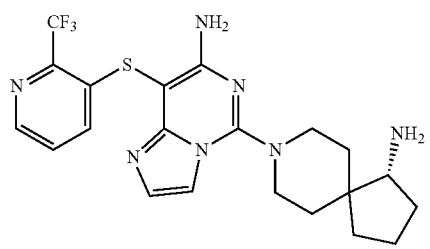
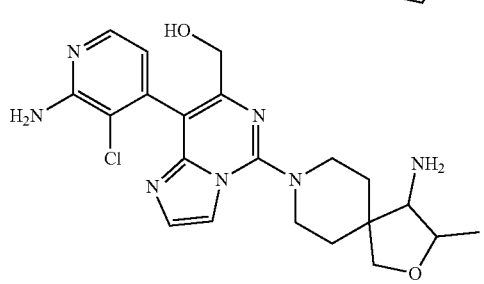
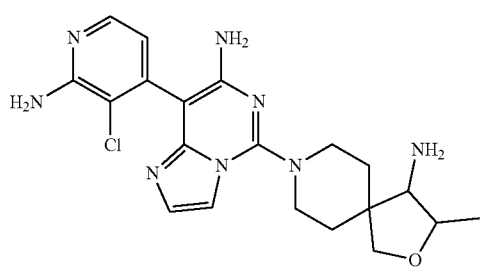
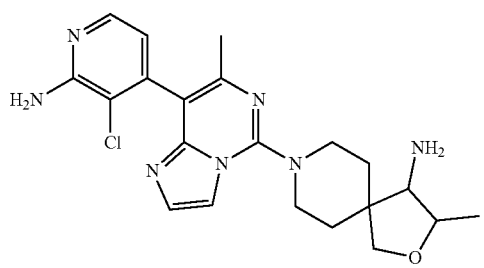
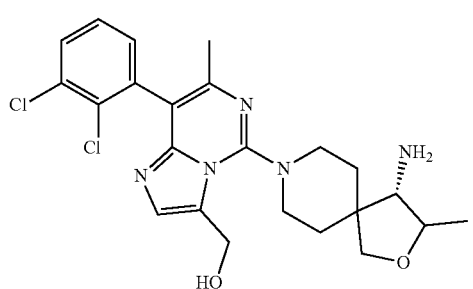
156
-continued
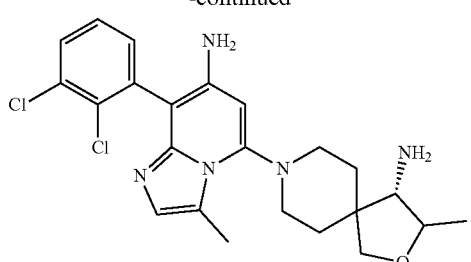
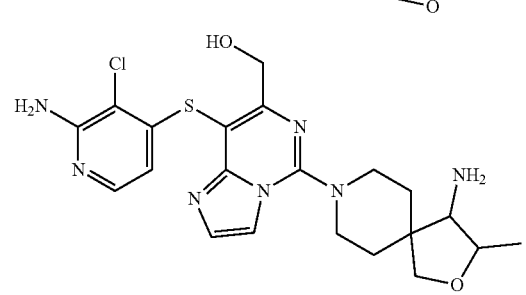
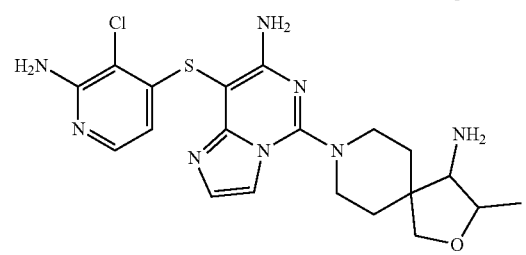
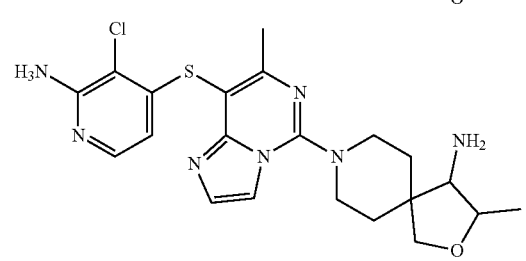
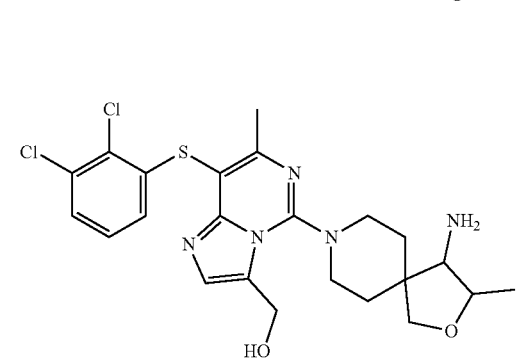
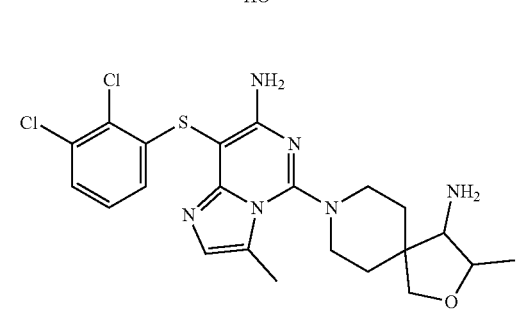

157
-continued
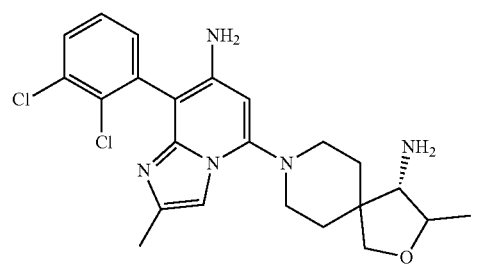
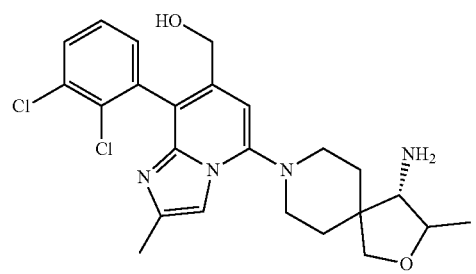
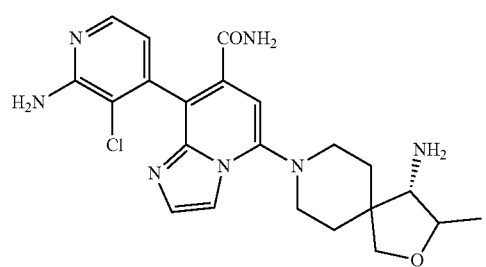
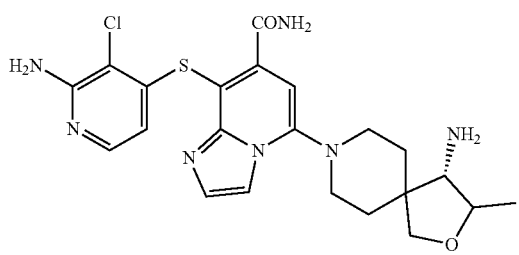
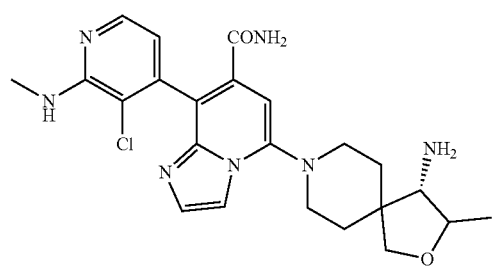
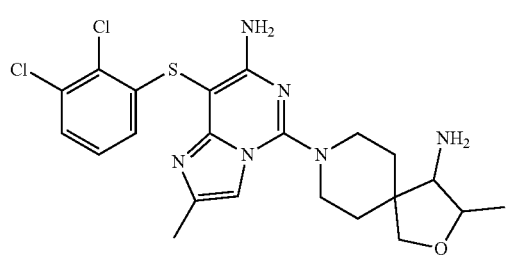
158
-continued
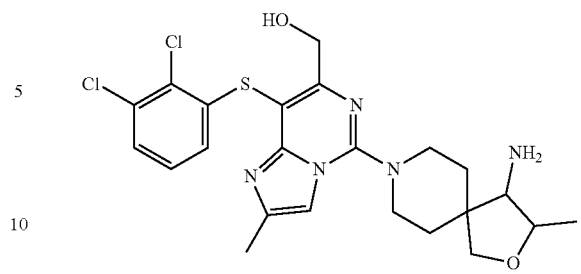
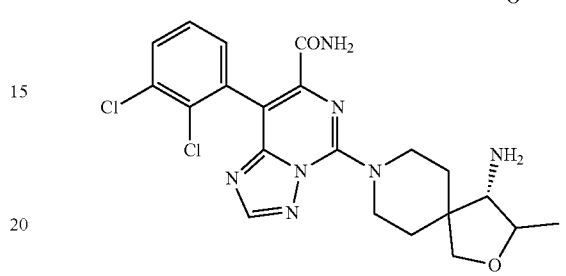
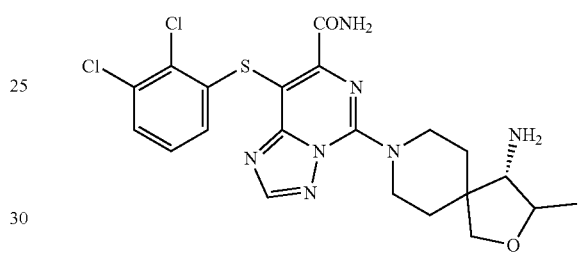
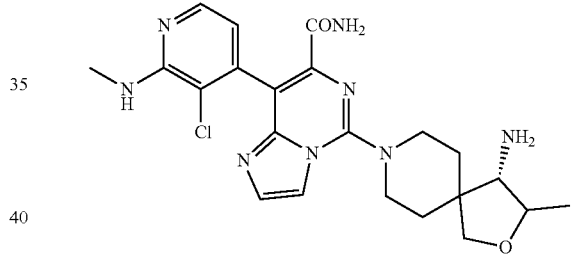
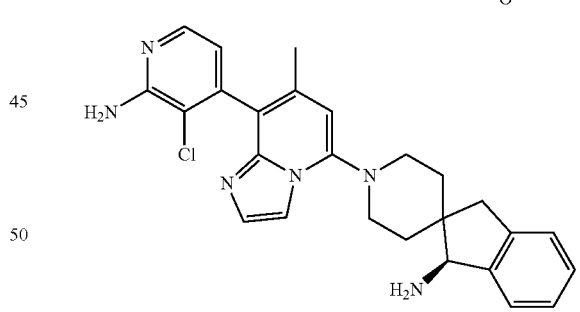
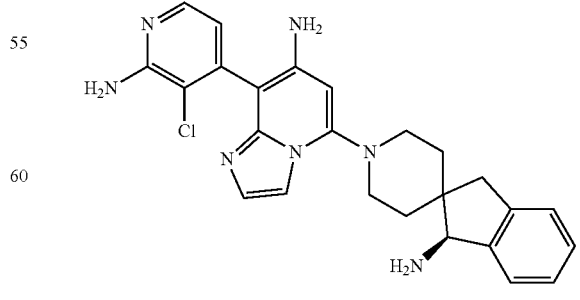

-continued
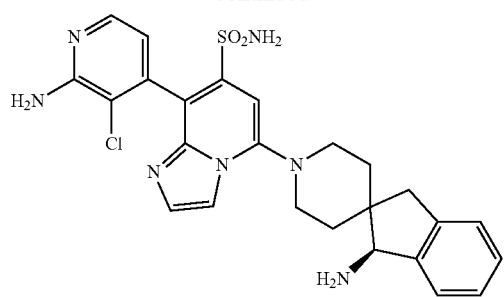
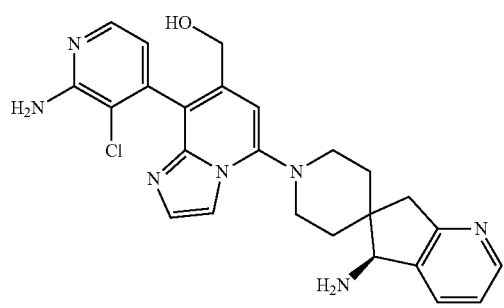
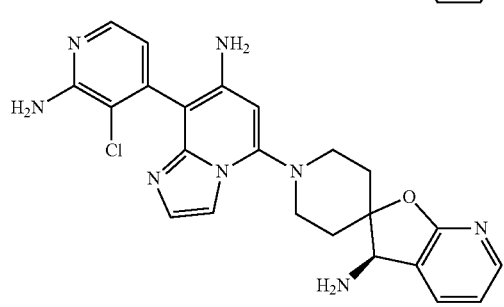
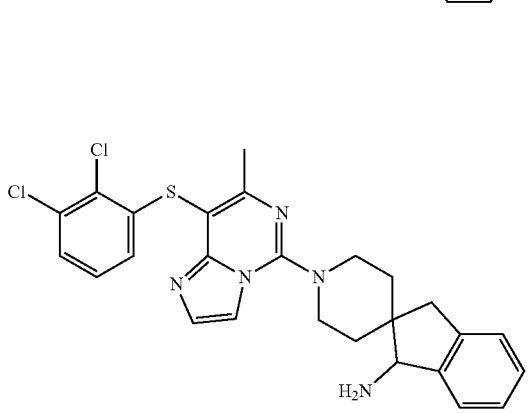
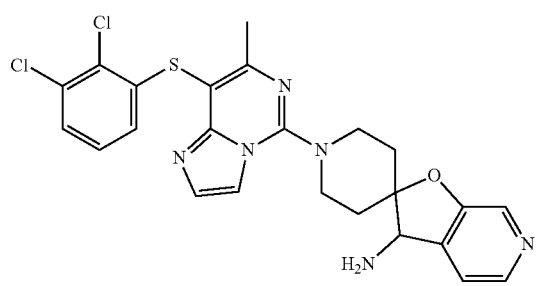
-continued
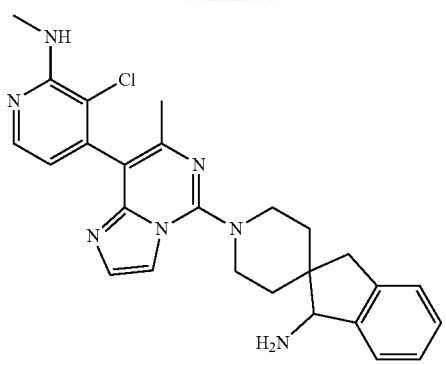
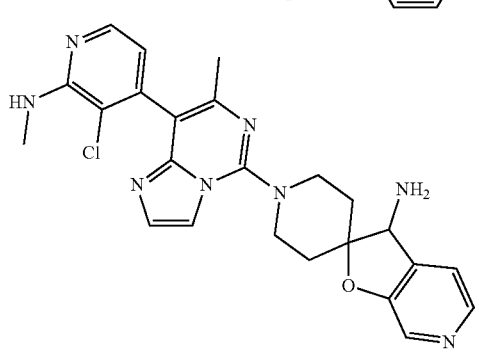
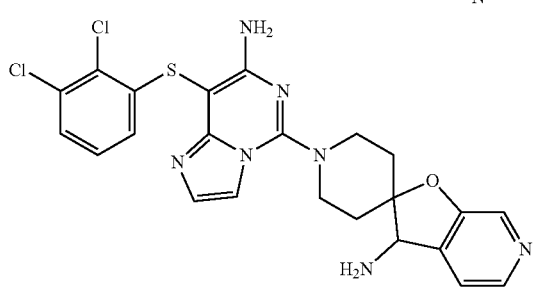
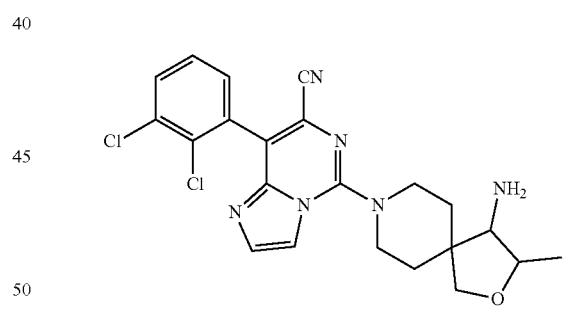
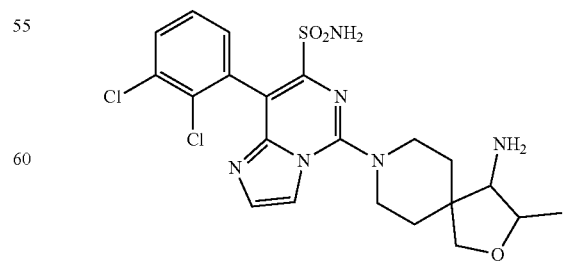

161
-continued
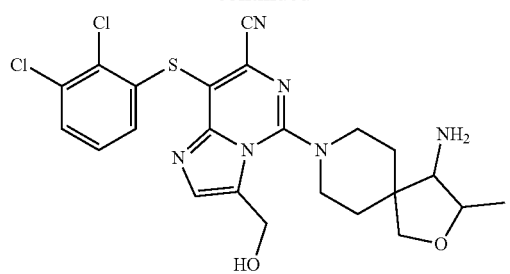
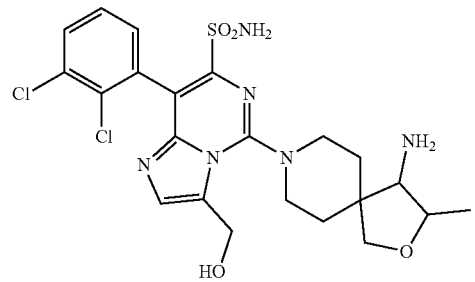
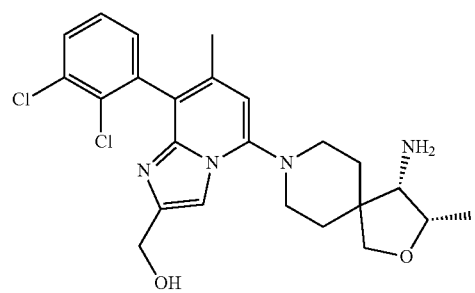
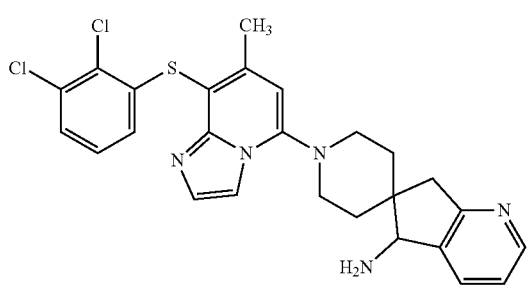
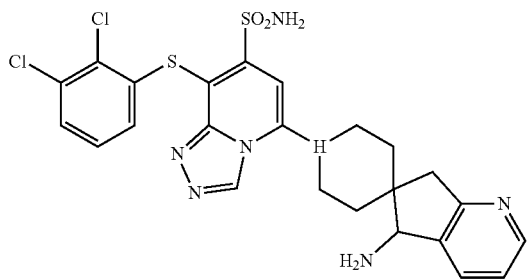
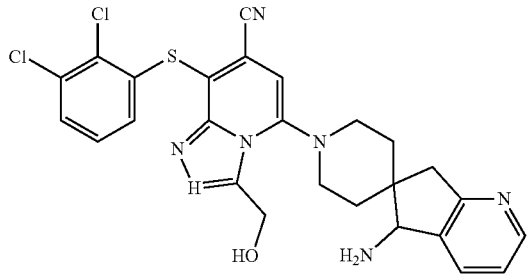
162
-continued
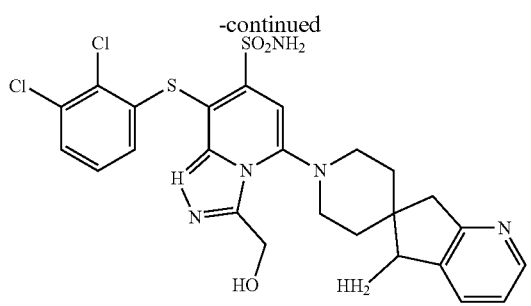
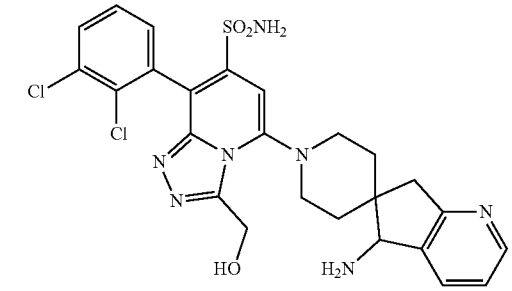
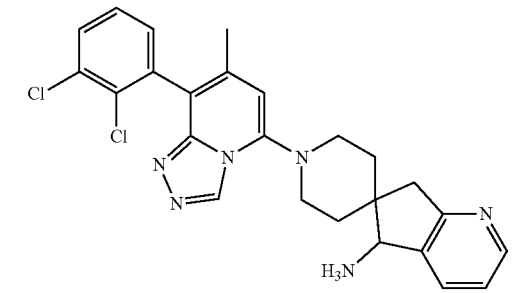
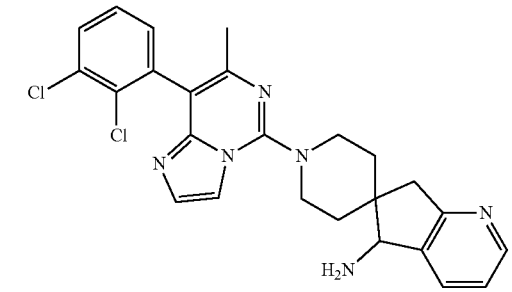
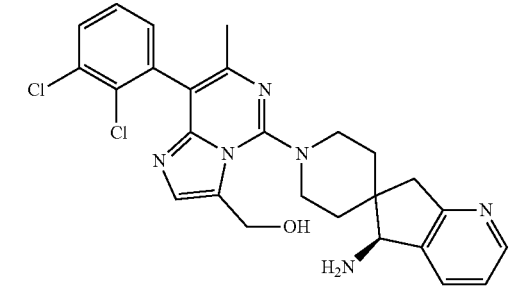
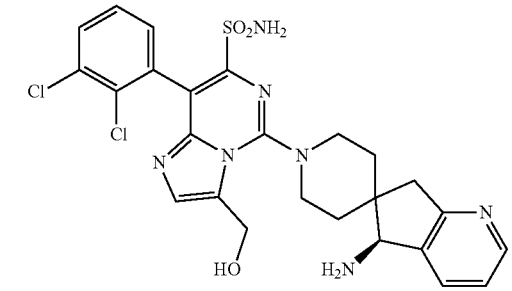

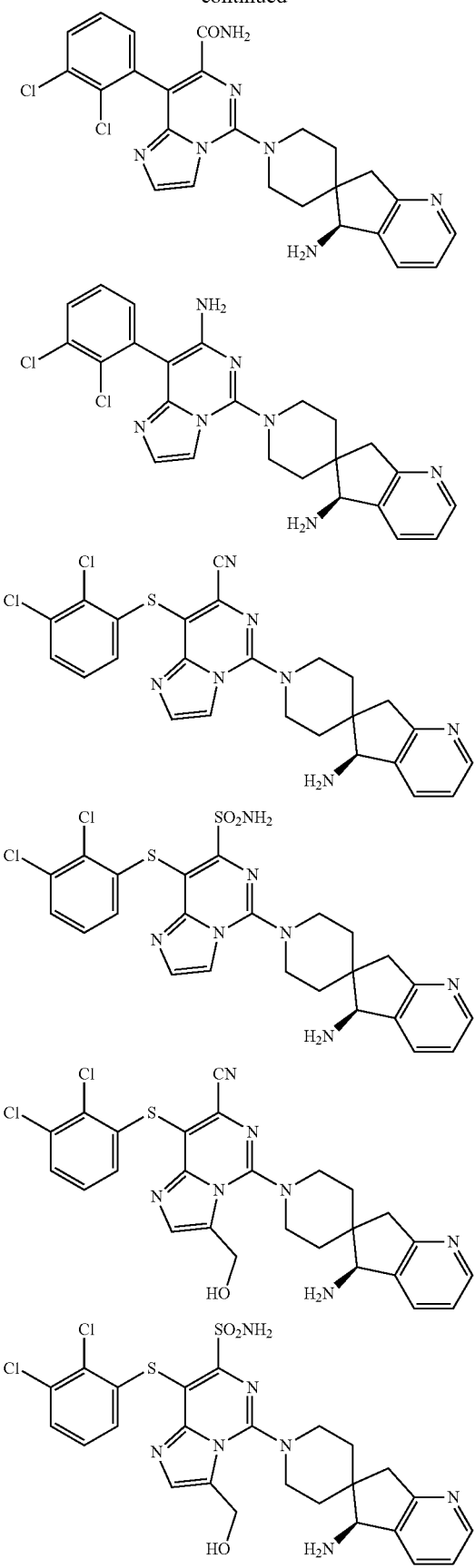
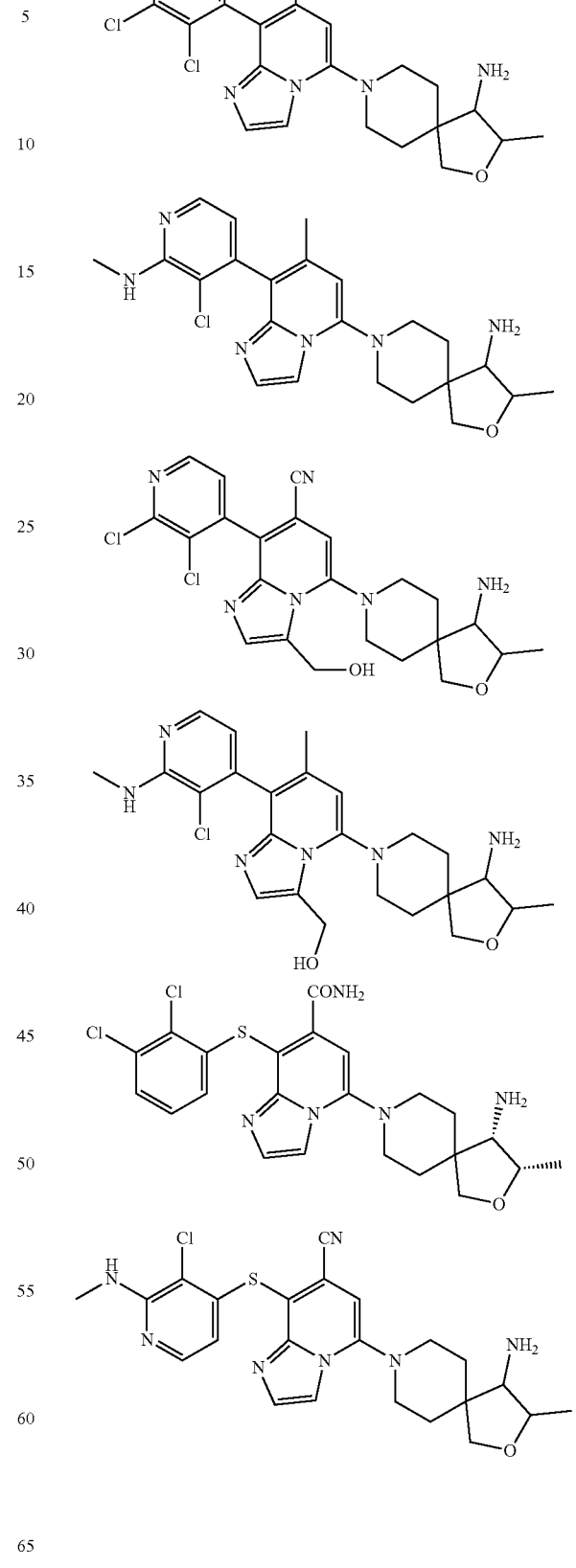

165
-continued

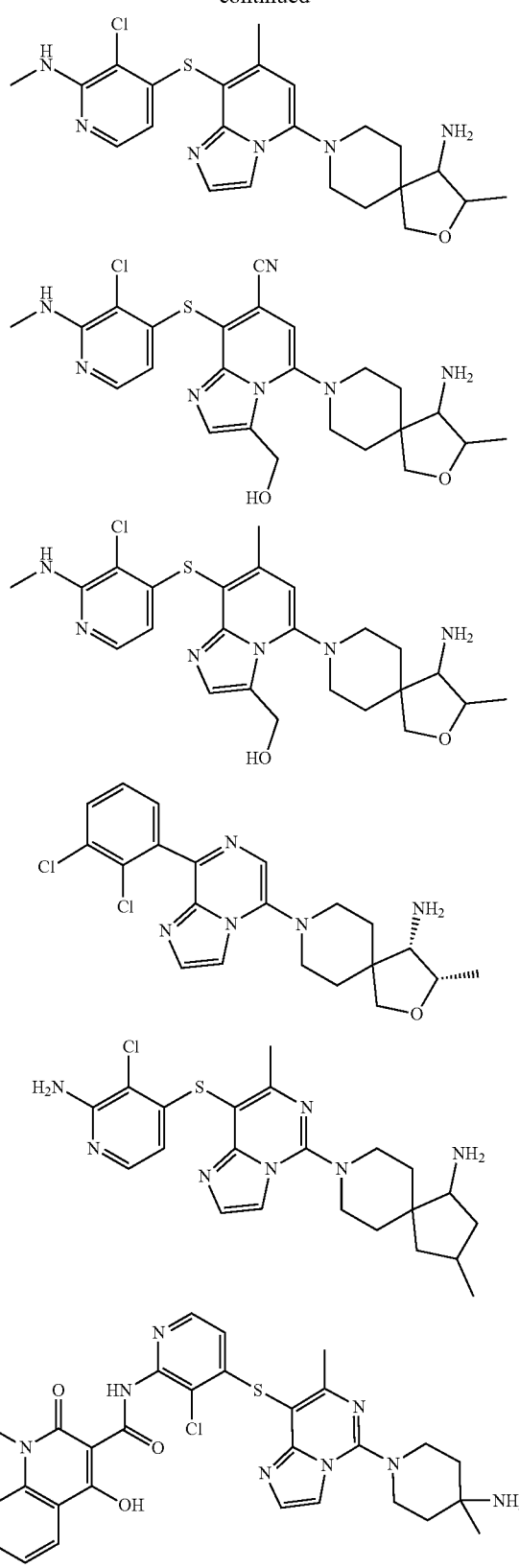

166
-continued

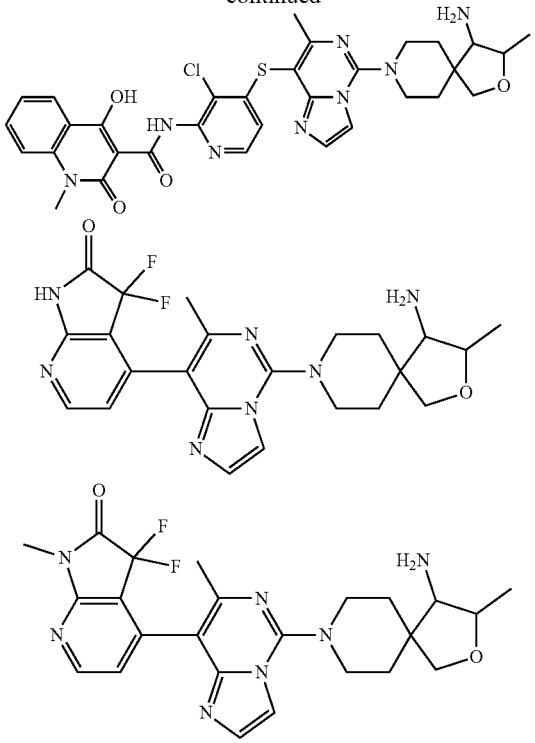

Another object of the present disclosure is to provide a drug for treating or preventing tumors and a composition thereof. The technical scheme to achieve the above object is as follows:

A pharmaceutical composition for treating tumors, consisting of a nitrogen-containing fused heterocyclic compound represented by formula (I-3) described above, or a pharmaceutically acceptable salt thereof, or an enantiomer, a diastereomer, a tautomer, a solvate, a polymorph or a prodrug thereof, and a pharmaceutically acceptable carrier.

Another object of the present disclosure is to provide a use of one of the compounds described above. The technical scheme to achieve the above object is as follows:

the nitrogen-containing fused heterocyclic compound represented by formula (I), or a pharmaceutically acceptable salt thereof, or an enantiomer, a diastereomer, a tautomer, a solvate, a polymorph or a prodrug thereof is used to prepare a drug for treating diseases associated with the activity or expression of proteins such as SHP2, particularly a drug for treating a tumor, an immune disease and an inflammatory disease.

The present disclosure relates to a compound with structural characteristics of a formula (I), wherein the compound can inhibit a variety of tumor cells, particularly can efficiently kill tumors associated with abnormal signaling pathways such as Ras-Raf-ERK, PD-L1, etc., and is a class of therapeutic drugs with a novel mechanism of action.

Terms

Unless otherwise defined, all technical terms herein have the same meaning as generally understood by those skilled in the art to which the subject of the claims are concerned. Unless otherwise indicated, all patents, patent applications, and publications cited herein are incorporated herein by reference in their entirety.

It should be understood that the foregoing brief description and the following detailed description are exemplary and only for explanation, but do not impose any limitation on the subject of the present invention. The singular forms used in the application include the meaning of the plural forms unless otherwise specified. It must be noted that the singular forms used in the specification and claims include the plural forms of the things indicated, unless otherwise clearly indicated herein. It should also be noted that "or", "alternatively" is used to represent "and/or" unless otherwise indicated. In addition, the terms "include" and other forms thereof, such as "including", "containing" and "comprising" used are not restrictive.

Definitions of standard chemical terms are available in references (including Carey and Sundberg "ADVANCED ORGANIC CHEMISTRY 4TH ED." Vols. A (2000) and B (2001), Plenum Press, New York). Unless otherwise indicated, conventional methods within the technical scope of the art, such as mass spectrometry, NMR, IR and UV/VIS spectroscopy, and pharmacological methods are used. Unless specifically defined, the terms used herein in the descriptions of analytical chemistry, synthetic organic chemistry, and pharmaceutical and medicinal chemistry are known in the art. Standard techniques can be used in chemical synthesis, chemical analysis, drug preparation, formulation and delivery, and treatment of patients. For example, reaction and purification may be performed according to the manufacturer's instructions for use of the kit, or in a manner known in the art or in accordance with the Specification of the present disclosure. The techniques and methods described above may generally be implemented according to conventional methods well known in the art based on the descriptions in the multiple schematic and more specific references cited and discussed in the Specification. In the Specification, groups and substituents thereof can be selected by those skilled in the art to provide stable structural moieties and compounds.

When a substituent is described by a conventional chemical formula written from left to right, the substituent also includes a chemically equivalent substituent obtained when the structural formula is written from right to left. For example, —CH$_2$O— is equivalent to —OCH$_2$—.

The section headings used herein are only for the purpose of arranging the article and should not be construed as limiting the subject described above. References, in whole or in part, cited herein including but not limited to patents, patent applications, articles, books, operating manuals, and papers, are hereby incorporated by reference in their entirety.

Some chemical groups defined herein are preceded by simplified symbols to represent the total number of carbon atoms present in the groups. For example, C$_{1-6}$ alkyl refers to the alkyl with a total of 1 to 6 carbon atoms as defined below. The total number of the carbon atoms in the simplified symbol does not include carbon that may be present in a substituent of the group.

In addition to those as described above, when used in the Specification and claims of the application, the following terms have the meanings as described below unless otherwise specified.

In the application, the term "halogen" refers to fluorine, chlorine, bromine, or iodine; "hydroxy" refers to a —OH group; "hydroxyalkyl" refers to the alkyl substituted with the hydroxy (—OH) as defined below; "carbonyl" refers to a —C(=O)— group; "nitro" refers to —NO$_2$; "cyano" refers to —CN; "amino" refers to —NH$_2$; "substituted amino" refers to the amino substituted with one or two of the alkyl, alkylcarbonyl, arylalkyl and heteroarylalkyl as defined below, for example, monoalkylamino, dialkylamino, alkylamido, arylalkylamino, and heteroarylalkylamino; "carboxyl" refers to —COOH.

In the application, as a group or a part of other group (e.g., used in groups such as a halogen substituted alkyl, etc.), the term "alkyl" refers to a straight or branched hydrocarbon chain group which only consists of carbon atoms and hydrogen atoms, contains no unsaturated bonds, has, for example, 1-12 (preferably 1-8, more preferably 1-6) carbon atoms, and is linked to the rest of a molecule by a single bond. Examples of alkyl include, but are not limited to, methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, nonyl, decyl, etc.

In the application, as a group or a part of other group, the term "alkenyl" refers to a straight or branched hydrocarbon chain group which only consists of carbon atoms and hydrogen atoms, contains at least one double bond, has, for example, 2-14 (preferably 2-10, more preferably 2-6) carbon atoms, and is linked to the rest of a molecule by a single bond, e.g. but not limited to, vinyl, propenyl, allyl, but-1-alkenyl, but-2-alkenyl, pent-1-enyl, pent-1,4-dienyl, etc.

In the application, as a group or a part of other group, the term "alkynyl" refers to a straight or branched hydrocarbon chain group which only consists of carbon atoms and hydrogen atoms, contains at least one triple bond and optionally one or more double bonds, has, for example, 2-14 (preferably 2-10, more preferably 2-6) carbon atoms, and is linked to the rest of a molecule by a single bond, e.g. but not limited to, ethynyl, prop-1-alkynyl, but-1-alkynyl, pent-1-en-4-ynyl, etc.

In the application, as a group or a part of other group, the term "cycloalkyl" refers to a stable non-aromatic monocyclic or polycyclic alkyl only consisting of carbon atoms and hydrogen atoms, wherein the cycloalkyl may include a fused ring system, a bridged ring system, or a spiro system with 3-15 carbon atoms, preferably 3-10 carbon atoms, more preferably 3-8 carbon atoms, and the cycloalkyl is saturated or unsaturated and may be linked to the rest of a molecule by a single bond via any suitable carbon atom. Unless otherwise specified in the Specification, the carbon atoms in the cycloalkyl may optionally be oxidized. Examples of cycloalkyl include, but are not limited to, cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-dihydroindenyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo [2.2.1] heptyl, 7,7-dimethyl-bicyclo [2.2.1] heptyl, bicyclo [2.2.1] heptenyl, bicyclo [2.2.2] octyl, bicyclo [3.1.1] heptyl, bicyclo [3.2.1] octyl, bicyclo [2.2.2] octenyl, bicyclo [3.2.1] octenyl, adamantyl, octahydro-4,7-methylene-1H-indenyl and octahydro-2,5-methylene-cyclopentadienyl, etc.

In the application, as a group or a part of other group, the term "heterocyclyl" refers to a stable 3-20 membered non-aromatic cyclic group consisting of 2-14 carbon atoms and 1-6 heteroatoms selected from nitrogen, phosphorus, oxygen, and sulfur. Unless otherwise specified in the Specification, the heterocyclyl may be a monocyclic, bicyclic, tricyclic or more-ring system, wherein the heterocyclyl may include a fused ring system, a bridged ring system, or a spiro system; nitrogen, carbon or sulfur atom in the heterocyclyl thereof may optionally be oxidized; the nitrogen atom may optionally be quaternized; and the heterocyclyl may be partially or completely saturated. The heterocyclyl may be linked to the rest of a molecule by a single bond via carbon atoms or heteroatoms. In the heterocyclyl containing a fused ring, one or more rings may be aryl or heteroaryl as defined below, provided that a junction to the rest of a molecule is a non-aromatic ring atom. For the objects of the present disclosure, the heterocyclyl is preferably a stable 4-11 membered non-aromatic monocyclic, bicyclic, bridged ring or spiro group containing 1-3 heteroatoms selected from nitrogen, oxygen and sulfur, and more preferably a stable 4-8 membered non-aromatic monocyclic, bicyclic, bridged ring or spiro group containing 1-3 heteroatoms selected from nitrogen, oxygen and sulfur. Examples of the heterocyclyl include, but are not limited to, pyrrolidinyl, morpholinyl, piperazinyl, homopiperazinyl, piperidinyl, thiomorpholinyl, 2,7-diaza-spiro [3.5]nonane-7-yl, 2-oxa-6-aza-spiro [3.3] heptan-6-yl, 2,5-diaza-bicyclo [2.2.1] heptan-2-yl, azetidinyl, pyranyl, tetrahydropyranyl, thienyl, tetrahydrofuranyl, oxazinyl, dioxolane, tetrahydroisoquinolinyl, decahydroisoquinolinyl, imidazolidinyl, imidazolidinyl, quinazinyl, thiazolidinyl, isothiazolidinyl, isoxazolidinyl, dihydroindolyl, octahydroindolyl, octahydroisoindolyl, pyrrolidinyl, pyrazolidinyl, phthalimide, etc.

In the application, as a group or a part of other group, the term "aryl" refers to a conjugated hydrocarbon ring system group with 6-18 carbon atoms (preferably 6-10 carbon atoms). For the object of the present disclosure, the aryl may be a monocyclic, bicyclic, tricyclic or more-ring system, or may be fused to the cycloalkyl or heterocyclyl as defined above, provided that the aryl is linked to the rest part of a molecule by a single bond via atoms on the aromatic ring. Examples of the aryl include, but are not limited to, phenyl, naphthyl, anthryl, phenanthryl, fluorenyl, 2,3-dihydro-1H-isoindolyl, 2-benzoxazolinone, 2H-1,4-benzoxazin-3 (4H)-keto-7-yl, etc.

In the application, the term "arylalkyl" refers to the alkyl as defined above which is substituted with the aryl as defined above.

In the application, as a group or a part of other group, the term "heteroaryl" refers to a 5-16 membered conjugated ring group with 1-15 carbon atoms (preferably 1-10 carbon atoms) and 1-6 heteroatoms selected from nitrogen, oxygen and sulfur in the ring. Unless otherwise specified in the Specification, the heteroaryl may be a monocyclic, bicyclic, tricyclic or more-ring system, or may be fused to the cycloalkyl or heterocyclyl as defined above, provided that the aryl is linked to the rest part of a molecule by a single bond via atoms on the aromatic ring. Nitrogen, carbon or sulfur atoms in the heteroaryl may optionally be oxidized; the nitrogen atoms may optionally be quaternized. For the objects of the present disclosure, the heteroaryl is preferably a stable 5-12 membered aromatic group containing 1-5 heteroatoms selected from nitrogen, oxygen and sulfur, and more preferably a stable 5-10 membered aromatic group containing 1-4 heteroatoms selected from nitrogen, oxygen and sulfur or a 5-6 membered aromatic group containing 1-3 heteroatoms selected from nitrogen, oxygen and sulfur. Examples of the heteroaryl include, but are not limited to, thienyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furyl, pyrrolyl, triazolyl, tetrazolyl, triazinyl, indazinyl, isoazinylindolyl, indazolyl, isoindazolyl, purinyl, quinolinyl, isoquinolinyl, diazonaphthyl, naphthyridyl, quinoxolinyl, pteridinyl, carbazolyl, carbazolyl, phenanthridyl, phenanthrolinyl, acridyl, phenazinyl, isothiazolyl, benzothiazolyl, benzothiophenyl, oxotriazolyl, cinnolinyl, quinazolyl, thiophenyl, phenylthio, indolizinyl, o-phenanthroline, isoxazolyl, phenoxazinyl, phenothiazinyl, 4,5,6,7-tetrahydrobenzo [b]thienyl, naphthopyridyl, [1,2,4] triazolo [4,3-b] pyridazine, [1,2,4] triazolo [4,3-a]pyrazine, [1,2,4] triazolo [4,3-c] pyrimidine, [1,2,4] triazolo [4,3-a] pyridine, imidazo [1,2-a] pyridine, imidazo [1,2-b] pyridazine, imidazo [1,2-a] pyrazine, etc.

In the application, the term "heteroarylalkyl" refers to the alkyl as defined above which is substituted with the heteroaryl as defined above.

In the application, "optional" or "optionally" indicates that an event or condition described herein below may or may not occur, and the description includes both the presence and absence of the event or condition at the same time. For example, "optionally substituted aryl" indicates that the aryl is substituted or unsubstituted, and the description includes both the substituted aryl and the unsubstituted aryl at the same time.

The terms "moiety", "structural moiety", "chemical moiety", "group" and "chemical group" used herein refer to specific fragments or functional groups in a molecule. The chemical moiety is generally considered to be a chemical entity embedded or linked to the molecule.

"Stereoisomer" refers to a compound which consists of the same atoms bonded by the same bonds, but with different three-dimensional structures. The present disclosure covers various stereoisomers and mixtures thereof.

When a compound of the present disclosure contains an ene double bond, the compound of the present disclosure is intended to contain E- and Z-geometric isomers, unless otherwise indicated.

"Tautomer" refers to an isomer formed by transferring a proton from an atom of a molecule to another atom of the same molecule. All tautomeric forms of the compound of the present disclosure are included within the scope of the present disclosure.

The compound of the present disclosure or a pharmaceutically acceptable salt thereof may contain one or more chiral carbon atoms and thus may yield an enantiomer, a diastereoisomer, and other stereoisomeric forms. Each chiral carbon atom may be defined as (R)- or (S)-based on stereo chemistry. The present disclosure is intended to include all possible isomers, as well as racemic and optically pure forms thereof. A racemate, a diastereomer or an enantiomer may be selected as raw materials or intermediates for the preparation of the compound of the present disclosure. Optically active isomers can be prepared using chiral synthons or chiral reagents, or resolved using conventional techniques such as crystallization and chiral chromatography.

Conventional techniques for preparing/separating individual isomers include chiral synthesis from suitable optically pure precursors, or resolution of racemates (or racemates of salts or derivatives) using, for example, chiral high performance liquid chromatography, for example, see Gerald Gubitz and Martin G. Schmid (Eds.), Chiral Separations, Methods and Protocols, Methods in Molecular Biology, Vol. 243, 2004; A. M. Stalcup, Chiral Separations, Annu. Rev. Anal. Chem. 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, Acc. Chem. Res. 1990, 23, 128.

In the application, the term "Pharmaceutically Acceptable Salt" includes a pharmaceutically acceptable acid addition salt and a pharmaceutically acceptable base addition salt.

The "Pharmaceutically Acceptable Acid Addition Salt" refers to a salt which is formed with an inorganic acid or an organic acid and can retain the biological effectiveness of a free base without other side effects, wherein the inorganic acid salt includes, but is not limited to, hydrochloride, hydrobromide, sulfate, nitrate, phosphate, etc.; the organic acid salt includes, but is not limited to, formate, acetate, 2,2-dichloroacetate, trifluoroacetate, propionate, hexanoate, caprylate, decanoate, undecylenate, glycolate, gluconate, lactate, sebacate, adipate, glutarate, malonate, oxalate, maleate, succinate, fumarate, tartrate, citrate, palmitate, stearate, oleate, cinnamate, laurate, malate, glutamate, pyroglutamate, aspartate, benzoate, methanesulfonate, benzene sulfonate, p-tosylate, alginate, ascorbate, salicylate, 4-aminosalicylate, naphthalene disulfonate, etc. The salts can be prepared by methods known in the art.

The "Pharmaceutically Acceptable Base Addition Salt" refers to a salt which is formed with an inorganic base or an organic base and can retain the biological effectiveness of a free acid without other side effects. Salts derived from the inorganic base include, but are not limited to, sodium salts, potassium salts, lithium salts, ammonium salts, calcium salts, magnesium salts, iron salts, zinc salts, copper salts, manganese salts, aluminum salts, etc. Preferred inorganic salts are the ammonium salts, the sodium salts, the potassium salts, the calcium salts and the magnesium salts. Salts derived from the organic base include, but are not limited to, the following salts of primary, secondary and tertiary amines, substituted amines including naturally substituted amines, cyclic amines, and basic ion exchange resins, such as ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin, etc. Preferred organic bases include isopropylamine, diethylamine, ethanolamine, trimethylamine, dicyclohexylamine, choline, and caffeine. The salts can be prepared by methods known in the art.

"Polymorph" refers to different solid crystalline phases of some compounds of the present disclosure in the solid state due to the presence of two or more different molecular arrangements. The some compounds of the present disclosure may be present in more than one crystalline form, and the present disclosure is intended to include various crystal forms and mixtures thereof.

Typically, crystallization may produce a solvate of the compound of the present disclosure. The term "solvate" used in the present disclosure refers to an aggregate containing one or more molecules of the compound of the present disclosure and one or more molecules of a solvent, wherein the solvent may be water, in which case the solvate is a hydrate. Alternatively, the solvent may be an organic solvent. Thus, the compound of the present disclosure may be present in hydrates, including monohydrates, dihydrates, hemihydrates, sesquihydrates, trihydrates, tetrahydrates, etc., and corresponding solvated forms. The compound of the present invention can form a true solvate, but in some cases, the compound can also retain only indeterminate water or a mixture of water and a part of indeterminate solvent. The compound of the present disclosure may be reacted in the solvent or precipitated or crystallized from the solvent. The solvate of the compound of the present disclosure is also included within the scope of the present disclosure.

The present disclosure further comprises a prodrug of the compound described above. In the present application, the term "prodrug" indicates a compound of the bioactive compound of the present disclosure that can be converted to cost under physiological conditions or by solvolysis. Therefore, the term "prodrug" refers to a pharmaceutically acceptable metabolic precursor of the compound of the present disclosure. When the prodrug is administered to an individual in need, the prodrug may be inactive but is converted into the active compound of the present disclosure in vivo. The prodrug is usually converted rapidly in vivo to produce the parent compound of the present disclosure, for example, by hydrolysis in the blood. The prodrug compound generally provides the advantages of solubility, histocompatibility, or sustained release in mammalian organisms. The prodrug includes known amino protective groups and carboxy protective groups. For specific preparation method for the prodrug, refer to Saulnier, M. G., et al., Bioorg. Med. Chem. Lett. 1994, 4, 1985-1990; Greenwald, R. B., et al., J. Med. Chem. 2000, 43, 475.

In the present application, the "Pharmaceutical Composition" refers to the compound of the present disclosure and a formulation of a medium generally accepted in the art for delivering a bioactive compound to a mammal (e.g., human). The medium includes a pharmaceutically acceptable carrier. The object of the pharmaceutical composition is to promote the administration of an organism, and facilitate the absorption of active ingredients, thereby exerting the bioactivity.

The term "Pharmaceutically Acceptable" used herein refers to a substance (e.g., a carrier or a diluent) that does not affect the bioactivity or nature of the compound of the present disclosure and is relatively nontoxic, i.e. the substance can be administered to an individual without causing any adverse biological reactions or interacting adversely with any component contained in the composition.

In the application, the "Pharmaceutically Acceptable Carrier" includes, but is not limited to, any adjuvants, carriers, excipients, fluidizers, sweeteners, diluents, preservatives, dyes/colouring agents, flavoring agents, surfactants, wetting agents, dispersants, suspensions, stabilizers, isotonic agents, solvents, or emulsifiers which are licensed by the relevant government authorities to be acceptable for use in humans or livestocks.

The terms such as "Tumor", "Diseases Associated with Abnormal Cell Proliferation", etc. of the present disclosure include, but are not limited to, leukemia, gastrointestinal stromal tumors, histiocytic lymphoma, non-small cell lung cancer, small cell lung cancer, pancreatic cancer, lung squamous cell carcinoma, lung adenocarcinoma, breast cancer, prostate cancer, liver cancer, skin cancer, epithelial cell cancer, cervical cancer, ovarian cancer, intestinal cancer, nasopharyngeal cancer, brain cancer, bone cancer, esophageal cancer, melanoma, renal cancer, buccal cavity cancer, etc.

The terms "Prevented," "Prevent", and "Preventing" used herein include reduction of the possibility of occurrence or exacerbation of diseases or conditions to patients.

The term "Treatment" and other similar synonyms used herein include the following meanings:
(i) Preventing the occurrence of diseases or conditions in the mammals, especially when such mammals are susceptible to such diseases or conditions but have not been diagnosed with the diseases or conditions;
(ii) Inhibiting the diseases or conditions, i.e., restraining the development of the diseases or conditions;

(iii) Alleviating the diseases or conditions, i.e., resolving the diseases or conditions; or (iv) Relieving symptoms caused by the diseases or conditions.

The terms "Effective Amount", "Therapeutically Effective Amount" or "Pharmaceutically Effective Amount" used herein refer to an amount of at least one agent or compound sufficient to alleviate one or more symptoms of the disease or condition being treated to a certain extent after administration. The outcome may be a resolution and/or remission of signs, symptoms or etiology, or any other desired change in a biological system. For example, the "effective amount" for treatment refers to an amount of the composition containing the compound disclosed herein that is required to provide a clinically significant remission effect. The effective amount suitable for any individual case may be determined using techniques such as dose escalation trials.

The terms "Taking", "Administering", "Administration", etc. used herein refer to methods capable of delivering the compound or the composition to a desired site for a biological action. The methods include, but are not limited to, oral route, transduodenal route, parenteral injection (including intravenous, subcutaneous, intraperitoneal, intramuscular, intraarterial injection or infusion), topical administration, and transrectal administration. Those skilled in the art are familiar with administration techniques that can be used for the compound and methods described herein, for example, techniques discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compound and the composition discussed herein are administered orally.

The terms "Pharmaceutical Combination", "in Combination with A Drug", "Co-Administration", "Administer Other Therapy", "Administer Other Therapeutic Agent", etc. used herein refer to a drug therapy obtained by mixing or combining more than one active ingredient, wherein the drug therapy includes fixed and unfixed combinations of active ingredients. The term "Fixed Combination" refers to the simultaneous administration of at least one compound described herein and at least one synergistic agent to a patient in the form of a single entity or a single dosage form. The term "Unfixed Combination" refers to the simultaneous administration, co-administration, or sequential administration in turn of at least one compound and at least one synergistic formulation described herein to a patient in the form of a separate entity. The terms are also applied in the cocktail therapy, for example by administering three or more active ingredients.

Those skilled in the art should also understand that in the methods described below, a functional group of the intermediate compound may need to be protected by an appropriate protective group. Such functional group includes hydroxyl, amino, mercapto and carboxylic acid. Appropriate hydroxy protective groups include trialkylsilyl or diarylalkylsilyl (e.g., tert-butyldimethylsilyl, tert-butyldiphenylsilyl or trimethylsilyl), tetrahydropyranyl, benzyl, etc. Appropriate amino, amidino and guanidino protective groups include tert-butoxycarbonyl, benzyloxycarbonyl, etc. Appropriate mercapto protective groups include —C(O)—R" (wherein R" is alkyl, aryl or arylalkyl), p-methoxybenzyl, triphenylmethyl, etc. Appropriate carboxyl protective groups include alkyl, aryl or arylalkyl esters.

The protective groups may be introduced and removed in accordance with standard techniques known to those skilled in the art and described herein. The use of the protective groups is detailed in Greene, T. W. and P. G. M. Wuts, Protective Groups in Organic Synthesis, (1999), $4^{th}$ Ed., Wiley. The protective group may also be a polymer resin.

Amino protective groups are well known in the art and include those described in detail in Protective Groups in Organic Synthesis, T. W. Greene and P. G. M. Wuts, 3rd edition, John Wiley & Sons, 1999, incorporated herein by reference. For example, nitrogen protective groups such as acylamino include, but are not limited to, formamide, acetamide, and benzamide; the nitrogen protective groups (e.g., carbamate groups) include, but are not limited to, methylcarbamate, ethylcarbamate, 9-fluorenylmethylcarbamate (Fmoc), 2,7-di-tert-butyl-[9-(10,10-dioxo-10,10,10,10-tetrahydrothixol)] methylcarbamate (DBD-Tmoc), 4-methoxybenzoylcarbamate (Phenoc), 2,2,2-trichloroethylcarbamate (Troc), 2-trimethylsilyl ethylcarbamate (Teoc), 2-phenylethylcarbamate (hZ), 1-(1-adamantyl)-1-methylethylcarbamate (Adpoc), 1,1-dimethyl-2,2-dibromoethylcarbamate (DB-t-BOC), 1,1-dimethyl-2,2,2-trichloroethylcarbamate (TCBOC), 1-methyl-1-(4-diphenyl) ethylcarbamate (Bpoc), 1-(3,5-di-tert-butylphenyl)-1-methylethylcarbamate (t-Bumeoc), 2-(2'- and 4'-pyridyl) ethylcarbamate (Pyoc), tert-butylcarbamate (BOC), 1-adamantylcarbamate (Adoc), vinyl carbamate (Voc), allyl carbamate (Alloc), 1-isopropylallyl carbamate (ipaoc), cinnamyl carbamate (Coc), 4-nitrocinnamyl carbamate (Noc), benzyl carbamate (Cbz), p-methoxybenzyl carbamate (Moz), 4-methylsulfinylbenzyl carbamate (Msz), [2-(1,3-cyclopentyl disulfide)] methylcarbamate (Dmoc), 4-methylphenylthiocarbamate (Mtpc), 2,4-dimethylphenylthiocarbamate (Bmpc), 2-ethylphosphoramate (Peoc), 2-triphenylisopropylcarbamate (Ppoc), 5-benzisoxazolylmethylcarbamate, and 2-(trifluoromethyl)-6-chromone methylcarbamate (Tcroc); The nitrogen protective groups (e.g., sulfonamide groups) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-Dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), P-trimethylsilyl ethanesulfonamide (SES), and 4-(4',8'-dimethoxynaphthylmethyl) benzenesulfonamide (DNMBS); other nitrogen protective groups include, but are not limited to, N-1,1,4,4-tetramethyldisilylazolane adduct (STABASE), N-[2-(trimethylsilyl) ethoxy] methylamine (SEM), N-triphenylmethylamine (Tr), N-[(4-methoxyphenyl) diphenylmethyl] amine (MMTr), N-9-phenylfluorenamine (PhF), N-ferrocenylmethylamino (Fcm), N-cyclohexylideneamine, N-borane derivatives, N-copper chelates, N-zinc chelates, N-nitramine, N-nitrosamine, amine N-oxide, diphenylphosphine amine (Dpp), dimethyl phosphorothioamine (Mpt), diphenyl phosphonothioamine (Ppt), o-nitrobenzenesulfinamide (Nps), and 3-nitropyridine sulfinamide (Npys).

Without violating common sense in the art, each preferred conditions described above may be arbitrarily combined to obtain each preferred example of the present disclosure.

Reagents and raw materials used in the present disclosure are commercially available.

The present disclosure has the positive progressive that the nitrogen-containing fused heterocyclic SHP2 inhibitor compound of the present disclosure has high inhibitory activity for an SHP2 enzyme and MV4-11 cell proliferation, and has good druggability.

DETAILED DESCRIPTION OF THE EMBODIMENT

The following examples further illustrate the present disclosure, but the present disclosure is not limited thereto. In the following examples, experimental methods without specific conditions are selected according to conventional methods and conditions, or according to the product specification.

Preparation of Intermediates

By reference to the synthetic route and method of patent WO2018172984A1, preparing an aryl spiro intermediates 1A-1T.

| No. | Structure | LC-MS(M + H) |
|---|---|---|
| 1A | | 307.1 |
| 1B | | 308.1 |
| 1C | | 325.1 |
| 1D | | 309.1 |
| 1E | 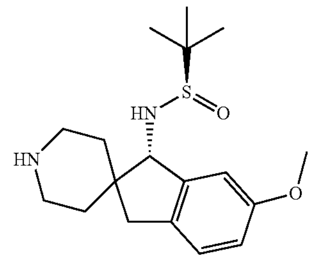 [SMILES: COc1ccc2c(c1)[C@@H](N[S@](=O)C(C)(C)C)C1(CCNCC1)C2] | 337.1 |
| 1F | 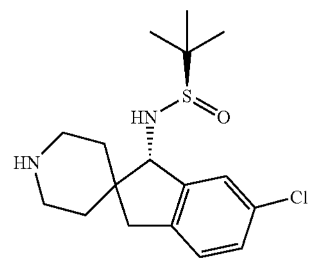 | 341.1/343.1 |
| 1G | 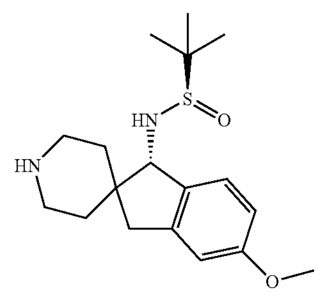 [SMILES: COc1ccc2c(c1)CC1(CCNCC1)[C@@H]2N[S@](=O)C(C)(C)C] | 337.1 |
| 1H | 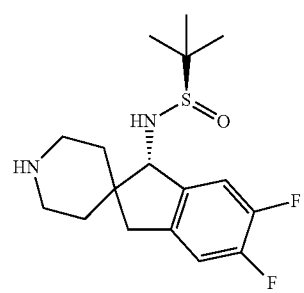 [SMILES: CC(C)(C)[S@@](=O)N[C@@H]1c2cc(F)c(F)cc2CC12CCNCC2] | 343.1 |
| 1I | 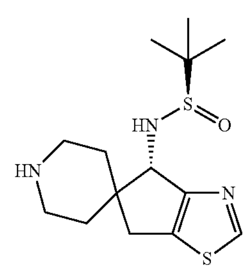 [SMILES: CC(C)(C)[S@@](=O)N[C@@H]1c2ncsc2CC12CCNCC2] | 314.1 |

-continued

| No. | Structure | LC-MS(M + H) |
|---|---|---|
| 1J | 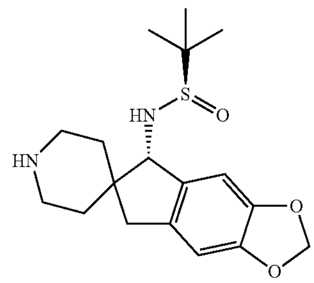 [SMILES: CC(C)(C)[S@@](=O)N[C@@H]1c2cc3c(cc2CC12CCNCC2)OCO3] | 351.1 |
| 1K | 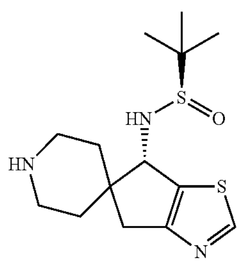 [SMILES: CC(C)(C)[S@@](=O)N[C@@H]1c2scnc2CC12CCNCC2] | 314.1 |
| 1L | 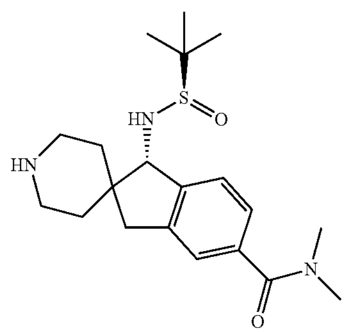 [SMILES: CN(C)C(=O)c1ccc2c(c1)CC1(CCNCC1)[C@@H]2N[S@](=O)C(C)(C)C] | 378.1 |
| 1M | 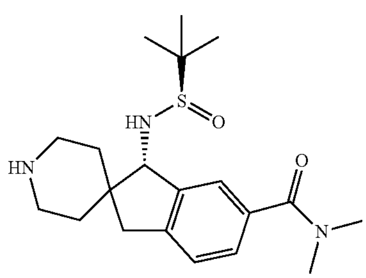 [SMILES: CN(C)C(=O)c1ccc2c(c1)[C@@H](N[S@](=O)C(C)(C)C)C1(CCNCC1)C2] | 378.1 |
| 1N | 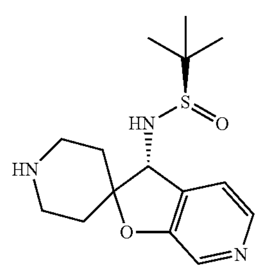 [SMILES: CC(C)(C)[S@@](=O)N[C@@H]1c2ccncc2OC12CCNCC2] | 310.1 |

-continued

| No. | Structure | LC-MS(M + H) |
|---|---|---|
| 1O | 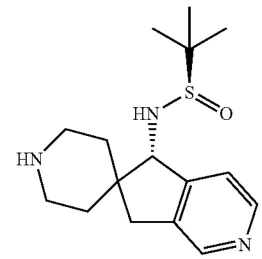 [SMILES: CC(C)(C)[S@@](=O)N[C@@H]1c2ccncc2CC12CCNCC2] | 308.1 |
| 1P | 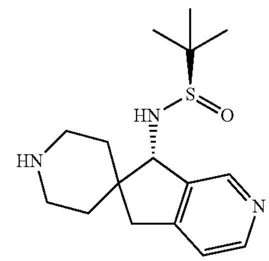 [SMILES: CC(C)(C)[S@@](=O)N[C@@H]1c2cnccc2CC12CCNCC2] | 308.1 |
| 1Q | 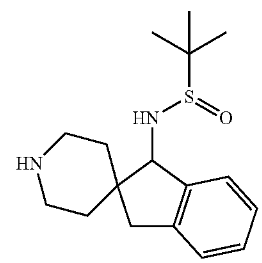 [SMILES: CC(C)(C)S(=O)NC1c2ccccc2CC12CCNCC2] | 307.1 |
| 1R | 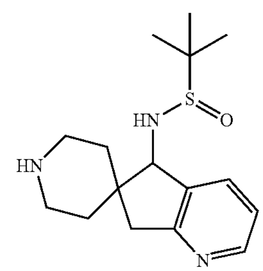 [SMILES: CC(C)(C)S(=O)NC1c2cccnc2CC12CCNCC2] | 308.1 |
| 1S | 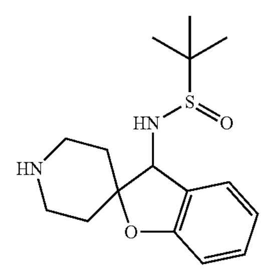 [SMILES: CC(C)(C)S(=O)NC1c2ccccc2OC12CCNCC2] | 309.1 |
| 1T | 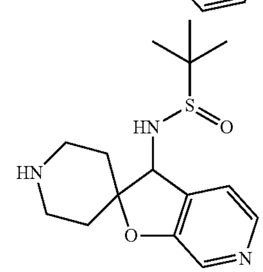 | 310.1 |

With intermediates 1A-1T and other commercial reagents as raw materials, preparing and synthesizing compounds of the following examples sequentially by synthetic methods of the examples, respectively.

Example 1: (S)-1'-(8-((2-amino-3-chloropyridin-4-yl) thio)-7-methylimidazo [1,2-c] pyrimidin-5-yl)-1,3-dihydrospiro [indene-2,4'-piperidine]-1-amine

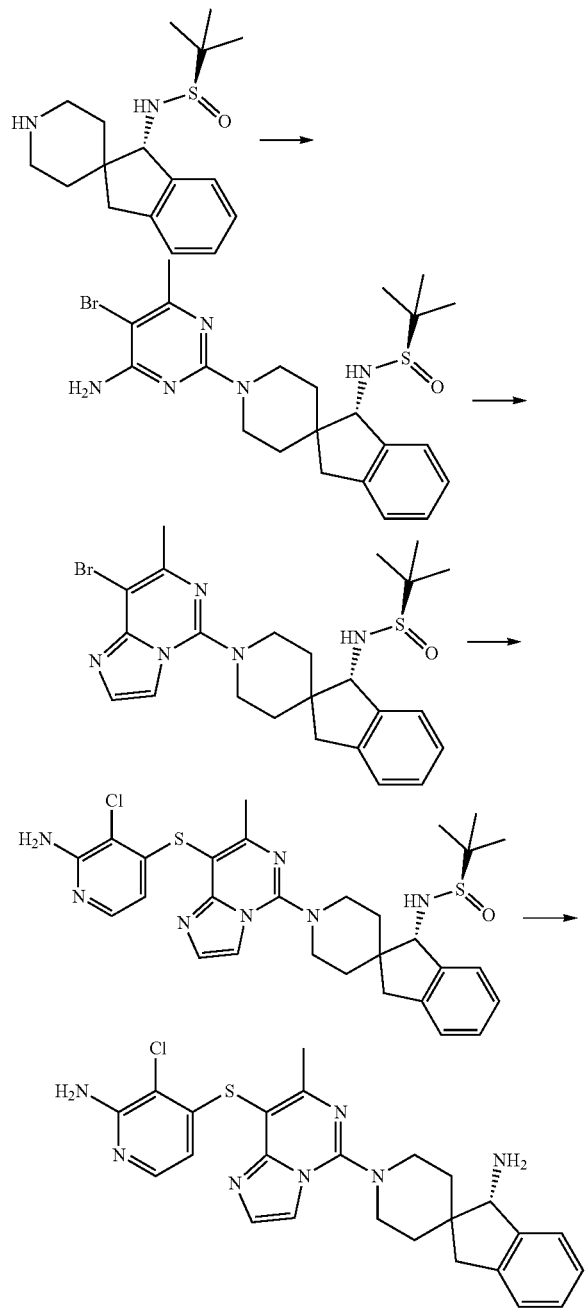

Step 1: Suspending (R)—N—((S)-1,3-dihydrospiro [indene-2,4'-piperidin]-1-yl)-2-methylpropan-2-sulfinamide (488 mg, 1.6 mmol), 5-bromo-2-chloro-6-methylpyrimidin-4-amine (356 mg, 1.6 mmol) and potassium carbonate (662.3 mg, 4.8 mmol) in N,N-dimethylformamide (DMF) (8 mL), and heating to 100° C. for reaction overnight. Cooling a reaction solution to room temperature, pouring the reaction solution into water, extracting with ethyl acetate, drying, concentrating under reduced pressure, and purifying residues by column chromatography to obtain (R)—N—((S)-1'-(4-amino-5-bromo-6-methylpyrimidin-2-yl)-1,3-dihydrospiro [indene-2,4'-piperidin]-1-yl)-2-methylpropan-2-sulfinamide (370 mg, yellow solids). MS(ESI): m/z=491.9/493.9[M+H].

Step 2: Suspending the (R)—N—((S)-1'-(4-amino-5-bromo-6-methylpyrimidin-2-yl)-1,3-dihydrospiro [indene-2,4'-piperidin]-1-yl)-2-methylpropan-2-sulfinamide (450 mg, 0.92 mmol), 40% aqueous chloroacetaldehyde (1.8 g, 9.2 mmol) and sodium acetate (302 mg, 3.7 mmol) in a mixed solvent (20 mL/20 mL) of aqueous ethanol/phosphate buffer solution (pH=6.7), heating to 100° C. and stirring for 16 hours. Cooling the reaction solution to the room temperature, concentrating, extracting with the ethyl acetate, drying, concentrating under the reduced pressure, and purifying by the column chromatography to obtain (R)—N—((S)-1'-(8-bromo-7-methylimidazo [1,2-c] pyrimidin-5-yl)-1,3-dihydrospiro [indene-2,4'-piperidin]-1-yl)-2-methylpropan-2-sulfinamide (340 mg, yellow oil). MS(ESI): m/z=515.8/517.8[M+H]; 1H-NMR (400 MHz, DMSO_d6) δ7.67 (d, J=1.2 Hz, 1H), 7.59 (d, J=1.2 Hz, 1H), 7.29-7.31 (m, 1H), 7.21-7.23 (m, 3H), 5.68 (d, J=10.4 Hz, 1H), 4.47 (d, J=10.4 Hz, 1H), 3.70-3.78 (m, 2H), 3.09-3.45 (m, 6H), 2.71-2.75 (m, 1H), 2.17-2.24 (m, 1H), 1.93-1.99 (m, 1H), 1.54-1.67 (m, 1H), 1.39-1.42 (m, 1H), 1.22 (s, 9H).

Step 3: Suspending the (R)—N—((S)-1'-(8-bromo-7-methylimidazolo [1,2-c]pyrimidin-5-yl)-1,3-dihydrospiro [indene-2,4'-piperidin]-1-yl)-2-methylpropan-2-sulfinamide (340 mg, 0.66 mmol), sodium 2-amino-3-chloropyridine-4-thiophenolate (121 mg, 0.66 mmol), 3,4,7,8-tetramethylphenanthroline (32 mg, 0.13 mmol), copper iodide (CuI) (25 mg, 0.13 mmol) and the potassium carbonate (255 mg, 1.8 mmol) in dimethylsulfoxide (DMSO) (2 mL), exchanging with nitrogen for three times, and raising the temperature to 120° C. for reaction overnight. Cooling the reaction solution to the room temperature, pouring the reaction solution into water, extracting with the ethyl acetate, drying, concentrating under the reduced pressure, and purifying the residue by preparative chromatography to obtain (R)—N—((S)-1'-(8-((2-amino-3-chloropyridin-4-yl) thio)-7-methylimidazo [1,2-c] pyrimidin-5-yl)-1,3-dihydrospiro [indene-2,4'-piperidin]-1-yl)-2-methylpropan-2-sulfinamide (56 mg, colorless oil). MS(ESI): m/z=596.2[M+H].

Step 4: Dissolving the (R)—N—((S)-1'-(8-((2-amino-3-chloropyridin-4-yl) thio)-7-methylimidazo [1,2-c] pyrimidin-5-yl)-1,3-dihydrospiro [indene-2,4'-piperidin]-1-yl)-2-methylpropan-2-sulfinamide (56 mg, 0.094 mmol) in a 2M hydrogen chloride/methanol (HCl/MeOH) solution (5 mL) and stirring at room temperature for 1 hour. After the reaction is completed, concentrating under the reduced pressure, and purifying the residue by preparative chromatography to obtain the target compound: (S)-1'-(8-((2-amino-3-chloropyridin-4-yl) thio)-7-methylimidazo [1,2-c] pyrimidin-5-yl)-1,3-dihydrospiro [indene-2,4'-piperidine]-1-amine (27 mg, white solids). MS(ESI): m/z=492.1/494.1 [M+H]; 1H-NMR (400 MHz, CD3OD) δ7.92 (d, J=2.0 Hz, 1H), 7.69 (d, J=1.6 Hz, 1H), 7.54-7.57 (m, 2H), 7.36-7.48 (m, 3H), 6.18 (d, J=6.4 Hz, 1H), 4.50 (s, 1H), 4.11-4.25 (m, 2H), 3.50-3.64 (m, 2H), 3.26 (s, 2H), 2.64 (s, 3H), 1.67-2.20 (m, 4H).

Example 2: (S)-1'-(7-methyl-8-(2-(trifluoromethyl) pyridin-3-yl) thio) imidazo [1,2-c] pyrimidin-5-yl)- 1,3-dihydrospiro [indene-2,4'-piperidine]-1-amine

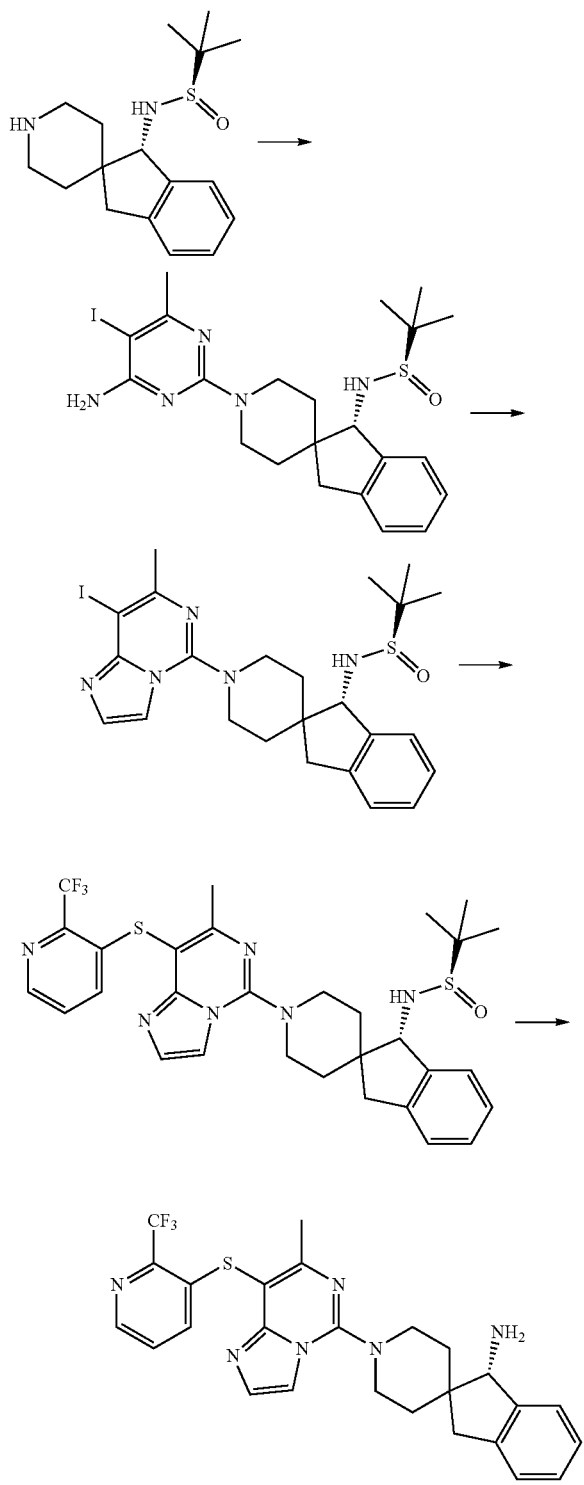

Step 1: Suspending (R)—N—((S)-1,3-dihydrospiro [indene-2,4'-piperidin]-1-yl)-2-methylpropan-2-sulfinamide (603 mg, 1.97 mmol), 5-iodo-2-chloro-6-methylpyrimidin-4-amine (530 mg, 1.976 mmol) and potassium carbonate (662.3 mg, 4.8 mmol) in N,N-dimethylformamide (DMF) (15 mL), and heating to 100° C. for reaction for 16 hours. Cooling a reaction solution to room temperature, pouring the reaction solution into water, extracting with dichloromethane for four times, drying in an organic phase, concentrating under reduced pressure, and purifying by column chromatography to obtain (R)—N—((S)-1'-(4-amino-5-iodo-6-methylpyrimidin-2-yl)-1,3-dihydrospiro [indene-2,4'-piperidin]-1-yl)-2-methylpropan-2-sulfinamide (670 mg, yellow solids). MS(ESI): m/z=540.3[M+H].

Step 2: Suspending the (R)—N—((S)-1'-(4-amino-5-iodo-6-methylpyrimidin-2-yl)-1,3-dihydrospiro [indene-2,4'-piperidin]-1-yl)-2-methylpropan-2-sulfinamide (520 mg, 0.96 mmol), 40% aqueous chloroacetaldehyde (1.9 g, 9.6 mmol) and sodium acetate (524.7 mg, 6.4 mmol) in a mixed solvent (24 mL/24 mL) of aqueous ethanol/phosphate buffer solution (pH=6.7), heating to 60° C. and stirring for 16 hours. Cooling the reaction solution to the room temperature, concentrating, extracting with the ethyl acetate, drying, concentrating under the reduced pressure, and purifying by the column chromatography to obtain (R)—N—((S)-1'-(8-iodo-7-methylimidazo [1,2-c] pyrimidin-5-yl)-1,3-dihydrospiro [indene-2,4'-piperidin]-1-yl)-2-methylpropan-2-sulfinamide (120 mg, yellow oil). MS(ESI): m/z=564.1[M+H].

Step 3: Suspending the (R)—N—((S)-1'-(8-iodo-7-methylimidazolo [1,2-c]pyrimidin-5-yl)-1,3-dihydrospiro [indene-2,4'-piperidin]-1-yl)-2-methylpropan-2-sulfinamide (30.0 mg, 0.053 mmol), 2-(trifluoromethyl) pyridine-3-thiophenol (49.0 mg, 0.27 mmol), 3,4,7,8-tetramethylphenanthroline (2.64 mg, 0.011 mmol), copper iodide (CuI) (2.13 mg, 0.011 mmol) and the potassium carbonate (21.6 mg, 0.16 mmol) in DMSO (2 mL), exchanging with nitrogen, and then raising the temperature to 120° C. for reaction for 16 hours. Cooling the reaction solution to the room temperature, pouring the reaction solution into water, extracting with the ethyl acetate, drying, concentrating under the reduced pressure, and purifying the residue by preparative chromatography to obtain (R)—N—((S)-1'-(8-((2-(trifluoromethyl)-pyridin-3-yl) thio)-7-methylimidazo [1,2-c] pyrimidin-5-yl)-1,3-dihydrospiro [indene-2,4'-piperidin]-1-yl)-2-methylpropan-2-sulfinamide (30 mg, yellow oil). MS(ESI): m/z=615.5[M+H].

Step 4: Dissolving the (R)—N—((S)-1'-(8-((2-amino-3-chloropyridin-4-yl) thio)-7-methylimidazo [1,2-c] pyrimidin-5-yl)-1,3-dihydrospiro [indene-2,4'-piperidin]-1-yl)-2-methylpropan-2-sulfinamide (30 mg, 0.049 mmol) in methanol (3 mL), adding 3 M HCl/MeOH (1 mL), and then stirring at room temperature for 2 hour. After the reaction is completed, concentrating under the reduced pressure, and purifying the residue by preparative chromatography to obtain the target compound: (S)-1'-(7-methyl-8-(2-(trifluoromethyl) pyridin-3-yl) thio) imidazo [1,2-c] pyrimidin-5-yl)-1,3-dihydrospiro [indene-2,4'-piperidine]-1-amine (5 mg, white solids). MS(ESI): m/z=511.5[M+H]; 1H-NMR (400 MHz, CD3OD) δ8.46 (d, J=3.2 Hz, 1H), 7.98-8.02 (m, 1H), 7.83 (br s, 1H), 7.53 (d, J=7.6 Hz, 1H), 7.34-7.44 (m, 5H), 4.48 (s, 1H), 4.11-4.28 (m, 2H), 3.56-3.68 (m, 2H), 3.25-3.33 (m, 2H), 2.59 (s, 3H), 1.72-2.20 (m, 4H).

Example 3: (S)-1'-(8-((3-chloro-2-(cyclopropylamino) pyridin-4-yl) thio)-7-methylimidazo [1,2-c] pyrimidin-5-yl)-1,3-dihydrospiro [indene-2,4'-piperidine]-1-amine

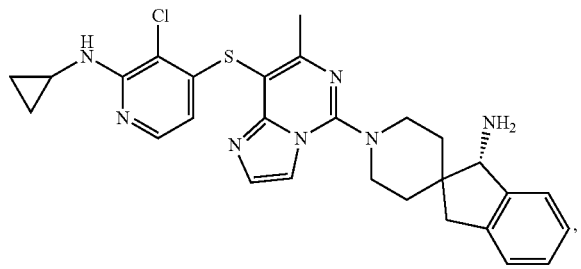 [SMILES: Cc1nc(N2CCC3(CC2)Cc2ccccc2[C@H]3N)n2ccnc2c1Sc1ccnc(NC2CC2)c1Cl]

and with sodium 3-chloro-2-(cyclopropylamino) pyridine-4-thiophenolate as a raw material, the operation is the same as that in Example 2. MS(ESI): m/z=532.6[M+H]; $^1$H-NMR (400 MHz, CD3OD) δ8.13 (br s, 1H), 7.91 (br s, 1H), 7.74 (d, J=4.0 Hz, 1H), 7.54 (d, J=7.6 Hz, 1H), 7.35-7.42 (m, 3H), 6.70 (d, J=3.6 Hz, 1H), 4.50 (s, 1H), 4.26-4.41 (m, 2H), 3.68-3.72 (m, 2H), 3.26-3.31 (m, 2H), 2.73-2.76 (m, 1H), 2.64 (s, 3H), 1.73-2.23 (m, 4H), 1.07-1.12 (m, 2H), 0.84 (br s, 2H).

Example 4: (S)-1'-(7-amino-8-((2-amino-3-chloropyridin-4-yl) thio) imidazo [1,2-c] pyrimidin-5-yl)-1,3-dihydrospiro [indene-2,4'-piperidine]-1-amine

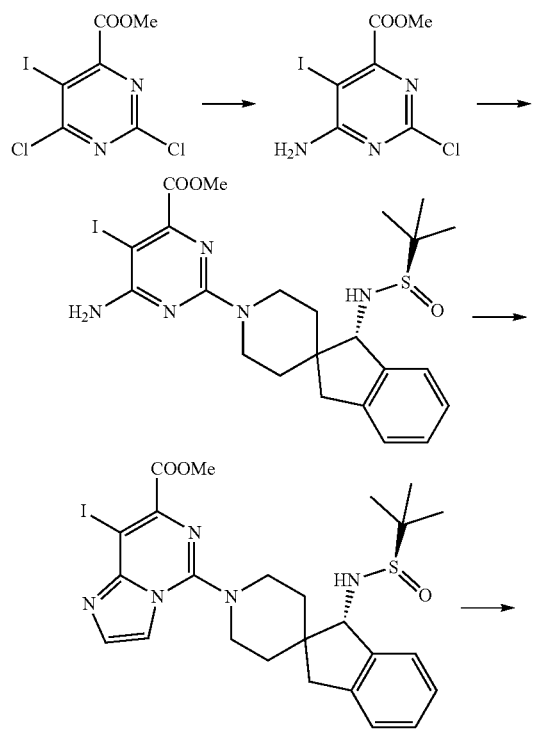

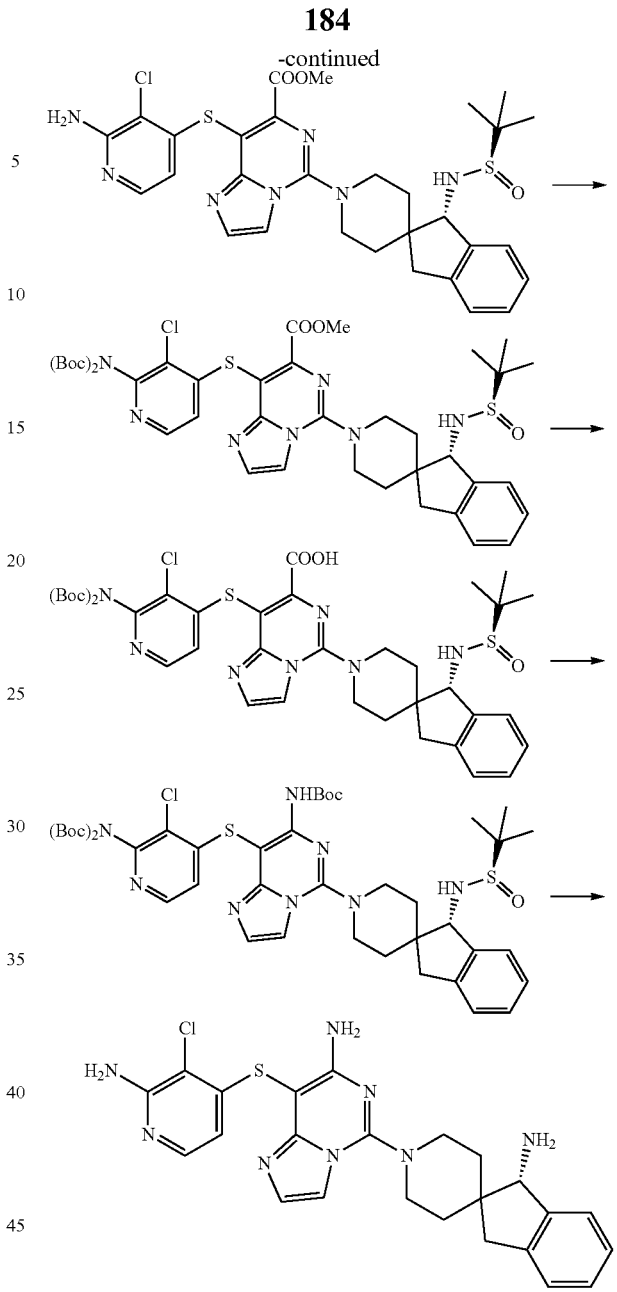

Step 1: Dissolving methyl 2,6-dichloro-5-iodopyrimidine-4-carboxylate (4.0 g, 12 mmol) in dioxane (40 mL), adding a 2M ammonia/methanol solution (40 mL), and stirring at room temperature for 2 hours. Concentrating under reduced pressure, and purifying by column chromatography to obtain methyl 6-amino-2-chloro-5-iodopyrimidine-4-carboxylate (2.4 g, white solids). MS(ESI): m/z=313.7[M+H]; $^1$H-NMR (400 MHz, DMSO-d6) δ8.53 (brs, 1H), 7.38 (brs, 1H), 3.87 (s, 3H).

Step 2: Dissolving methyl 6-amino-2-chloro-5-iodopyrimidine-4-carboxylate (376 mg, 1.2 mmol) and (R)—N—((S)-1,3-dihydrospiro [indene-2,4'-piperidin]-1-yl)-2-methylpropan-2-sulfinamide (TFA salt, 420 mg, 1.0 mmol) in N,N-dimethylformamide (DMF) (20 mL), adding potassium carbonate (690 mg, 5.0 mmol), heating to 80° C. for reaction for 2 hours, cooling a reaction solution to room temperature, diluting with ethyl acetate, washing with saturated saline, drying and concentrating under the reduced pressure to obtain 6-amino-2-((1S)-1-((tert-butylsulfinyl) amino)-1,3-dihydrospiro [indene-2,4'-piperidin]-1'-yl)-5-iodopyrimidin-4-methyl carboxylate (yellow solids) for direct used in the next reaction. MS(ESI): m/z=583.8[M+H].

Step 3: Dissolving the 6-amino-2-((1S)-1-((tert-butylsulfinyl) amino)-1,3-dihydrospiro [indene-2,4'-piperidin]-1'-yl)-5-iodopyrimidin-4-methyl carboxylate (crude, 1.0 mmol) in ethanol (40 mL), adding phosphate buffer solution (40 mL, pH=6.7), sodium acetate (848 mg, 10.3 mmol) and 40% aqueous chloroacetaldehyde (2.0 g, 10.3 mmol), and heating to 100° C. for reaction overnight. Cooling the reaction solution to room temperature, concentrating to remove most of organic solvents, extracting with the ethyl acetate, drying, concentrating under the reduced pressure, and purifying by the column chromatography to obtain 5-((1S)-1-((tert-butylsulfinyl) amino)-1,3-dihydrospiro [indene-2,4'-piperidin]-1'-yl)-8-iodoimidazo [1,2-c] pyrimidine-7-methyl carboxylate (167 mg, yellow solids). MS(ESI): m/z=607.8[M+H]; $^1$H-NMR (400 MHz, DMSO_d6) δ7.88 (d, J=1.2 Hz, 1H), 7.75 (d, J=1.2 Hz, 1H), 7.20-7.31 (m, 4H), 5.69 (d, J=10.4 Hz, 1H), 4.48 (d, J=10.0 Hz, 1H), 3.88 (s, 3H), 3.74-3.81 (m, 2H), 3.12-3.28 (m, 3H), 2.72-2.75 (m, 1H), 2.15-2.22 (m, 1H), 1.93-1.97 (m, 1H), 1.65-1.69 (m, 1H), 1.41-1.44 (m, 1H), 1.21 (s, 9H).

Step 4: Suspending the 5-((1S)-1-((tert-butylsulfinyl) amino)-1,3-dihydrospiro [indene-2,4'-piperidin]-1'-yl)-8-iodoimidazo [1,2-c] pyrimidine-7-methyl carboxylate (135 mg, 0.22 mmol), 2-amino-3-chloropyridine-4-thiophenolate (61 mg, 0.38 mmol), 3,4,7,8-tetramethylphenanthroline (10 mg, 0.042 mmol), copper iodide (CuI) (8 mg, 0.042 mmol) and the potassium carbonate (91 mg, 0.66 mmol) in DMSO (20 mL), exchanging with nitrogen, and then raising the temperature to 120° C. for reaction for 1 hour. Cooling the reaction solution to the room temperature, diluting with ethyl acetate, washing with saturated saline, drying in an organic phase, concentrating under the reduced pressure, and purifying by the column chromatography to obtain 8-((2-amino-3-chloropyridin-4-yl) thio)-5-((1S)-1-((tert-butylsulfinyl) amino)-1,3-dihydrospiro [indene-2,4'-piperidin]-1'-yl) imidazo [1,2-c] pyrimidin-7-methyl carboxylate (80 mg, yellow solids). MS(ESI): m/z=640.3[M+H]; $^1$H-NMR (400 MHz, CD3OD) δ7.86 (d, J=1.2 Hz, 1H), 7.51 (d, J=1.2 Hz, 1H), 7.40 (d, J=6.0 Hz, 1H), 7.11-7.26 (m, 4H), 5.83 (d, J=5.6 Hz, 1H), 4.50 (s, 1H), 3.99-4.05 (m, 2H), 3.76 (s, 3H), 3.15-3.34 (m, 3H), 2.76 (d, J=16.0 Hz, 1H), 2.23-2.30 (m, 1H), 1.97-2.05 (m, 1H), 1.67-1.71 (m, 1H), 1.44-1.48 (m, 1H), 1.24 (s, 9H).

Step 5: Dissolving the 8-((2-amino-3-chloropyridin-4-yl) thio)-5-((1S)-1-((tert-butylsulfinyl) amino)-1,3-dihydrospiro [indene-2,4'-piperidin]-1'-yl) imidazo [1,2-c]pyrimidin-7-methyl carboxylate (70 mg, 0.11 mmol), Boc anhydride (Boc2O) (119 mg, 0.55 mmol), N,N-dimethylaminopyridine (DMAP) (1 mg, 0.01 mmol) and triethylamine (33 mg, 0.33 mmol) in anhydrous dichloromethane (10 mL), reacting at room temperature for 24 hours, concentrating under the reduced pressure, and purifying by the column chromatography to obtain 8-((2-di-tert-butoxycarbonylamino-3-chloropyridin-4-yl) thio)-5-((1S)-1-((tert-butylsulfinyl) amino)-1,3-dihydrospiro [indene-2,4'-piperidin]-1'-yl) imidazo [1,2-c] pyrimidine-7-methyl carboxylate (60 mg, yellow solids). MS(ESI): m/z=840.4[M+H].

Step 6: Dissolving the 8-((2-di-tert-butoxycarbonylamino-3-chloropyridin-4-yl) thio)-5-((1S)-1-((tert-butylsulfinyl) amino)-1,3-dihydrospiro [indene-2,4'-piperidin]-1'-yl) imidazo [1,2-c] pyrimidine-7-methyl carboxylate (50 mg, 0.06 mmol) and sodium hydroxide (10 mg, 0.25 mmol) in methanol (10 mL), adding water (2 mL), heating to 50° C. for reaction for 1 hour, neutralizing in 2M diluted hydrochloric acid, concentrating under the reduced pressure, and purifying by the column chromatography to obtain 8-((2-di-tert-butoxycarbonylamino-3-chloropyridin-4-yl) thio)-5-((1S)-1-((tert-butylsulfinyl) amino)-1,3-dihydrospiro [indene-2,4'-piperidin]-1'-yl) imidazo [1,2-c] pyrimidine-7-carboxylic acid (40 mg, white solids). MS(ESI): m/z=826.3[M+H]; $^1$H-NMR (400 MHz, DMSO-d6) δ7.98 (d, J=5.2 Hz, 1H), 7.59 (s, 1H), 7.42 (s, 1H), 7.21-7.32 (m, 4H), 6.62 (d, J=5.2 Hz, 1H), 5.70 (d, J=10.0 Hz, 1H), 4.50 (d, J=10.0 Hz, 1H), 3.85-3.91 (m, 2H), 3.15-3.24 (m, 3H), 2.77 (d, J=16.0 Hz, 1H), 2.18-2.24 (m, 1H), 1.96-2.01 (m, 1H), 1.68-1.72 (m, 1H), 1.45-1.49 (m, 1H), 1.41 (s, 18H), 1.23 (s, 9H).

Step 7: Dissolving the 8-((2-di-tert-butoxycarbonylamino-3-chloropyridin-4-yl) thio)-5-((1S)-1-((tert-butylsulfinyl) amino)-1,3-dihydrospiro [indene-2,4'-piperidin]-1'-yl) imidazo [1,2-c] pyrimidine-7-carboxylic acid (35 mg, 0.042 mmol), diphenyl azidophosphate (DPPA) (35 mg, 0.13 mmol) and the triethylamine (17 mg, 0.17 mmol) in tert-butanol (10 mL), and heating to 100° C. for reaction for 3 hours, and after LC-MS shows complete reaction, concentrating under the reduced pressure to obtain (R)—N—((S)-1'-(8-((2-di-tert-butoxycarbonylamino-3-chloropyridin-4-yl) thio)-7-tert-butoxycarbonylaminoimidazo [1,2-c] pyrimidin-5-yl)-1,3-dihydrospiro [indene-2,4'-piperidin]-1-yl)-2-methylpropan-2-sulfinamide (yellow oil) for direct use in the next reaction. MS(ESI): m/z=897.6[M+H].

Step 8: Dissolving the (R)—N—((S)-1'-(8-((2-di-tert-butoxycarbonylamino-3-chloropyridin-4-yl) thio)-7-tert-butoxycarbonylaminoimidazo [1,2-c] pyrimidin-5-yl)-1,3-dihydrospiro [indene-2,4'-piperidin]-1-yl)-2-methylpropan-2-sulfinamide (crude, 0.042 mmol) in the 2M HCl/MeOH (5 mL) and stirring at room temperature for 5 hour. After the reaction is completed, concentrating under the reduced pressure, and purifying the residue by preparative chromatography to obtain the target compound: (S)-1'-(7-amino-8-((2-amino-3-chloropyridin-4-yl) thio) imidazo [1,2-c] pyrimidin-5-yl)-1,3-dihydrospiro [indene-2,4'-piperidine]-1-amine. MS(ESI): m/z=493.1[M+H]; $^1$H-NMR (400 MHz, CD3OD) δ7.54 (d, J=5.6 Hz, 1H), 7.50 (d, J=1.6 Hz, 1H), 7.42-7.44 (m, 1H), 7.20-7.29 (m, 5H), 6.00 (d, J=5.6 Hz, 1H), 4.09 (s, 1H), 3.98-4.02 (m, 2H), 3.33-3.42 (m, 2H), 3.20 (d, J=15.6 Hz, 1H), 2.90 (d, J=15.6 Hz, 1H), 1.99-2.11 (m, 2H), 1.55-1.72 (m, 2H).

Example 5: (S)-1'-(7-amino-8-(2-(trifluoromethyl) pyridin-3-yl) thio) imidazo [1,2-c] pyrimidin-5-yl)-1,3-dihydrospiro [indene-2,4'-piperidine]-1-amine

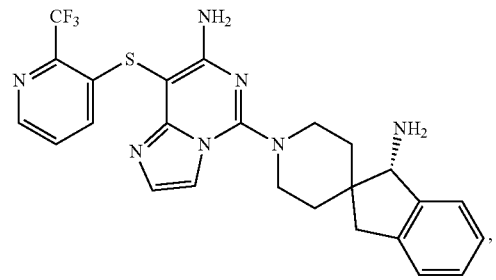 [SMILES: Nc1nc(N2CCC3(CC2)Cc2ccccc2[C@H]3N)n2ccnc2c1Sc1cccnc1C(F)(F)F]

and with 2-(trifluoromethyl) pyridine-3-thiophenol as a raw material, the operation is the same as that in Example 4. MS(ESI): m/z=512.1[M+H]; $^1$H-NMR (400 MHz, CD3OD)

δ 8.37 (t, J=2.4 Hz, 1H), 7.48-7.53 (m, 2H), 7.31-7.37 (m, 5H), 7.23 (d, J=1.6 Hz, 1H), 4.31 (d, J=2.8 Hz, 1H), 3.98-4.07 (m, 2H), 3.37-3.45 (m, 2H), 3.06-3.24 (m, 2H), 2.01-2.10 (m, 2H), 1.69-1.73 (m, 2H).

Example 6: (S)-1'-(8-((2-amino-3-chloropyridin-4-yl) thio)-7-methylimidazo [1,2-c] pyrimidin-5-yl)-5,7-dihydrospiro [cyclopentano [b] pyridine-6,4'-piperidine]-5-amine

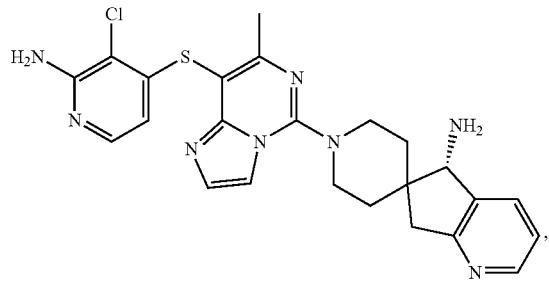 [SMILES: Cc1nc(N2CCC3(CC2)Cc2ncccc2[C@H]3N)n2ccnc2c1Sc1ccnc(N)c1Cl]

and with an intermediate 1B as a raw material, the operation is the same as that in Example 2. MS(ESI): m/z=493.2/495.2 [M+H]; ¹H-NMR (400 MHz, CD₃OD) δ 8.53 (d, 1H), 7.92 (d, J=2.0 Hz, 1H), 7.69-7.73 (m, 2H), 7.50 (d, J=1.6 Hz, 1H), 7.23 (m, 1H), 6.12 (d, J=6.4 Hz, 1H), 4.50 (s, 1H), 4.11-4.25 (m, 2H), 3.50-3.64 (m, 2H), 3.26 (s, 2H), 2.64 (s, 3H), 1.67-2.20 (m, 4H).

Example 7: (S)-1'-(8-((2-amino-3-chloropyridin-4-yl) thio)-7-methylimidazo [1,2-c] pyrimidin-5-yl)-6-methoxy-1,3-dihydrospiro [indene-2,4'-piperidine]-1-amine

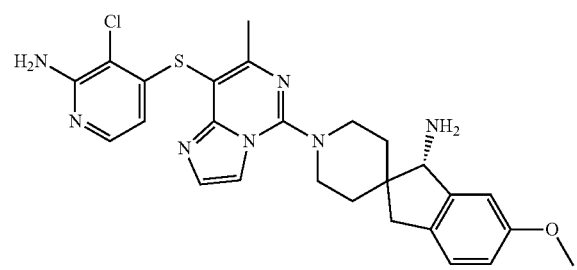 [SMILES: COc1ccc2c(c1)[C@@H](N)C1(CCN(c3nc(C)c(Sc4ccnc(N)c4Cl)c4nccn34)CC1)C2]

and with an intermediate 1E as a raw material, the operation is the same as that in Example 2. MS(ESI): m/z=522.2/524.2 [M+H]; ¹H-NMR (400 MHz, CD₃OD) δ 7.92 (d, J=2.0 Hz, 1H), 7.69 (d, J=1.6 Hz, 1H), 7.50 (d, J=1.6 Hz, 1H), 6.95-7.28 (m, 3H), 6.20 (d, J=6.4 Hz, 1H), 4.50 (s, 1H), 4.11-4.25 (m, 2H), 3.70 (s, 3H), 3.50-3.64 (m, 2H), 3.26 (s, 2H), 2.64 (s, 3H), 1.67-2.20 (m, 4H).

Example 8: (S)-1'-(8-((2-amino-3-chloropyridin-4-yl) thio)-7-methylimidazo [1,2-c] pyrimidin-5-yl)-5,6-difluoro-1,3-dihydrospiro [indene-2,4'-piperidine]-1-amine

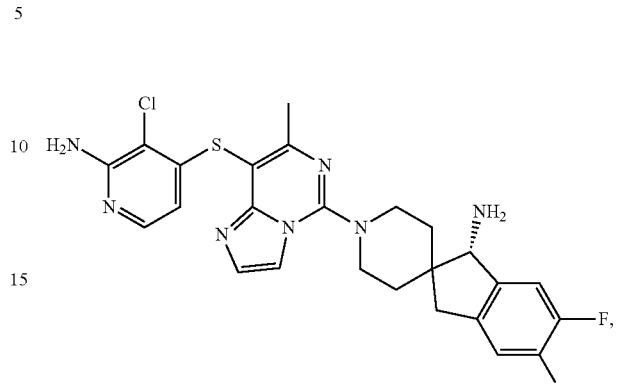

and with an intermediate 1H as a raw material, the operation is the same as that in Example 2. MS(ESI): m/z=528.2/530.2 [M+H].

Example 9: (S)-1'-(8-((2-amino-3-chloropyridin-4-yl) thio)-2,7-dimethylimidazo [1,2-c] pyrimidin-5-yl)-1,3-dihydrospiro [indene-2,4'-piperidine]-1-amine

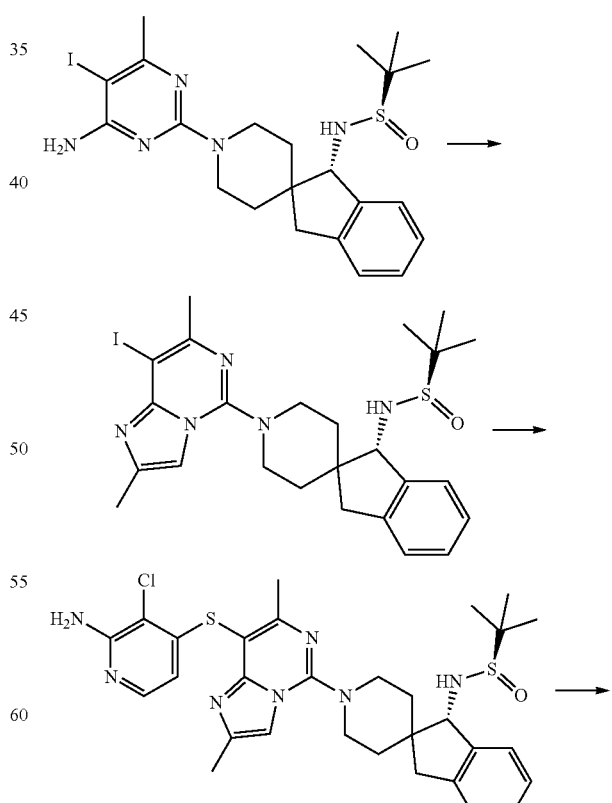

-continued

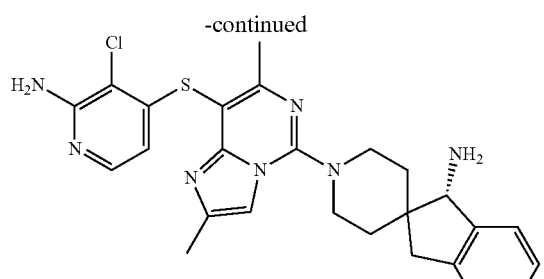

Dissolving the (R)—N—((S)-1'-(4-amino-5-iodo-6-methylpyrimidin-2-yl)-1,3-dihydrospiro [indene-2,4'-piperidin]-1-yl)-2-methylpropan-2-sulfinamide (1.5 mmol) in tetrahydrofuran (THF) (10 mL), adding monochloroacetone (0.9 eq.), stirring at room temperature overnight, and filtering precipitated solids. Dissolving the obtained solids in ethanol (30 mL), heating to reflux, and stirring for 4 hours. Cooling a reaction solution to room temperature, concentrating under reduced pressure, adding saturated aqueous sodium carbonate, extracting with ethyl acetate, drying, and concentrating under the reduced pressure to obtain a methylimidazole intermediate (white solids). MS(ESI): m/z=578.1[M+H].

Subsequent operation steps are the same as that in Example 2. MS(ESI): m/z=506.2/508.2[M+H]; $^1$H-NMR (400 MHz, CD$_3$OD) δ7.92 (d, J=2.0 Hz, 1H), 7.54-7.58 (m, 2H), 7.36-7.48 (m, 3H), 6.18 (d, J=6.4 Hz, 1H), 4.50 (s, 1H), 4.11-4.25 (m, 2H), 3.50-3.64 (m, 2H), 3.26 (s, 2H), 2.64 (s, 3H), 2.45 (s, 3H), 1.67-2.20 (m, 4H).

Example 10: (S)-1'-(8-((2-amino-3-chloropyridin-4-yl) thio)-2,7-dimethylimidazo [1,2-c] pyrimidin-5-yl)-5,7-dihydrospiro [cyclopentano [b] pyridine-6,4'-piperidine]-5-amine

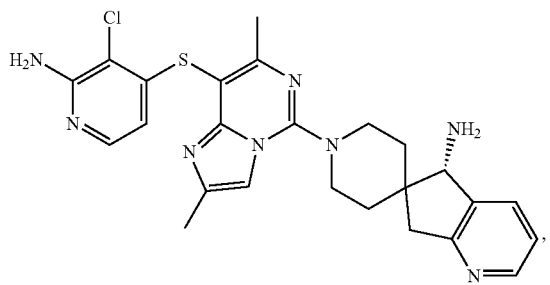 [SMILES: Cc1cn2c(N3CCC4(CC3)Cc3ncccc3[C@H]4N)nc(C)c(Sc3ccnc(N)c3Cl)c2n1]

and the operation is the same as that in Example 9, MS (ESI): m/z=507.2/509.2 [M+H].

Example 11: (S)-1'-(8-((2-amino-3-chloropyridin-4-yl) thio)-2,7-dimethylimidazo [1,2-c] pyrimidin-5-yl)-6-methoxy-1,3-dihydrospiro [indene-2,4'-piperidine]-1-amine

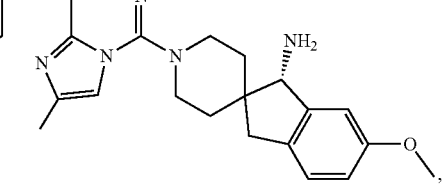

and the operation is the same as that in Example 9, MS(ESI): m/z=536.2/538.2[M+H].

Example 12: (S)-1'-(8-((2-amino-3-chloropyridin-4-yl) thio)-7-(fluoromethyl) imidazo [1,2-c] pyrimidin-5-yl)-1,3-dihydrospiro [indene-2,4'-piperidine]-1-amine

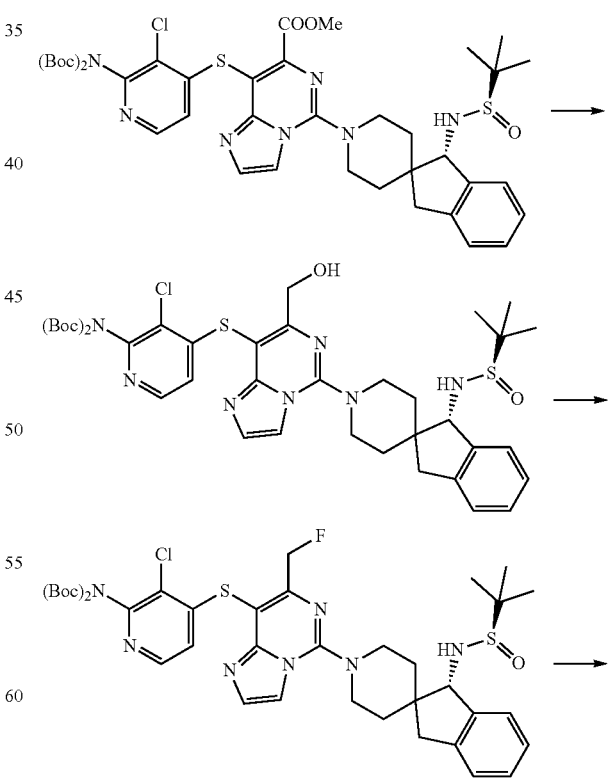

-continued

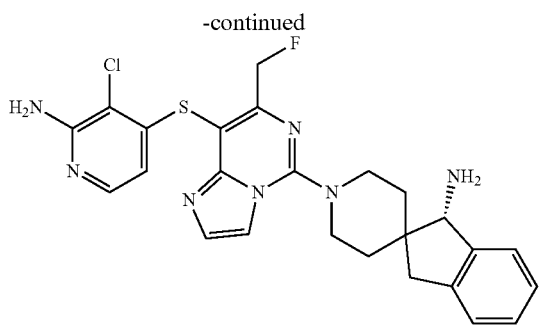

Step 1: Dissolving 8-((2-di-tert-butoxycarbonylamino-3-chloropyridin-4-yl) thio)-5-((1S)-1-((tert-butylsulfinyl) amino)-1,3-dihydrospiro [indene-2,4'-piperidin]-1'-yl) imidazo [1,2-c] pyrimidine-7-methyl carboxylate (0.19 mmol) in dichloromethane (15 mL), cooling to −78° C., slowly adding DIBAL-H (0.56 mmol, 1M toluene solution), raising to room temperature, stirring for 2 hours, diluting with ether, adding 2 drops of 15% sodium hydroxide for a quenching reaction, drying, concentrating under reduced pressure, and purifying by column chromatography to obtain 8-((2-di-tert-butoxycarbonylamino-3-chloropyridin-4-yl) thio)-5-((1S)-1-((tert-butylsulfinyl) amino)-1,3-dihydrospiro [indene-2,4'-piperidin]-1'-yl) imidazo [1,2-c] pyrimidine-7-yl) methanol (white solids). MS(ESI): m/z=812.3[M+H].

Step 2: Dissolving the 8-((2-di-tert-butoxycarbonylamino-3-chloropyridin-4-yl) thio)-5-((1S)-1-((tert-butylsulfinyl) amino)-1,3-dihydrospiro [indene-2,4'-piperidin]-1'-yl) imidazo [1,2-c] pyrimidine-7-yl) methanol (0.12 mmol) in the dichloromethane (10 mL), cooling to 0° C., slowly adding diethylamine sulfur trifluoride (DAST) (0.18 mmol), raising to room temperature, stirring overnight, concentrating, and purifying by the column chromatography to obtain (S)-1'-(8-((2-di-tert-butoxycarbonylamino-3-chloropyridin-4-yl) thio)-7-(fluoromethyl) imidazo [1,2-c] pyrimidin-5-yl)-1,3-dihydrospiro [indene-2,4'-piperidine]-1-amine (white solids). MS(ESI): m/z=814.3[M+H].

Step 3: Dissolving the (S)-1'-(8-((2-di-tert-butoxycarbonylamino-3-chloropyridin-4-yl) thio)-7-(fluoromethyl) imidazo [1,2-c] pyrimidin-5-yl)-1,3-dihydrospiro [indene-2,4'-piperidine]-1-amine (0.04 mmol) in the 2M HCl/MeOH (5 mL) and stirring at room temperature for 5 hour. After the reaction is completed, concentrating under the reduced pressure, and purifying the residue by preparative chromatography to obtain the target compound: (S)-1'-(8-((2-amino-3-chloropyridin-4-yl) thio)-7-(fluoromethyl) [1,2-c] pyrimidin-5-yl)-1,3-dihydrospiro [indene-2,4'-piperidine]-1-amine (white solids). MS(ESI): m/z=510.2/512.2[M+H]; $^1$H-NMR (400 MHz, CD$_3$OD) δ7.93 (d, J=2.0 Hz, 1H), 7.69 (d, J=1.6 Hz, 1H), 7.54-7.58 (m, 2H), 7.36-7.48 (m, 3H), 6.17 (d, J=6.4 Hz, 1H), 5.01-5.25 (m, 2H), 4.50 (s, 1H), 4.12-4.25 (m, 2H), 3.50-3.64 (m, 2H), 3.26 (s, 2H), 1.68-2.21 (m, 4H).

Example 13: (R)-1'-(8-((2-amino-3-chloropyridin-4-yl) thio)-7-methylimidazo [1,2-c] pyrimidin-5-yl)-3H-spiro [benzofuran-2,4'-piperidine]-3-amine

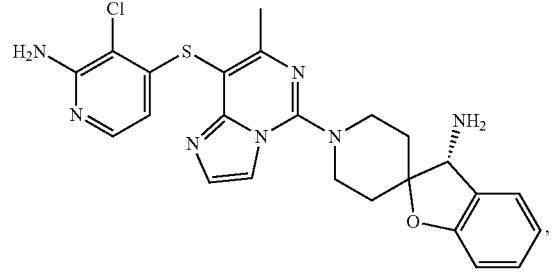

and with an intermediate 1D as a raw material, the operation is the same as that in Example 2, MS(ESI): m/z=494.2/496.2 [M+H]; $^1$H-NMR (400 MHz, CD$_3$OD) δ7.92 (d, J=2.0 Hz, 1H), 7.69 (d, J=1.6 Hz, 1H), 7.50 (d, J=1.6 Hz, 1H), 6.92-7.38 (m, 4H), 6.18 (d, J=6.4 Hz, 1H), 4.45 (s, 1H), 4.10-4.20 (m, 2H), 3.40-3.54 (m, 2H), 2.64 (s, 3H), 1.62-2.10 (m, 4H).

Example 14: (S)-1'-(8-((2-amino-3-chloropyridin-4-yl) thio)-7-methylimidazo [1,2-c] pyrimidin-5-yl)-4,6-dihydrospiro [cyclopentano [d] thiazol-5,4'-piperidine]-6-amine

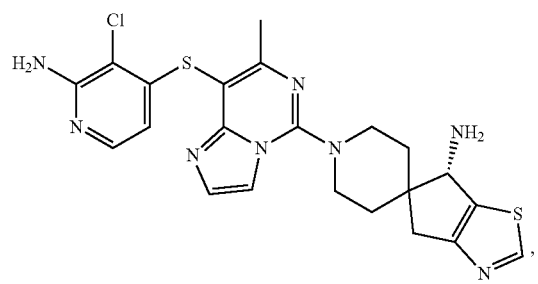 [SMILES: Cc1nc(N2CCC3(CC2)Cc2ncsc2[C@H]3N)n2ccnc2c1Sc1ccnc(N)c1Cl]

and with an intermediate 1D as a raw material, the operation is the same as that in Example 2, MS(ESI): m/z=499.2/501.2 [M+H]; $^1$H-NMR (400 MHz, CD$_3$OD) δ9.02 (s, 1H), 7.92 (d, J=2.0 Hz, 1H), 7.69 (d, J=1.6 Hz, 1H), 7.50 (d, J=1.6 Hz, 1H), 6.18 (d, J=6.4 Hz, 1H), 4.23-4.45 (m, 3H), 4.10-4.20 (m, 2H), 3.40-3.54 (m, 2H), 2.64 (s, 3H), 1.62-2.10 (m, 4H).

Example 15: (S)-1'-(8-(2-amino-3-chloropyridin-4-yl)-7-methylimidazo [1,2-c]pyrimidin-5-yl)-1,3-dihydrospiro [indene-2,4'-piperidine]-1-amine

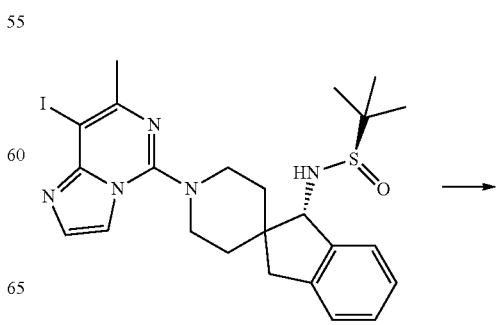

-continued

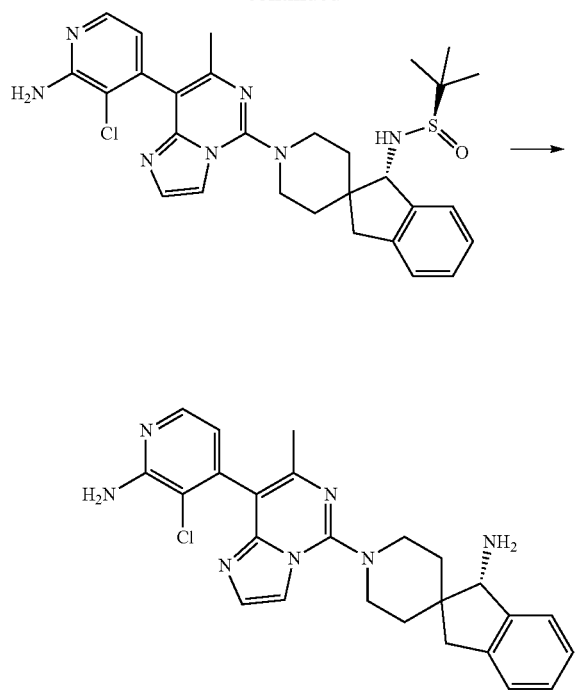

Step 1: Dissolving (R)—N—((S)-1'-(8-iodo-7-methylimidazolo [1,2-c] pyrimidin-5-yl)-1,3-dihydrospiro [indene-2,4'-piperidin]-1-yl)-2-methylpropan-2-sulfinamide (0.42 mmol) and 2-amino-3-chloro-4-pyridineboronic acid pinacol ester (0.64 mmol) in N,N-dimethylformamide (DMF) (15 mL), adding potassium phosphate (1.68 mmol) and tetraphenylphosphine palladium (Pd(PPh$_3$)$_4$) (0.042 mmol), exchanging with argon and heating to 80° C. overnight until LCMS shows complete reaction. Diluting with ethyl acetate, washing with saturated saline, drying, concentrating, and purifying by the column chromatography to obtain (R)—N—((S)-1'-(8-(2-amino-3-chloropyridin-4-yl)-7-methylimidazo [1,2-c] pyrimidin-5-yl)-1,3-dihydrospiro [indene-2,4'-piperidin]-1-yl)-2-methylpropan-2-sulfinamide (yellow solids). MS(ESI): m/z=564.2/566.2[M+H].

Step 2: Dissolving the (R)—N—((S)-1'-(8-(2-amino-3-chloropyridin-4-yl)-7-methylimidazo [1,2-c] pyrimidin-5-yl)-1,3-dihydrospiro [indene-2,4'-piperidin]-1-yl)-2-methylpropan-2-sulfinamide (0.07 mmol) in 2M HCl/MeOH (10 mL) and stirring at room temperature for 5 hour. After the reaction is completed, concentrating under the reduced pressure, and purifying the residue by preparative chromatography to obtain the target compound: (S)-1'-(8-(2-amino-3-chloropyridin-4-yl)-7-methylimidazo [1,2-c] pyrimidin-5-yl)-1,3-dihydrospiro [indene-2,4'-piperidine]-1-amine (yellow solids). MS(ESI): m/z=460.2/462.2[M+H]; $^1$H-NMR (400 MHz, CD$_3$OD) δ8.27 (d, J=2.0 Hz, 1H), 7.69 (d, J=1.6 Hz, 1H), 7.54-7.57 (m, 2H), 7.36-7.48 (m, 3H), 7.28 (d, J=6.4 Hz, 1H), 4.50 (s, 1H), 4.11-4.25 (m, 2H), 3.50-3.64 (m, 2H), 3.26 (s, 2H), 2.64 (s, 3H), 1.67-2.20 (m, 4H).

Example 16: (S)-1'-(7-methyl-8-(2-(trifluoromethyl)pyridin-3-yl) imidazo [1,2-c] pyrimidin-5-yl)-1,3-dihydrospiro [indene-2,4'-piperidine]-1-amine

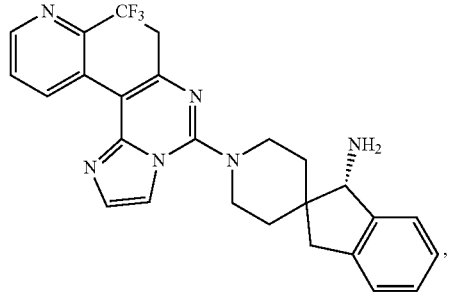

and with 2-trifluoromethyl-3-boronic acid pinacol ester as a raw material, the operation is the same as that in Example 15, MS (ESI): m/z=479.2/481.2 [M+H].

Example 17: (S)-1'-(8-((2-amino-3-chloropyridin-4-yl) thio)-7-methylimidazo [1,2-a] pyridin-5-yl)-1,3-dihydrospiro [indene-2,4'-piperidine]-1-amine

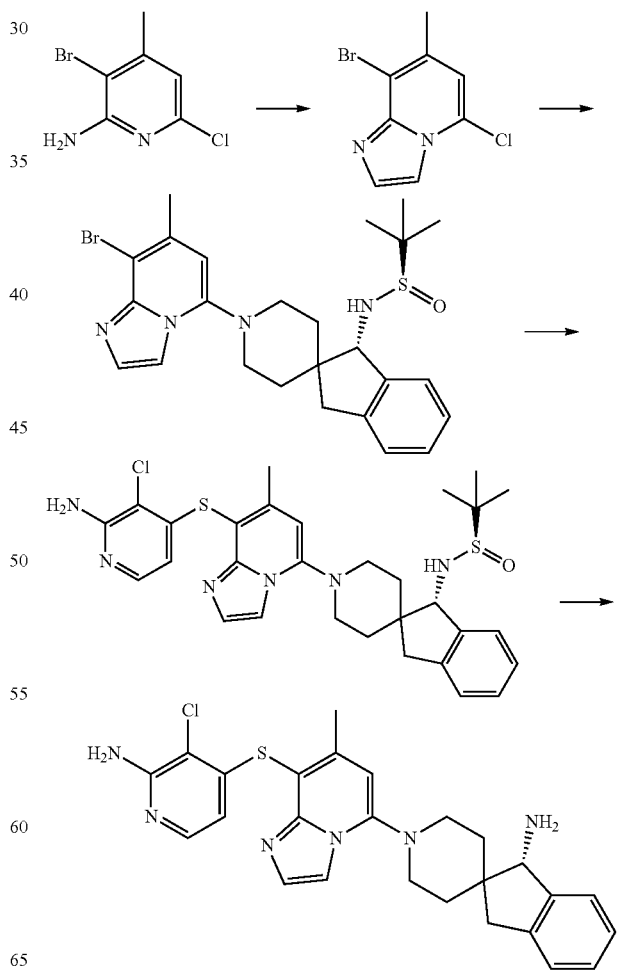

Dissolving 3-bromo-6-chloro-4-methylpyridin-2-amine (400 mg, 1.82 mmol) in ethanol (EtOH) (40 mL), adding phosphate buffer (pH=6.7, 40 mL), sodium acetate (600 mg, 7.32 mmol) and 40% aqueous chloroacetaldehyde (1.42 g, 7.28 mmol), and stirring at 90° C. for 16 hours. Cooling to room temperature, extracting with ethyl acetate for three times, washing with saturated saline after merging with an organic phase, drying, concentrating, and purifying by column chromatography to obtain 8-bromo-5-chloro-7-methylimidazo [1,2-a] pyridine (360 mg, yellow solids). MS(ESI): m/z=244.9/246.9[M+H]. $^1$H-NMR (400 MHz, CDCl$_3$) δ7.78 (d, J=1.6 Hz, 1H), 7.70 (d, J=1.2 Hz, 1H), 6.81 (s, 1H), 2.50 (s, 3H).

Subsequent operation steps are the same as that in Example 1. MS(ESI): m/z=491.2/493.2[M+H]; $^1$H-NMR (400 MHz, CD$_3$OD) δ7.92 (d, J=2.0 Hz, 1H), 7.70 (d, J=1.6 Hz, 1H), 7.54-7.57 (m, 2H), 7.36-7.48 (m, 3H), 6.54 (s, 1H), 6.18 (d, J=6.4 Hz, 1H), 4.50 (s, 1H), 4.11-4.25 (m, 2H), 3.50-3.64 (m, 2H), 3.26 (s, 2H), 2.64 (s, 3H), 1.67-2.20 (m, 4H).

Example 18: (S)-1'-(8-((2-amino-3-chloropyridin-4-yl) thio)-7-methyl-[1,2,4]triazolo [4,3-a] pyridin-5-yl)-1,3-dihydrospiro [indene-2,4'-piperidine]-1-amine

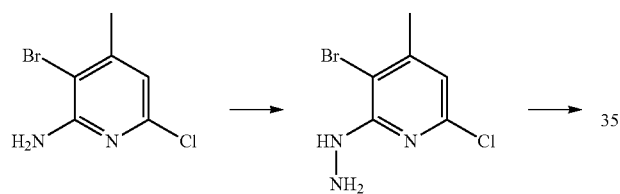

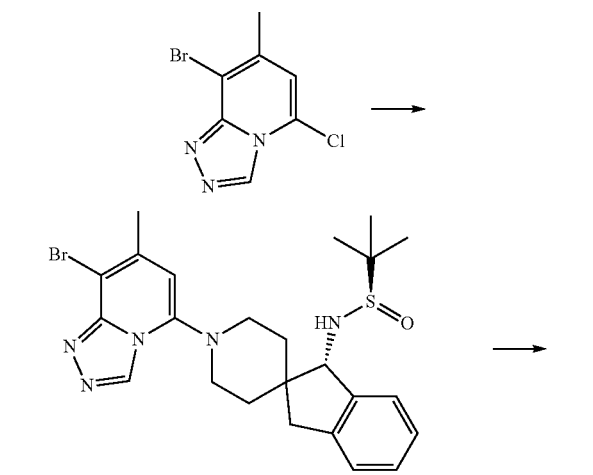

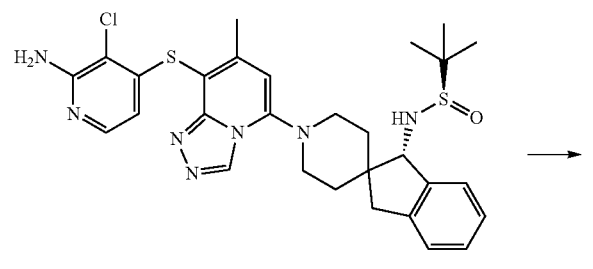

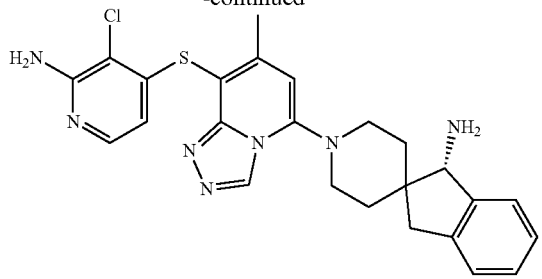

Dissolving 2,6-dichloro-3 bromo-4-methylpyridine (4.15 mmol) in ethanol (10 mL), adding a 85% hydrazine hydrate solution (2 mL), and heating for reflux and reaction overnight until TLC shows complete reaction. Cooling a reaction solution to room temperature, concentrating under reduced pressure and purifying by column chromatography to obtain 2-hydrazino-3-bromo-4-methyl-6-chloropyridine (white solids), MS (ESI): m/z=236.1/238.1 [M+H].

Dissolving 2-hydrazino-3-bromo-4-methyl-6-chloropyridine (2.96 mmol) in trimethyl orthoformate (6 mL), raising the temperature to 100° C. under protection of nitrogen for 16 hours, cooling the reaction solution to room temperature, concentrating under the reduced pressure, purifying by the column chromatography to obtain 8-bromo-5-chloro-7-methyl-[1,2,4] triazolo [4,3-a] pyridine (white solids), MS (ESI): m/z=246.2/248.2 [M+H]; $^1$H-NMR (400 MHz, CDCl3) δ8.95 (s, 1H), 6.83 (s, 1H), 2.52 (s, 3H).

Subsequent operation steps are the same as that in Example 1. MS(ESI): m/z=492.2/494.2[M+H].

Example 19: (S)-1'-(8-((2-amino-3-chloropyridin-4-yl) thio)-7-methyl-[1,2,4]triazolo [1,5-a] pyridin-5-yl)-1,3-dihydrospiro [indene-2,4'-piperidine]-1-amine

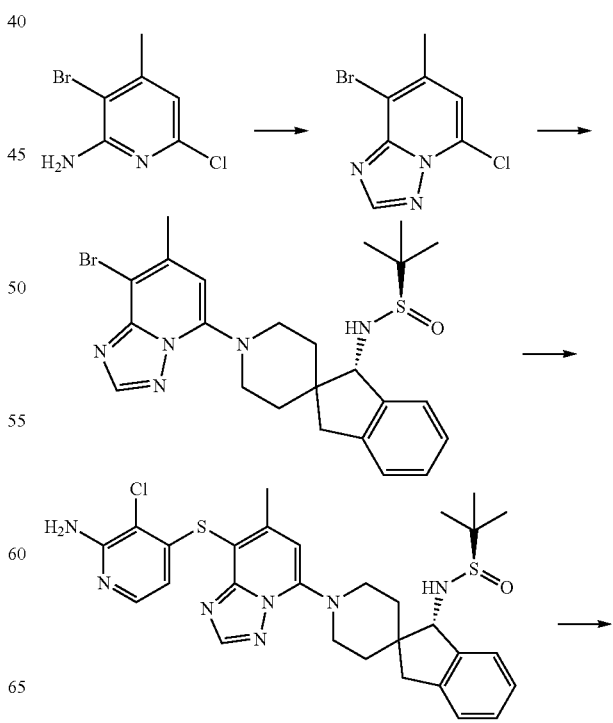

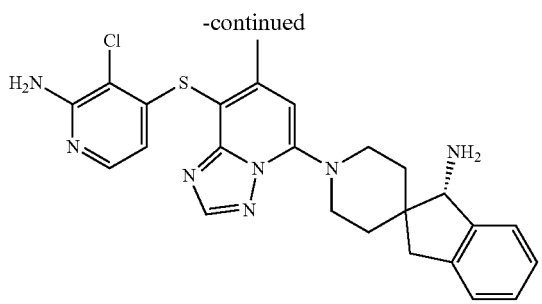

Dissolving 2-amino-3-bromo-4-methyl-6-chloropyridine (5.4 mmol) in 60 mL of methanol, and adding dimethylformamide-dicarboxal (3 eq.) dropwise to the mixture described above at room temperature. Then stirring a reaction solution at 60° C. overnight, cooling to room temperature, then adding hydroxylamine hydrochloride (3 eq.) and pyridine (3 eq.) to the reaction solution, and stirring at room temperature for 2.5 hours. Concentrating the reaction solution under reduced pressure, suspending residues in anhydrous tetrahydrofuran (80 mL), cooling in an ice bath, and slowly adding trifluoroacetic anhydride (3 eq.) dropwise. Then removing the ice bath and stirring at room temperature overnight. Concentrating the reaction solution under the reduced pressure, and purifying by column chromatography to obtain 8-bromo-5-chloro-7-methyl-[1,2,4] triazole [4,3-a] pyridine (white solids). MS(ESI): m/z=246.2/248.2[M+H]; $^1$H-NMR (400 MHz, CDCl$_3$) δ8.40 (s, 1H), 7.07 (s, 1H), 2.58 (s, 3H).

Subsequent operation steps are the same as that in Example 1. MS(ESI): m/z=492.2/494.2[M+H]. $^1$H-NMR (400 MHz, CD$_3$OD) δ8.39 (s, 1H), 7.65 (d, J=1.6 Hz, 1H), 7.52-7.56 (m, 2H), 7.34-7.45 (m, 2H), 7.03 (s, 1H), 6.19 (d, J=6.4 Hz, 1H), 4.49 (s, 1H), 4.13-4.24 (m, 2H), 3.51-3.64 (m, 2H), 3.27 (s, 2H), 2.64 (s, 3H), 1.67-2.20 (m, 4H).

Example 20: 1'-(8-((2-amino-3-chloropyridin-4-yl)thio)-7-methylimidazo [1,2-c] pyrimidin-5-yl)-1,3-dihydrospiro [indene-2,4'-piperidine]-1-amine

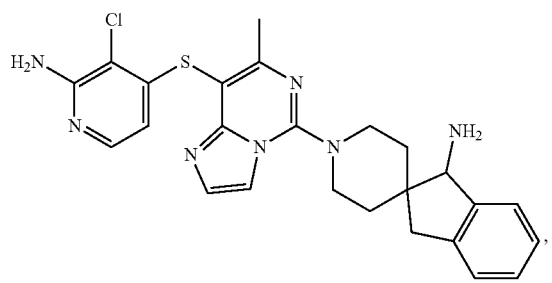

and the operation is the same as that in Example 2. MS(ESI): m/z=492.1/494.1[M+H]; $^1$H-NMR (400 MHz, CD$_3$OD) δ7.92 (d, J=2.0 Hz, 1H), 7.69 (d, J=1.6 Hz, 1H), 7.54-7.57 (m, 2H), 7.36-7.48 (m, 3H), 6.18 (d, J=6.4 Hz, 1H), 4.50 (s, 1H), 4.11-4.25 (m, 2H), 3.50-3.64 (m, 2H), 3.26 (s, 2H), 2.64 (s, 3H), 1.67-2.20 (m, 4H).

Example 21: 1-(8-(2,3-dichlorophenyl)-7-methyl-[1,2,4] triazole [1,5-c]pyrimidin-5-yl)-4-methylpiperidin-4-amine

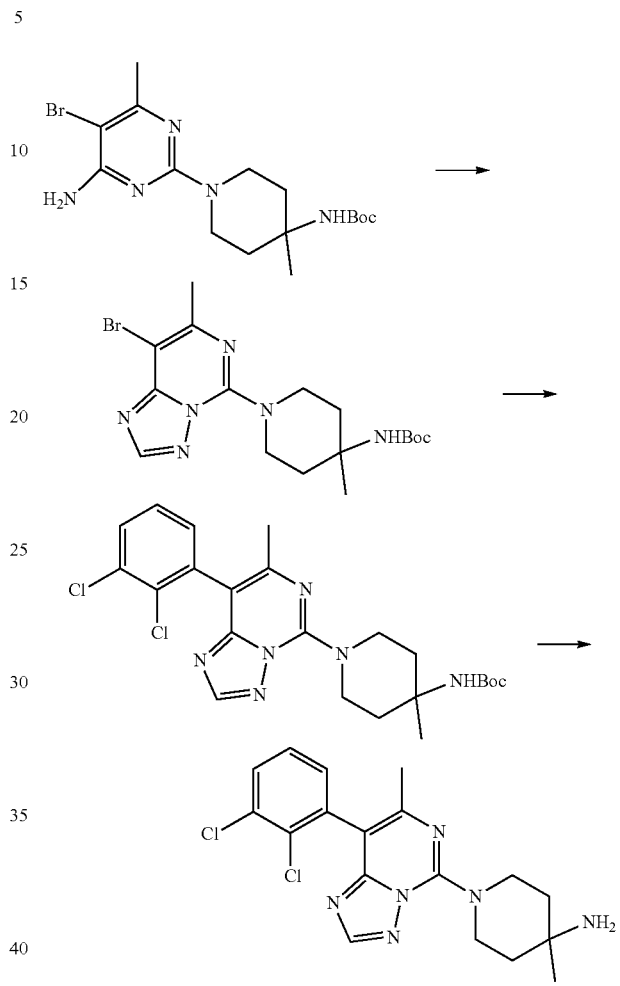

Step 1: Dissolving tert-butyl (1-(4-amino-5-bromo-6-methylpyrimidin-2-yl)-4-methylpiperidin-4-yl) carbamate (120 mg, 0.3 mmol) in methanol (10 mL), adding N,N-dimethyl dimethoxyacetal (DMF-DMA) (72 mg, 0.6 mmol), heating to 80° C. and stirring for 1 hour. Cooling to room temperature, and concentrating under reduced pressure. Dissolving residues and hydroxylamine hydrochloride (62 mg, 0.9 mmol) in methanol (5 mL), adding pyridine (71 mg, 09 mmol), stirring at room temperature for 1 hour, and concentrating under the reduced pressure. Dissolving the residues in anhydrous tetrahydrofuran (10 mL), adding trifluoroacetic anhydride (TFAA) (189 mg, 0.9 mmol) dropwise under an ice bath for cooling, and reacting at room temperature overnight. Concentrating and purifying by the column chromatography to obtain (1-(8-bromo-7-methyl-[1,2,4] triazole [1,5-c] pyrimidin-5-yl)-4-methylpiperidin-4-yl) tert-butyl carbamate (80 mg, yellow solids). MS(ESI): m/z=425.1/427.1[M+H]; $^1$H-NMR (400 MHz, DMSO-d6): δ8.46 (s, 1H), 6.66 (brs, 1H), 4.33-4.40 (m, 2H), 3.50-3.56 (m, 2H), 2.48 (s, 3H), 2.14-2.18 (m, 2H), 1.53-1.60 (m, 2H), 1.39 (s, 9H), 1.27 (s, 3H).

Step 2: Dissolving the (1-(8-bromo-7-methyl-[1,2,4] triazole [1,5-c] pyrimidin-5-yl)-4-methylpiperidin-4-yl) tert-butyl carbamate (55 mg, 0.13 mmol) and 2,3-dichlorophenylboronic acid (37 mg, 0.19 mmol) in DMF (10 mL), adding potassium phosphate (83 mg, 0.39 mmol) and Pd (PPh3) 4 (15 mg, 0.013 mmol), exchanging with argon, and heating to 80° C. for reaction overnight until LCMS shows complete reaction. Diluting with ethyl acetate, washing with saturated saline, drying in an organic phase, concentrating, and purifying by the column chromatography to obtain (1-(8-(2,3-dichlorophenyl)-7-methyl-[1,2,4] triazole [1,5-c] pyrimidin-5-yl)-4-methylpiperidin-4-yl) tert-butyl carbamate (30 mg, pale yellow solids). MS(ESI): m/z=491.2/493.2 [M+H]; $^1$H-NMR (400 MHz, CD$_3$OD): δ8.11 (s, 1H), 7.55 (dd, J=1.6, 8.0 Hz, 1H), 7.32 (t, J=8.0 Hz, 1H), 7.23 (dd, J=1.6, 7.6 Hz, 1H), 4.55-4.58 (m, 2H), 3.54-3.58 (m, 2H), 2.07-2.17 (m, 2H), 2.11 (s, 3H), 1.59-1.66 (m, 2H), 1.36 (s, 9H), 1.29 (s, 3H).

Step 3: Dissolving the (1-(8-(2,3-dichlorophenyl)-7-methyl-[1,2,4] triazole [1,5-c] pyrimidin-5-yl)-4-methylpiperidin-4-yl) tert-butyl carbamate (30 mg, 0.06 mmol) in anhydrous dichloromethane (5 mL), adding trifluoroacetic acid (TFA) (1 mL) dropwise, reacting at room temperature for 1 hour, concentrating under the reduced pressure, and purifying by preparative chromatography to obtain 1-(8-(2,3-dichlorophenyl)-7-methyl-[1,2,4] triazole [1,5-c] pyrimidin-5-yl)-4-methylpiperidin-4-amine (15 mg, pale yellow solids). MS(ESI): m/z=391.1/393.1; $^1$H-NMR (400 MHz, CD$_3$OD) δ8.42 (s, 1H), 8.00 (bs, 3H), 7.76 (dd, J=1.6, 6.4 Hz, 1H), 7.50 (t, J=8.0 Hz, 1H), 7.40 (dd, J=1.6, 8.0 Hz, 1H), 4.58-4.64 (m, 2H), 3.66-3.73 (m, 2H), 2.32 (s, 3H), 1.84-1.93 (m, 4H), 1.43 (s, 3H).

Example 22: 1-(8-(2,3-dichlorophenyl)-7-methyl-[1,2,4] triazole [4,3-c]pyrimidin-5-yl)-4-methylpiperidin-4-amine

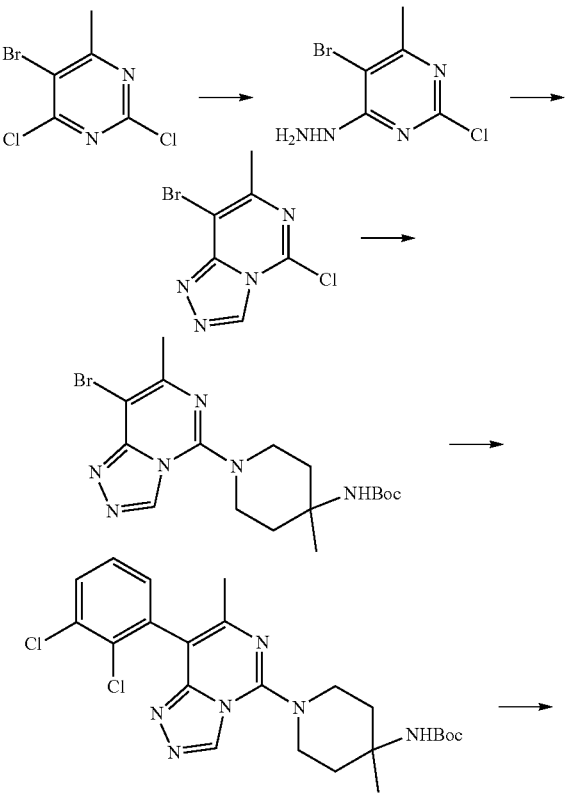

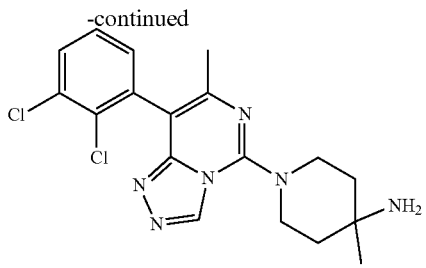

Step 1: Dissolving 5-bromo-2,4-dichloro-6-methylpyrimidine (242 mg, 1 mmol) in ethanol (10 mL), slowly adding 85% hydrazine hydrate (59 mg, 1 mmol) under cooling in an ice bath, and stirring at 0° C. for 1 hour. Concentrating under reduced pressure, and purifying by pulping with petroleum ether to obtain 5-bromo-2-chloro-4-hydrazino-6-methylpyrimidine (150 mg, white solids). MS(ESI): m/z=236.9/238.9[M+H]; $^1$H-NMR (400 MHz, DMSO-d6): δ8.88 (brs, 1H), 4.61 (brs, 2H), 2.35 (s, 3H).

Step 2: Dissolving the 5-bromo-2-chloro-4-hydrazino-6-methylpyrimidine (150 mg, 0.64 mmol) in trimethyl orthoformate (5 mL), and heating to 100° C. for reaction overnight. Cooling to room temperature, concentrating under the reduced pressure, and purifying by column chromatography to obtain 8-bromo-5-chloro-7-methyl-[1,2,4]triazolo [4,3-c] pyrimidine (77 mg, yellow solids). MS(ESI): m/z=246.9/248.9[M+H]; $^1$H-NMR (400 MHz, CDCl$_3$): δ8.93 (s, 1H), 2.67 (s, 3H).

Step 3: Dissolving the 8-bromo-5-chloro-7-methyl-[1,2,4] triazolo [4,3-c]pyrimidine (77 mg, 0.31 mmol) and (4-methylpiperidin-4-yl) tert-butyl carbamate (100 mg, 0.47 mmol) in N,N-dimethylformamide (DMF) (10 mL), adding potassium carbonate (86 mg, 0.62 mmol), and stirring for at room temperature 2 hours. Diluting with ethyl acetate, washing with saturated saline, drying, concentrating, and purifying by the column chromatography to obtain (1-(8-bromo-7-methyl-[1,2,4] triazolo [4,3-c] pyrimidin-5-yl)-4-methylpiperidin-4-yl) tert-butyl carbamate (70 mg, white solids). MS(ESI): m/z=425.1/427.1[M+H]; $^1$H-NMR (400 MHz, CD$_3$OD): 9.22 (s, 1H), 3.75-3.80 (m, 2H), 3.39-3.46 (m, 2H), 2.55 (s, 3H), 2.25-2.28 (m, 2H), 1.74-1.82 (m, 2H), 1.47 (s, 9H), 1.40 (s, 3H).

Step 4: Dissolving the (1-(8-bromo-7-methyl-[1,2,4] triazolo [4,3-c] pyrimidin-5-yl)-4-methylpiperidin-4-yl) tert-butyl carbamate (55 mg, 0.13 mmol) and 2,3-dichlorophenylboronic acid (37 mg, 0.19 mmol) in DMF (10 mL), adding potassium phosphate (83 mg, 0.39 mmol) and Pd (PPh$_3$) 4 (15 mg, 0.013 mmol), exchanging with argon, and heating to 80° C. for reaction overnight until LCMS shows complete reaction. Diluting with ethyl acetate, washing with saturated saline, drying, concentrating, and purifying by the column chromatography to obtain (1-(8-(2,3-dichlorophenyl)-7-methyl-[1,2,4] triazolo [4,3-c] pyrimidin-5-yl)-4-methylpiperidin-4-yl) tert-butyl carbamate (15 mg, pale yellow solids). MS(ESI): m/z=491.1/493.1[M+H]; $^1$H-NMR (400 MHz, CD$_3$OD): δ9.20 (s, 1H), 7.68 (dd, J=1.6, 8.0 Hz, 1H), 7.46 (t, J=8.0 Hz, 1H), 7.38 (dd, J=1.6, 8.0 Hz, 1H), 3.84-3.87 (m, 2H), 3.46-3.52 (m, 2H), 2.29-2.32 (m, 2H), 2.21 (s, 3H), 1.80-1.87 (m, 2H), 1.48 (s, 9H), 1.43 (s, 3H).

Step 5: Dissolving the (1-(8-(2,3-dichlorophenyl)-7-methyl-[1,2,4] triazolo [4,3-c] pyrimidin-5-yl)-4-methylpiperidin-4-yl) tert-butyl carbamate (15 mg, 0.03 mmol) in anhydrous dichloromethane (5 mL), adding trifluoroacetic acid (TFA) (1 mL) dropwise, reacting at room temperature for 1 hour, concentrating, and purifying by preparative chromatography to obtain 1-(8-(2,3-dichlorophenyl)-7-methyl-[1,2,4] triazole [4,3-c]pyrimidin-5-yl)-4-methylpiperidin-4-amine (3.5 mg, yellow solids). MS(ESI): m/z=391.0/393.0; ¹H-NMR (400 MHz, CD₃OD) δ9.21 (s, 1H), 7.70 (dd, J=1.6, 8.0 Hz, 1H), 7.46 (t, J=8.0 Hz, 1H), 7.37 (dd, J=1.6, 8.0 Hz, 1H), 3.95-3.99 (m, 2H), 3.57-3.63 (m, 2H), 2.22 (s, 3H), 1.96-2.08 (m, 4H), 1.51 (s, 3H).

Example 23: 1-(8-(2,3-dichlorophenyl)-7-methyl-[1,2,4] triazole [4,3-a]pyridin-5-yl)-4-methylpiperidin-4-amine

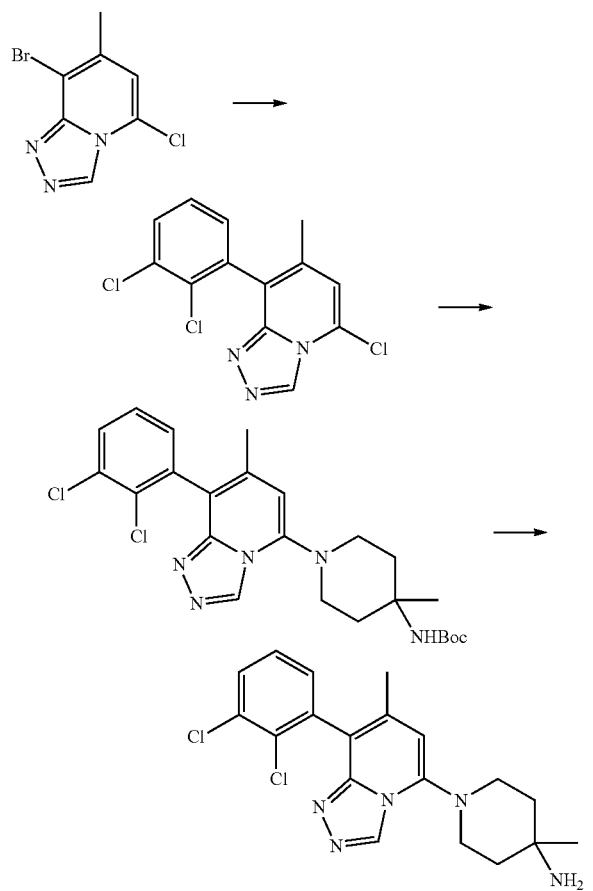

Step 1: Dissolving 8-bromo-5-chloro-7-methyl-[1,2,4] triazolo [4,3-a] pyridine (50 mg, 0.20 mmol) in a 1,4-dioxane/water mixed solution (2 mL, 4:1), adding 2,3-dichlorophenylboronic acid (43 mg, 0.22 mmol) and sodium bicarbonate (NaHCO₃) (51 mg, 0.61 mmol), adding Pd (dppf) Cl₂ (81 mg, 0.01 mmol) after exchanging withy nitrogen, raising the temperature to 100° C. and stirring for 16 hours. Cooling to room temperature, filtering, concentrating, and purifying by column chromatography to obtain 5-chloro-8-(2,3-dichlorophenyl)-7-methyl-[1,2,4] triazolo [4,3-a] pyridine (32 mg, brown solids). MS(ESI): m/z=311.9/313.9[M+H].

Step 2: Dissolving the 5-chloro-8-(2,3-dichlorophenyl)-7-methyl-[1,2-a] pyridine (30 mg, 0.09 mmol) in DMF (2 mL), adding (4-methylpiperidin-4-yl) tert-butyl carbamate (18 mg, 0.08 mmol) and potassium phosphate (K₃PO₄) (18 mg, 0.08 mmol), raising the temperature to 100° C. and stirring for 16 hours. Cooling to room temperature, filtering, concentrating, and purifying by the column chromatography to obtain (1-(8-(2,3-dichlorophenyl)-7-methyl-[1,2,4] triazolo [4,3-a] pyridin-5-yl)-4-methylpiperidin-4-yl) tert-butyl carbamate (yellow solids). MS(ESI): m/z=490.4/492.4[M+H].

Step 3: Dissolving the (1-(8-(2,3-dichlorophenyl)-7-methyl-[1,2,4] triazolo [4,3-a] pyridin-5-yl)-4-methylpiperidin-4-yl) tert-butyl carbamate (15 mg, 0.03 mmol) in dichloromethane (DCM) (1.5 mL), adding TFA (0.4 mL) and stirring at room temperature for 1 hour. Concentrating under reduced pressure, and purifying by preparative chromatography to obtain the 1-(8-(2,3-dichlorophenyl)-7-methyl-[1,2,4] triazole [4,3-a]pyridin-5-yl)-4-methylpiperidin-4-amine (2 mg, yellow solids). MS(ESI): m/z=390.1/392.0; ¹H-NMR (400 MHz, CD₃OD) δ9.06 (s, 1H), 7.68 (dd, J=1.6, 8.0 Hz, 1H), 7.45 (t, J=8.0 Hz, 1H), 7.31 (dd, J=1.6, 8.0 Hz, 1H), 6.61 (s, 1H), 3.46 (dd, J=5.2, 11.2 Hz, 2H), 3.20-3.26 (m, 2H), 2.13-2.20 (m, 5H), 2.03-2.07 (m, 2H), 1.54 (s, 3H).

Example 24: 1-(8-(2,3-dichlorophenyl)-7-methyl-imidazolo [1,2-a] pyridin-5-yl)-4-methylpiperidin-4-amine

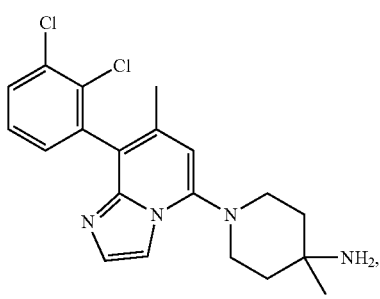 [SMILES: Cc1cc(N2CCC(C)(N)CC2)n2ccnc2c1-c1cccc(Cl)c1Cl]

and the operation is the same as that in Example 23. MS(ESI): m/z=389.1/391.0; H-NMR (400 MHz, CD₃OD) δ7.69 (d, J=1.2 Hz, 1H), 7.65 (dd, J=1.2, 8.0 Hz, 1H), 7.41-7.45 (m, 2H), 7.27 (dd, J=1.2, 7.6 Hz, 1H), 6.54 (s, 1H), 3.30-3.34 (m, 2H), 3.15-3.20 (m, 2H), 2.15 (s, 3H), 1.87-1.91 (m, 4H), 1.34 (s, 3H).

Example 25: 1-(8 ((2,3-dichlorophenyl) sulfanyl)-7-methylimidazole [1,2-c]pyrimidin-5-yl)-4-methylpiperidin-4-amine

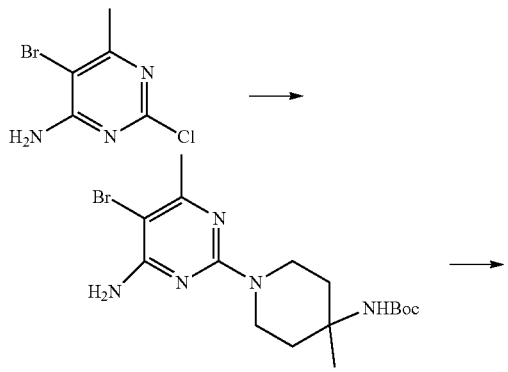

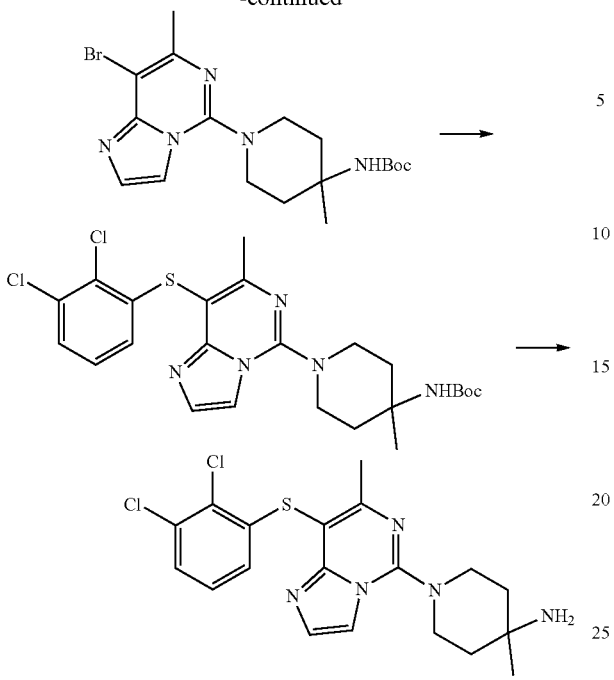

Step 1: Dissolving 5-bromo-2-chloro-6-methylpyrimidin-4-amine (450 mg, 2.04 mmol) and (4-methylpiperidin-4-yl) tert-butyl carbamate (514 mg, 2.40 mmol) in DMF (12 mL), adding potassium carbonate (559 mg, 4.05 mmol), heating to 60° C., stirring overnight, diluting with ethyl acetate, washing with saturated saline, drying, concentrating, and purifying by column chromatography to obtain (1-(4-amino-5-bromo-6-methylpyrimidin-2-yl)-4-methylpiperidin-4-yl) tert-butyl carbamate (550 mg, white solids). MS(ESI): m/z=400.3/402.3[M+H]; 1H-NMR (400 MHz, DMSO-d6): δ6.53 (brs, 2H), 3.92-3.95 (m, 2H), 3.22-3.28 (m, 2H), 2.22 (s, 3H), 1.95-1.99 (m, 2H), 1.38 (s, 9H), 1.27-1.33 (m, 2H), 1.22 (s, 3H).

Step 2: Dissolving the (1-(4-amino-5-bromo-6-methylpyrimidin-2-yl)-4-methylpiperidin-4-yl) tert-butyl carbamate (226 mg, 0.57 mmol) in ethanol (10 mL), adding a phosphate buffer solution (10 mL, pH=6.7), sodium acetate (186 mg, 2.27 mmol) and 40% aqueous chloroacetaldehyde (1.1 g, 5.6 mmol), heating to 100° C., stirring for 24 hours, diluting with ethyl acetate, washing with saturated saline, drying, concentrating, and purifying by the column chromatography to obtain (1-(8-bromo-7-methylimidazo [1,2-c] pyrimidin-5-yl)-4-methylpiperidin-4-yl) tert-butyl carbamate (180 mg, yellow solids). MS(ESI): m/z=424.3/426.3[M+H]; 1H-NMR (400 MHz, DMSO-d6): 7.79 (d, J=1.2 Hz, 1H), 7.55 (d, J=1.2 Hz, 1H), 6.63 (brs, 1H), 3.45-3.49 (m, 2H), 3.15-3.20 (m, 2H), 2.47 (s, 3H), 2.17-2.20 (m, 2H), 1.61-1.68 (m, 2H), 1.39 (s, 9H), 1.29 (s, 3H).

Step 3: Dissolving the (1-(8-bromo-7-methylimidazo [1,2-c] pyrimidin-5-yl)-4-methylpiperidin-4-yl) tert-butyl carbamate (240 mg, 0.57 mmol) and 2,3-dichlorothiophenol (152 mg, 0.85 mmol) in dioxane (15 mL), adding potassium phosphate (180 mg, 0.85 mmol), 1,10-phenanthroline (21 mg, 0.11 mmol) and copper iodide (CuI) (22 mg, 0.11 mmol), exchanging with nitrogen, heating to 105° C. and stirring for 18 hours. Cooling to room temperature, filtering, concentrating, and purifying by the column chromatography to obtain (1-(8-((2,3-dichlorophenyl) sulfanyl)-7-methyl-imidazo [1,2-c]pyrimidin-5-yl)-4-methylpiperidin-4-yl) tert-butyl carbamate (17 mg, brown solids). MS(ESI): m/z=522.2/524.2[M+H].

Step 4: Dissolving the (1-(8-((2,3-dichlorophenyl) sulfanyl)-7-methylimidazo [1,2-c] pyrimidin-5-yl)-4-methylpiperidin-4-yl) tert-butyl carbamate (17 mg, 0.03 mmol) in DCM (1.5 mL), adding TFA (0.5 mL), and stirring at room temperature for 1 hour. Concentrating under reduced pressure, and purifying by preparative chromatography to obtain the 1-(8 ((2,3-dichlorophenyl) sulfanyl)-7-methylimidazole [1,2-c] pyrimidin-5-yl)-4-methylpiperidin-4-amine (9 mg, white solids). MS(ESI): m/z=422.1/424.1; ¹H-NMR (400 MHz, CD₃OD) δ7.73 (d, J=1.6 Hz, 1H), 7.47 (d, J=1.6 Hz, 1H), 7.27 (dd, J=1.2, 8.0 Hz, 1H), 7.02 (t, J=8.0 Hz, 1H), 6.49 (dd, J=1.2, 8.0 Hz, 1H), 3.58-3.76 (m, 4H), 2.57 (s, 3H), 1.77-1.86 (m, 4H), 1.30 (s, 3H).

Example 26: (R)-8-(8-((2-amino-3-chloropyridin-4-yl) thio)-7-methylimidazole [1,2-c] pyrimidin-5-yl)-8-azaspiro [4.5] quin-1-amine

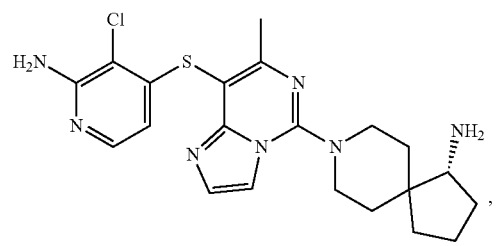 [SMILES: Cc1nc(N2CCC3(CCC[C@H]3N)CC2)n2ccnc2c1Sc1ccnc(N)c1Cl]

and the target compound is prepared according to the method of Example 1. MS(ESI): m/z=444.1/446.1[M+H]; ¹H-NMR (400 MHz, CD₃OD) δ7.95 (s, 1H), 7.75 (s, 1H), 7.58 (d, J=6.4 Hz, 1H), 6.27 (t, J=7.2 Hz, 1H), 4.15-4.24 (m, 2H), 3.45-3.48 (m, 2H), 2.63 (s, 3H), 2.25-2.32 (m, 1H), 1.67-2.03 (m, 10H).

Example 27: 5-(4-amino-4-methylpiperidin-1-yl)-8-(2,3-dichlorophenyl) imidazole [1,2-c] pyrimidin-7-amine

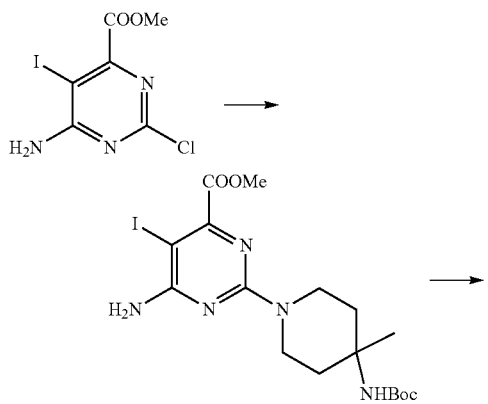

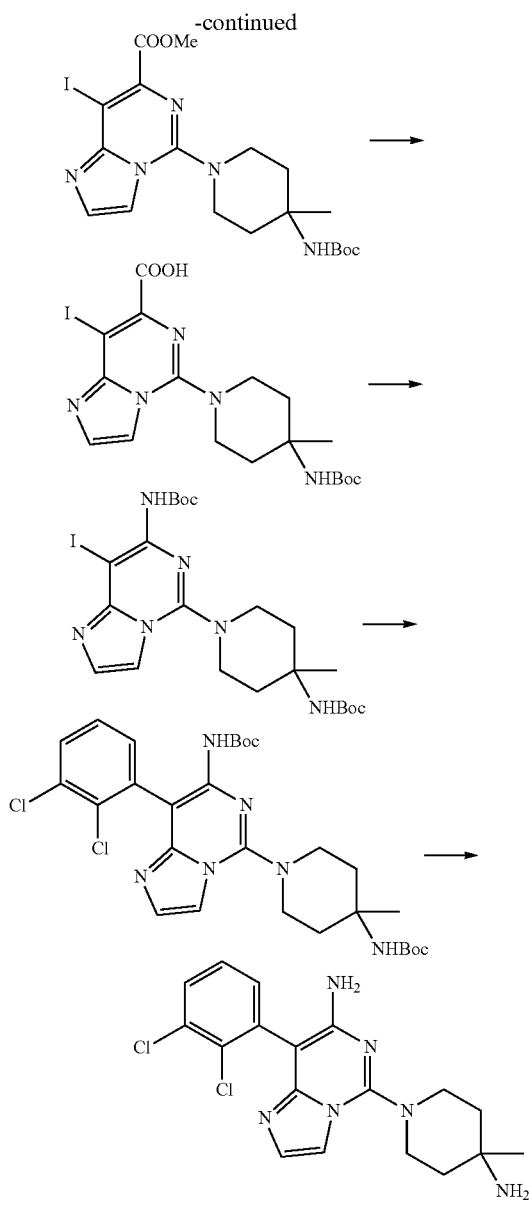

Step 1: Dissolving 6-amino-2-chloro-5-iodopyrimidine-4-methyl carboxylate (572 mg, 1.83 mmol) and (4-methylpiperidin-4-yl) tert-butyl carbamate (586 mg, 2.74 mmol) in N,N-dimethylformamide (DMF) (50 mL), adding potassium carbonate (506 mg, 3.67 mmol), and heating to 60° C. for reaction for 24 hours. Cooling a reaction solution to room temperature, diluting with ethyl acetate, washing with saturated saline, drying and concentrating under reduced pressure to obtain 6-amino-2-(4-((tert-butoxycarbonyl) amino)-4-methylpiperidin-1-yl)-5-iodopyrimidine-4-methyl carboxylate (710 mg, yellow solids). MS(ESI): m/z=491.8 [M+H]; $^1$H-NMR (400 MHz, DMSO_d6) δ6.82 (brs, 2H), 6.55 (brs, 1H), 3.89-3.93 (m, 2H), 3.81 (s, 3H), 3.22-3.27 (m, 2H), 1.97-1.99 (m, 2H), 1.38 (s, 9H), 1.31-1.38 (m, 2H), 1.22 (s, 3H).

Step 2: Dissolving the 6-amino-2-(4-((tert-butoxycarbonyl) amino)-4-methylpiperidin-1-yl)-5-iodopyrimidine-4-methyl carboxylate (491 mg, 1.0 mmol) in ethanol (40 mL), adding phosphate buffer solution (40 mL, pH=6.7), sodium acetate (848 mg, 10.3 mmol) and 40% aqueous chloroacetaldehyde (2.0 g, 10.3 mmol), and heating to 100° C. for reaction overnight. Cooling the reaction solution to room temperature, concentrating to remove most of organic solvents, extracting with the ethyl acetate, drying, concentrating under the reduced pressure, and purifying by the column chromatography to obtain 5-(4-((tert-butoxycarbonyl) amino)-4-methylpiperidin-1-yl)-8-iodoimidazo [1,2-c] pyrimidine-7-methyl carboxylate (395 mg, yellow solids). MS(ESI): m/z=516.1[M+H]; $^1$H-NMR (400 MHz, DMSO_d6) δ8.01 (d, J=1.2 Hz, 1H), 7.72 (d, J=1.2 Hz, 1H), 6.64 (brs, 1H), 3.88 (s, 3H), 3.50-3.53 (m, 2H), 3.17-3.23 (m, 2H), 2.17-2.21 (m, 2H), 1.61-1.68 (m, 2H), 1.39 (s, 9H), 1.29 (s, 3H).

Step 3: Dissolving the 5-(4-((tert-butoxycarbonyl) amino)-4-methylpiperidin-1-yl)-8-iodoimidazo [1,2-c] pyrimidine-7-methyl carboxylate (200 mg, 0.39 mmol) and sodium hydroxide (31 mg, 0.78 mmol) in methanol (10 mL), adding water (2 mL), heating to 50° C. for reaction for 3 hours, neutralizing by 2M dilute hydrochloric acid, concentrating under reduced pressure, and purifying by column chromatography to obtain 5-(4-((tert-butoxycarbonyl) amino)-4-methylpiperidin-1-yl)-8-iodoimidazo [1,2-c]pyrimidine-7-carboxylic acid (122 mg, yellow solids). MS(ESI): m/z=501.7[M+H]; $^1$H-NMR (400 MHz, DMSO-d6) δ7.76 (d, J=1.6 Hz, 1H), 7.48 (d, J=1.6 Hz, 1H), 6.63 (brs, 1H), 3.38-3.42 (m, 2H), 3.10-3.15 (m, 2H), 2.17-2.20 (m, 2H), 1.61-1.67 (m, 2H), 1.39 (s, 9H), 1.29 (s, 3H).

Step 4: Dissolving the 5-(4-((tert-butoxycarbonyl) amino)-4-methylpiperidin-1-yl)-8-iodoimidazo [1,2-c] pyrimidine-7-carboxylic acid (100 mg, 0.2 mmol), diphenyl azidophosphate (DPPA) (110 mg, 0.4 mmol) and triethylamine (61 mg, 0.6 mmol) in tert-butanol (10 mL), heating to 100° C. for reaction for 2 hours, after LC-MS shows complete reaction, concentrating under reduced pressure, and purifying by the column chromatography to obtain (5-(4-((tert-butoxycarbonyl) amino)-4-methylpiperidin-1-yl)-8-iodoimidazo [1,2-c] pyrimidin-7-yl) tert-butyl carbamate (15 mg, yellow solids). MS(ESI): m/z=573.2[M+H]; $^1$H-NMR (400 MHz, CD$_3$OD) δ7.70 (d, J=1.6 Hz, 1H), 7.43 (d, J=1.6 Hz, 1H), 3.54-3.57 (m, 2H), 3.20-3.24 (m, 2H), 2.12-2.15 (m, 2H), 1.64-1.71 (m, 2H), 1.44 (s, 9H), 1.34 (s, 9H), 1.28 (s, 3H).

Step 5: Dissolving the (5-(4-((tert-butoxycarbonyl) amino)-4-methylpiperidin-1-yl)-8-iodoimidazo [1,2-c] pyrimidin-7-yl) tert-butyl carbamate (10 mg, 0.017 mmol) and 2,3-dichlorophenylboronic acid (5 mg, 0.026 mmol) in an ethanol/water mixed solvent (4 mL/0.2 mL), adding sodium carbonate (5 mg, 0.048 mmol), adding Pd (dppf)Cl$_2$ (2 mg, 0.0027 mmol) after exchanging with nitrogen, raising the temperature to 80° C. and stirring for 2 hours. Cooling to room temperature, filtering, concentrating, and purifying by the column chromatography to obtain 5-(4-((tert-butoxycarbonyl) amino)-4-methylpiperidin-1-yl)-8-(2,3-dichlorophenyl) imidazo [1,2-c] pyrimidin-7-yl) tert-butyl carbamate (6 mg, yellow solids). MS(ESI): m/z=591.4/593.4[M+H].

Step 6: Dissolving the 5-(4-((tert-butoxycarbonyl) amino)-4-methylpiperidin-1-yl)-8-(2,3-dichlorophenyl) imidazo [1,2-c] pyrimidin-7-yl) tert-butyl carbamate (6 mg, 0.01 mmol) in DCM (4 mL), adding TFA (1 mL), and stirring at room temperature for 2 hours. Concentrating under reduced pressure, and purifying by preparative chromatography to obtain the 5-(4-amino-4-methylpiperidin-1-yl)-8-(2,3-dichlorophenyl) imidazole [1,2-c] pyrimidin-7-amine (2 mg, yellow solids). MS(ESI): m/z=391.1/393.0; $^1$H-NMR (400 MHz, CD$_3$OD) δ7.64 (dd, J=1.2, 8.0 Hz, 1H), 7.55 (d, J=2.4 Hz, 1H), 7.37-7.42 (m, 2H), 7.31 (dd, J=1.2, 8.0 Hz, 1H), 3.81-3.85 (m, 2H), 3.38-3.45 (m, 2H), 1.87-2.02 (m, 4H), 1.45 (s, 3H).

Example 28: 1-(8-(2,3-dichlorophenyl)-7-(fluoromethylene) imidazole [1,2-c]pyrimidin-5-yl)-4-methylpiperidin-4-amine

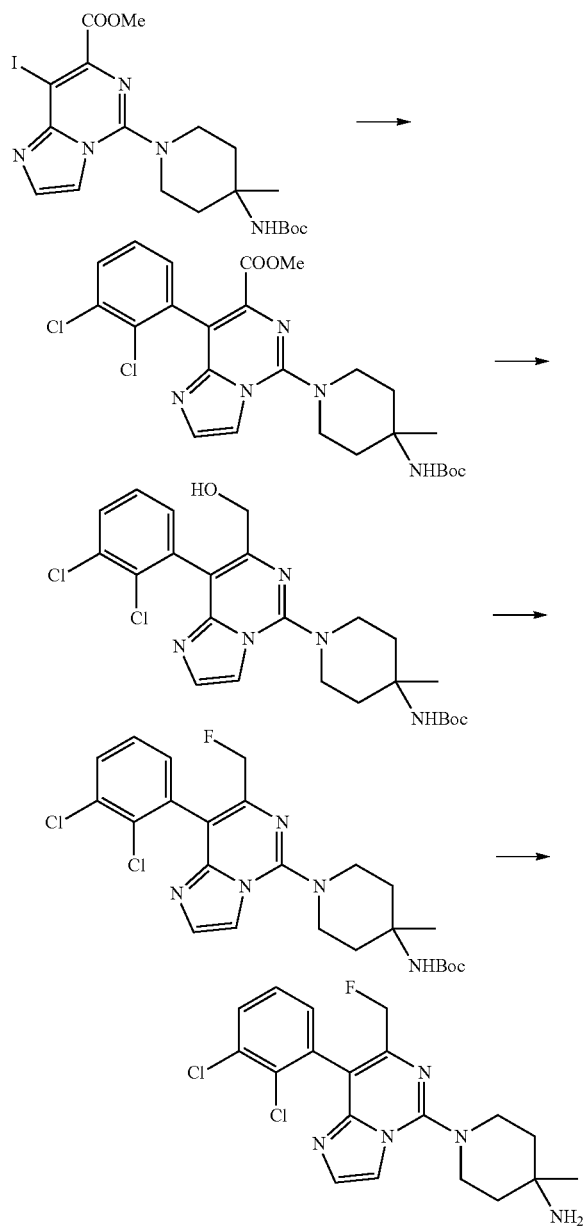

Step 1: Dissolving 5-(4-((tert-butoxycarbonyl) amino)-4-methylpiperidin-1-yl)-8-iodoimidazo [1,2-c] pyrimidine-7-methyl carboxylate (137 mg, 0.27 mmol) and 2,3-dichlorophenylboronic acid (101 mg, 0.53 mmol) in an ethanol/water mixed solvent (10 mL/0.5 mL), adding sodium carbonate (83 mg, 0.78 mmol), adding Pd (dppf)Cl$_2$ (27 mg, 0.04 mmol) after exchanging with nitrogen, raising the temperature to 80° C. and stirring for 2 hours. Cooling to room temperature, filtering, concentrating, and purifying by the column chromatography to obtain 5-(4-((tert-butoxycarbonyl) amino)-4-methylpiperidin-1-yl)-8-(2,3-dichlorophenyl) imidazo [1,2-c] pyrimidin-7-yl) tert-butyl carbamate (110 mg, yellow solids). MS(ESI): m/z=533.9/535.9[M+H]; $^1$H-NMR (400 MHz, DMSO-d6) δ7.97 (d, J=1.2 Hz, 1H), 7.70 (d, J=1.2 Hz, 1H), 7.67 (dd, J=1.6, 8.0 Hz, 1H), 7.40-7.44 (m, 1H), 7.32 (dd, J=1.6, 7.6 Hz, 1H), 6.68 (brs, 1H), 3.63 (s, 3H), 3.60-3.63 (m, 2H), 3.26-3.28 (m, 2H), 2.22-2.25 (m, 2H), 1.67-1.75 (m, 2H), 1.41 (s, 9H), 1.32 (s, 3H).

Step 2: Dissolving the 5-(4-((tert-butoxycarbonyl) amino)-4-methylpiperidin-1-yl)-8-(2,3-dichlorophenyl) imidazo [1,2-c] pyrimidin-7-yl) tert-butyl carbamate (100 mg, 0.19 mmol) in dichloromethane (15 mL), cooling to −78° C., slowly adding DIBAL-H (0.56 mL, 0.56 mmol, 1M toluene solution), raising to room temperature, stirring for 2 hours, diluting with ether, adding 2 drops of 15% sodium hydroxide for a quenching reaction, drying, concentrating under reduced pressure, and purifying by column chromatography to obtain (1-(8-(2,3-dichlorophenyl)-7-(hydroxymethyl) imidazo [1,2-c]pyrimidin-5-yl)-4-methylpiperidin-4-yl) tert-butyl carbamate (yellow solids). MS(ESI): m/z=505.9/507.9[M+H].

Step 3: Dissolving the (1-(8-(2,3-dichlorophenyl)-7-(hydroxymethyl) imidazo [1,2-c] pyrimidin-5-yl)-4-methylpiperidin-4-yl) tert-butyl carbamate (80 mg, 0.16 mmol) in dichloromethane (10 mL), cooling to 0° C., slowly adding diethylamine sulfur trifluoride (DAST) (38 mg, 0.24 mmol), raising to room temperature, stirring overnight, concentrating, and purifying by the column chromatography to obtain ((1-(8-(2,3-dichlorophenyl)-7-(fluoromethyl) imidazo [1,2-c] pyrimidin-5-yl)-4-methylpiperidin-4-yl) tert-butyl carbamate (51 mg, yellow solids). MS(ESI): m/z=508.3/510.3 [M+H]; $^1$H-NMR (400 MHz, DMSO-d6) δ7.88 (d, J=1.2 Hz, 1H), 7.76 (dd, J=1.6, 8.0 Hz, 1H), 7.57 (d, J=1.2 Hz, 1H), 7.46-7.50 (m, 1H), 7.40 (dd, J=1.6, 7.6 Hz, 1H), 6.67 (brs, 1H), 5.15 (dd, J=10.4, 34.0 Hz, 1H), 5.03 (dd, J=10.4, 34.0 Hz, 1H), 3.58-3.63 (m, 2H), 3.25-3.28 (m, 2H), 2.22-2.25 (m, 2H), 1.67-1.73 (m, 2H), 1.41 (s, 9H), 1.32 (s, 3H).

Step 4: Dissolving the ((1-(8-(2,3-dichlorophenyl)-7-(fluoromethyl) imidazo [1,2-c] pyrimidin-5-yl)-4-methylpiperidin-4-yl) tert-butyl carbamate (50 mg, 0.098 mmol) in DCM (5 mL), adding TFA (5 mL), and stirring at room temperature for 2 hours. Concentrating under reduced pressure, and purifying by preparative chromatography to obtain the 1-(8-(2,3-dichlorophenyl)-7-(fluoromethylene) imidazole [1,2-c] pyrimidin-5-yl)-4-methylpiperidin-4-amine (22 mg, white solids). MS(ESI): m/z=408.1/410.1; $^1$H-NMR (400 MHz, CD$_3$OD) δ7.83 (s, 1H), 7.70 (dd, J=1.6, 8.0 Hz, 1H), 7.58 (d, J=1.2 Hz, 1H), 7.45 (t, J=8.0 Hz, 1H), 7.37 (dd, J=1.6, 8.0 Hz, 1H), 5.01-5.25 (m, 2H), 3.72-3.79 (m, 2H), 3.53-3.61 (m, 2H), 1.87-1.91 (m, 4H), 1.37 (s, 3H).

Comparative Compound 1: 1-(8-(2,3-dichlorophenyl)-7-methylimidazo [1,2-c]pyrimidin-5-yl)-4-methylpiperidin-4-amine

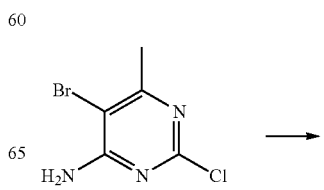

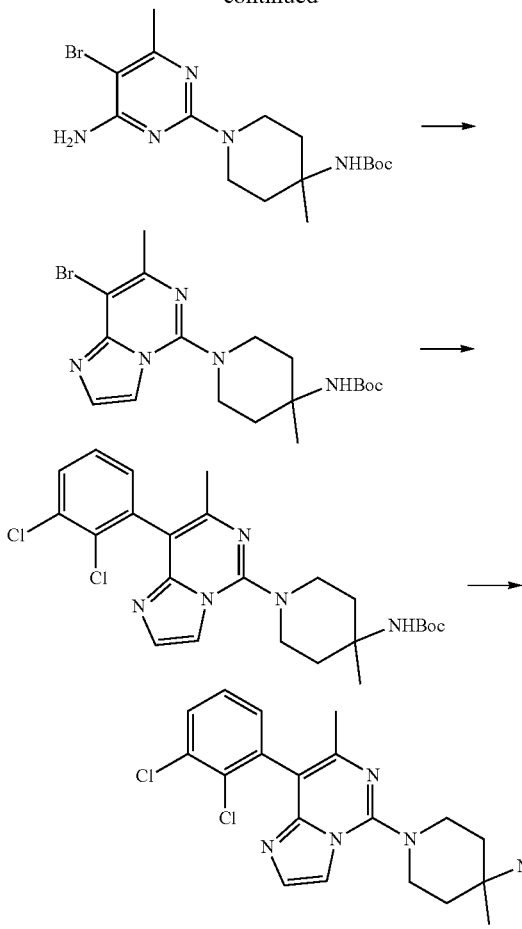

Step 1: Dissolving 5-bromo-2-chloro-6-methylpyrimidin-4-amine (300 mg, 1.35 mmol) and (4-methylpiperidin-4-yl) tert-butyl carbamate (372 mg, 2.7 mmol) in DMF (12 mL), adding potassium carbonate (559 mg, 4.05 mmol), heating to 60° C., stirring overnight, diluting with ethyl acetate, washing with saturated saline, drying, concentrating, and purifying by column chromatography to obtain (1-(4-amino-5-bromo-6-methylpyrimidin-2-yl)-4-methylpiperidin-4-yl) tert-butyl carbamate (261 mg, white solids). MS(ESI): m/z=400.3/402.3[M+H]; 1H-NMR (400 MHz, DMSO-d6): δ6.53 (brs, 2H), 3.92-3.95 (m, 2H), 3.22-3.28 (m, 2H), 2.22 (s, 3H), 1.95-1.99 (m, 2H), 1.38 (s, 9H), 1.27-1.33 (m, 2H), 1.22 (s, 3H).

Step 2: Dissolving the (1-(4-amino-5-bromo-6-methylpyrimidin-2-yl)-4-methylpiperidin-4-yl) tert-butyl carbamate (226 mg, 0.57 mmol) in ethanol (10 mL), adding a phosphate buffer solution (10 mL, pH=6.7), sodium acetate (186 mg, 2.27 mmol) and 40% aqueous chloroacetaldehyde (1.1 g, 5.6 mmol), heating to 100° C., stirring for 24 hours, diluting with ethyl acetate, washing with saturated saline, drying, concentrating, and purifying by the column chromatography to obtain (1-(8-bromo-7-methylimidazo [1,2-c] pyrimidin-5-yl)-4-methylpiperidin-4-yl) tert-butyl carbamate (180 mg, yellow solids). MS(ESI): m/z=424.3/426.3[M+H]; 1H-NMR (400 MHz, DMSO-d6): 7.79 (d, J=1.2 Hz, 1H), 7.55 (d, J=1.2 Hz, 1H), 6.63 (brs, 1H), 3.45-3.49 (m, 2H), 3.15-3.20 (m, 2H), 2.47 (s, 3H), 2.17-2.20 (m, 2H), 1.61-1.68 (m, 2H), 1.39 (s, 9H), 1.29 (s, 3H).

Step 3: Dissolving the (1-(8-bromo-7-methylimidazo [1,2-c] pyrimidin-5-yl)-4-methylpiperidin-4-yl) tert-butyl carbamate (180 mg, 0.42 mmol) and (2,3-dichlorophenyl) boric acid (122 mg, 0.64 mmol) in DMF (15 mL), adding potassium phosphate (356 mg, 1.68 mmol) and Pd(PPh$_3$)$_4$ (50 mg, 0.043 mmol), exchanging with argon, heating to 80° C. for reaction overnight until LCMS shows complete reaction. Cooling to room temperature, diluting with ethyl acetate, washing with saturated saline, drying, concentrating, and purifying by the column chromatography to obtain (1-(8-(2,3-dichlorophenyl)-7-methylimidazo [1,2-c] pyrimidin-5-yl)-4-methylpiperidin-4-yl) tert-butyl carbamate (35 mg, light yellow solids). MS(ESI): m/z=490.2[M+H]; 1H-NMR (400 MHz, DMSO-d6): δ7.71-7.73 (m, 2H), 7.47 (t, J=8.0 Hz, 1H), 7.44 (d, J=1.6 Hz, 1H), 7.37 (dd, J=1.6, 8.0 Hz, 1H), 6.65 (brs, 1H), 3.53-3.56 (m, 2H), 3.23-3.29 (m, 2H), 2.20-2.23 (m, 2H), 2.11 (s, 3H), 1.65-1.72 (m, 2H), 1.41 (s, 9H), 1.32 (s, 3H).

Step 5: Dissolving the (1-(8-(2,3-dichlorophenyl)-7-methylimidazo [1,2-c]pyrimidin-5-yl)-4-methylpiperidin-4-yl) tert-butyl carbamate (35 mg, 0.072 mmol) in anhydrous dichloromethane (5 mL), adding TFA (1 mL) dropwise, reacting at room temperature for 1 hour, concentrating, purifying by preparative chromatography and lyophilizing to obtain the 1-(8-(2,3-dichlorophenyl)-7-methylimidazo [1,2-c] pyrimidin-5-yl)-4-methylpiperidin-4-amine (7.6 mg, yellow solids). MS(ESI): m/z=390.0/392.1[M+H]; 1H-NMR (400 MHz, DMSO_d6) δ7.69-7.74 (m, 2H), 7.37-7.48 (m, 3H), 3.42-3.50 (m, 4H), 2.11 (s, 3H), 1.57-1.71 (m, 4H), 1.17 (s, 3H).

Comparative Compound 2: 1-(8-(2,3-dichlorophenyl) imidazo [1,2-c] pyrimidin-5-yl)-4-methylpiperidin-4-amine

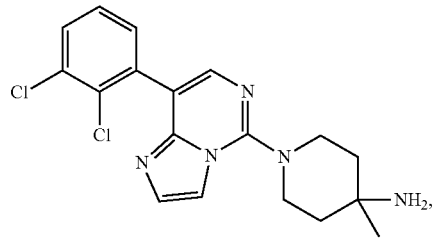 [SMILES: CC1(N)CCN(c2ncc(-c3cccc(Cl)c3Cl)c3nccn23)CC1]

and with 5-bromo-2-chloropyrimidin-4-amine as a raw material, and the operation is the same as that of the comparative compound 1. MS(ESI): m/z=376.1/378.1[M+H]; 1H-NMR (400 MHz, CD$_3$OD) δ7.66 (d, J=1.6 Hz, 1H), 7.62 (s, 1H), 7.53-7.55 (m, 1H), 7.45 (d, J=1.6 Hz, 1H), 7.30-7.31 (m, 2H), 3.52-3.55 (m, 4H), 1.70-1.75 (m, 4H), 1.20 (s, 3H).

Comparative Compound 3

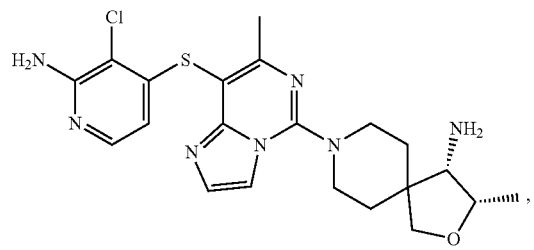 [SMILES: Cc1nc(N2CCC3(CC2)CO[C@@H](C)[C@H]3N)n2ccnc2c1Sc1ccnc(N)c1Cl]

and the target compound is prepared according to the method of Example 2. MS(ESI): m/z=460.4; $^1$H-NMR (400 MHz, CD$_3$OD) δ7.92 (brs, 1H), 7.72 (br s, 1H), 7.56 (d, J=4.8 Hz, 1H), 6.22 (d, J=6.4 Hz, 1H), 4.32-4.35 (m, 1H), 4.09-4.19 (m, 2H), 4.03 (d, J=8.8 Hz, 1H), 3.92 (d, J=9.2 Hz, 1H), 3.30-3.53 (m, 3H), 2.61 (s, 3H), 1.82-2.11 (m, 4H), 1.34 (d, J=6.4 Hz, 3H).

Test Example 1: Test of Inhibitory Activity of Compounds of Examples Against an SHP2 Enzyme (1) Preparing 1×Reaction Buffer according to the BPS Biosciences' Instructions for Use of the SHP2 enzyme. (2) Preparing a compound concentration gradient: Test the test compound at 10 µM under 3× dilution for 10 concentrations, diluting to a 100% dimethyl sulfoxide solution at a 100× final concentration in a 384-well plate, and diluting the compound with Precision 4× for 10 concentrations. Transferring 250 nL of the compound at the 100× final concentration to a target plate OptiPlate-384F using a dispenser Echo 550. Adding 250 nL of dimethyl sulfoxide to a positive control and 250 nL of 1 mM SHP099 to a negative control. (3) Preparing the activation peptide solution at a 5× final concentration with the 1×Reaction Buffer, adding 5 µL of the solution to a reaction plate, respectively, and centrifuging at 1000 rpm for 1 min. (4) Preparing an enzyme solution at a 2.5× final concentration with the 1×Reaction Buffer, adding 10 µL of the solution to the reaction plate, respectively, centrifuging at 1000 rpm for 1 min, and incubating at room temperature for 60 min. (5) Preparing a substrate peptide solution at a 2.5× final concentration with the 1×Reaction Buffer, centrifuging at 1000 rpm for 1 min, and incubating at room temperature for 30 min. (6) Adding 30 µL of stop test solution to stop the reaction, centrifuging at 1000 rpm for 60 see, and mixing well by shaking. (7) Reading the conversion rate with a Caliper EZ Reader. (7) Data analysis:

$$\% \text{ Inhibition} = \frac{\text{Conversion \%\_max} - \text{Conversion \%\_sample}}{\text{Conversion \%\_max} - \text{Conversion \%\_min}} \times 100$$

Wherein: Conversion %/_sample is the reading of a conversion rate of a sample; Conversion %_min: mean of negative control wells, which represents the reading of a conversion rate in absence of enzyme activity wells; Conversion %_max: mean of a ratio of positive control wells, which represents the reading of a conversion rate in absence of compound inhibition wells. (8) Fitting a dose-response curve: With a log value of the concentration as the X-axis and the % inhibition as the Y-axis, fitting the dose-response curve using the log (inhibitor) vs. response-Variable slope of an analytical software GraphPad Prism 5, and thereby obtaining IC50 values for each compound against enzyme activity (the specific results are shown in Table 1).

TABLE 1

| No. | SHP2 Enzyme Inhibition IC$_{50}$ Value/nM |
|---|---|
| Example 1 | 4.4 |
| Example 2 | 6.3 |
| Example 3 | 1.0 |
| Example 4 | 1.9 |
| Example 5 | 0.8 |
| Example 6 | 1.3 |
| Example 7 | 2.1 |
| Example 8 | 3.7 |
| Example 9 | NT |

TABLE 1-continued

| No. | SHP2 Enzyme Inhibition IC$_{50}$ Value/nM |
|---|---|
| Example 10 | NT |
| Comparative Compound 1 | 141 |
| Example 11 | NT |
| Example 12 | 2.9 |
| Example 13 | 1.8 |
| Example 14 | 3.1 |
| Example 15 | 12.1 |
| Example 16 | 9.5 |
| Example 17 | 9.1 |
| Example 18 | 24.6 |
| Example 19 | 29.5 |
| Example 20 | 3.8 |
| Comparative Compound 2 | 3460 |
| Example 21 | >1 uM |
| Example 22 | >1 uM |
| Example 23 | >1 uM |
| Example 24 | 706 |
| Example 25 | 65 |
| Example 26 | 6.1 |
| Example 27 | 287 |
| Example 28 | 53 |
| SHP099 | 73 |
| Comparative Compound 3 | 6.8 |

Result: Fused heterocyclic compounds of examples of the present disclosure have high inhibitory activity against the SHP2 enzyme, and most of IC50 values of the fused heterocyclic compounds are less than 50 nM, showing significant advantages compared to the comparative compounds 1, 2 and SHP099.

Test Example 2: Test of Inhibitory Activity of Compounds of Examples Against Proliferation of MV4-11 Leukemia Cells Specific experimental procedures: 1) At Day 0: Inoculating trypsin-digested cells in 96-well plate and suspending the plate in cell culture medium; measure cell density using an automatic cell counter, diluting the cells with the culture medium to appropriate density, adding 100 µl of cell suspension in the 96-well plate, and incubating a cell-free medium as a control well in a cell incubator with 500 CO$_2$ at 37° C. overnight; 2) Day 1: Treating test compounds of the cells using a drug for a total of 8 concentrations, and diluting at a 3× concentration, wherein 10 µM is a starting test concentration of the test compounds. Specific steps: Preparing a 200× compound mother liquid, diluting compounds to a 3× final concentration with the culture medium, i.e., adding 3 µL of 200× compound to 197 µL of culture medium, adding 50 µL of diluted compound to the cells in each well of the 96-well plate, and incubating the plate in the cell incubator with 5% CO$_2$ at 37° C. for 72 h; 3) Day 4: Testing the cell viability by equilibrating the 96-well to room temperature first, adding 40 µl of CellTiter-Glo® reagent to each well, mixing in a shaker for 2 min to fully lysing the cells, incubating at room temperature for 10 minutes to stabilize luminescence signals, and reading luminescence value using an Envision plate reader; 4) Using GraphPad Prism 5.0 software for analyzing data at the time of data processing, fitting the data using non-linear S-curve regression to obtain a dose-response curve, and thereby calculating the IC50 values. % Inhibition=(DMSO-treated cell wells–compound-treated cell wells)/(DMSO-treated cell wells–cell-free medium well)×100. IC50 values are obtained by a four-parameter regression using software attached to the plate reader (the specific results are shown in Table 2).

TABLE 2

| No. | $IC_{50}$ value/nM |
|---|---|
| Example 1 | 11.0 |
| Example 2 | 31.3 |
| Example 3 | 2.8 |
| Example 4 | 4.7 |
| Example 5 | <1.5 |
| Example 6 | 8.7 |
| Example 7 | 9.3 |
| Example 8 | 12.0 |
| Example 9 | NT |
| Example 10 | NT |
| Comparative Compound 1 | 1412 |
| Example 11 | NT |
| Example 12 | 24.7 |
| Example 13 | 39.2 |
| Example 14 | 18.4 |
| Example 15 | 135.3 |
| Example 16 | 107.6 |
| Example 17 | 48.0 |
| Example 18 | 860.2 |
| Example 19 | 687.4 |
| Example 20 | 9.4 |
| Comparative Compound 2 | >10000 |
| Example 21 | >10 uM |
| Example 22 | >10 uM |
| Example 23 | >10 uM |
| Example 24 | 5.4 uM |
| Example 25 | 1360 |
| Example 26 | 147 |
| Example 27 | 2546 |
| Example 28 | 2013 |
| SHP099 | 1669 |
| Comparative Compound 3 | 43 |

Note:
NTs in Tables 1 and 2 indicate not tested.

Result: The aromatic-substituted spiro-substituted fused heterocyclic compounds of examples of the present disclosure have high inhibitory activity against MV 4-11 cell proliferation inhibitors; most of the compounds have $IC_{50}$ values less than 1000 nM, and some compounds have cell activity $IC_{50}$ even less than 10 nM, showing significant in vitro antitumor activity advantages compared to the comparative compounds 1, 2 and SHP099.

Test Example 3: Test of Inhibitory Activity of Some Compounds of Examples Against Different Cell Proliferation Incubating cells such as KYSE520 (oesophageal cancer cells), H358 (lung cancer cells), Colo-205 (colorectal cancer cells), MiaPaca-2 (pancreas cancer cells), MOLM 13 (leukemia cells), NCI—H 1666 (lung cancer cells), NCI—H 508 (lung cancer), KATO III (gastric cancer), HEK 293A (normal cells), H3255 (lung cancer), H1975 (lung cancer), PC-9 (lung cancer), A549 (lung cancer), SNU16 (gastric cancer), and H1299 (lung cancer) in a 96-well plate at 100 l/well and 20,000 cells/mL, and supplementing 10% fetal bovine serum and 1% penicillin/streptomycin sulfate. With 0.5% dimethyl sulfoxide as a blank control, treating the cells in a solution of the test compounds under 3× dilution at an initial concentration of 10 μM in eight gradients, and incubating the plate in an incubator with 5% $CO_2$ for a certain period of time. At the end of the incubation, adding 10 μL of an MTT stock solution (5 mg/mL) to each well. Incubating the plates at 37° C. for 4 hours, and then removing the culture medium. Adding the dimethyl sulfoxide (100 μL) to each well, and then shaking well. Measuring the absorbance of a formazan product at 570 nm on a Thermo Scientific Varioskan Flash multi-mode reader. Fitting dose-response data to a three-parameter nonlinear regression model using GraphPad Prism 6.0 software to obtain $IC_{50}$ values.

Conclusion: Some examples of the present disclosure, such as Example 1 and Example 4, have good cell proliferation inhibitory activity against different tumor cell lines such as KYSE520, H358, MOLM 13, NCI-H1666, NCI—H 508, SNU 16, KATO III, etc., with IC50 values less than 1 uM, especially susceptible to tumor cell lines driven by receptor tyrosine kinase or Ras-Raf-MEK mutations, e.g. for KYSE520, H358, MOLM 13, NCI-H1666, NCI—H 508 cell proliferation inhibition, all IC50 values are less than 100 nM, some even less than 10 nM, showing higher in vitro antitumor activity which is much higher than that of the comparative compounds 1, 2 and SHP099.

Test Example 4: Inhibitory Activity Some Compounds of Examples Against Different Enzymes Allowing compound solutions (10 μM, 3× dilution at eight gradients) of examples reacted with phosphatases such as SHP1, LMW-PTP, LYP, MKP3, PTP1B, PTPN2, PTPN6, VHR, CDC25A, PTPRR, etc. according to a similar method shown in Test Example 1 to test the inhibitory activity of the compounds on the phosphatases described above.

Conclusion: Some examples of the present disclosure, such as Example 1 and Example 4, have weak inhibitory activity against phosphatases such as SHP1 and PTP1B, with IC50 values greater than 500 nM, showing a high selectivity compared to the SHP2 enzyme.

Test Example 5: ADME Test of Some Compounds of Examples

Metabolic stability test: Incubating 150 μL of liver microsomes (final concentration 0.5 mg/mL) containing NADPH (final concentration 1 mM), 1 μM of test compound and a positive control midazolam or a negative control atenolol for metabolic stability, terminating the reaction with acetonitrile containing tinidazole at 0 min, 5 min, 10 min and 30 min, respectively, vortexing for 10 min, centrifuging at 15,000 rmp for 10 min, and injecting 50 μL of supernatant into a 96-well plate. Calculating the metabolic stability of the compounds by determining the relative reduction of a parent drug.

Direct inhibition test (DI test): Incubating 100 μL of human liver microsomes (final concentration 0.2 mg/mL) containing NADPH (final concentration 1 mM), 10 μM of compound, a positive inhibitor cocktail (ketoconazole 10 μM, quinidine 10 μM, sulfaphenazole 100 μM, a-naphthoflavone 10 μM, and tranylcypromine 1,000 μM), a negative control (BPS containing 0.1% dimethyl sulfoxide) and a mixed probe substrate (midazolam 10 μM, testosterone 100 μM, dextromethorphan 10 μM, diclofenac 20 μM, phenacetin 100 μM, and mephenytoin 100 μM) for direct inhibition, and terminating the reaction after 20 min of the incubation. Calculating the relative enzyme activity by measuring the relative production of metabolites.

Conclusion: Some examples of the present disclosure, such as Example 1 and Example 4, have high metabolic stability on liver microsomes of different species (mice, rats, dogs, monkeys, and human), with half-lives greater than 60 min, showing high metabolic stability and small species differences.

Some examples of the present disclosure, such as Example 1 and Example 4, have the inhibitory activity ($IC_{50}$ values greater than 25 uM) against common CYP enzymes such as CYP1A2, 2C8, 2C9, 2C19, 2D6 and 3A4, showing good druggability.

Test Example 6: Test of In Vivo Pharmacokinetic Parameters of Some Compounds in Rats, Mice and Dogs Dividing 6 SPF-grade laboratory animals into two groups, and preparing the test compound to a suitable solution or suspension; intravenously administering animals in one group, and orally administering animals in the other group. Collecting blood via jugular vein puncture at approximately 0.2 mL/time point for each sample, anticoagulating with sodium heparin, wherein the time points for blood collection is as follows: pre-dose, and 5, 15 and 30 min, and 1, 2, 4, 6, 8, and 24 h post-dose; placing the collected blood samples on ice, separating plasma by centrifugation (centrifugation conditions: 8,000 rpm, 6 min, 2-8° C.), and storing the collected plasma at −80° C. before analysis. Analyzing plasma samples using LC-MS/MS.

Based on the plasma concentration data of the drug, pharmacokinetic parameters such as $AUC_{0-t}$, $AUC_{0-\infty}$, $MRT_{0-\infty}$, $C_{max}$, $T_{max}$, $T_{1/2}$ and $V_d$ of a test sample, as well as mean and standard deviations thereof are calculated using a pharmacokinetic calculation software WinNonlin 5.2 non-compartmental model. In addition, the bioavailability (F) is calculated by the following formula.

$$F = \frac{AUC_{(0-t)(PO)} \times Dose_{IV}}{AUC_{(0-t)(IV)} \times Dose_{(PO)}} \times 100\%.$$

For samples with concentrations below the lower limit of quantification, samples taken before reaching $C_{max}$ should be calculated as zero for calculations of the pharmacokinetic parameter, and samples taken at sampling points after reaching $C_{max}$ should be calculated as non-quantifiable (BLQ) (specific results are shown in Table 3).

TABLE 3

| Test Items | Mouse po, 5 mg/kg Example 1 | Rat po, 5 g/kg Example 4 | Beagle Dog po, 5 mg/kg Example 1 | Example 1 |
|---|---|---|---|---|
| Maximum plasma concentration $C_{max}$ (nM) | 306 | 79 | 211 | 907 |
| Area under the curve AUC (uM * h) | 5845 | 557 | 3541 | 18248 |
| Half-life $T_{1/2}$ (h) | 11.8 | 10.9 | 22.3 | 10.9 |
| Bioavailability F | 61% | 20% | 64% | 162% |

Test Example 7: Test of Some Compounds of Examples on Growth Inhibition of Xenograft in Nude Mice Experimental method: 1) Culturing MV 4-11/KYSE520/NCI-H358 cells in a culture medium containing 10% fetal bovine serum. Harvesting tumor cells at an exponential growth phase, and resuspending in PBS to suitable concentrations for subcutaneous tumor inoculation in nude mice. 2) Subcutaneously inoculating 2-8×10$^7$ tumor cells at the right back of a mouse, and resuspending the cells in PBS and matrigel (1:1); observing tumor growth regularly, and randomizing mice for administration based on tumor size and mouse body weight when tumors grow to a mean volume of ~120 mm$^3$-1800 mm$^3$. 3) Defining the day of tumor cell inoculation as Day 0. Prior to the start of dosing, weighing all animals and measuring the tumor volume with a vernier caliper. 3) Administering orally compound of examples (prepared with water for injection containing 1% Tween80 to a desired concentration for use) at a given dose for three consecutive weeks, and giving an equal amount of solvent animals in a solvent control group. Measuring diameters of the xenograft twice a week throughout the experiment, and weighing the mice were at the same time.

The calculation formula of tumor volume (TV) is: $TV = \frac{1}{2} \times a \times b^2$, wherein a and b represent length and width, respectively. The relative tumor volume (RTV) is calculated based on the measured results using the formula: $RTV = Vt/V0$, wherein V0 is the tumor volume measured at the time of dosing in separate cages (i.e., Day 0) and Vt is the tumor volume at each measurement. The anti-tumor activity is evaluated by the following measures: 1) relative tumor proliferation rate T/C (%), which is calculated by the following formula: T/C (%)=(TRTV/CRTV)×100%, wherein TRTV: RTV of ae treatment group; CRTV: RTV of a negative control group; 2) inhibition rate of tumor volume growth GI %, which is calculated by the following formula: GI %=[1−(TVt−TV0)/(CVt−CT0)]×100%, wherein TVt is the tumor volume at each measurement in the treatment group; TV0 is the tumor volume obtained at the time of dosing in separate cages in the treatment group; CVt is the tumor volume at each measurement in the control group; CV0 is the tumor volume obtained at the time of dosing in separate cages in the control group (specific data are shown in Table 4).

TABLE 4

| Tumor Cell Xenograft Model | Dose, Route, and Frequency of Administration | | T/C |
|---|---|---|---|
| MV 4-11 | Example 1 | 2 mg/kg, orally, once daily, for 21 consecutive days | 28% |
| | | 5 mg/kg, orally, once daily, for 21 consecutive days | 3.0% |
| | SHP099 | 30 mg/kg, orally, once daily, for 21 consecutive days | 47% |
| KYSE520 | Example 1 | 2 mg/kg, orally, once daily, for 21 consecutive days | 30% |
| | | 6 mg/kg, orally, once daily, for 21 consecutive days | 18% |
| | SHP099 | 30 mg/kg, orally, once daily, for 21 consecutive days | 43% |
| NCI-H358 | Example 1 | 0.8 mg/kg, orally, once daily, for 21 consecutive days | 39% |
| | | 2.5 mg/kg, orally, once daily, for 21 consecutive days | 13% |
| | Comparative Compound 3 | 10 mg/kg, orally, once daily, for 21 consecutive days | 39% |

Conclusion: The compound 1 of the example have excellent inhibitory effect on MV 4-11/KYSE520/NCI-H358 tumor cell xenografts in nude mice with a low effective dose, a significant dose-response relationship and a long-acting effect (as shown in westernblot assay of tumor tissues, the experimental drug can still inhibit the signaling pathway in tumor tissues continuously 24 hours after the last dosing), and the experimental animals are well tolerated; the compound 1 of the example has far higher in vivo inhibitory effect against the three tumors described above that that of the comparative compound 3 and SHP099.

Test Example 8: Test of Compounds of Examples on Growth Inhibition of MC38 Colorectal Cancer Xenografts in C57BL-6 Mice Experimental method: 1) Culturing MC38 cells in a culture medium containing 10% fetal bovine serum. Harvesting tumor cells at an exponential growth phase, and resuspending in PBS to suitable concentrations for subcutaneous tumor inoculation in nude mice. 2) Subcutaneously inoculating $5 \times 10^7$ tumor cells at the right back of a mouse, and resuspending the cells in PBS and matrigel (1:1); observing tumor growth regularly, and randomizing mice for administration based on tumor size and mouse body weight when tumors grow to a mean volume of ~50 mm³-60 mm³. 3) Defining the day of tumor cell inoculation as Day 0. Prior to the start of dosing, weighing all animals and measuring the tumor volume with a vernier caliper. 3) Administering orally compound of examples (prepared with water for injection containing 1% Tween80 to a desired concentration for use) at a given dose, intraperitoneally injecting an anti-PD-L1 antibody twice a week, for two consecutive weeks, and giving an equal amount of solvent animals in a solvent control group. Measuring diameters of the xenograft twice a week throughout the experiment, and weighing the mice were at the same time.

The calculation formula of tumor volume (TV) is: $TV = \frac{1}{2} \times a \times b^2$, wherein a and b represent length and width, respectively. The relative tumor volume (RTV) is calculated based on the measured results using the formula: RTV=Vt/V0, wherein V0 is the tumor volume measured at the time of dosing in separate cages (i.e., Day 0) and Vt is the tumor volume at each measurement. The anti-tumor activity is evaluated by the following measures: 1) relative tumor proliferation rate T/C (%), which is calculated by the following formula: T/C (%)=(TRTV/CRTV)×100%, wherein TRTV: RTV of ae treatment group; CRTV: RTV of a negative control group; 2) inhibition rate of tumor volume growth GI %, which is calculated by the following formula: GI %=[1−(TVt−TV0)/(CVt−CT0)]×100%, wherein TVt is the tumor volume at each measurement in the treatment group; TV0 is the tumor volume obtained at the time of dosing in separate cages in the treatment group; CVt is the tumor volume at each measurement in the control group; CV0 is the tumor volume obtained at the time of dosing in separate cages in the control group (specific data are shown in Table 5).

TABLE 5

| No. | Dose, Route, and Frequency of Administration | T/C |
| --- | --- | --- |
| Example 1 | 1 mg/kg, orally, once daily | 60% |
| Anti PD-L1 | 10 mg/kg, intraperitoneally, twice a week | 39% |
| Example 1 + Anti PD-L1 | 1 mg/kg, orally, once daily + 10 mg/kg, intraperitoneally, twice a week | 13% |

Conclusion: The Compound 1 of the example and the PD-L1 antibody (InVivoMab anti-mouse PD-L1/B7-H1, Clone: 10F.9G2; Lot: 66571701B) used in the C57BL-6 murine model have a significant synergistic effect on the growth inhibition of MC38 tumor cell xenografts and good tolerance in experimental animals.

Although the detailed embodiments of the present disclosure are described above, technicians skilled in the art should understand that the embodiments are only examples, and many changes or modifications can be made to the embodiments without departing from principles and essence of the present disclosure. Therefore, the protection scope of the present disclosure is defined by the appended claims.

What is claimed is:

1. A nitrogen-containing fused heterocyclic compound, a pharmaceutically acceptable salt thereof, an enantiomer thereof, a diastereomer thereof, a tautomer thereof, a solvate thereof, a polymorph thereof or a prodrug:

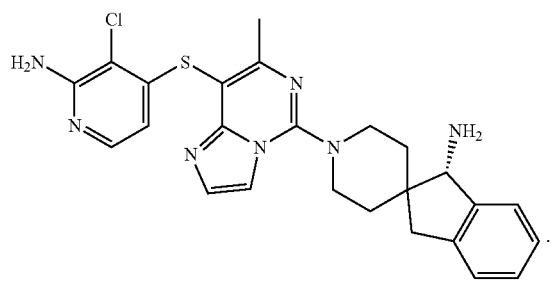 [SMILES: Cc1nc(N2CCC3(CC2)Cc2ccccc2[C@H]3N)n2ccnc2c1Sc1ccnc(N)c1Cl]

2. A pharmaceutical combination comprising the nitrogen-containing fused heterocyclic compound as defined in claim 1, a pharmaceutically acceptable salt thereof, an enantiomer thereof, a diastereomer thereof, a tautomer thereof, a solvate thereof, a polymorph thereof or a prodrug thereof, and a PD-1 inhibit or the PD-1 inhibitor is a PD-L1 antibody.

3. A pharmaceutical composition, comprising the nitrogen-containing fused heterocyclic compound as defined in claim 1, a pharmaceutically acceptable salt thereof, an enantiomer thereof, a diastereomer thereof, a tautomer thereof, a solvate thereof, a polymorph thereof or a prodrug thereof, and a pharmaceutically acceptable carrier.

4. A nitrogen-containing fused heterocyclic compound, a pharmaceutically acceptable salt thereof, an enantiomer thereof, a diastereomer thereof, a tautomer thereof, a solvate thereof, a polymorph thereof or a prodrug:

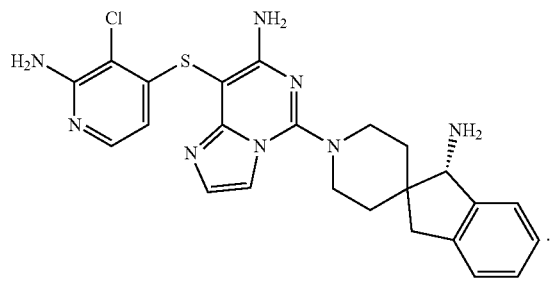 [SMILES: Nc1nccc(Sc2c(N)nc(N3CCC4(CC3)Cc3ccccc3[C@H]4N)n3ccnc23)c1Cl]

5. A pharmaceutical composition, comprising the nitrogen-containing fused heterocyclic compound as defined in claim 4, a pharmaceutically acceptable salt thereof, an enantiomer thereof, a diastereomer thereof, a tautomer thereof, a solvate thereof, a polymorph thereof or a prodrug thereof, and a pharmaceutically acceptable carrier.

6. A pharmaceutical combination comprising the nitrogen-containing fused heterocyclic compound as defined in claim 4, a pharmaceutically acceptable salt thereof, an enantiomer thereof, a diastereomer thereof, a tautomer thereof, a solvate thereof, a polymorph thereof or a prodrug thereof, and a PD-1 inhibit or the PD-1 inhibitor is a PD-L1 antibody.

* * * * *